US011865173B2

(12) United States Patent
Palese et al.

(10) Patent No.: US 11,865,173 B2
(45) Date of Patent: Jan. 9, 2024

(54) INFLUENZA VIRUS HEMAGGLUTININ PROTEINS AND USES THEREOF

(71) Applicant: ICAHN SCHOOL OF MEDICINE AT MOUNT SINAI, New York, NY (US)

(72) Inventors: Peter Palese, New York, NY (US); Adolfo Garcia-Sastre, New York, NY (US); Megan Ermler, New York, NY (US); Florian Krammer, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 17/583,088

(22) Filed: Jan. 24, 2022

(65) Prior Publication Data
US 2022/0257749 A1 Aug. 18, 2022

Related U.S. Application Data

(62) Division of application No. 16/305,845, filed as application No. PCT/US2017/037384 on Jun. 14, 2017, now Pat. No. 11,266,734.

(60) Provisional application No. 62/355,679, filed on Jun. 28, 2016, provisional application No. 62/350,701, filed on Jun. 15, 2016.

(51) Int. Cl.
| | | |
|---|---|---|
| *A61K 39/145* | (2006.01) | |
| *A61K 39/12* | (2006.01) | |
| *A61K 35/76* | (2015.01) | |
| *C07K 14/005* | (2006.01) | |
| *C07K 14/11* | (2006.01) | |
| *A61K 39/00* | (2006.01) | |

(52) U.S. Cl.
CPC .......... *A61K 39/145* (2013.01); *C07K 14/005* (2013.01); *A61K 2039/525* (2013.01); *A61K 2039/53* (2013.01); *A61K 2039/545* (2013.01); *A61K 2039/70* (2013.01); *C12N 2760/16122* (2013.01); *C12N 2760/16134* (2013.01); *C12N 2760/16171* (2013.01); *C12N 2760/16222* (2013.01); *C12N 2760/16234* (2013.01); *C12N 2760/16271* (2013.01)

(58) Field of Classification Search
CPC .. A61K 39/12; A61K 39/145; A61K 2039/70; A61K 2039/525; A61P 31/16
See application file for complete search history.

(56) References Cited

U.S. PATENT DOCUMENTS

| | | |
|---|---|---|
| 4,444,887 A | 4/1984 | Hoffmann |
| 4,522,811 A | 6/1985 | Eppstein et al. |
| 4,603,112 A | 7/1986 | Paoletti et al. |
| 4,693,981 A | 9/1987 | Wiesehahn et al. |
| 4,716,111 A | 12/1987 | Osband et al. |
| 4,722,848 A | 2/1988 | Paoletti et al. |
| 4,769,330 A | 9/1988 | Paoletti et al. |
| 5,057,540 A | 10/1991 | Kensil et al. |
| 5,106,619 A | 4/1992 | Wiesehahn et al. |
| 5,110,587 A | 5/1992 | Paoletti et al. |
| 5,166,057 A | 11/1992 | Palese et al. |
| 5,174,993 A | 12/1992 | Paoletti |
| 5,182,192 A | 1/1993 | Steplewski et al. |
| 5,413,923 A | 5/1995 | Kucherlapati et al. |
| 5,484,719 A | 1/1996 | Lam et al. |
| 5,545,806 A | 8/1996 | Lonberg et al. |
| 5,569,825 A | 10/1996 | Lonberg et al. |
| 5,571,709 A | 11/1996 | Devauchelle et al. |
| 5,573,916 A | 11/1996 | Cheronis et al. |
| 5,589,174 A | 12/1996 | Okuno et al. |
| 5,612,487 A | 3/1997 | Lam et al. |
| 5,625,126 A | 4/1997 | Lonberg et al. |
| 5,631,350 A | 5/1997 | Okuno et al. |
| 5,633,425 A | 5/1997 | Lonberg et al. |
| 5,643,576 A | 7/1997 | Johnston et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,891,705 A | 4/1999 | Budowsky et al. |
| 5,916,771 A | 6/1999 | Hori et al. |
| 5,929,304 A | 7/1999 | Radin et al. |
| 6,001,634 A | 12/1999 | Palese et al. |
| 6,022,726 A | 2/2000 | Palese et al. |
| 6,034,298 A | 3/2000 | Lam et al. |
| 6,136,320 A | 10/2000 | Arntzen et al. |
| 6,146,642 A | 11/2000 | Garcia-Sastre et al. |
| 6,165,476 A | 12/2000 | Strom et al. |

(Continued)

FOREIGN PATENT DOCUMENTS

| | | |
|---|---|---|
| CA | 2121559 A1 | 10/1994 |
| CA | 2718923 A1 | 9/2009 |

(Continued)

OTHER PUBLICATIONS

Abe et al., 2004, "Effect of the addition of oligosaccharides on the biological activities and antigenicity of influenza A/H3N2 virus hemagglutinin," J Virol., 78(18):9605-9611.

(Continued)

*Primary Examiner* — Barry A Chestnut
(74) *Attorney, Agent, or Firm* — JONES DAY

(57) ABSTRACT

Provided herein are chimeric hemagglutinin (HA) polypeptides and uses thereof for inducing an immune response (e.g., an antibody response) against influenza virus. Also provided herein are methods of generating antibodies to the chimeric HA polypeptides in a subject.

27 Claims, 57 Drawing Sheets

Specification includes a Sequence Listing.

(56) References Cited

U.S. PATENT DOCUMENTS

| | | |
|---|---|---|
| 6,265,189 B1 | 7/2001 | Paoletti et al. |
| 6,337,070 B1 | 1/2002 | Okuno et al. |
| 6,468,544 B1 | 10/2002 | Egorov et al. |
| 6,544,785 B1 | 4/2003 | Palese et al. |
| 6,551,820 B1 | 4/2003 | Mason et al. |
| 6,573,079 B1 | 6/2003 | Palese et al. |
| 6,635,246 B1 | 10/2003 | Barrett et al. |
| 6,649,372 B1 | 11/2003 | Palese et al. |
| 6,669,943 B1 | 12/2003 | Palese et al. |
| 6,720,409 B2 | 4/2004 | Okuno et al. |
| 6,770,799 B2 | 8/2004 | Mor et al. |
| 6,852,522 B1 | 2/2005 | Palese et al. |
| 6,867,293 B2 | 3/2005 | Andrews et al. |
| 6,887,699 B1 | 5/2005 | Palese et al. |
| 6,942,861 B2 | 9/2005 | McKee et al. |
| 6,951,754 B2 | 10/2005 | Hoffmann |
| 7,312,064 B2 | 12/2007 | Hoffmann |
| 7,384,774 B2 | 6/2008 | Palese et al. |
| 7,442,379 B2 | 10/2008 | Garcia-Sastre et al. |
| 7,494,808 B2 | 2/2009 | Palese et al. |
| 7,504,560 B2 | 3/2009 | Arntzen et al. |
| 7,566,458 B2 | 7/2009 | Yang et al. |
| 7,968,101 B2 | 6/2011 | Kawaoka et al. |
| 8,367,077 B2 | 2/2013 | Zurbriggen et al. |
| 8,603,467 B2 | 12/2013 | Chen et al. |
| 8,673,314 B2 | 3/2014 | Garcia Sastre et al. |
| 8,828,406 B2 | 9/2014 | Garcia-Sastre et al. |
| 9,051,359 B2 | 6/2015 | Garcia-Sastre et al. |
| 9,175,069 B2 | 11/2015 | Garcia-Sastre et al. |
| 9,371,366 B2 | 6/2016 | Garcia-Sastre et al. |
| 9,452,211 B2 | 9/2016 | Meijberg et al. |
| 9,701,723 B2 | 7/2017 | Garcia-Sastre et al. |
| 9,707,288 B2 | 7/2017 | Schrader |
| 9,708,373 B2 | 7/2017 | Garcia-Sastre et al. |
| 9,849,172 B2 | 12/2017 | Garcia-Sastre et al. |
| 9,908,930 B2 | 3/2018 | Palese et al. |
| 9,968,670 B2 | 5/2018 | Garcia-Sastre et al. |
| 10,131,695 B2 | 11/2018 | Garcia-Sastre et al. |
| 10,137,189 B2 | 11/2018 | Garcia-Sastre et al. |
| 10,179,806 B2 | 1/2019 | Garcia-Sastre et al. |
| 10,544,207 B2 | 1/2020 | Palese et al. |
| 10,583,188 B2 | 3/2020 | Garcia-Sastre et al. |
| 10,736,956 B2 | 8/2020 | Palese et al. |
| 11,254,733 B2 | 2/2022 | Palese et al. |
| 11,266,734 B2 | 3/2022 | Palese et al. |
| 2002/0054882 A1 | 5/2002 | Okuno et al. |
| 2002/0164770 A1 | 11/2002 | Hoffman |
| 2003/0134338 A1 | 7/2003 | Makarocskiy |
| 2004/0002061 A1 | 1/2004 | Kawaoka |
| 2004/0073011 A1 | 4/2004 | Hagay et al. |
| 2005/0009008 A1 | 1/2005 | Robinson et al. |
| 2005/0042229 A1 | 2/2005 | Yang et al. |
| 2005/0048074 A1 | 3/2005 | Cardineau et al. |
| 2005/0064391 A1 | 3/2005 | Segal et al. |
| 2005/0106178 A1 | 5/2005 | O'hagan et al. |
| 2005/0201946 A1 | 9/2005 | Friede et al. |
| 2006/0008473 A1 | 1/2006 | Yana et al. |
| 2006/0019350 A1 | 1/2006 | Palese et al. |
| 2006/0204487 A1 | 9/2006 | Shaaltiel et al. |
| 2006/0217338 A1 | 9/2006 | Lu et al. |
| 2006/0280754 A1 | 12/2006 | Garry et al. |
| 2007/0020238 A1 | 1/2007 | Baltimore et al. |
| 2007/0036809 A1 | 2/2007 | Michl et al. |
| 2007/0207171 A1 | 9/2007 | Dubensky et al. |
| 2007/0275014 A1 | 11/2007 | Yusibov et al. |
| 2008/0019998 A1 | 1/2008 | Wang et al. |
| 2008/0032921 A1 | 2/2008 | Alexander et al. |
| 2008/0038232 A1 | 2/2008 | Shaaltiel et al. |
| 2008/0152657 A1 | 6/2008 | Horowitz et al. |
| 2008/0176247 A1 | 7/2008 | Chou et al. |
| 2008/0193455 A1 | 8/2008 | Stassen et al. |
| 2008/0248066 A1 | 10/2008 | Dubensky et al. |
| 2008/0254060 A1 | 10/2008 | Palese et al. |
| 2009/0053762 A1 | 2/2009 | Shaaltiel |
| 2009/0068221 A1 | 3/2009 | Morrison |
| 2009/0081255 A1 | 3/2009 | Bublot et al. |
| 2009/0082548 A1 | 3/2009 | Shaaltiel et al. |
| 2009/0169547 A1 | 7/2009 | Sahin et al. |
| 2009/0208477 A1 | 8/2009 | Shaaltiel et al. |
| 2009/0246830 A1 | 10/2009 | Kawaoka et al. |
| 2009/0291472 A1 | 11/2009 | Lu et al. |
| 2009/0304730 A1 | 12/2009 | Amon et al. |
| 2009/0304739 A1 | 12/2009 | Rappouli et al. |
| 2009/0311265 A1 | 12/2009 | Van Den Brink et al. |
| 2009/0311669 A1 | 12/2009 | Kawaoka |
| 2010/0184192 A1 | 7/2010 | Smith et al. |
| 2010/0247571 A1 | 9/2010 | Wong et al. |
| 2010/0297165 A1 | 11/2010 | Berzofsky et al. |
| 2010/0297174 A1 | 11/2010 | Garcia-Sastre et al. |
| 2011/0027270 A1 | 2/2011 | Garcia-Sastre et al. |
| 2011/0111494 A1 | 5/2011 | Hill et al. |
| 2011/0182938 A1 | 7/2011 | Weiner et al. |
| 2011/0300604 A1 | 12/2011 | Kawaoka et al. |
| 2012/0039898 A1 | 2/2012 | Throsby et al. |
| 2012/0058538 A1 | 3/2012 | Palese et al. |
| 2012/0122185 A1 | 5/2012 | Palese et al. |
| 2012/0189658 A1 | 7/2012 | Couture et al. |
| 2012/0244183 A1 | 9/2012 | Garcia-Sastre et al. |
| 2012/0294796 A1 | 11/2012 | Johnson et al. |
| 2013/0022623 A1 | 1/2013 | Karsunky et al. |
| 2013/0129747 A1 | 5/2013 | Schrader |
| 2013/0129761 A1 | 5/2013 | Garcia-Sastre et al. |
| 2013/0209499 A1 | 8/2013 | Garcia-Sastre et al. |
| 2013/0224187 A1 | 8/2013 | Rother et al. |
| 2013/0315929 A1 | 11/2013 | Bock |
| 2014/0004149 A1 | 1/2014 | Tobin et al. |
| 2014/0170163 A1 | 6/2014 | Garcia Sastre et al. |
| 2014/0193484 A1 | 7/2014 | Bertholet Girardin et al. |
| 2014/0328875 A1 | 11/2014 | Garcia Sastre et al. |
| 2015/0132253 A1 | 5/2015 | Sahin et al. |
| 2015/0132330 A1 | 5/2015 | Garcia-Sastre et al. |
| 2015/0239960 A1 | 8/2015 | Garcia-Sastre et al. |
| 2015/0252103 A1 | 9/2015 | Sahin et al. |
| 2015/0266951 A1 | 9/2015 | Song |
| 2015/0297712 A1 | 10/2015 | Garcia-Sastre et al. |
| 2015/0299270 A1 | 10/2015 | Galarza et al. |
| 2015/0335729 A1 | 11/2015 | Garcia-Sastre et al. |
| 2015/0352202 A1 | 12/2015 | Osorio et al. |
| 2016/0015828 A1 | 1/2016 | Torgov et al. |
| 2016/0017025 A1 | 1/2016 | Samira et al. |
| 2016/0022806 A1 | 1/2016 | Weiner et al. |
| 2016/0024196 A1 | 1/2016 | Majeti et al. |
| 2016/0038585 A1 | 2/2016 | Dormitzer et al. |
| 2016/0137721 A1 | 5/2016 | Palese et al. |
| 2016/0185860 A1 | 6/2016 | Sahin et al. |
| 2016/0311918 A1 | 10/2016 | Wang et al. |
| 2016/0355553 A1 | 12/2016 | Meijberg et al. |
| 2016/0355590 A1 | 12/2016 | Epstein |
| 2016/0361408 A1 | 12/2016 | Garcia-Sastre et al. |
| 2016/0362455 A1 | 12/2016 | Meijberg et al. |
| 2016/0376347 A1 | 12/2016 | Saelens et al. |
| 2017/0204177 A1 | 7/2017 | Wang et al. |
| 2017/0327565 A1 | 11/2017 | Schrader |
| 2018/0002385 A1 | 1/2018 | Garcia-Sastre et al. |
| 2018/0008696 A1 | 1/2018 | Palese et al. |
| 2018/0022804 A1 | 1/2018 | Peters et al. |
| 2018/0265573 A1 | 9/2018 | Palese et al. |
| 2018/0312592 A1 | 11/2018 | Junutula et al. |
| 2018/0333479 A1 | 11/2018 | Garcia-Sastre et al. |
| 2019/0048324 A1 | 2/2019 | Kawaoka et al. |
| 2019/0099484 A1 | 4/2019 | Garcia-Sastre et al. |
| 2019/0106461 A1 | 4/2019 | Garcia-Sastre et al. |
| 2019/0125859 A1 | 5/2019 | Palese et al. |
| 2019/0292229 A1 | 9/2019 | Blackledge et al. |
| 2019/0314485 A1 | 10/2019 | Palese et al. |
| 2020/0223905 A1 | 7/2020 | Palese et al. |
| 2021/0260179 A1 | 8/2021 | Palese et al. |
| 2022/0153873 A1 | 5/2022 | Krammer et al. |

(56) References Cited

U.S. PATENT DOCUMENTS

| | | |
|---|---|---|
| 2022/0249652 A1 | 8/2022 | Palese et al. |
| 2022/0363736 A1 | 11/2022 | Palese et al. |

FOREIGN PATENT DOCUMENTS

| | | | |
|---|---|---|---|
| CN | 1196788 C | | 4/2005 |
| CN | 103665155 A | | 3/2014 |
| CN | 104185476 A | | 12/2014 |
| CN | 105263516 A | | 1/2016 |
| EP | 0621339 A2 | | 10/1994 |
| EP | 0702085 A1 | | 3/1996 |
| EP | 0780475 A1 | | 6/1997 |
| EP | 2540312 A1 | | 1/2013 |
| JP | H 789992 A | | 4/1995 |
| JP | H 10-502168 A | | 2/1998 |
| JP | 2004258814 A | | 9/2004 |
| JP | 2006347922 A | | 12/2006 |
| JP | 2008249712 A | | 10/2008 |
| JP | 2009022186 A | | 2/2009 |
| JP | 2009131237 A | | 6/2009 |
| JP | 2012521786 A | | 10/2010 |
| JP | 2011057653 A | | 3/2011 |
| JP | 2012530499 A | | 12/2012 |
| JP | 2014530003 A | | 11/2014 |
| JP | 2016508133 A | | 3/2016 |
| WO | WO 1984000687 A1 | | 3/1984 |
| WO | WO 1991010741 A1 | | 7/1991 |
| WO | WO 1992001047 A1 | | 1/1992 |
| WO | WO 1994009136 A1 | | 4/1994 |
| WO | WO 1994012629 A1 | | 6/1994 |
| WO | WO 1994016109 A1 | | 7/1994 |
| WO | WO 1994017826 A1 | | 8/1994 |
| WO | WO 1995034324 A1 | | 12/1995 |
| WO | WO 1996011279 A2 | | 4/1996 |
| WO | WO 1996033735 A1 | | 10/1996 |
| WO | WO 1996034096 A1 | | 10/1996 |
| WO | WO 1996034625 A1 | | 11/1996 |
| WO | WO 1997006270 A1 | | 2/1997 |
| WO | WO 1997012032 A1 | | 4/1997 |
| WO | WO 1997040161 A1 | | 10/1997 |
| WO | WO 1997040177 A1 | | 10/1997 |
| WO | WO 1998002530 A1 | | 1/1998 |
| WO | WO 1998013501 A2 | | 4/1998 |
| WO | WO 1998016654 A1 | | 4/1998 |
| WO | WO 1998024893 A2 | | 6/1998 |
| WO | WO 1998046645 A2 | | 10/1998 |
| WO | WO 1998050433 A1 | | 11/1998 |
| WO | WO 1998053078 A1 | | 11/1998 |
| WO | WO 1999002657 A1 | | 1/1999 |
| WO | WO 1999015672 A1 | | 4/1999 |
| WO | WO 2001004333 A1 | | 1/2001 |
| WO | WO 2002000885 A2 | | 1/2002 |
| WO | WO 2003068923 A2 | | 8/2003 |
| WO | WO 2003068923 A3 | | 8/2003 |
| WO | WO 2005000901 A2 | | 1/2005 |
| WO | WO 2007045674 A2 | | 4/2007 |
| WO | WO 2007064802 A1 | | 6/2007 |
| WO | WO 2007103322 A2 | | 9/2007 |
| WO | WO 2007109812 A2 | | 9/2007 |
| WO | WO 2007109813 A1 | | 9/2007 |
| WO | WO 2007110776 A1 | | 10/2007 |
| WO | WO 2007134237 A2 | | 11/2007 |
| WO | WO 2007134327 A2 | | 11/2007 |
| WO | WO 2008005777 A2 | | 1/2008 |
| WO | WO 2008028946 A2 | | 3/2008 |
| WO | WO 2008032219 A2 | | 3/2008 |
| WO | WO 2009001217 A2 | | 12/2008 |
| WO | WO 2009009876 A1 | | 1/2009 |
| WO | WO 2009012489 A1 | | 1/2009 |
| WO | WO 2009025770 A2 | | 2/2009 |
| WO | WO 2009036157 A1 | | 3/2009 |
| WO | WO 2009068992 A1 | | 6/2009 |
| WO | WO 2009076778 A1 | | 6/2009 |
| WO | WO 2009079259 A2 | | 6/2009 |
| WO | WO 2009092038 A1 | | 7/2009 |
| WO | WO 2009121004 A2 | | 10/2009 |
| WO | WO 2009150532 A1 | | 12/2009 |
| WO | WO 2009156405 A1 | | 12/2009 |
| WO | WO 2010003235 A1 | | 1/2010 |
| WO | WO 2010036170 A1 | | 4/2010 |
| WO | WO 2010036948 A2 | | 4/2010 |
| WO | WO 2010117786 A1 | | 10/2010 |
| WO | WO 2010130636 A1 | | 11/2010 |
| WO | WO 2010138564 A1 | | 12/2010 |
| WO | WO 2010148511 A1 | | 12/2010 |
| WO | WO 2011014645 A1 | | 2/2011 |
| WO | WO 2011044152 A1 | | 4/2011 |
| WO | WO 2011087092 A1 | | 7/2011 |
| WO | WO 2011103453 A2 | | 8/2011 |
| WO | WO 2011111966 A2 | | 9/2011 |
| WO | WO 2011123495 A1 | | 10/2011 |
| WO | WO 2011126370 A1 | | 10/2011 |
| WO | WO 2012009790 A1 | | 1/2012 |
| WO | WO 2013043729 A1 | | 3/2013 |
| WO | WO 2013079473 A1 | | 6/2013 |
| WO | WO 2014159960 A1 | | 1/2014 |
| WO | WO 2014099931 A1 | | 6/2014 |
| WO | WO 2014152841 A1 | | 9/2014 |
| WO | WO 2015199564 A1 | | 12/2015 |
| WO | WO 2016005480 A1 | | 1/2016 |
| WO | WO 2016005482 A1 | | 1/2016 |
| WO | WO 2016118937 A1 | | 7/2016 |
| WO | WO 2016205347 A1 | | 12/2016 |
| WO | WO 2017021893 A1 | | 2/2017 |
| WO | WO 2017035479 A1 | | 3/2017 |
| WO | WO 2017053413 A1 | | 3/2017 |
| WO | WO 2017136575 A1 | | 8/2017 |
| WO | WO 2017136575 A8 | | 8/2017 |
| WO | WO 2017148889 A1 | | 9/2017 |
| WO | WO 2017210445 A1 | | 12/2017 |
| WO | WO 2018148383 A1 | | 8/2018 |
| WO | WO 2018187706 A2 | | 10/2018 |
| WO | WO 2019032463 A1 | | 2/2019 |
| WO | WO 2019246363 A1 | | 12/2019 |
| WO | WO 2020219719 A1 | | 10/2020 |
| WO | WO 2020264141 A1 | | 12/2020 |
| WO | WO 2021081120 A1 | | 4/2021 |

OTHER PUBLICATIONS

Abed et al., 2002, "Divergent evolution of hemagglutinin and neuraminidase genes in recent influenza A:H3N2 viruses isolated in Canada," J. Med. Virol., 67(4):589-595.

Air et al., 1985, "Location of antigenic sites on the three-dimensional structure of the influenza N2 virus neuraminidase," Virology, 145(2):237-248.

Air et al., 1990, "Antigenic, sequence, and crystal variation in influenza B neuraminidase," Virology, 177(2):578-587.

Air et al., 2012, "Influenza neuraminidase," Influenza Other Respir Viruses, 6(4):245-256 (Epub 2011).

Air, 2015, "Influenza virus antigenicity and broadly neutralizing epitopes," Curr. Opin. Virol. 11:113-121.

Altman et al., 2018, "Antibody Immunodominance: The Key to Understanding Influenza Virus Antigenic Drift," Viral. Immunol., 31(2):142-149.

Altschul et al., 1997, "Gapped BLAST and PSI-BLAST: a new generation of protein database search programs," Nucleic Acids Res., 25(17):3389-3402.

Amanat et al., 2019, "Cross-reactive antibodies binding to H4 hemagglutinin protect against a lethal H4N6 influenza virus challenge in the mouse model," Emerg. Microbes. Infect., 8(1):155-168.

Angeletti et al., 2017, "Defining B cell immunodominance to viruses," Nat Immunol., 18(4):456-463.

Angeletti et al., 2018, "Is It Possible to Develop a "Universal" Influenza Virus Vaccine? Outflanking Antibody Immunodominance on the Road to Universal Influenza Vaccination," Cold Spring Harb Perspect Biol., 10(7):a028852 (9 pages).

Anonymous, "alignment" IBIS—Integrated Biotechnological Information, European Patent Office, retrieved from ibis.internal.epo.org/exam/jobResult?id=285344, on Sep. 26, 2014 (1 page).

(56) References Cited

OTHER PUBLICATIONS

Anonymous, "Amino Acids Reference Chart—Sigma-Aldrich" retrieved from www.sigmaaldrich.com/life-science/metabolomics/learning-center/amino-acid-reference-chart.html, on Jul. 17, 2015 (3 pages).
Anthony et al., 2012, "Emergence of fatal avian influenza in New England harbor seals," MBio., 3(4):e00166-12.
Antoine et al., 1998, "The complete genomic sequence of the modified vaccinia Ankara strain: comparison with other orthopoxviruses," Virology, 244(2):365-396.
Arzey et al., 2012, "Influenza virus A (H10N7) in chickens and poultry abattoir workers, Australia," Emerg Infect Dis., 18(5):814-816.
Babai et al., 2001, "A novel liposomal influenza vaccine (INFLUSOME-VAC) containing hemagglutinin-neuraminidase and IL-2 or GM-CSF induces protective anti-neuraminidase antibodies cross-reacting with a wide spectrum of influenza A viral strains," Vaccine 20(3-4):505-515.
Babu et al., 2014, "Live attenuated H7N7 influenza vaccine primes for a vigorous antibody response to inactivated H7N7 influenza vaccine," Vaccine 32:6798-6804.
Bailey et al., 2018, "A Method to Assess Fc-mediated Effector Functions Induced by Influenza Hemagglutinin Specific Antibodies," J. Vis. Exp., (132):e56256 (5 pages).
Baker et al., 1976, "Effect of Ca++ on the stability of influenza virus neuraminidase," Arch Virol., 52(1-2):7-18.
Baker et al., 2013, "Protection against lethal influenza with a viral mimic," J Virol., 87(15):8591-8605.
Basler et al., 1999, "Mutation of neuraminidase cysteine residues yields temperature-sensitive influenza viruses," J Virol., 73(10):8095-8103.
Baz et al., 2013, "Replication and immunogenicity of swine, equine, and avian h3 subtype influenza viruses in mice and ferrets," J Virol., 87(12):6901-6910.
Beare et al., 1975, "Trials in man with live recombinants made from A/PR/8/34 (H0 N1) and wild H3 N2 influenza viruses," Lancet, 2(7938):729-732.
Belongia et al., 2016, "Variable influenza vaccine effectiveness by subtype: a systematic review and meta-analysis of test-negative design studies," Lancet Infect. Dis., 16(8):942-951.
Belshe, 2007, "Translational research on vaccines: influenza as an example," Clin Pharmacol Ther., 82(6):745-749.
Benjamin et al., 2014, "A broadly neutralizing human monoclonal antibody directed against a novel conserved epitope on the influenza virus H3 hemagglutinin globular head," J. Virol., 88(12):6743-6750.
Benne et al., 1998, "Comparison of neutralizing and hemagglutination-inhibiting antibody responses to influenza A virus vaccination of human immunodeficiency virus-infected individuals," Clin. Diagn. Lab Immunol., 5(1):114-117.
Benoit et al., 2015, "Hemagglutination Inhibition Antibody Titers as a Correlate of Protection Against Seasonal A/H3N2 Influenza Disease," Open Forum Infect. Dis., 2(2):ofv067 (8 pages).
Berry, 2007, "Cross-reactive MAb to the binding domain of botulinum neurotoxin A, B, and E developed using a sequential immunization strategy: anti-botulinum neurotoxin," Hybridoma 26(6):435-436.
Bett et al., 1993, "Packaging capacity and stability of human adenovirus type 5 vectors," J Virol., 67(10):5911-5921.
Beyer et al., 2013, "Cochrane re-arranged: support for policies to vaccinate elderly people against influenza," Vaccine, 31(50):6030-6033.
Bhatt et al., 2011, "The genomic rate of molecular adaptation of the human influenza A virus," Mol. Biol. Evol., 28(9):2443-2451.
Bianchi et al., 2005, "Universal influenza B vaccine based on the maturational cleavage site of the hemagglutinin precursor," J. Virol. 79(12):7380-7388.
Bommakanti et al., 2010, "Design of an HA2-based *Escherichia coli* expressed influenza immunogen that protects mice from pathogenic challenge," Proc. Natl. Acad. Sci. USA 107:13701-13706.
Bommakanti et al., 2012, "Design of *Eschericia coli*-Expressed Stalk Domain Immunogens of H1N1 Hemagglutinin That Protect Mice from Lethal Challenge," J. Virol. 86(24):13434-13444.
Boni et al., 2010, "Guidelines for identifying homologous recombination events in influenza A virus," PLoS One 5(5):e10434.
Boni et al., 2012, "No evidence for intra-segment recombination of 2009 H1N1 influenza virus in swine," Gene 494(2):242-245.
Bouvier et al., 2008, "Oseltamivir-resistant influenza A viruses are transmitted efficiently among guinea pigs by direct contact but not by aerosol," J Virol., 82(20):10052-10058.
Bouvier et al., 2010, "Animal Models for Influenza Virus Pathogenesis and Transmission," Viruses, 2(8):1530-1563.
Bowie et al., 1990, "Deciphering the Message in Protein Sequences: Tolerance to Amino Acid Substitutions," Science 247:1306-1310.
Bright et al., 2007, "Influenza virus-like particles elicit broader immune responses than whole virion inactivated influenzavirus or recombinant hemagglutinin," Vaccine, 25(19):3871-3878.
Broecker et al., 2018, "Immunodominance of Antigenic Site B in the Hemagglutinin of the Current H3N2 Influenza Virus in Humans and Mice," J Virol., 92(20):e01100-18.
Broecker et al., 2019, "A Mosaic Hemagglutinin-Based Influenza Virus Vaccine Candidate Protects Mice From Challenge With Divergent H3N2 Strains," NPJ Vaccines, 4:31 (9 pages).
Broecker et al., 2019, "Extending the Stalk Enhances Immunogenicity of the Influenza Virus Neuraminidase," J. Virol., 93(18):e00840-19 (12 pages).
Brottet et al., 2014, "Influenza season in Réunion dominated by influenza B virus circulation associated with numerous cases of severe disease, France, 2014," Eurosurveillance (4 pages).
Bruhn et al., 2014, "Crystal structure of the nipah virus phosphoprotein tetramerization domain," J Virol., 88(1):758-762 (Epub 2013).
Budd et al., 2018, "Update: Influenza Activity—United States, Oct. 1, 2017-Feb. 3, 2018," MMWR Morb Mortal Wkly Rep., 67(6):169-179.
Bullough et al., 1994, "Structure of influenza haemagglutinin at the pH of membrane fusion," Nature 371:37-43.
Carter et al., 2016, "Design and Characterization of a Computationally Optimized Broadly Reactive Hemagglutinin Vaccine for H1N1 Influenza Viruses," J Virol., 90(9):4720-4734.
Casali et al., 2008, "Site-directed mutagenesis of the hinge peptide from the hemagglutinin protein: enhancement of the pH-responsive conformational change," Protein Eng. Des. Sel. 21(6):395-404.
Castrucci et al., 1993, "Biologic importance of neuraminidase stalk length in influenza A virus," J. Virol., 67(2):759-764.
Caton et al., 1982, "The antigenic structure of the influenza virus A/PR/8/34 hemagglutinin (H1 subtype)," Cell, 31(2 Pt 1):417-427.
Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf, pp. A32-A108 (2007).
Centers for Disease Control and Prevention (CDC), 2009, "Swine influenza A (H1N1) infection in two children—Southern California, Mar.-Apr. 2009," MMWR Morb Mortal Wkly Rep., 58(15):400-402.
Centers for Disease Control and Prevention (CDC), 2009, "Update on influenza A (H1N1) 2009 monovalent vaccines," MMWRMorb Mortal Wkly Rep., 58(39):1100-1101.
Centers for Disease Control and Prevention (CDC), 2010, "Estimates of deaths associated with seasonal influenza—United States, 1976-2007," MMWR Morb Mortal Wkly Rep., 59(33):1057-1062.
Centers for Disease Control and Prevention (CDC), 2011, "Influenza-Associated Pediatric Deaths—United States, Sep. 2010--Aug. 2011," MMWR Morb Mortal Wkly Rep., 60(36):1233-1267.
Centers for Disease Control and Prevention (CDC), 2012, "Notes from the field: Highly pathogenic avian influenza A (H7N3) virus infection in two poultry workers—Jalisco, Mexico, Jul. 2012," MMWR Morb Mortal Wkly Rep., 61(36):726-727.
Centers for Disease Control and Prevention (CDC), 2012, "Notes from the field: Outbreak of influenza A (H3N2) virus among persons and swine at a county fair—Indiana, Jul. 2012," MMWR Morb Mortal Wkly Rep., 61(29):561.

(56) References Cited

OTHER PUBLICATIONS

Centers for Disease Control and Prevention (CDC), 2018, "Interim Estimates of 2017-18 Seasonal Influenza Vaccine Effectiveness—United States, Feb. 2018," MMWR Morb Mortal Wkly Rep., 67(6);180-185.
Chen et al., 1999, "N- and C-terminal residues combine in the fusion-pH influenza hemagglutinin $HA_2$ subunit to form an N cap that terminates the triple-stranded coiled coil," Proc. Natl. Acad. Sci. 96(16):8967-8972.
Chen et al., 2000, "Cross-protection against a lethal influenza virus infection by DNA vaccine to neuraminidase," Vaccine, 18(28):3214-3222.
Chen et al., 2007, "Exploration of the emergence of the Victoria lineage of influenza B virus," Arch Virol., 152(2):415-422 (Epub 2006).
Chen et al., 2007, "Influenza Virus Hemagglutinin and Neuraminidase, but Not the Matrix Protein, Are Required for Assembly and Budding of Plasmid-Derived Virus-Like Particles," J. Virol. 81(13):7111-7123.
Chen et al., 2009, "Evaluation of live attenuated influenza a virus h6 vaccines in mice and ferrets," J Virol., 83(1):65-72.
Chen et al., 2010, "Generation of Live Attenuated Novel Influenza Virus A/California/7/09 (H1N1) Vaccines with High Yield in Embryonated Chicken Eggs," J. Virol. 84(1):44-51.
Chen et al., 2011, "Vaccine design of hemagglutinin glycoprotein against influenza," Trends Biotechnol. 29(9):426-434.
Chen et al., 2012, "The 2009 pandemic H1N1 virus induces anti-neuraminidase (NA) antibodies that cross-react with the NA of H5N1 viruses in ferrets," Vaccine, 30(15):2516-2522.
Chen et al., 2014, "Clinical and epidemiological characteristics of a fatal case of avian influenza A H10N8 virus infection: a descriptive study," Lancet, 383(9918):714-721.
Chen et al., 2016, "Influenza A viruses expressing intra- or intergroup chimeric hemagglutinins," 90:3789-3793, doi:10.1128/JVI.03060-15.
Chen et al., 2018, "Influenza Infection in Humans Induces Broadly Cross-Reactive and Protective Neuraminidase-Reactive Antibodies," Cell, 173(2):417-429.
Chromikova et al., 2017, "Generation of a serum free CHO DG44 cell line stably producing a broadly protective anti-influenza virus monoclonal antibody," PLoS One, 12(9):e0183315 (11 pages).
Claas et al., 1998, "Human influenza A H5N1 virus related to a highly pathogenic avian influenza virus," Lancet, 351(9101):472-477.
Clementi et al., 2011, "A Human Monoclonal Antibody with Neutralizing Activity against Highly Divergent Influenza Subtypes," PLoS ONE 6(12):e28001.
Clements et al., 1986, "Serum and nasal wash antibodies associated with resistance to experimental challenge with influenza A wild-type virus," J. Clin. Microbiol., 24(1):157-160.
Cobey et al., 2017, "Immune history and influenzavirus susceptibility," Curr. Opin. Virol., 22:105-111.
Cohen et al., 2013, "Influenza A penetrates host mucus by cleaving sialic acids with neuraminidase," Virol J., 10:321 (13 pages).
Communie et al., 2013, "Structure of the tetramerization domain of measles virus phosphoprotein," J. Virol., 87(12):7166-7169.
Copeland et al., 2005, "Functional chimeras of human immunodeficiency virus type 1 Gp120 and influenza A virus (H3) hemagglutinin," J. Virol. 79:6459-6471.
Corti et al., 2010, "Heterosubtypic neutralizing antibodies are produced by individuals immunized with a seasonal influenza vaccine," J Clin Invest, 120(5):1663-1673.
Corti et al., 2011, "A neutralizing antibody selected from plasma cells that binds to group 1 and group 2 influenza A hemagglutinins," Science 333(6044):850-856.
Cotter et al., 2014, "A Single Amino Acid in the Stalk Region of the H1N1pdm Influenza Virus HA Protein Affects Viral Fusion, Stability and Infectivity," PLoS Pathogens 10(1):e1003831.
Couch et al., 1974, "Induction of partial immunity to influenza by a neuraminidase-specific vaccine," J Infect Dis., 129(4):411-420.
Couch et al., 2012, "A randomized clinical trial of an inactivated avian influenza A (H7N7) vaccine," PLoS One, 7(12):e49704 (6 pages).
Couch et al., 2012, "Randomized comparative study of the serum antihemagglutinin and antineuraminidase antibody responses to six licensed trivalent influenza vaccines," Vaccine, 31(1):190-195.
Couch et al., 2013, "Antibody correlates and predictors of immunity to naturally occurring influenza in humans and the importance of antibody to the neuraminidase," J Infect Dis., 207(6):974-981.
Coudeville et al., 2010, "Relationship between haemagglutination-inhibiting antibody titres and clinical protection against influenza: development and application of a bayesian random-effects model," BMC Med. Res. Methodol., 10:18 (11 pages).
Cox et al., 1998, "Influenza," Infect. Dis. Clin. North Am. 12(1):27-38.
Cox, 2013, "Correlates of protection to influenza virus, where do we go from here?," Hum. Vaccin. Immunother., 9(2):405-408.
Crotty et al., 2004, "Tracking human antigen-specific memory B cells: a sensitive and generalized ELISPOT system," J. Immunol. Methods 286 (1-2):111-122.
D'Aoust et al., 2008, "Influenza virus-like particles produced by transient expression in Nicotiana benthaminana induce a protective immune response against a lethal viral challenge in mice," J. Plant Biotechnol, 6(9):930-940.
D'Aoust et al., 2010, "The production of hemagglutinin-based virus-like particles in plants: a rapid, efficient and safe response to pandemic influenza," Plant Biotechnol. 8(5):607-619.
Da Silva et al., 2013, "Assembly of subtype 1 influenza neuraminidase is driven by both the transmembrane and head domains," J Biol Chem., 288(1):644-653 (Epub 2012).
Dalakouras et al., 2006, "Development of recombinant protein-based influenza vaccine. Expression and affinity purification of H1N1 influenza virus neuraminidase," J Chromatogr A., 1136(1):48-56.
Das et al., 2010, "Glycosylation Focuses Sequence Variation in the Influenza A Virus H1 Hemagglutinin Globular Domain," PLoS Pathogens 6(11):e1001211.
Das et al., 2013, "Defining influenza A virus hemagglutinin antigenic drift by sequential monoclonal antibody selection," Cell Host Microbe, 13(3):314-323.
Database Geneseq "Influenza A virus hemagglutinin protein, H1PR8", Accession No. AJG95109, dated Nov. 15, 2007.
Database GenPept "Hemagglutinin precursor [Contains: Hemagglutinin HA1 chain; Hemagglutinin HA2 chain]", Accession No. P03437, dated Jul. 21, 1986.
De Jong et al., 2000, "Mismatch between the 1997/1998 influenza vaccine and the major epidemic A(H3N2) virus strain as the cause of an inadequate vaccine-induced antibody response to this strain in the elderly," J Med Virol., 61(1):94-99.
Deroo et al., 1996, "Recombinant neuraminidase vaccine protects against lethal influenza," Vaccine, 14(6):561-569.
Desselberger et al., 1978, "Biochemical evidence that "new" influenza virus strains in nature may arise by recombination (reassortment)," Proc Natl Acad Sci USA, 75(7):3341-3345.
Dijkstra et al., 2009, "Long time trends in influenza-like illness and associated determinants in The Netherlands," Epidemiol Infect., 137(4):473-479.
Dilillo et al., 2014, "Broadly neutralizing hemagglutinin stalk-specific antibodies require FcγR interactions for protection against influenza virus in vivo," Nat Med., 20(2):143-151.
Dilillo et al., 2016, "Broadly neutralizing anti-influenza antibodies require Fc receptor engagement for in vivo protection," J Clin Invest, 126(2):605-610.
Dillon et al., 1992, "Induction of protective class I MHC-restricted CTL in mice by a recombinant influenza vaccine in aluminum hydroxide adjuvant," Vaccine 10(5):309-318.
Domnich et al., 2017, "Effectiveness of MF59-adjuvanted seasonal influenza vaccine in the elderly: A systematic review and meta-analysis," Vaccine, 35(4):513-520.
Doms et al., 2000, "HIV-1 Membrane Fusion: Targets of Opportunity," JCB, 151(2): F9-F13.
Dowdle et al., 1973, "Inactivated influenza vaccines. 2. Laboratory indices of protection," Postgrad Med J., 49(569):159-163.

(56) References Cited

OTHER PUBLICATIONS

Doyle et al., 1986, "Analysis of Progressive Deletions of the Transmembrane and Cytoplasmic Domains of Influenza Hemagglutinin," JCB 103:1193-1204.
Doyle et al., 2013, "A monoclonal antibody targeting a highly conserved epitope in influenza B neuraminidase provides protection against drug resistant strains," Biochem. Biophys. Res. Commun. 441(1):226-229.
Doyle et al., 2013, "Universal anti-neuraminidase antibody inhibiting all influenza A subtypes," Antiviral Res., 100(2):567-574.
Dreyflus et al., 2012, "Highly conserved protective epitopes on influenza B viruses," Science, 337(6100):1343-1348.
Dubensky et al., 1996, "Sindbis virus DNA-based expression vectors: utility for in vitro and in vivo gene transfer," J Virol., 70(1):508-519.
Dunand et al., 2016, "Both Neutralizing and Non-Neutralizing Human H7N9 Influenza Vaccine-Induced Monoclonal Antibodies Confer Protection," Cell Host Microbe., 19(6):800-813.
Durrant et al., 2016, "Microsecond Molecular Dynamics Simulations of Influenza Neuraminidase Suggest a Mechanism for the Increased Virulence of Stalk-Deletion Mutants," J. Phys. Chem. B., 120(33):8590-8599.
Easterbrook et al., 2012, "Protection against a lethal H5N1 influenza challenge by intranasal immunization with virus-like particles containing 2009 pandemic H1N1 neuraminidase in mice," Virology, 432(1):39-44.
Eda et al., 2006, "Sequential immunization with V3 peptides from primary human immunodeficiency virus type 1 produces cross-neutralizing antibodies against primary isolates with a matching narrow-neutralization sequence motif," J. Virol, 80(11):5552-5562.
Edwards et al., 2003, "The remarkable flexibility of the human antibody repertoire; isolation of over one thousand different antibodies to a single protein, BLyS," J. Mol. Biol., 334(1):103-118.
Ekiert et al., 2009, "Antibody recognition of a highly conserved influenza virus epitope", Science; 324(5924):246-251.
Ekiert et al., 2011, "A highly conserved neutralizing epitope on group 2 influenza A viruses", Science 333:843-850.
Ekiert et al., 2012, , "Broadly neutralizing antibodies against influenza virus and prospects for universal therapies," Curr Opin Virol., 2(2):134-141.
Ekiert et al., 2012, "Cross-neutralization of influenza A viruses mediated by a single antibody loop," Nature 489:526-532.
Ellebedy et al., 2014, "Induction of broadly cross-reactive antibody responses to the influenza HA stem region following H5N1 vaccination in humans," Proc Natl Acad Sci USA, 111(36):13133-13138.
EMA Guideline on the exposure to medicinal products during pregnancy: need for post-authorization data (Doc. Ref. EMEA/CHMP/313666/2005), adopted at Community level in May 2006; http://www.ema.europa.eu/docs/en_GB/document_library/Regulatory_and_procedural_guideline_2009/11/WC500011303.pdf (21 pages).
Eriksson et al., 2007, "Local and systemic cytokine and chemokine responses after parenteral influenza vaccination," Influenza Other Respir Viruses, 1(4):139-146.
Ermler et al., 2017, "Chimeric Hemagglutinin Constructs Induce Broad Protection against Influenza B Virus Challenge in the Mouse Model," J. Virol. 91(12): e00286-17.
Extended European Search Report for European Application No. 11763347.9, dated Feb. 2, 2015.
Fields et al., 1981, "Structure of the neuraminidase gene in human influenza virus A/PR/8/34," Nature, 290(5803):213-217.
Fiore et al., 2010, "Prevention and control of influenza with vaccines: recommendations of the Advisory Committee on Immunization Practices (ACIP), 2010," MMWR Recomm. Rep., 59(RR-8):1-62.
Fiore et al., 2011, "Antiviral agents for the treatment and chemoprophylaxis of influenza—recommendations of the Advisory Committee on Immunization Practices (ACIP)," MMWR Recomm Rep., 60(1):1-24.
Fitch et al., 1997, "Long term trends in the evolution of H(3) HA1 human influenza type A," Proc. Natl. Acad. Sci. USA, 94(15):7712-7718.
Flandorfer et al., 2003, "Chimeric Influenza A Viruses with a Functional Influenza B Virus Neuraminidase or Hemagglutinin," J. Virol. 77(17):9116-9123.
Fleury, et al., 2007, GenBank Acc. No. P03437, Updated Apr. 3, 2007.
Fluzone®, 2009-2010 Fluzone Seasonal influenza vaccine package insert, 2009.
Fodor et al., 1999, "Rescue of influenza A virus from recombinant DNA," J. Virol. 73:9679-9682 (1999).
Fouchier et al., 2004, "Avian influenza A virus (H7N7) associated with human conjunctivitis and a fatal case of acute respiratory distress syndrome," Proc Natl Acad Sci USA, 101(5):1356-1361.
Fox et al., 1982, "Influenzavirus infections in Seattle families, 1975-1979. II. Pattern of infection in invaded households and relation of age and prior antibody to occurrence of infection and related illness," Am J Epidemiol., 116(2):228-242.
Friesen et al., 2014, "A common solution to group 2 influenza virus neutralization," Proc. Natl. Acad. Sci. USA, 111(1):445-450 (Epub 2013).
Fujii et al., 2002, "Selective incorporation of influenzavirus RNA segments into virions," Proc. Natl. Acad. Sci. USA 100:2002-2007.
Fulton et al., 2018, "The Influenza B Virus Hemagglutinin Head Domain Is Less Tolerant to Transposon Mutagenesis than That of the Influenza A Virus," J Virol., 92(16):e00754-18 (13 pages).
Gamblin et al., 2004, "The structure and receptor binding properties of the 1918 influenza hemagglutinin," Science, 303(5665):1838-1842.
Gao et al., 2009, "Rewiring the RNAs of influenzavirus to prevent reassortment," Proc. Natl. Acad. Sci. USA 106:15891-15896.
Gao et al., 2013, "Human infection with a novel avian-origin influenza A(H7N9) virus," N. Engl. J. Med. 368:1888-1897.
Gao et al., 2016, "Measuring Influenza Neuraminidase Inhibition Antibody Titers by Enzyme-linked Lectin Assay," J. Vis. Exp., (115):e54573 (9 pages).
Gao et al., 2019, "Antigenic Drift of the Influenza A(H1N1)pdm09 Virus Neuraminidase Results in Reduced Effectiveness of A/California/7/2009 (H1N1pdm09)-Specific Antibodies," mBio, 10(2):e00307-19 (17 pages).
García-Sastre et al., 1994, "Introduction of foreign sequences into the genome of influenza A virus," Dev. Biol. Stand 82:237-246.
García-Sastre et al., 1994, "Use of a mammalian internal ribosomal entry site element for expression of a foreign protein by a transfectant influenza virus," J. Virol. 68:6254-6261.
Garcon et al., 2012, "Development and evaluation of AS03, an Adjuvant System containing α-tocopherol and squalene in an oil-in-water emulsion," Expert Rev Vaccines, 11(3):349-366.
Gauger et al., 2011, "Enhanced pneumonia and disease in pigs vaccinated with an inactivated humanlike (δ-cluster) H1N2 vaccine and challenged with pandemic 2009 H1N1 influenzavirus," Vaccine 29(15):2712-2719.
Gavigan et al., 2019, "Influenza: annual seasonal severity," Curr. Opin. Pediatr., 31(1):112-118.
Gaymard et al., 2016, "Functional balance between neuraminidase and haemagglutinin in influenza viruses," Clin. Microbiol. Infect., 22(12):975-983.
GenBan Accession No. AAA43397.1, neuraminidase [Influenza A virus (A/WSN/1933(H1N1))], 1982.
GenBan Accession No. ABG23658.1, neuraminidase, partial [Influenza A virus (A/Zhejiang/16/2006(H5N1))], 2007.
GenBank Accession No. AAA43412.1, neuraminidase [Influenza A virus (A/Puerto Rico/8/1934(H1N1))], 1981.
GenBank Accession No. AAQ90293.1, neuraminidase [Influenza A virus (A/equine/Santiago/77(H7N7))], 2003.
GenBank Accession No. AAS89005.1, neuraminidase [Influenza A virus (A/Thailand/3(SP-83)/2004(H5N1))], 2005.
GenBank Accession No. ABE97718.1, neuraminidase [Influenza A virus (A/Vietnam/CL100/2004(H5N1))], 2006.
GenBank Accession No. ABE97719.1, neuraminidase [Influenza A virus (A/Vietnam/CL105/2005(H5N1))], 2006.

(56) References Cited

OTHER PUBLICATIONS

GenBank Accession No. ABE97720.1, neuraminidase [Influenza A virus (A/Vietnam/CL115/2005(H5N1))], 2006.
GenBank Accession No. ACQ76318, hemagglutinin [Influenza A virus (A/California/04/2009(H1N1))], 2009.
GenBank Accession No. ACS71642, haemagglutinin [Influenza A virus (A/Perth/16/2009(H3N2))], 2009.
GenBank Accession No. AEX30531.1, neuraminidase [Influenza A virus (A/chicken/N101/Iran/2011(H9N2))], 2011.
GenBank Accession No. AEX30532.1, neuraminidase [Influenza A virus (A/chicken/N102/Iran/2011(H9N2))], 2011.
GenBank Accession No. AG018161.1, *Homo sapiens* genomic DNA, 21q region, clone: B396A17A4a015, genomic survey sequence, 1999.
GenBank Accession No. AIA62041.1, nemaminidase [Influenza A virus (A/goose/Guangxi/020G/2009(H3N8))], 2014.
GenBank Accession No. AII30325.1, neuraminidase [Influenza A virus (A/pigeon/Guangxi/020P/2009(H3N6))] , 2015.
GenBank Accession No. BAF48478-2007, haemagglutinin [Influenza A virus (A/duck/Czech/1956(H4N6))], 2007.
GenBank Accession No. CRI06477.1, neuraminidase [Influenza A virus (A/England/10740685/2010(H1N1))], 2015.
GenBank Accession No. CY209719.1, Influenza B virus (B/Arizona/36/2016) NB protein (NB) and neuraminidase (NA) genes, complete cds, last modified Dec. 21, 2016.
GenBank Accession No. DQ017504.1, Influenza A virus (A/mallard/Alberta/24/01(H7N3)) from Canada segment 4, complete sequence, 2005.
GenBank Accession No. KY090574.1, Influenza B virus (B/Pennsylvania/34/2015) segment 6 NB protein (NB) and neuraminidase (NA) genes, complete cds, last modified Aug. 24, 2017.
GenBank Accession No. NP 040981.1, nemaminidase [Influenza A virus (A/Puerto Rico/8/1934(H1N1))], 1981.
Genbank, NCBI Reference Sequence: YP_163736.1, HA2 [Influenza A virus (A/Puerto Rico/8/1934(H1N1))].
Georgiev et al., 2018, "Two-Component Ferritin Nanoparticles for Multimerization of Diverse Trimeric Antigens," ACS Infect Dis., 4(5):788-796.
Gerdil, 2003, "The annual production cycle for influenza vaccine," Vaccine, 21(16):1776-1779.
Gerhard et al., 1981, "Antigenic structure of influenza virus haemagglutinin defined by hybridoma antibodies," Nature, 290(5808):713-717.
Gerhard et al., 2006, "Prospects for universal influenza virus vaccine," Emerging Infectious Diseases; 12(4):569-574.
Gibbs et al., 2001, "Recombination in the hemagglutinin gene of the 1918 Spanish Flu," Science 293(5536):1842-1845.
Giddings et al., 2000, "Transgenic plants as factories for biopharmaceuticals," Nat. Biotechnol. 18:1151-1155.
Giles et al., 2012, "Computationally optimized antigens to overcome influenza viral diversity," Expert Rev Vaccines, 11(3):267-269.
Glezen et al., 1978, "Interpandemic influenza in the Houston area, 1974-76," N Engl J Med., 298(11):587-592.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Goel et al., 2004, "Plasticity within the antigen-combining site may manifest as molecular mimicry in the humoral immune response," J. Immunol., 173(12):7358-7367.
Goff et al., 2013, "Induction of cross-reactive antibodies to novel H7N9 influenza virus by recombinant Newcastle disease virus expressing a North American lineage H7 subtype hemagglutinin," *J. Virol.*, 87 (14): 8235-40.
Goff et al., 2013, "Adjuvants and immunization strategies to induce influenza virus hemagglutinin stalk antibodies", PLoS One 8:e79194.
Gomord et al., 2005, "Biopharmaceutical production in plants: problems, solutions and opportunities." TRENDS in Biotechnology, 23(11):559-565.
Goto et al., 2013, "The genome-packaging signal of the influenza A virus genome comprises a genome incorporation signal and a genome-bundling signal," J. Virol., 87(21):11316-11322.
Gould et al., 1987, "Mouse H-2k-Restricted Cytotoxic T Cells Recognize Antigenic Determinants in Both The HA1 and HA2 Subunits of the Influenza A/PR/8/34 Hemagglutinin," J. Exp. Med., 166:693-701.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Gravel et al., 2010, "Qualitative and quantitative analyses of virtually all subtypes of influenza A and B viral neuraminidases using antibodies targeting the universally conserved sequences," Vaccine 28(36):5774-5784.
Graves et al., 1983, "Preparation of influenza virus subviral particles lacking the HAI subunit of hemagglutinin: unmasking of cross-reactive HA2 determinants," Virology 126(1):106-116.
Grohskopf et al., 2017, "Prevention and Control of Seasonal Influenza with Vaccines: Recommendations of the Advisory Committee on Immunization Practices—United States, 2017-18 Influenza Season," MMWRRecomm, Rep., 66(2):1-20.
Gross et al., 1995, "The efficacy of influenza vaccine in elderly persons. A meta-analysis and review of the literature," Ann Intern Med., 123(7):518-527.
Gubareva et al., 2000, "Influenza virus neuraminidase inhibitors," Lancet, 355(9206):827-835.
Gulati et al., 2002, "Antibody epitopes on the neuraminidase of a recent H3N2 influenza virus (A/Memphis/31/98)," J Virol., 76(23):12274-12280.
Haffer et al., 1990, "Human immunodeficiency virus-like, nonreplicating, gag-env particles assemble in a recombinant vaccinia virus expression system," J Virol., 64(6):2653-2659.
Hagnesee et al., 1991, "Self-assembly of human papillomavirus type 1 capsids by expression of the L1 protein alone or by coexpression of the L1 and L2 capsid proteins," J Virol., 67(1):315-322.
Hai et al., 2008, "Influenza B virus NS 1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Hai et al., 2013, "Influenza A(H7N9) virus gains neuraminidase inhibitor resistance without loss of in vivo virulence or transmissibility," Nat Commun., 4:2854 (9 pages).
Halbherr et al., 2015, "Biological and protective properties of immune sera directed to the influenza virus neuraminidase," J Virol., 89(3):1550-1563 (Epub Nov. 12, 2014).
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Hamilton et al., 2016, "Club cells surviving influenza A virus infection induce temporary nonspecific antiviral immunity," Proc Natl Acad Sci USA, 113(14):3861-3866.
Hanks et al., 2005, "Re-engineered CD40 receptor enables potent pharmacological activation of dendritic-cell cancer vaccines in vivo," Nat Med., 11(2):130-137 and supplemental materials.
Harris et al., 2006, "Influenzavirus pleiomorphy characterized by cryoelectron tomography," Proc Natl Acad Sci USA, 103(50):19123-19127.
Harvey et al., 2011, "Improved antigen yield in pandemic H1N1 (2009) candidate vaccine viruses with chimeric hemagglutinin molecules," J Virol., 85(12):6086-6090.
Haynes, 2009, "Influenza virus-like particle vaccines", Expert Rev. Vaccines, 8(4): 435-445.
He et al., 2014, "Infection of influenza virus neuraminidase-vaccinated mice with homologous influenza virus leads to strong protection against heterologous influenza viruses," J Gen Virol., 95(Pt 12):2627-2637.

(56) References Cited

OTHER PUBLICATIONS

He et al., 2017, "Alveolar macrophages are critical for broadly-reactive antibody-mediated protection against influenza A virus in mice," Nat. Commun., 8(1):846 (14 pages).
Heaton et al., 2013, "Genome-wide mutagenesis of influenzavirus reveals unique plasticity of the hemagglutinin and NS1 proteins," Proc Natl Acad Sci USA, 110(50):20248-20253.
Heaton et al., 2013, "In Vivo Bioluminescent Imaging of Influenza A Virus Infection and Characterization of Novel Cross-Protective Monoclonal Antibodies," J. Virol. 87(15):8272-8281.
Heikkinen et al., 2014, ",Impact of influenza B lineage-level mismatch between trivalent seasonal influenza vaccines and circulating viruses, 1999-2012" Clin Infect Dis., 59(11):1519-1524.
Heinonen et al., 2010, "Early oseltamivir treatment of influenza in children 1-3 years of age: a randomized controlled trial," Clin Infect Dis., 51(8):887-894.
Hobson et al., 1972, "The role of serum haemagglutination-inhibiting antibody in protection against challenge infection with influenza A2 and B viruses," J Hyg (Lond), 70(4):767-777.
Hoffmann et al., 2000, "A DNA transfection system for generation of influenza A virus from eight plasmids," Proc Natl Acad Sci USA, 97(11):6108-6113.
Hong et al., 2013, "Antibody recognition of the pandemic H1N1 Influenza virus hemagglutinin receptor binding site," J. Virol. 87(22):12471-12480.
Horimoto et al., 2003, "Generation of influenza A viruses with chimeric (type A/B) hemagglutinins." J Virol. 77(14):8031-8038.
Horimoto et al., 2004, "Influenza A viruses possessing type B hemagglutinin and neuraminidase: potential as vaccine components," Microbes and Infection, 6(6):579-583.
Horvath et al., 1998, "Hemagglutinin-based multipeptide construct elicits enhanced protective immune response in mice against influenza A virus infection", Immunology Letters; 60(2/03):127-136.
Hu et al., 2013, "Fully human broadly neutralizing monoclonal antibodies against influenza A viruses generated from the memory B cells of a 2009 pandemic H1N1 influenza vaccine recipient," Virology 435(2):320-328.
Huang et al., 2004, "The Reverse Genetics Systems for Human and Animal RNA Viruses," Chinese Journal of Biotechnology, vol. 20, Issue 3, which is also published in Lian Yu, "Molecular Biology of Infectious Bursal Disease Virus and Research on New Vaccines," Zhejiang University Press, pp. 254-266, published on Dec. 31, 2007 (in Chinese with English abstract).
Hutchinson et al., 2010, "Genome packaging in influenza A virus," J. Gen. Virol., 91(Pt 2):313-328 (Epub 2009).
Iba et al., 2014, "Conserved neutralizing epitope at globular head of hemagglutinin in H3N2 influenza viruses" J. Virol., 88(13):7130-7144.
Igarashi et al.: 2008, "Genetically destined potentials for N-linked glycosylation of influenza virus hemagglutinin" Virology, 376:323-329.
Impagliazzo et al., 2015, "A stable trimeric influenza hemagglutinin stem as a broadly protective immunogen." Science, 349(6254):1301-1306 and supplemental materials.
Influenza Research Database, strain name: A/Anhui/1/2005, Collection Date: 2005 (2 pages).
Influenza Research Database, strain name: A/Bar-headed Goose/ Qinghai/59/05, Collection Date: 2005 (2 pages).
Influenza Research Database, strain name: A/California/07/2009, Collection Date: Apr. 9, 2009 (3 pages).
Influenza Research Database, strain name: A/Indonesia/5/2005, Collection Date: 2005 (3 pages).
Influenza Research Database, strain name: A/turkey/Turkey/1/2005, Collection Date: 2005 (2 pages).
Influenza Research Database, strain name: A/Viet Nam/1203/2004, Collection Date: 2004 (3 pages).
Influenza Research Database, strain name: A/whooper swan/Mongolia/ 244/2005, Collection Date: 2005 (2 pages).
Influenza Research Database, strain name: B/Brisbane/60/2008, Collection Date: 2008 (2 pages).
Influenza Research Database, strain name: B/Florida/04/2006, Collection Date: Nov. 1, 2006 (1 page).
Influenza Research Database, strain name: B/Florida/4/2006, Collection Date: Nov. 1, 2006 (1 page).
Influenza Research Database, strain name: B/lee/40, Collection Date: 1940 (1 page).
Influenza Research Database, strain name: B/Malaysia/2506/2004, Collection Date: May 12, 2004 (2 pages).
Influenza Research Database, strain name: B/Massachusetts/02/ 2012, Collection Date: Mar. 13, 2012 (1 page).
Influenza Research Database, strain name: B/New Jersey/01/2012, Collection Date: Apr. 26, 2012 (1 page).
Influenza Research Database, strain name: B/Texas/02/2013, Collection Date: Jan. 9, 2013 (1 page).
Influenza Research Database, strain name: B/Victoria/2/87, Collection Date: 1987 (1 page).
Influenza Research Database, strain name: B/Wisconsin/01/2010, Collection Date: 2010 (1 page).
Influenza Research Database, strain name: B/Yamagata/16/88, Collection Date: 1988 (2 pages).
International Preliminary Report on Patentability of International application No. PCT/US2011/030441, dated Oct. 2, 2012.
International Search Report and Corrected Written Opinion for International Patent Application No. PCT/US2020/029582 (Pub No. WO 2020219719) dated Sep. 28, 2020 (30 pages).
International Search Report and Written Opinion for International Patent Application No. PCT/US2020/039588 (Pub No. WO 2020264141) dated Nov. 9, 2020 (18 pages).
International Search Report and Written Opinion for International Patent Application No. PCT/US2020/056703 (Pub No. WO 2021081120) dated Feb. 9, 2021 (13 pages).
International Search Report and Written Opinion dated Oct. 29, 2019 of International Patent Application No. PCT/US2019/038178 (16 pages).
International Search Report dated Feb. 19, 2013 or PCT Application No. PCT/US2012/056122, Published as WO 2013/043729.
International Search Report dated Apr. 28, 2014 of PCT Application No. PCT/US2013/075697, Published as WO 2014/099931.
International Search Report dated Jun. 26, 2014 for PCT Application No. PCT/US2014/025526, Published as WO 2014/159960.
International Search Report dated Jul. 13, 2011 of PCT Application No. PCT/US2011/030441, Published as WO 2011/123495.
International Search Report dated Aug. 24, 2010 or PCT Application No. PCT/US2010/029202, Published as WO 2010/117786.
International Search Report of International Application No. PCT/ US2010/036170, dated Aug. 17, 2010.
International Search Report of International Application No. PCT/ US2011/025467, dated Oct. 19, 2011.
International Search Report of International Application No. PCT/ US2016/014640, dated Jun. 3, 2016.
International Search Report of International Application No. PCT/ US2016/037595, dated Sep. 15, 2016.
International Search Report of International Application No. PCT/ US2017/035479, dated Oct. 25, 2017.
International Search Report of International Application No. PCT/ US2017/037384, dated Nov. 3, 2017.
International Search Report of International Application No. PCT/ US2018/026489, dated Aug. 27, 2018.
International Search Report of International Application No. PCT/ US2018/045399, dated Nov. 29, 2018.
Isakova-Sivak et al., 2011, "Genetic bases of the temperature-sensitive phenotype of a master donor virus used in live attenuated influenza vaccines: A/Leningrad/134/17/57 (H2N2)," Virology, 412(2):297-305.
Isakova-Sivak et al., 2015, "Safety, immunogenicity and infectivity of new live attenuated influenza vaccines," Expert Rev Vaccines, 14(10):1313-1329.
Izurieta et al., 2000, "Influenza and the rates of hospitalization for respiratory disease among infants and young children," *NEJM* 342(4):232-239.
Jacobsen et al., 2017, "Influenza Virus Hemagglutinin Stalk-Specific Antibodies in Human Serum are a Surrogate Marker for In

(56) References Cited

OTHER PUBLICATIONS

Vivo Protection in a Serum Transfer Mouse Challenge Model," mBio, 8(5):e01463-17 (13 pages).
Jayasundara et al., 2014, "Natural attack rate of influenza in unvaccinated children and adults: a meta-regression analysis," BMC Infect Dis., 14:670 (9 pages).
Jefferson et al., 2005, "Assessment of the efficacy and effectiveness of influenza vaccines in healthy children: systematic review," Lancet, 365(9461):773-780.
Jefferson et al., 2005, "Efficacy and effectiveness of influenza vaccines in elderly people: a systematic review," Lancet, 366(9492):1165-1174.
Jeoung et al., 1995, "Effects of tumor necrosis factor-alpha on antimitogenicity and cell cycle-related proteins in MCF-7 cells." J Biol Chem., 270(31):18367-18373.
Jerne et al., 1982, "Recurrent idiotopes and internal images," EMBO J., 1(2):243-247.
Jin et al., 2003, "Multiple amino acid residues confer temperature sensitivity to human influenza virus vaccine strains (FluMist) derived from cold-adapted A/Ann Arbor/6/60," Virology, 306(1):18-24.
Job et al., 2018, "Broadened immunity against influenza by vaccination with computationally designed influenza virus N1 neuraminidase constructs," NPJ Vaccines, 3:55 (11 pages).
Joh Hira et al., 2004, "Production of monoclonal antibodies against a conserved region of Hemagglutinin of Influenza A virus and enzymatic activity of the light chain," Lectures in the Chemical Society of Japan, 84(2):1156, 2 J6-15 in Japanese with English translation of Abstract (4 pages).
Johansson et al., 1987, "Antigen-presenting B cells and helper T cells cooperatively mediate intravirionic antigenic competition between influenza A virus surface glycoproteins," Proc Natl Acad Sci USA, 84(19):6869-6873.
Johansson et al., 1987, "Immunologic response to influenza virus neuraminidase is influenced by prior experience with the associated viral hemagglutinin. II. Sequential infection of mice simulates human experience," J. Immunol., 139(6):2010-2014.
Johansson et al., 1989, "Purified influenza virus hemagglutinin and neuraminidase are equivalent in stimulation of antibody response but induce contrasting types of immunity to infection," J. Virol., 63(3):1239-1246.
Johansson et al., 1993, "Dissociation of influenzavirus hemagglutinin and neuraminidase eliminates their intravirionic antigenic competition," J Virol., 67(10):5721-5723.
Johansson et al., 1994, "Immunization with purified N1 and N2 influenza virus neuraminidases demonstrates cross-reactivity without antigenic competition," Proc Natl Acad Sci USA, 91(6):2358-2361.
Johansson et al., 1998, "Supplementation of conventional influenza A vaccine with purified viral neuraminidase results in a balanced and broadened immune response," Vaccine, 16(9-10):1009-1015.
Johansson et al., 2011, "Influenza viral neuraminidase: the forgotten antigen," Expert Rev. Vaccines, 10(12):1683-1695.
Johnson et al., 2002, "Updating the accounts: global mortality of the 1918-1920 "Spanish" influenza pandemic," Bull Hist Med., 76(1):105-115.
Joseph et al., 2007, "Evaluation of replication and pathogenicity of avian influenza a H7 subtype viruses in a mouse model," J Virol., 81(19):10558-10566.
Kabat et al., 1971, "Attempts to locate complementarity-determining residues in the variable positions of light and heavy chains," Ann N Y Acad Sci., 190:382-393.
Kamlangdee et al., 2016, "Mosaic H5 Hemagglutinin Provides Broad Humoral and Cellular Immune Responses Against Influenza Viruses," J Virol., 90(15):6771-6783.
Kanekiyo et al., 2013, "Self-assembling influenza nanoparticle vaccines elicit broadly neutralizing H1N1 antibodies." Nature, 499(7456):102-6.
Karlin et al., 1990, "Methods for assessing the statistical significance of molecular sequence features by using general scoring schemes," Proc Natl Acad Sci USA, 87(6):2264-2268.
Karlin et al., 1993, "Applications and statistics for multiple high-scoring segments in molecular sequences," Proc Natl Acad Sci USA, 90(12):5873-5877.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Kawai et al., 2006, "A comparison of the effectiveness of oseltamivir for the treatment of influenza A and influenza B: a Japanese multicenter study of the 2003-2004 and 2004-2005 influenza seasons," Clin Infect Dis., 43(4):439-444.
Kawai et al., 2007, "Longer virus shedding in influenza B than in influenza A among outpatients treated with oseltamivir," J Infect., 55(3):267-272.
Kayali et al., 2011, "Evidence of infection with H4 and H11 avian influenza viruses among Lebanese chicken growers," PLoS One, 6(10):e26818.
Khanna et al., 2014, "Protective Immunity Based on the Conserved Hemagglutinin Stalk Domain and Its Prospects for Universal Influenza Vaccine Development," Biomed Res Int., 2014:546274 (7 pages).
Khiabanian et al., 2009, "Differences in patient age distribution between influenza A subtypes," PLoS One, 4(8):e6832 (5 pages).
Khurana et al., 2011, "MF59 adjuvant enhances diversity and affinity of antibody-mediated immune response to pandemic influenza vaccines," Sci. Transl. Med., 3(85):85ra48 (10 pages).
Khurana et al., 2013, "Vaccine-induced anti-HA2 antibodies promote virus fusion and enhance influenza virus respiratory disease," Sci Transl Med., 5(200):200ra114.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Kilbourne et al., 1976, "Comparative efficacy of neuraminidase-specific and conventional influenza virus vaccines in induction of antibody to neuraminidase in humans," J Infect Dis., 134(4):384-394.
Kilbourne et al., 1987, "Immunologic response to the influenza virus neuraminidase is influenced by prior experience with the associated viral hemagglutinin. I. Studies in human vaccinees," J Immunol., 138(9):3010-3013.
Kilbourne et al., 1990, "Independent and disparate evolution in nature of influenza A virus hemagglutinin and neuraminidase glycoproteins," Proc Natl Acad Sci USA, 87(2):786-790.
Kilbourne et al., 1995, "Purified influenza A virus N2 neuraminidase vaccine is immunogenic and non-toxic in humans," Vaccine, 13(18):1799-1803.
Kirnbauer et al., 1992, "Papillomavirus L1 major capsid protein self-assembles into virus-like particles that are highly immunogenic," Proc Natl Acad Sci USA, 89(24):12180-12184.
Kistner et al., 2007, "Cell culture (Vero) derived whole virus (H5N1) vaccine based on wild-type virus strain induces cross-protective immune responses," Vaccine 25(32):6028-6036.
Klausberger et al., 2014, "One-shot vaccination with an insect cell-derived low-dose influenza A H7 virus-like particle preparation protects mice against H7N9 challenge," Vaccine, 32(3):355-362 (Epub 2013).
Koel et al., 2013, "Substitutions near the receptor binding site determine major antigenic change during influenza virus evolution," Science, 342(6161):976-979.
Kon et al., 2016, "Influenza Vaccine Manufacturing: Effect of Inactivation, Splitting and Site of Manufacturing. Comparison of Influenza Vaccine Production Processes," PLoS One, 11(3):e0150700 (19 pages).
Kosik et al., 2019, "Neuraminidase inhibition contributes to influenza A virus neutralization by antihemagglutinin stem antibodies," J. Exp. Med., 216(2):304-316.
Krammer et al., 2010. "Trichoplusia ni cells (High Five) are highly efficient for the production of influenza A virus-like particles: a

(56) References Cited

OTHER PUBLICATIONS comparison of two insect cell lines as production platforms for influenza vaccines," Mol Biotechnol., 45(3):226-234.
Krammer et al., 2012, "A carboxy-terminal trimerization domain stabilizes conformational epitopes on the stalk domain of soluble recombinant hemagglutinin substrates," PLoS One. 7:e43603.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2013, "Influenza virus hemagglutinin stalk-based antibodies and vaccines," Curr. Opin. Virol., 3(5):521-530.
Krammer et al., 2013, "Chimeric hemagglutinin influenza virus vaccine constructs elicit broadly protective stalk-specific antibodies", J Virol. 87:6542-6550.
Krammer et al., 2014, "An H7N1 influenzavirus vaccine induces broadly reactive antibody responses against H7N9 in humans," Clin Vaccine Immunol., 21(8):1153-1163.
Krammer et al., 2014, "Divergent H7 immunogens offer protection from H7N9 virus challenge," J Virol., 88(8):3976-3985.
Krammer et al., 2014, "Assessment of influenza virus hemagglutinin stalk-based immunity in ferrets," J. Virol., 88:3432-3442.
Krammer et al., 2014, "H3 stalk-based chimeric hemagglutinin influenza virus constructs protect mice from H7N9 challenge", J Virol, 88:2340-2343.
Krammer et al., 2015, "Advances in the development of influenza virus vaccines," Nat Rev Drug Discov., 14(3):167-182.
Krammer et al., 2018, "Influenza," Nat. Rev. Dis. Primers, 4(1):3 (21 pages).
Krammer et al., 2018, "NAction! How Can Neuraminidase-Based Immunity Contribute to Better Influenza Virus Vaccines?," mBio, 9(2):e02332-17 (12 pages).
Krammer et al., 2019, "Emerging from the Shadow of Hemagglutinin: Neuraminidase Is an Important Target for Influenza Vaccination," Cell Host Microbe., 26(6):712-713.
Krammer et al., 2019, "Universal Influenza Virus Vaccines That Target the Conserved Hemagglutinin Stalk and Conserved Sites in the Head Domain," J. Infect. Dis., 219(Suppl_1):S62-S67.
Krammer, 2015, "Emerging influenza viruses and the prospect of a universal influenza virus vaccine," Biotechnol. J., 10(5):690-701.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Krammer, 2017, "Annex I: Sequence comparison of the J&J, VRC and MSSM headless HA constructs (tentative H3 numbering included)" (3 pages).
Krammer, 2017, "Strategies to induce broadly protective antibody responses to viral glycoproteins," Expert Rev. Vaccines, 16(5):503-513.
Krammer, 2019, "The human antibody response to influenza A virus infection and vaccination," Nat. Rev. Immunol., 19(6):383-397.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Krause et al., 2012, "Human monoclonal antibodies to pandemic 1957 H2N2 and pandemic 1968 H3N2 influenza viruses", J. Virol. 86:6334-6340.
Laguio-Vila et al., 2015, "Comparison of serum hemagglutinin and neuraminidase inhibition antibodies after 2010-2011 trivalent inactivated influenza vaccination in healthcare personnel," Open Forum Infect. Dis., 2(1):ofu115 (9 pages).
Lambe et al., 2013, "Immunity against heterosubtypic influenza virus induced by adenovirus and MVA expressing nucleoprotein and matrix protein-1," Sci Rep., 3:1443 (8 pages).
Landry et al., 2008, "Three-dimensional structure determines the pattern of CD4+ T-cell epitope dominance in influenzavirus hemagglutinin", Journal of Virology; 82(3):1238-1248.

Landry et al., 2010, "Preclinical and Clinical Development of Plant-Made Virus-Like Particle Vaccine against Avian H5N1 Influenza", PLoS One, 5(12): e15559. (12 pages).
Larkin et al., 2007, "Clustal W and Clustal X version 2.0," Bioinformatics, 23(21):2947-2948.
Laver et al., 1981, "Mechanism of antigenic drift in influenza virus. Amino acid sequence changes in an antigenically active region of Hong Kong (H3N2) influenza virus hemagglutinin," J Mol Biol., 145(2):339-361.
Laver et al., 1988, "Crystallization and preliminary X-ray analysis of type B influenza virus neuraminidase complexed with antibody Fab fragments," Virology, 167(2):621-624.
Lebendiker, 2006, "Purification Protocols." The Wolfson Centre for Applied Structural Biology, http://wolfson.huji.ac.il/purification/Purification_Protocols.html. Apr. 5, 2006 (30 pages).
Ledgerwood et al., 2011, "DNA priming and influenza vaccine immunogenicity: two phase 1 open label randomised clinical trials," Lancet Infect Dis., 11(12):916-924.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lee et al., 2012, "Heterosubtypic antibody recognition of the influenza virus hemagglutinin receptor binding site enhanced by avidity", Proc. Natl. Acad. Sci. USA 109:17040-17045.
Lee et al., 2014, "Receptor mimicry by antibody F045-092 facilitates universal binding to the H3 subtype of influenzavirus," Nat. Commun., 5:3614 (9 pages).
Leon et al., 2016, "Optimal activation of Fc-mediated effector functions by influenza virus hemagglutinin antibodies requires two points of contact," Proc. Natl. Acad. Sci. USA, 113(40):E5944-E5951.
Leroux-Roels, et al. 2008. "Broad Glade 2 cross-reactive immunity induced by an adjuvanted Glade 1 rH5N1 pandemic influenza vaccine", PLOS One; 3(2):e1665 (5 pages).
Li et al., 1992, "Influenza A virus transfectants with chimaeric haemagglutinins containing epitopes from different subtypes", Journal of Virology, 67:399-404.
Li et al., 1999, "Recombinant influenza A virus vaccines for the pathogenic human A/Hong Kong/97 (H5N1) viruses," J Infect Dis., 179(5):1132-1138.
Li et al., 2011, "A novel tetrameric PilZ domain structure from xanthomonads," PLoS One, 6(7):e22036 (13 pages).
Li et al., 2011, "Emergence and genetic variation of neuraminidase stalk deletions in avian influenza viruses," PLoS One, 6(2):e14722 (11 pages).
Li et al., 2012, "Pandemic H1N1 influenza vaccine induces a recall response in humans that favors broadly cross-reactive memory B cells," Proc Natl Acad Sci USA, 109(23):9047-9052.
Liang et al., 1994, "Heterosubtypic immunity to influenza type A virus in mice. Effector mechanisms and their longevity," J Immunol., 152(4):1653-1661.
Liang et al., 2005, "cis-Acting packaging signals in the influenza virus PB1, PB2, and PA genomic RNA segments," J. Virol., 79(16):10348-10355.
Liu et al., 2015, "Cross-Reactive Neuraminidase-Inhibiting Antibodies Elicited by Immunization with Recombinant Neuraminidase Proteins of H5N1 and Pandemic H1N1 Influenza A Viruses," J. Virol., 89(14):7224-7234.
Liu et al., 2019, "Sequential Immunization With Live-Attenuated Chimeric Hemagglutinin-Based Vaccines Confers Heterosubtypic Immunity Against Influenza A Viruses in a Preclinical Ferret Model," Front. Immunol., 10:756 and Supplemental Figs. SI to S7 (25 pages).
Lloyd et al., 2009, "Modelling the human immune response: performance of a 1011 human antibody repertoire against a broad panel of therapeutically relevant antigens," Protein Eng. Des. Sel., 22(3):159-168 (Epub 2008).
Lorieau et al., 2010, "The complete influenza hemagglutinin fusion domain adopts a tight helical hairpin arrangement at the lipid:water interface," PNAS, 107(25):11341-11346.

(56) References Cited

OTHER PUBLICATIONS

Lowen et al., 2006, "The guinea pig as a transmission model for human influenza viruses," Proc Natl Acad Sci USA, 103(26):9988-9992.
Lowen et al., 2009, "Blocking interhost transmission of influenza virus by vaccination in the guinea pig model," J. Virol. 83(7):2803-2818.
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Luo et al., 1993, "Alterations of the stalk of the influenza virus neuraminidase: deletions and insertions," Virus Res., 29(2):141-153.
Maier et al., 2020, "Pre-existing Antineuraminidase Antibodies Are Associated With Shortened Duration of Influenza A(H1N1)pdm Virus Shedding and Illness in Naturally Infected Adults," Clin Infect Dis., 70(11):2290-2297.
Mallajosyula et al., 2014, "Influenza hemagglutinin stem-fragment immunogen elicits broadly neutralizing antibodies and confers heterologous protection." PNAS, 111(25):E2514-23.
Manini et al., 2015, "Flucelvax (Optaflu) for seasonal influenza," Expert Rev. Vaccines, 14(6):789-804.
Marasco et al.. 2007, "The growth and potential of human antiviral monoclonal antibody therapeutics", Nat. Biotechnol: 25(12):1421-1434.
Marathe et al., 2016, "Combinations of Oseltamivir and T-705 Extend the Treatment Window for Highly Pathogenic Influenza A(H5N1) Virus Infection in Mice," Sci Rep., 6:26742 (14 pages).
Marcelin et al., 2012, "Contribution of antibody production against neuraminidase to the protection afforded by influenza vaccines," Rev Med Virol., 22(4):267-279.
Margine et al., 2013, "Expression of functional recombinant hemagglutinin and neuraminidase proteins from the novel H7N9 influenza virus using the baculovirus expression system," J Vis Exp., (81):e51112 (10 pages).
Margine et al., 2013, "H3N2 influenza virus infection induces broadly reactive hemagglutinin stalk antibodies in humans and mice", J. Virol. 87(8):4728-4737.
Margine et al., 2013, "Hemagglutinin stalk-based universal vaccine constructs protect against group 2 influenza A viruses", J Virol, 10435-10446.
Marsh et al., 2007, "Specific residues of the influenza A virus hemagglutinin viral RNA are important for efficient packaging into budding virions," J. Virol., 81(18):9727-9736.
Martinez-Romero et al., 2013, "Substitutions T200A and E227A in the hemagglutinin of pandemic 2009 influenza A virus increase lethality but decrease transmission," J Virol., 87(11):6507-6511.
Martinez-Sobrido et al., 2010, "Generation of recombinant influenza virus from plasmid DNA," J Vis Exp., 3(42):e2057 (5 pages).
Matias et al., 2016, "Model estimates of the burden of outpatient visits attributable to influenza in the United States," BMC Infect. Dis., 16(1):641 (11 pages).
Matrosovich et al., 2004, "Neuraminidase is important for the initiation of influenza virus infection in human airway epithelium," J Virol., 78(22):12665-12667.
Matsuzaki et al., 2014, "Epitope mapping of the hemagglutinin molecule of A/(H1N1)pdm09 influenza virus by using monoclonal antibody escape mutants," J. Virol., 88(21):12364-12373.
Matthews et al., 2006, "A tryptophan amphiphilic tetramerization domain-containing acetylcholinesterase from the bovine lungworm, *Dictyocaulus viviparus*," Parasitology, 133(Pt 3):381-387.
Mbawuike et al., 1994, "Influenza A subtype cross-protection after immunization of outbred mice with purified chimeric NS1/HA2 influenza virus protein", Vaccine, 1994: 12(14):1340-1348.
McAuley et al., 2019, "Influenza Virus Neuraminidase Structure and Functions," Front Microbiol., 10:39 (13 pages).
McMahon et al., 2019, "Mucosal Immunity against Neuraminidase Prevents Influenza B Virus Transmission in Guinea Pigs," mBio, 10(3):e00560-19 (12 pages).
Memoli et al., 2016, "Evaluation of Antihemagglutinin and Antineuraminidase Antibodies as Correlates of Protection in an Influenza A/H1N1 Virus Healthy Human Challenge Model," mBio, 7(2):e00417-16 (12 pages).
Mendez-Legaza et al., 2019, "Heterotypic Neuraminidase Antibodies Against Different A(H1N1) Strains are Elicited after Seasonal Influenza Vaccination," Vaccines (Basel), 7(1):30 (15 pages).
Meseda et al., 2018, "Immunogenicity and Protection Against Influenza H7N3 in Mice by Modified Vaccinia Virus Ankara Vectors Expressing Influenza Virus Hemagglutinin or Neuraminidase," Sci. Rep., 8(1):5364 (14 pages).
Mett et al., 2008, "A plant-produced influenza subunit vaccine protects ferrets against virus challenge", Influenza and Other Respiratory Viruses, 2(1):33-40.
Miller et al., 2013, "1976 and 2009 H1N1 influenzavirus vaccines boost anti-hemagglutinin stalk antibodies in humans", J. Infect. Dis. 207:98-105.
Mo et al., 2003. "Coexpression of complementary fragments of CIC-5 and restoration of chloride channel function in a Dent's disease mutation", Am J Physiol Cell Physiol; 286:C79-C89.
Mok et al., 2008, "Enhancement of the CD8<+> T cell response to a subdominant epitope respiratory syncytial virus by deletion of an immunodominant epitope", Vaccine: 26(37):4775-4782.
Molinari et al., 2007, "The annual impact of seasonal influenza in the US: measuring disease burden and costs," Vaccine, 25(27):5086-5096.
Montgomery et al., 1993, "Heterologous and homologous protection against influenza A by DNA vaccination: optimization of DNA vectors," DNA Cell Biol. 12(9):777-783.
Monto et al., 2015, "Antibody to Influenza Virus Neuraminidase: An Independent Correlate of Protection," J Infect Dis., 212(8):1191-1199.
Montplaisir et al., 2009, "Risk of narcolepsy associated with inactivated adjuvanted (AS03) A/H1N1 (2009) pandemic influenza vaccine in Quebec," *PLoS One* 9 (9): e108489 (9 pages).
Moody et al., 2011, "H3N2 influenza infection elicits more cross-reactive and less clonally expanded anti-hemagglutinin antibodies than influenza vaccination," PLoS One, 6(10):e25797 (14 pages).
Morel et al., 2011, "Adjuvant System AS03 containing α-tocopherol modulates innate immune response and leads to improved adaptive immunity," Vaccine, 29(13):2461-2473.
Moscona, 2005, "Neuraminidase inhibitors for influenza," N Engl J Med., 353(13):1363-1373.
Mullarkey et al., 2016, "Broadly Neutralizing Hemagglutinin Stalk-Specific Antibodies Induce Potent Phagocytosis of Immune Complexes by Neutrophils in an Fc-Dependent Manner," mBio, 7(5):e01624-16 (12 pages).
Muramoto et al., 2006, "Hierarchy among viral RNA (vRNA) segments in their role in vRNA incorporation into influenza A virions," J. Virol., 80(5):2318-2325.
Murphy et al., 1972, "Association of serum anti-neuraminidase antibody with resistance to influenza in man," N. Engl. J. Med., 286(25):1329-1332.
Nachbagauer et al., 2014, "Induction of broadly reactive anti-hemagglutinin stalk antibodies by an H5N1 vaccine in humans," *J. Virol.* 88 (22): 13260-13268.
Nachbagauer et al., 2015, "Hemagglutinin stalk immunity reduces influenza virus replication and transmission in ferrets," J Virol., 90(6):3268-3273.
Nachbagauer et al., 2016, "A chimeric haemagglutinin-based influenza split virion vaccine adjuvanted with AS03 induces protective stalk-reactive antibodies in mice," Npj Vaccines 1:16015 (10 pages).
Nachbagauer et al., 2016, "Age Dependence and Isotype Specificity of Influenza Virus Hemagglutinin Stalk-Reactive Antibodies in Humans," MBio., 7(1):e01996-15 (10 pages).
Nachbagauer et al., 2017, "A universal influenza virus vaccine candidate confers protection against pandemic H1N1 infection in preclinical ferret studies," NPJ Vaccines, 2:26 (13 pages).
Nakajima et al., 2000, "Variation in response among individuals to antigenic sites on the HA protein of human influenza virus may be

(56) References Cited

OTHER PUBLICATIONS responsible for the emergence of drift strains in the human population," Virology, 274(1):220-231.
Nakaya et al., 2001, "Recombinant Newcastle disease virus as a vaccine vector," J Virol., 75(23):11868-11873.
National Insitutes of Health Pubchem, "Zanamivir," found at https://pubchem.ncbi.nim.nih.gov/zompound/Zanamivir (Year: 2021).
NCT01676402, Clinical Trial, "Seasonal Influenza HA DNA With Trivalent Inactivated Vaccine (TIV) Administered ID or IM in Healthy Adults 18-70 Years," last updated Jul. 17, 2014 (6 pages).
Nelson et al., 2008, "Lehninger Principles of Biochemistry—Fifth Edition," Chapter 4.3, p. 123, W.H. Freeman and Company.
Neumann et al., 1999, "Generation of influenza A viruses entirely from cloned cDNAs", PNAS 96:9345-9350.
Ni et al, 2013, "Structural basis for the divergent evolution of influenza B virus hemagglutinin," Virology 446(1-2):112-122.
Nichol et al., 1995, "The effectiveness of vaccination against influenza in healthy, working adults," N Engl J Med., 333(14):889-893.
Nicholson et al., 2000, "Efficacy and safety of oseltamivir in treatment of acute influenza: a randomised controlled trial," Lancet, 355(9218):1845-1850.
O'Brien et al. 2004, "Incidence of outpatient visits and hospitalizations related to influenza in infants and young children," Pediatrics, 113:585-593.
Ogburn et al., 2007, "Impact of clinic interventions on the rate of influenza vaccination in pregnant women," J Reprod Med., 52(9):753-756.
Ohkura et al., 2012, "Epitope mapping of neutralizing monoclonal antibody in avian influenza A H5N1 virus hemagglutinin," Biochem. Biophys. Res. Commun. 418(1):38-43 (Epub 2011).
Ohmit et al., 2011, "Influenza hemagglutination-inhibition antibody titer as a correlate of vaccine-induced protection," J Infect Dis., 204(12):1879-1885.
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among E11 and H2 strains," J. Virol., 68(1):517-520.
Olson et al., 2007, "Monitoring the impact of influenza by age: emergency department fever and respiratory complaint surveillance in New York City," PLoS Med., 4(8):e247 (13 pages).
Oshima et al., 2011, "Naturally Occurring Antibodies in Humans Can Neutralize a Variety of Influenza Virus Strains, Including H3, H1, H2, and H5". Journal of Virology, 85(21):11048-11057.
Ott et al., 2000. The Adjuvant MF59: A 10-Year Perspective, p. 211-228. In O'Hagan DT (ed.), Vaccine Adjuvants, vol. 42. Springer.
Oxford, 2013, "Towards a universal influenza vaccine: volunteer virus challenge studies in quarantine to speed the development and subsequent licensing," Br J Clin Pharmacol., 76(2):210-216.
Ozawa et al., 2007, "Contributions of two nuclear localization signals of influenza A virus nucleoprotein to viral replication," J. Virol., 81(1):30-41 (Epub 2006).
Ozawa et al., 2009, "Nucleotide sequence requirements at the 5' end of the influenza A virus M RNA segment for efficient virus replication," J. Virol., 83(7):3384-3388.
Palese et al., 1974, "Characterization of temperature sensitive influenza virus mutants defective in neuraminidase," Virology, 61(2):397-410.
Palese et al., 2007, "Orthomyxoviridae: The Viruses and Their Replication," in Fields Virology, D.M. Knipe, & P. M. Howley (Eds.), Philadelphia, PA: Wolters Kluwer Lippincott Williams & Wilkins, pp. 1647-1689.
Palese, 2004, "Influenza: old and new threats," Nat Med., 10(12 Suppl):S82-87.
Pan et al., 2011, "Selective pressure to increase charge in immunodominant epitopes of the H3 hemagglutinin influenza protein," J Mol Evol., 72(1):90-103.

Pantua et al., 2006, "Requirements for the assembly and release of Newcastle disease virus-like particles," J Virol, 80(22):11062-11073.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Park et al., 2006, "Engineered viral vaccine constructs with dual specificity: avian influenza and Newcastle disease," Proc Natl Acad Sci USA, 103(21):8203-8208.
Pearson et al., 1988, "Improved tools for biological sequence comparison," Proc Natl Acad Sci USA, 85(8):2444-2448.
Perricone et al., 2013, "Autoimmune/inflammatory syndrome induced by adjuvants (ASIA) 2013: Unveiling the pathogenic, clinical and diagnostic aspects," J Autoimmun., 47:1-16.
Pettersen et al., 2004, "UCSF Chimera—a visualization system for exploratory research and analysis," J Comput Chem., 25(13):1605-1612.
Pica et al., 2012, "Hemagglutinin stalk antibodies elicited by the 2009 pandemic influenza virus as a mechanism for the extinction or seasonal H1N1 viruses." Proc Nat Acad Sci USA, 109(7):2573-2578.
Piepenbrink et al., 2019, "Broad and Protective Influenza B Virus Neuraminidase Antibodies in Humans after Vaccination and their Clonal Persistence as Plasma Cells," mBio, 10(2):e00066-19 (17 pages).
Ping et al., 2015, "Development of high-yield influenza A virus vaccine viruses," Nat. Commun., 6:8148 (15 pages).
Pleschka et al., 1996, "A plasmid-based reverse genetics system for influenza A virus", J Virol 70:4188-4192.
Ponomarenko et al., 2009, "B-Cell Epitope Prediction" Ch. 35 in Structural Bioinformatics, 2nd Edition, Gu and Bourne Editors, John Wiley & Sons. Inc., pp. 849-879.
Popova et al., 2012, "Immunodominance of antigenic site B over site A of hemagglutinin of recent H3N2 influenza viruses," PLoS One, 7(7):e41895 (11 pages).
Potter et al., 1979, "Determinants of immunity to influenza infection in man," Br. Med. Bull., 35(1):69-75.
Powers et al., 1996, "Neuraminidase-specific antibody responses to inactivated influenza virus vaccine in young and elderly adults," Clin. Diagn. Lab. Immunol., 3(5):511-516.
Q0PZR5, UniProtKB Accession No. Q0PZR5, Oct. 29, 2014 [online]. [Retrieved on Sep. 2, 2016]. Retrieved from the internet <URL:http://www.uniprot.org/uniprot/Q0PZR5.txt?version=53> (2 pages).
Quinlivan et al., 2005, "Attenuation of equine influenza viruses through truncations of the NS1 protein," J Virol., 79(13):8431-8439.
Rajendran et al., 2017, "Analysis of Anti-Influenza Virus Neuraminidase Antibodies in Children, Adults, and the Elderly by ELISA and Enzyme Inhibition: Evidence for Original Antigenic Sin" mBio, 8(2):e02281-16 (12 pages).
Rambaut et al., 2008, "The genomic and epidemiological dynamics of human influenza A virus," Nature, 453(7195):615-619.
Rasala et al., 2010, "Production of therapeutic proteins in algae, analysis of expression of seven human proteins in the chloroplast of Chlamydomonas reinhardtii," Plant Biotechnol J., 8(6):719-733.
Reid et al., Hemagglutinin [Influenza A virus (A/South Carolina/1/1918(H1N1))]. GenBank Acc. No. AAD17229.1. Dep. Oct. 11, 2000.
Retamal et al., 2014, "Epitope mapping of the 2009 pandemic and the A/Brisbane/59/2007 seasonal (H1N1) influenza virus haemagglutinins using mAbs and escape mutants," J. Gen. Virol., 95(Pt 11):2377-2389.
Ridenour et al., 2015, "Development of influenza A(H7N9) candidate vaccine viruses with improved hemagglutinin antigen yield in eggs," Influenza Other Respir Viruses, 9(5):263-270.
Rivera et al., 1995, "Probing the structure of influenza B hemagglutinin using site-directed mutagenesis," Virology 206(2):787-795.
Roberts el al., 1993, "Role of conserved glycosylation sites in maturation and transport of influenza A virus hemagglutinin." J Virol, 67(6):3048-3060.
Robertson, 1987, "Sequence Analysis of the Haemagglutinin of A/Taiwan/1/86, a New Variant of Human Influenza A(H1/N1) Virus," J. Gen. Virol., 68(4):1205-1208.

(56) References Cited

OTHER PUBLICATIONS

Rockman et al., 2013, "Neuraminidase-inhibiting antibody is a correlate of cross-protection against lethal H5N1 influenza virus in ferrets immunized with seasonal influenza vaccine," J Virol., 87(6):3053-3061.
Rolfes et al., 2014, "Update: influenza activity—United States, Sep. 28-Dec. 6, 2014," MMWR Morb Mortal Wkly Rep., 63(50):1189-1194.
Rolfes et al., 2018, "Annual estimates of the burden of seasonal influenza in the United States: A tool for strengthening influenza surveillance and preparedness," Influenza Other Respir Viruses, 12(1):132-137.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Rudikoff et al., 1982, "Single amino acid substitution altering antigen-binding specificity." Proc Nat Acad Sci USA., 79(6):1979-1983.
Rumpler et al., 2018, "A conserved leucine zipper-like motif accounts for strong tetramerization capabilities of SEPALLATA-like MADS-domain transcription factors," J Exp Bot., 69(8):1943-1954.
Runstadler et al., 2013, "Connecting the study of wild influenza with the potential for pandemic disease," Infect Genet Evol., 17:162-187.
Ryder et al., 2016, "Vaccination with VSV-vectored chimeric hemagglutinins protects mice against divergent influenza virus challenge strains", J. Virol., 90(5):2544-2550.
Sagawa et al., 1996, "The immunological activity of a deletion mutant of influenza virus haemagglutinin lacking the globular region", J Gen Virol; 77:1483-1487.
Salem, 2000, "In vivo acute depletion of CD8(+) T cells before murine cytomegalovirus infection upregulated innate antiviral activity of natural killer cells", Int. J. Immunopharmacol. 22:707-718.
Sandbulte et al., 2007, "Cross-reactive neuraminidase antibodies afford partial protection against H5N1 in mice and are present in unexposed humans," PLoS Med., 4(2):e59 (8 pages).
Sandbulte et al., 2011, "Discordant antigenic drift of neuraminidase and hemagglutinin in H1N1 and H3N2 influenza viruses," Proc. Natl. Acad. Sci. USA, 108(51):20748-20753.
Santak, 2012, "Old and new ways to combat human influenza virus." Periodicus Biologorum, 114(2):221-234.
Sautto et al., 2018, "Towards a Universal Influenza Vaccine: Different Approaches for One Goal," Virol J., 15(1):17 (12 pages).
Scheiffele et al., 1997, "Interaction of influenza virus haemagglutinin with sphingolipid-cholesterol membrane domains via its transmembrane domain," EMBO J., 16(18):5501-5508.
Scheres, 2012, "RELION: implementation of a Bayesian approach to cryo-EM structure determination," J Struct Biol., 180(3):519-530.
Schneeman et al., 2012, "A Virus-Like Particle That Elicits Cross-Reactive Antibodies to the Conserved Stem of Influenza Virus Hemagglutinin," J. Virol., 86(21):11686-22697.
Schuind et al., 2015, "Immunogenicity and Safety of an EB66 Cell-Culture-Derived Influenza A/Indonesia/5/2005(H5N1) AS03-Adjuvanted Vaccine: A Phase 1 Randomized Trial," J Infect Dis., 212(4):531-541.
Schulman et al., 1968, "Protective effects of specific immunity to viral neuraminidase on influenza virus infection of mice," J Virol., 2(8):778-786.
Schulman, 1969, "The role of antineuraminidase antibody in immunity to influenza virus infection," Bull World Health Organ., 41(3):647-650.
Schulze, 1997, "Effects of Glycosylation on the Properites and Functions of Influenza Virus Hemagglutinin", The Journal of Infectious Diseases, 176(S1):S24-S28.
Seibert et al., 2010, "Oseltamivir-resistant variants of the 2009 pandemic H1N1 influenza A virus are not attenuated in the guinea pig and ferret transmission models," J Virol., 84(21):11219-11226.
Seibert et al., 2013, "Recombinant IgA is sufficient to prevent influenza virus transmission in guinea pigs," J Virol., 87(14):7793-7804.
Shaw et al., 2013, "Chapter 40: Orthomyxoviridae," in Fields Virology, 6th Ed., Lippincott Williams & Wilkins, a Wolters Kluwer, Philadelphia, PA, pp. 1151-1181 and references (107 pages).
Shoji et al., 2008, "Plant-expressed HA as a seasonal influenza vaccine candidate", Vaccine, 26(23):2930-2934.
Shoji et al., 2011, "An influenza N1 neuraminidase-specific monoclonal antibody with broad neuraminidase inhibition activity against H5N1 HPAI viruses," Hum Vaccin., 7 Suppl:199-204.
Simmons et al., 2007. "Prophylactic and therapeutic efficacy of human monoclonal antibodies against H5N1 Influenza", PLOS Medicine; 4(5):928-936.
Singleton et al., 1995, "Dictionary of Microbiology and Molecular Biology—Second Edition." A Wiley-Interscience Publication (3 pages).
Skehel et al., 1984, "A carbohydrate side chain on hemagglutinins of Hong Kong influenza viruses inhibits recognition by a monoclonal antibody," Proc. Natl. Acad. Sci. USA, 81(6):1779-1783.
Skowronski et al., 2013, "Virus-host interactions and the unusual age and sex distribution of human cases of influenza A(H7N9) in China, Apr. 2013," Euro Surveill., 18(17):20465 (4 pages).
Smith et al., 1981, "Comparison of biosequences," Advances in Applied Mathematics, 2(4):482-489.
Smith et al., 2004, "Mapping the antigenic and genetic evolution of influenza virus," Science, 305(5682):371-376.
Smith et al., 2017, "Neuraminidase-based recombinant virus-like particles protect against lethal avian influenza A(H5N1) virus infection in ferrets," Virology, 509:90-97.
Song et al., 2007, "Influenza A Virus Hemagglutinin Protein, H1PR8," Geneseq, XP002595511.
Sparrow et al., 2016, "Passive immunization for influenza through antibody therapies, a review of the pipeline, challenges, and potential applications." Vaccine, 34: 5442-5448.
Stadlbauer et al., 2018, "Cross-reactive mouse monoclonal antibodies raised against the hemagglutinin of A/Shanghai/1/2013 (H7N9) protect against novel H7 virus isolates in the mouse model," Emerg. Microbes. Infect., 7(1):110 (12 pages).
Stadlbauer et al., 2019, "Broadly Protective Human Antibodies That Target the Active Site of Influenza Virus Neuraminidase," Science, 366(6464):499-504.
Stech et al., 2005, "A new approach to an influenza live vaccine: modification of the cleavage site of hemagglutinin", Nat. Med. 11(6):683-689.
Steel et al., 2009, "Live attenuated influenza viruses containing NS1 truncations as vaccine candidates against H5N1 highly pathogenic avian influenza," J Virol., 83(4):1742-1753.
Steel et al., 2010, "Influenza Virus Vaccine Based on the Conserved Hemagglutinin Stalk Domain," mBIO 1(1). pii: e00018-10 (9 pages).
Stephenson et al., 2005, "Cross-reactivity to highly pathogenic avian influenza H5N1 viruses alter vaccination with nonadjuvanted and MF59-adjuvanted influenza A/Duck/Singapore/97 (H5N3) vaccine: a potential priming strategy." J Infect Dis., 191(8):1210-1215.
Steuler et al., 1984, "Sequence of the neuraminidase gene of an avian influenza A virus (A/parrot/ulster/73, H7N1)," Virology, 135(1):118-124.
Stevens et al., 2006, "Structure and Receptor Specificity of the Hemagglutinin from an H5N1 Influenza Virus" Science, 312:404-409.
Stoute et al., 1997, "A preliminary evaluation of a recombinant circumsporozoite protein vaccine against Plasmodium falciparum malaria. RTS,S Malaria Vaccine Evaluation Group," N Engl J Med., 336(2):86-91.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Su et al., 2014, "Comparing clinical characteristics between hospitalized adults with laboratory-confirmed influenza A and B virus infection," Clin Infect Dis., 59(2):252-255.
Subbarao et al., 2013, "The prospects and challenges of universal vaccines for influenza," Trends Microbiol., 21(7):350-358.

(56) References Cited

OTHER PUBLICATIONS

Sugaya et al., 2007, "Lower clinical effectiveness of oseltamivir against influenza B contrasted with influenza A infection in children," Clin Infect Dis., 44(2):197-202 (Epub 2006).
Sui et al., 2011, "Wide prevalence of heterosubtypic broadly neutralizing human anti-influenza A antibodies," Clin Infect Dis., 52(8):1003-1009.
Sui et al., 2009, "Structural and functional bases for broad-spectrum neutralization of avian and human influenza A viruses", Nat Struct Mol Biol; 16(3):265-273 with Supplementary Information (31 pages).
Sultana et al., 2014, "Stability of neuraminidase in inactivated influenza vaccines," Vaccine, 32(19):2225-2230.
Sun et al., 2011, "Glycosylation Site Alteration in the Evolution of Influenza A (H1N1) Viruses." PLoS Pathogens, 6(7):e22844 (9 pages).
Sun et al., 2019, "Development of Influenza B Universal Vaccine Candidates Using the "Mosaic" Hemagglutinin Approach," J Virol., 93(12):e00333-19 (17 pages).
Sutter et al., 1992, "Nonreplicating vaccinia vector efficiently expresses recombinant genes," Proc Natl Acad Sci USA, 89(22):10847-10851.
Swayne et al., 2003, "Recombinant paramyxovirus type 1-avian influenza-H7 virus as a vaccine for protection of chickens against influenza and Newcastle disease," Avian Dis., 47(3 Suppl):1047-1050.
Sylte et al., 2007, "Influenza neuraminidase antibodies provide partial protection for chickens against high pathogenic avian influenza infection," Vaccine, 25(19):3763-3772.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacy in vivo", J. Virol. 86:6179-6188.
Tan et al., 2014, "Characterization of a broadly neutralizing monoclonal antibody that targets the fusion domain of group 2 influenza A virus hemagglutinin," J. Virol., 88(23):13580-13592.
Tan et al., 2018, "Universal influenza virus vaccines and therapeutics: where do we stand with influenza B virus?," Curr Opin Immunol., 53:45-50.
Tao et al., 2009, "Enhanced protective immunity against H5N1 influenzavirus challenge by vaccination with DNA expressing a chimeric hemagglutinin in combination with an MHC class I-restricted epitope of nucleoprotein in mice", Antiviral research, 2009; 81(3); 253-260.
Tarbouriech et al., 2000, "Tetrameric coiled coil domain of Sendai virus phosphoprotein," Nat Struct Biol., 7(9):777-781.
Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Tete et al., 2016, "Dissecting the hemagglutinin head and stalk-specific IgG antibody response in healthcare workers following pandemic H1N1 vaccination," *Nature Partner Journals (NPJ) Vaccine*, Article No. 16001 doi:10.1038/npjvaccines.2016.1 (9 pages).
Thoennes et al., 2008, "Analysis of residues near the fusion peptide in the influenza hemagglutinin structure for roles in triggering membrane fusion", Virology; 370(2):403-414.
Thompson et al., 2003, "Mortality associated with influenza and respiratory syncytial virus in the United States," JAMA, 289(2):179-186.
Thomson et al., 2012, "Pandemic H1N1 Influenza Infection and Vaccination in Humans Induces Cross-Protective Antibodies that Target the Hemagglutinin Stem", Front. Immunol. 3:87 (19 pages).
Throsby et al., 2008, "Heterosubtypic neutralizing monoclonal antibodies cross-protective against H5N1 and H1N1 recovered from human IgM+ memory B cells", PLoS ONE; 3(12):e3942 (15 pages).
Tong et al., 2013. "New world bats harbor diverse influenza A viruses," PLoS Pathog. 9: e1003657 (12 pages).
Tran et al., 2016, "Cryo-electron microscopy structures of chimeric hemagglutinin displayed on a universal influenza vaccine candidate", MBio, 7(2): e00257-16 (9 pages).
Treanor et al., 2007, "Safety and immunogenicity of a baculovirus-expressed hemagglutinin influenza vaccine: a randomized controlled trial," JAMA, 297(14):1577-1582.
Tricco et al., 2013, "Comparing influenza vaccine efficacy against mismatched and matched strains: a systematic review and meta-analysis," BMC Med., 11:153 (19 pages).
Truelove et al., 2016, "A comparison of hemagglutination inhibition and neutralization assays for characterizing immunity to seasonal influenza A," Influenza Other Respir Viruses, 10(6):518-524.
Tscherne et al., 2010, "An enzymatic virus-like particle assay for sensitive detection of virus entry," J Virol Methods, 163(2):336-343.
Tsibane et al., 2012, "Influenza human monoclonal antibody 1F1 interacts with three major antigenic sites and residues mediating human receptor specificity in H1N1 viruses," PLoS Pathog., 8(12):e1003067 (9 pages).
Turbelin et al., 2013, "Age distribution of influenza like illness cases during post-pandemic A(H3N2): comparison with the twelve previous seasons, in France," PLoS One, 8(6):e65919 (9 pages).
Tweed et al., 2004, "Human illness from avian influenza H7N3, British Columbia," Emerg Infect Dis., 10(12):2196-2199.
UniProtKB: P16199.1, Influenza B virus (B/Memphis/3/89), last modified Dec. 11, 2019.
UniProtKB: P16203.1, Influenza B virus (B/Singapore/222/79), last modified Apr. 22, 2020.
UniProtKB: P16205.1, Influenza B virus (B/USSR/100/83), last modified Dec. 11, 2019.
UniProtKB: P16207.1, Influenza B virus (Strain B/VICTORIA/3/85), last modified Dec. 11, 2019.
UniProtKB: P27907, Influenza B virus (strain B/Beijing/1/1987), last modified Dec. 11, 2019.
UniProtKB: Q90021.1, Influenza B virus (B/Yamagata/16/1988), last modified Dec. 11, 2019.
Vahey et al., 2019, "Low-Fidelity Assembly of Influenza A Virus Promotes Escape from Host Cells," Cell, 176(1-2):281-294.e19 (Epub 2018).
Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Van Der Brand et al., 2011, "Efficacy of vaccination with different combinations of MF59-adjuvanted and nonadjuvantcd seasonal and pandemic influenza vaccines against pandemic H1N1 (2009) influenzavirus infection in ferrets," J Virol., 85(6):2851-2858.
Van Der Lubbe, 2018, "Mini-HA Is Superior to Full Length Hemagglutinin Immunization in Inducing Stem-Specific Antibodies and Protection Against Group 1 Influenza Virus Challenges in Mice," Front Immunol., 9:2350 (13 pages).
Van Der Most et al., 2014, "Seeking help: B cells adapting to flu variability," Sci Transl Med., 6(246):246ps8 (7 pages).
Van Reeth et al., 2009, "Prior infection with an H1N1 swine influenza virus partially protects pigs against a low pathogenic H5N1 avian influenza virus," Vaccine, 27(45):6330-6339.
Vanlandschoot et al., 1995. "A fairly conserved epitope on the hemagglutinin of influenza A (H3N2) virus with variable accessibility to neutralizing antibody." Virology, 212(2)526-534.
Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.
Vareckova et al., 2008, "HA2-specific monoclonal antibodies as tools for differential recognition of influenza A virus antigenic subtypes," Virus Research, 132:181-186.

(56) References Cited

OTHER PUBLICATIONS

Vaughn et al., 2014, "Safety of AS03-adjuvanted inactivated split virion A(H1N1)pdm09 and H5N1 influenza virus vaccines administered to adults: pooled analysis of 28 clinical trials," Hum Vaccin Immunother, 10(10):2942-2957.
Vavricka et al., 2011, "Structural and functional analysis of laninamivir and its octanoate prodrug reveals group specific mechanisms for influenza NA inhibition," PLoS Pathog., 7(10):e1002249 (10 pages).
Vigerust et al., 2007, "N-Linked Glycosylation Attenuates H3N2 Influenza Viruses", Journal of Virology, 81(16): 8593-8600.
Vincent et al., 2008, "Failure of protection and enhanced pneumonia with a US H1N2 swine influenza virus in pigs vaccinated with an inactivated classical swine H1N1 vaccine," Vet Microbiol., 126(4):310-323.
Wagner et al., 2002, "Functional balance between haemagglutinin and neuraminidase in influenza virus infections," Rev. Med. Virol., 12(3):159-166.
Walz et al., 2018, "Neuraminidase-Inhibiting Antibody Titers Correlate with Protection from Heterologous Influenza Virus Strains of the Same Nemaminidase Subtype," J Virol., 92(17):e01006-18 (15 pages).
Wan et al., 2013, "Molecularbasis for broad neuraminidase immunity: conserved epitopes in seasonal and pandemic H1N1 as well as H5N1 influenza viruses," J Virol., 87(16):9290-9300.
Wan et al., 2015, "Structural characterization of a protective epitope spanning A(H1N1)pdm09 influenzavirus neuraminidase monomers," Nat Commun., 6:6114 (10 pages).
Wang et al., 1992, "High-affinity laminin receptor is a receptor for Sindbis virus in mammalian cells," J Virol., 66(8):4992-5001.
Wang et al., 2006, "Hemagglutinin (HA) proteins from H1 and H3 serotypes of influenza A viruses require different antigen designs for the induction of optimal protective antibody responses as studied by codon-optimized HA DNA vaccines," J Virol., 80(23):11628-11637.
Wang et al., 2007, "Incorporation of High Levels of Chimeric Human Immunodeficiency Virus Envelope Glycoproteins into Virus-Like Particles", J. Virol., 81(20):10869-10878.
Wang et al., 2008, "Crystal structure of unliganded influenza B virus hemagglutinin," J. Virol. 82(6):3011-3020.
Wang et al., 2008, "Simplified recombinational approach for influenza A virus reverse genetics", J. Virol. Methods 151:74-78.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Wang et al., 2009, "Glycans on influenza hemagglutinin affect receptor binding and immune response." PNAS, 106(43):18137-18142.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):e1000796 (9 pages).
Wang et al., 2010, "Vaccination with a synthetic peptide from the influenza virus hemagglutinin provides protection against distinct viral subtypes". PNAS. 107(44):18979-18984.
Wang et al., 2011, "Biochemistry. Catching a moving target," Science, 333(6044):834-835.
Wang et al., 2012, "Generation of recombinant pandemic H1N1 influenza virus with the HA cleavable by bromelain and identification of the residues influencing HA bromelain cleavage." Vaccine, 30(4):872-878.
Ward et al., 1982, "Amino acid sequence of the Pronase-released heads of neuraminidase subtype N2 from the Asian strain A/Tokyo/3/67 of influenza virus," Biochem J., 207(1):91-95.
Webby et al., 2010, Hemagglutinin [Influenza A virus (A/Brisbane/59/2007(H1N1))]. GenBank Acc. No. ADE28750.1. Dep. Mar. 29, 2010.
Webster et al., 1968, "Reactions of antibodies with surface antigens of influenza virus," J Gen Virol., 3(3):315-326.
Webster et al., 1980, "Determination of the number of nonoverlapping antigenic areas on Hong Kong (H3N2) influenza virus hemagglutinin with monoclonal antibodies and the selection of variants with potential epidemiological significance," Virology, 104(1):139-148.
Webster et al., 1984, "Antigenic and biological characterization of influenza virus neuraminidase (N2) with monoclonal antibodies," Virology, 135(1):30-42.
Wei et al., 2010, "Induction of Broadly Neutralizing H1N1 Influenza Antibodies by Vaccination," Science; 329:1060-1064.
Wei et al., 2020, "Next-generation influenza vaccines: opportunities and challenges," Nat. Rev. Drug Discov., 19(4):239-252.
Weir et al., 2016, "An overview of the regulation of influenza vaccines in the United States," Influenza Other Respir Viruses, 10(5):354-360.
Weis et al., 1988, "Structure of the influenza virus haemagglutinin complexed with its receptor, sialic acid." Nature, 333:426-431.
Weis et al., 1990, "Refinement of the Influenza Virus Hemagglutinin by Simulated Annealing." J. Mol. Biol. 212:737-761.
Weldon et al., 2010, "Enhanced immunogenicity of stabilized trimeric soluble influenza hemagglutinin", PLoSONE 5(9):e12466 (8 pages).
Whittle et al., 2011, "Broadly neutralizing human antibody that recognizes the receptor-binding pocket of influenza virus hemagglutinin," Proc. Natl. Acad. Sci. USA, 108(34):14216-14221.
WHO World Health Organization Factsheet No. 211. Influenza Nov. 2016. https://www.who.int/mediacentre/factsheets/fs211/en.
Wiley et al., 1981, "Structural identification of the antibody-binding sites of Hong Kong influenza haemagglutinin and their involvement in antigenic variation," Nature, 289(5796):373-378.
Wiley et al., 1983, "The three-dimensional structure and antigenic variation of the influenza virus haemagglutinin." Division of Virology, 107-111.
Wiley, 1987, "The Structure And Function Of The Hemagglutinin Membrane Glycoprotein Of Influenza Virus." Ann. Rev. Biochem., 56:365-394.
Wilson et al., 1981, "Structure of the haemagglutinin membrane glycoprotein of influenza virus at 3 A resolution." Nature, 289:366-373.
Wilson et al., 1990, "Structural basis of immune recognition of influenza virus hemagglutinin," Annu. Rev. Immunol., 8:737-771.
Winokur et al., 1991, "The hepatitis A virus polyprotein expressed by a recombinant vaccinia virus undergoes proteolytic processing and assembly into viruslike particles," J Virol., 65(9):5029-5036.
Winter et al., 1981, "Nucleotide Sequence Of The Haemagglutinin Gene Of A Human Influenza Virus H1 Subtype" Nature, 292:72-75.
Wohlbold et al., 2014, "In the Shadow of Hemagglutinin: A Growing Interest in Influenza Viral Neuraminidase and Its Role as a Vaccine Antigen," Viruses 6(6):2465-2494.
Wohlbold et al., 2015, "An H10N8 influenza virus vaccine strain and mouse challenge model based on the human isolate A/Jiangxi-Donghu/346/13," Vaccine, 33(9):1102-1106.
Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Wohlbold et al., 2016, "Hemagglutinin Stalk- and Neuraminidase-Specific Monoclonal Antibodies Protect against Lethal H10N8 Influenza Virus Infection in Mice," J Virol., 90(2):851-861.
Wohlbold et al., 2017, "Broadly protective murine monoclonal antibodies against influenza B virus target highly conserved neuraminidase epitopes," Nat. Microbiol. 2(10):1415-1424 with supplemental materials.
Wohlbold, 2017, "The influenza virus neuraminidase as a vaccine antigen and the potential of neuraminidase antibodies to protect against infection," dissertation submitted to the Graduate Faculty of the Graduate School of Biomedical Sciences, Biomedical Sciences Doctoral Program, in partial fulfillment of the requirements for the degree of Doctor of Philosophy, Icahn School of Medicine at Mount Sinai (236 pages).

(56) References Cited

OTHER PUBLICATIONS

Worobey et al., 2002, "Questioning the Evidence for Genetic Recombination in the 1918 "Spanish Flu" Virus", Science, 296(5566):211a (3 pages).
Wrammert et al., 2008, "Rapid cloning of high-affinity human monoclonal antibodies against influenzavirus," Nature, 453(7195):667-671.
Wrammert et al., 2011, "Broadly cross-reactive antibodies dominate the human B cell response against 2009 pandemic H1N1 influenzavirus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jun. 26, 2014 for PCT Application No. PCT/US2014/025526, Published as WO 2014/159960.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.
Written Opinion of International application No. PCT/US2010/036170, dated Aug. 17, 2010.
Written Opinion of International application No. PCT/US2011/025467, dated Oct. 19, 2011.
Written Opinion of the International Searching Authority for International Application No. PCT/US2016/014640, dated Jun. 3, 2016.
Written Opinion of the International Searching Authority for International Application No. PCT/US2016/037595, dated Sep. 15, 2016.
Written Opinion of the International Searching Authority for International Application No. PCT/US2017/035479, dated Oct. 25, 2017.
Written Opinion of the International Searching Authority for International Application No. PCT/US2017/037384, dated Nov. 3, 2017.
Written Opinion of the International Searching Authority for International Application No. PCT/US2018/026489, dated Aug. 27, 2018.
Written Opinion of the International Searching Authority for International Application No. PCT/US2018/045399, dated Nov. 29, 2018.
Wu et al., 2018, "Structural insights into the design of novel anti-influenza therapies," Nat. Struct. Mol. Biol., 25(2):115-121.
Xiao et al., 1996, "High efficiency, long-term clinical expression of cottontail rabbit papillomavirus (CRPV) DNA in rabbit skin following particle-mediated DNA transfer," Nucleic Acids Res., 24(13):2620-2622.
Xie et al., 2011, "Revisiting the 1976 "swine flu" vaccine clinical trials: cross-reactive hemagglutinin and neuraminidase antibodies and their role in protection against the 2009 H1N1 pandemic virus in mice," Clin. Infect. Dis., 53(12):1179-1187.
Xu et al., 2008, "Structural characterization of the 1918 influenzavims H1N1 neuraminidase," J Virol., 82(21):10493-10501.
Xu et al., 2012, "Structural characterization of the hemagglutinin receptor specificity from the 2009 H1N1 influenza pandemic," J. Virol., 86(2):982-990 (Epub 2011).
Yan et al., 2012, "Microbial Resources and Utilization," Harbin Engineering University Press, pp. 100-101, in Chinese with machine English translation of Section 4 (11 pages).
Yang et al., 2006, "Targeting lentiviral vectors to specific cell types in vivo", PNAS 103: 11479-11484.
Yang et al., 2007, "Immunization by Avian H5 Influenza Hemagglutinin Mutants with Altered Receptor Binding Specificity", Science, 317(5839):825-828.
Yang et al., 2014, "A beneficiary role for neuraminidase in influenza virus penetration through the respiratory mucus," PLoS One, 9(10):e110026 (11 pages).
Yang et al., 2014, "Structural stability of influenza A(H1N1)pdm09 virus hemagglutinins." J. Virol., 88(9):4828-4838.
Yang, 2013, "Recombinant trivalent influenza vaccine (flublok(®)): a review of its use in the prevention of seasonal influenza in adults," Drugs, 73(12):1357-1366.
Yassine et al., 2015, "Hemagglutinin-stem nanoparticles generate heterosubtypic influenza protection." Nat. Med. 21(9):1065-1070.
Yasugi et al., 2013, "Human monoclonal antibodies broadly neutralizing against influenza B virus", PLoS Pathog. 9(2):e1003150 (12 pages).
Yasuhara et al., 2019, "Antigenic drift originating from changes to the lateral surface of the neuraminidase head of influenza A virus" Nat. Microbiol., 4(6):1024-1034.
Yen et al., 2011, "Hemagglutinin-neuraminidase balance confers respiratory-droplet transmissibility of the pandemic H1N1 influenza virus in ferrets," Proc. Natl. Acad. Sci. USA, 108(34):14264-14269.
Yewdell., 2013, "To dream the impossible dream: universal influenza vaccination," Curr Opin Virol., 3(3):316-321.
Yoshida et al., 2007, "Preparation of monoclonal antibodies against common region of influenza A virus hemagglutinin (HA)," Lectures in the Chemical Society of Japan, 87(2):1307, 2 J3-02 in Japanese with English translation of Abstract (4 pages).
Yoshida et al., 2009, "Cross-protective potential of a novel monoclonal antibody directed against antigenic site B of the hemagglutinin of influenza A viruses." PLoS Pathog., 5(3):e1000350 (9 pages).
Zamarin et al., 2006, "Influenza A virus PB1-F2 protein contributes to viral pathogenesis in mice," J Virol. 80(16):7976-7983.
Zerangue et al., 2000, "An artificial tetramerization domain restores efficient assembly of functional Shaker channels lacking T1," Proc Natl Acad Sci USA, 97(7):3591-3595.
Zhang et al., 2010, "Crystal structure of the swine-origin A (H1N1)-2009 influenza A virus hemagglutinin (HA) reveals similar antigenicity to that of the 1918 pandemic virus," Protein Cell 1(5):459-467.
Zhang et al., 2011, "Determination of serum neutralization antibodies against seasonal influenza A strain H3N2 and the emerging strains 2009 H1N1 and avian H5N1," Scand. J. Infect. Dis. 43(3):216-220.
Zhang et al., 2015, "A human-infecting H10N8 influenza virus retains a strong preference for avian-type receptors," Cell Host Microbe, 17(3):377-384.
Zhao et al., 2011, "Identification of a highly conserved H1 subtype-specific epitope with diagnostic potential in the hemagglutinin protein of influenza A virus," PLoS One, 6(8):e23374 (10 pages).
Zheng, et al., 1996, "Nonconserved nucleotides at the 3' and 5' ends of an influenza A virus RNA play an important role in viral RNA replication", Virology 217:242-251.
Zhou et al., 1994, "Adeno-associated virus 2-mediated high efficiency gene transfer into immature and mature subsets of hematopoietic progenitor cells in human umbilical cord blood," J Exp Med., 179(6):1867-1875.
Ziegler et al., 1995, "Type- and subtype-specific detection of influenza viruses in clinical specimens by rapid culture assay," J Clin Microbiol., 33(2):318-321.
Zost et al., 2017, "Contemporary H3N2 influenza viruses have a glycosylation site that alters binding of antibodies elicited by egg-adapted vaccine strains," Proc. Natl. Acad. Sci. USA, 114(47):12578-12583.
Zheng et al., 2020, "Enhancing Neuraminidase Immunogenicity of Influenza A Viruses by Rewiring RNA Packaging Signals," J. Virol., 94(16):e00742-20 (12 pages).
Centers of Excellence for Influenza Research and Surveillance (CEIRS), 2016, "9th Annual NIAID Centers of Excellence for Influenza Research and Surveillance Network Meeting," Memphis, Tennessee, Jun. 26-29, 2016, Program Book (37 pages)—"Design and incorporation of mosaic hemagglutinins as a universal vaccination strategy against influenza B viruses" by Megan Ermler on p. 21.
Dai et al., 2016, "Identification of Residues That Affect Oligomerization and/or Enzymatic Activity of Influenza Virus H5N1 Neuraminidase Proteins," J. Virol., 90(20): 9457-9470.
Gao et al., 2021, "Balancing the influenza neuraminidase and hemagglutinin responses by exchanging the vaccine virus backbone," PLoS Pathog., 17(4):e1009171 (22 pages).
International Preliminary Report on Patentability for International Patent Application No. PCT/US2010/043697 (Pub No. WO 2011014645) dated Jan. 31, 2012 (10 pages).

(56) References Cited

OTHER PUBLICATIONS

International Search Report and Written Opinion for International Patent Application No. PCT/US2010/043697 (Pub No. WO 2011014645) dated Nov. 17, 2010 (16 pages).

Lehninger et al., 1993, "Chapter 7: The Three-Dimensional Structure of Proteins," Principles of Biochemistry with an Extended Desicussion of Oxygen-Binding Proteins, Second Edition, Worth Publishers, pp. 160, 161 and 175-185.

Liao et al., 2020, "Chimeric hemagglutinin vaccine elicits broadly protective CD4 and CD8 T cell responses against multiple influenza strains and subtypes," Proc. Natl. Acad. Sci. USA, 117(30):17757-17763.

Liu et al., 2021, "Mosaic Hemagglutinin-Based Whole Inactivated Virus Vaccines Induce Broad Protection Against Influenza B Virus Challenge in Mice," Front. Immunol., 12:746447 (13 pages).

Lugovtsev et al., 2007, "Generation of the influenza B viruses with improved growth phenotype by substitution of specific amino acids of hemagglutinin," Virology, 365(2):315-323.

Madsen et al., 2020, "Human Antibodies Targeting Influenza B Virus Neuraminidase Active Site Are Broadly Protective," Immunity, 53(4):852-863.e7 (20 pages).

Myers et al., 2013, "Compensatory hemagglutinin mutations alter antigenic properties of influenza viruses," J. Virol., 87(20):11168-11172.

Nakagawa et al., 2002, "Emergence of an influenza B virus with antigenic change," J. Clin. Microbiol., 40(8):3068-3070.

Nakagawa et al., 2003, "Neutralizing epitopes specific for influenza B virus Yamagata group strains are in the loop," J. Gen. Virol., 84(Pt 4):769-773.

Strohmeier et al., 2021, "A Novel Recombinant Influenza Virus Neuraminidase Vaccine Candidate Stabilized by a Measles Virus Phosphoprotein Tetramerization Domain Provides Robust Protection from Virus Challenge in the Mouse Model," mBio., 12(6):e02241-21 (17 pages).

Strohmeier et al., 2022, "A CpG 1018 adjuvanted neuraminidase vaccine provides robust protection from influenza virus challenge in mice," NPJ Vaccines, 7(1):81 (13 pages).

Suntronwong et al., 2017, "Genetic and antigenic divergence in the influenza A(H3N2) virus circulating between 2016 and 2017 in Thailand," PLoS One, 12(12):e0189511 (12 pages).

Tan et al., 2022, "Murine Broadly Reactive Antineuraminidase Monoclonal Antibodies Protect Mice from Recent Influenza B Virus Isolates and Partially Inhibit Virus Transmission in the Guinea Pig Model," mSphere, 7(5):e0092721 (13 pages).

FIG. 1

B/Yam PNVTSRNG
A/H5  PYQGKSS

MDCK

■ B/Yamagata ectodomain (PR8 background)
▲ B/Yamagata ectodomain (PR8 background) + A/H5 150 loop

FIG. 4

B/Yamagata
ectodomain
(PR8 background)
+ A/H5 150 loop cH5/3

B/Yamagata
ectodomain
(PR8
background)

empty plasmid

Surface staining in 293T cells with anti-H5 serum

FIG. 5

B/Yam    NKNQMKN
A/H5     NDAAMQT

B/Yam RDNKTA
A/H5 KKNSTY

B/Yam AA to exchange: 90 131 133 137 144

B/Yam                                                 TIP
B/Yamagata ectodomain with A/H5    F<u>I</u>P

B/Yam
NIRLSTHNVINAERAPGGPYRL

B/Yamagata ectodomain with A/H5
K<u>I</u>QLST<u>K</u>NVINAE<u>H</u>APGGPYRL

```
                                        agcaaaagcagggga
                                               1
aaataaaaacaaccaaaATGAAGGCAAACC
        1                        2
TACTGGTCCTGTTAAGTGCACTTGCAGCTG
                       2
CAGATGCAGATCGAATCTGCACTGGGATAA
    2
CATCTTCAAACTCACCTCATGTGGTCAAAA
CAGCTACTCAAGGGGAAGTTAATGTGACTG
GTGTGATACCACTGACAACAACACCAACAA
AATCTCATTTTGCAAATCTCAAAGGAACAA
AGACCAGAGGGAAACTATGCCCAAACTGTC
TCAACTGCACAGATCTGGATGTGGCCTTGG
GCAGACCAATGTGTATGGGGCTAATACCTT
                       3
CGGCAAAAGCTTCAATACTCCACGAAGTCA
GACCTGTTACATCCGGGTGCTTTCCTATAA
TGCACGACAGAACAAAAATCAGACAGCTAC
CCAATCTTCTCAGAGGATATGAAAAGATCG
                              3        3
AATTATCAACCTCAAACGTTATCAACGCAG
 3              3
AAGTGGCACCAGGAGGACCCTACAGACTTG
   3
GAACCTCAAAATCTTGCAAATTCGGAAGCT
            4           5
CCAATTCTTTCTTCGCAACAATGGCTTGGG
 5
CTGTCCCACATCAATCAGGACATATACGA
         6
ATCCACTAACAGTAGAAGTACCATACATTT
GCACAAAAGGAGAAGACCAAATTACTGTTT
GGGGGTTCCATTCTGATGCCACACTGAAAA
                       7
TGCACCAACTCTATGGAGACTCAAATCCTC
   7
AAAAGTTCACCTCATCTGCCAATGGAGTAA
CCACACATTATGTTTCTCAGATTGGTGACT
TCCCAAATCAAACAGAAGACGGAGGGCTAC
CACAAAGCGGCAGAATTGTTGTTGATTACA
TGGTGCAAAAACCTGGGAAAACAGGAACAA
```

5'-<u>GCAAAAGCAGGGGTCACAATGGAG</u>AAGTTCATCATAATGGCAATGCTCTTGGTGAG
CACAAATGCATATGATAGGATATGCATTGGATACCAATCAAACAACTCCACTGACACAG
TAAACACACTCATAGAGCAAAATGTGCCAGTCACCCAGACAATGGAACTAGTGGAAACC
GAGAAACATCCTGCCTATTGCAATACTGATTTGGGTGCTCCACTAGAGTTGCGTGATTG
CAAGATTGAGGCGGTGATCTATGGGAACCCAAAATGTGACATCCACTTGAAAGACCAAG
GTTGGTCATACATAGTGGAGAGACCCAGTGCACCAGAGGGGATGTGCTACCCTGGATCA
GTGGAGAATCTCGAAGAGTTGAGGTTTGTTTTCTCCAGTGCTGCTTCCTACAAAAGGAT
AAGATTGTTTGATTACTCCAGATGGAATGTTACCAGATCTGGGACAAGCAAGGCATGCA
ATGCTTCAACAGGAGGCCAATCTTTCTATCGGAGCATCAATTGGCTAACTAAAAGAAA
CCCGACACCTATGACTTCAATGAGGGGACTTATATCAATAATGAAGATGGGACATAAT
TTTCTTATGGGGGATTCATCACCCACCGGATGCAAAAGAGCAAACAACACTGTACAAGA
ATGCAAATACTTTGAGTAGTGTTACTACCAACACTATAAACAGGAGCTTCCAACCCAAT
ATCGGGCCCAGGCCACTGGTGAGAGGGCAACAAGGGCGGATGGACTATTATTGGGGCAT
TTTGAAGAGGGGAGAAACTTTAAAAATTAGAACCAATGGGAACCTGATCGCGCCTGAAT
TCGGTTATCTGCTCAAAGGGGAGAGCCATGGCAGAATAATTCAAAATGAGGACATACCA
ATTGGGAGTTGTCACACGAAATGTCAGACATACGCAGGAGCAATTAATAGCAGCAAACC
CTTTCAGAATRCAAGCAGGCACTACATGGGAGAATGTCCCAAGTATGTGAAGAAGGAAA
GCTTACGGCTGGCAGTTGGACTTAGAAACACTCCTTCTATTGAACCCAGAGGCTTGTTT
GGAGCCATTGCTGGTTTTATTGAAGGGGGATGGTCTGGGATGATTGATGGATGGTATGG
GTTTCACCATAGTAATTCAGAAGGAACAGGAATGGCGGCCGATCAGAAATCGACACAAG
AAGCAATTGACAAAATCACCAATAAGGTCAATAATATAGTTGATAAAATGAACAGGGAA
TTTGAAGTAGTGAACCATGAGTTTTCCGAAGTCGAAAAAGAATAAACATGATAAATGA
CAAAATTGATGACCAGATTGAAGATCTTTGGGCCTACAATGCAGAGCTTCTGGTCCTCC
TAGAGAACCAGAAAACACTGGATGAACACGACTCCAATGTCAAAAATCTCTTTGATGAA
GTAAGAAGGAGACTTTCAGCCAATGCAATAGATACTGGGAATGGCTGCTTCGACATACT
CCACAAATGTGACAACGAGTGCATGGAGACCATAAAGAATGGGACTTATAACCATAAAG
AGTATGAGGAAGAGGCCAAGCTGGAAAGGAGCAAGATTAACGGAGTAAAGCTAGAGGAA
AATACCACCTATAAAATTCTCAGCATTTACAGTACGGTGGCGGCCAGTCTTTGCTTGGC
AATCCTGATTGCTGGAGGTCTAATCCTGGGCATGCAAAATGGATCTTGTAGATGCATGT
TCTGTATTTAAG<u>AAAAAACACCCTTGTTTCTACT</u>-3'

FIG. 21A

MEKFIIMAMLLVSTNAYDRICIGYQSNNSTDTVNTLIEQNVPVTQTMELVETEKHPAYC
NTDLGAPLELRDCKIEAVIYGNPKCDIHLKDQGWSYIVERPSAPEGMCYPGSVENLEEL
RFVFSSAASYKRIRLFDYSRWNVTRSGTSKACNASTGGQSFYRSINWLTKKKPDTYDFN
EGTYINNEDGDIIFLWGIHHPPDAKEQTTLYKNANTLSSVTTNTINRSFQPNIGPRPLV
RGQQGRMDYYWGILKRGETLKIRTNGNLIAPEFGYLLKGESHGRIIQNEDIPIGSCHTK
CQTYAGAINSSKPFQNXSRHYMGECPKYVKKESLRLAVGLRNTPSIEPRGLFGAIAGFI
EGGWSGMIDGWYGFHHSNSEGTGMAADQKSTQEAIDKITNKVNNIVDKMNREFEVVNHE
FSEVEKRINMINDKIDDQIEDLWAYNAELLVLLENQKTLDEHDSNVKNLFDEVRRRLSA
NAIDTGNGCFDILHKCDNECMETIKNGTYNHKEYEEEAKLERSKINGVKLEENTTYKIL
SIYSTVAASLCLAILIAGGLILGMQNGSCRCMFCI

FIG. 21B

```
CGGATGTTGCCCAGCCGGCGCCAGCGAGGAGGCTGGGACCATGCCGGCCAGCAAAAGCA
GGGGTTCAATCTGTCAAAATGGAGAAAATAGTGCTTCTTTTTGCAATAGTCAGTCTTGT
TAAAAGTGATCAGATTTGCATTGGTTACCATGCAAACAACTCGACAGAGCAGGTTGACA
CAATAATGGAAAAGAACGTTACTGTTACACATGCCCAAGACATACTGGAAAAGAAACAC
AACGGGAAGCTCTGCGATCTAGATGGAGTGAAGCCTCTAATTTTGAGAGATTGTAGCGT
AGCTGGATGGCTCCTCGGAAACCCAATGTGTGACGAATTCATCAATGTGCCGGAATGGT
CTTACATAGTGGAGAAGGCCAATCCAGTCAATGACCTCTGTTACCCAGGGGATTTCAAT
GACTATGAAGAATTGAAACACCTATTGAGCAGAATAAACCATTTTGAGAAAATTCAGAT
CATCCCCAAAAGTTCTTGGTCCAGTCATGAAGCCTCATTAGGGGTGAGCTCAGCATGTC
CATACCAGGGAAAGTCCTCCTTTTTCAGAAATGTGGTATGGCTTATCAAAAGAACAGT
ACATACCCAACAATAAGAGGAGCTACAATAATACCAACCAAGAAGATCTTTTGGTACT
GTGGGGATTCACCATCCTAATGATGCGGCAGAGCAGACAAAGCTCTATCAAACCCAA
CCACCTATATTTCCGTTGGGACATCAACACTAAACCAGAGATTGGTACCAAGAATAGCT
ACTAGATCCAAAGTAAACGGGCAAAGTGGAAGGATGGAGTTCTTCTGGACAATTTTAAA
GCCGAATGATGCAATCAACTTCGAGAGTAATGGAAATTTCATTGCTCCAGAATATGCAT
ACAAAATTGTCAAGAAGGGGACTCAACAATTATGAAAAGTGAATTGGAATATGGTAAC
TGCAACACCAAGTGTCAAACTCCAATGGGGCGATAAACTCTAGCATGCCATTCCACAA
TATACACCCTCTCACCATTGGGGAATGCCCCAAATATGTGAAATCAAACAGATTAGTCC
TTGCGACTGGGCTCAGAAATAGCCCTCAGCGGGAGACGCGGGGATTATTTGGAGCTATA
GCAGGTTTTATAGAGGGAGGATGGCAGGGAATGGTAGATGGTTGGTATGGGTACCACCA
TAGCAATGAGCAGGGGAGTGGGTACGCTGCAGACAAAGAATCCACTCAAAAGGCAATAG
ATGGAGTCACCAATAAGGTCAACTCGATCATTGACAAAATGAACACTCAGTTTGAGGCC
GTTGGAAGGGAATTTAACAACTTAGAAAGGAGAATAGAGAATTTAAACAAGAAGATGGA
AGACGGGTTCCTAGATGTCTGGACTTATAATGCTGAACTTCTGGTTCTCATGGAAAATG
AGAGAACTCTAGACTTTCATGACTCAAATGTCAAGAACCTTTACGACAAGGTCCGACTA
CAGCTTAGGGATAATGCAAAGGAGCTGGGTAACGGTTGTTTCGAGTTCTATCATAAATG
TGATAATGAATGTATGGAAAGTGTAAGAAATGGAACGTATGACTACCCGCAGTATTCAG
AAGAAGCGAGACTAAAAAGAGAGGAAATAAGTGGAGTAAAATTGGAATCAATAGGAATT
TACCAAATACTGTCAATTTATTCTACAGTGGCGAGTTCCCTAGCACTGGCAATCATGGT
AGCTGGTCTATCCTTATGGATGTGCTCCAATGGGTCGTTACAATGCAGAATTTGCATTT
AAATTTGTGAGTTCAGATTGTAGTTAAAAACACCCTTGTTTCTACTAATAACCCGGCGG
CCCAAAATGCC
```

FIG. 22A

MEKIVLLFAIVSLVKSDQICIGYHANNSTEQVDTIMEKNVTVTHAQDILEKKHNGKLCD
LDGVKPLILRDCSVAGWLLGNPMCDEFINVPEWSYIVEKANPVNDLCYPGDFNDYEELK
HLLSRINHFEKIQIIPKSSWSSHEASLGVSSACPYQGKSSFFRNVVWLIKKNSTYPTIK
RSYNNTNQEDLLVLWGIHHPNDAAEQTKLYQNPTTYISVGTSTLNQRLVPRIATRSKVN
GQSGRMEFFWTILKPNDAINFESNGNFIAPEYAYKIVKKGDSTIMKSELEYGNCNTKCQ
TPMGAINSSMPFHNIHPLTIGECPKYVKSNRLVLATGLRNSPQRETRGLFGAIAGFIEG
GWQGMVDGWYGYHHSNEQGSGYAADKESTQKAIDGVTNKVNSIIDKMNTQFEAVGREFN
NLERRIENLNKKMEDGFLDVWTYNAELLVLMENERTLDFHDSNVKNLYDKVRLQLRDNA
KELGNGCFEFYHKCDNECMESVRNGTYDYPQYSEEARLKREEISGVKLESIGIYQILSI
YSTVASSLALAIMVAGLSLWMCSNGSLQCRICIICEFRLLKTPLFLLITRRPKM

FIG. 22B

5'-<u>AAAGCAGGGGTTCTATTAAGAAATCAAAATGAAGAAAGCACTGCTATTTGCAGCTA</u>
TTTTCCTTTATGCAAAGGCAGATGAAATCTGTATCGGCTACTTAAGCAACAACTCAACA
GACAAAGTTGACACAATAATCGAGAACAATGTCACAGTGACTAGCTCAGTGGAACTAGT
CGAAACAGAACACACTGGGTCATTCTGCTCAATCAATGGAAAACAACCGATAAGTCTTG
GAGACTGCTCTTTTGCTGGGTGGATATTAGGTAATCCCATGTGTGATGATCTAATTGGT
AAGACTTCATGGTCCTACATTGTGGAGAAGCCCAACCCAACAAATGGAATTTGTTACCC
TGGAACTTTGGAGGATGAAGAAGAACTGAGACTGAAATTCAGTGGAGTCCTGGAATTCA
GCAAGTTCGAAGCATTCACATCAAATGGATGGGGTGCTGTGAATTCGGGAGCAGGAGTG
ACTGCTGCATGCAAATTCGGAAGCTCCAATTCTTTCTTCCGAAACATGGTATGGCTTAT
ACATCAATCAGGAACATATCCTGTAATAAAGAGGACTTTTAACAATACCAAAGGAAGAG
ATGTGTTGATCGTTTGGGGAATTCATCACCCTGCCACACTGAAAGAGCACCAAGACCTA
TACAAGAAAGACAGTTCCTATGTAGCAGTGGGTTCAGAAACTTACAACAGAAGATTCAC
CCCAGAAATCAGCACTAGGCCCAAAGTCAATGGACAGGCTGGACGGATGACATTTTATT
GGACAATGGTCAAACCAGGAGAGTCAATAACATTTGAGTCTAATGGTGCATTCTTGGCT
CCTAGATATGCTTTTGAGATTGTCTCTGTTGGAAATGGGAAATTATTCAGAAGCGAACT
GAGTATTGAATCATGCTCTACCAAATGCCAAACAGAAGTAGGAGGGATTAATACAAACA
AAAGTTTCCACAGTGTTCATAGGAACACTATTGGAGACTGTCCCAAATATGTGAATGTC
AAATCCCTAAAGCTTGCCACAGGACTTAGAAATGTTCCAGCAATAGCATCAAGAGGATT
GTTTGGAGCAATAGCCGGATTTATAGAAGGTGGGTGGCCAGGGCTTATCAATGGATGGT
ACGGTTTTCAACACAGAAATGAGGAAGGAACAGGCATAGCAGCAGACAGGGAGTCAACT
CAAAAGGCAGTAGACCAGATAACATCCAAAGTAAACAACATCGTCGACAGAATGAATAC
AAATTTCGAGTCTGTGCAACACGAATTCAGTGAAATAGAGGAGAGGATAAACCAATTGT
CGAAACACGTAGATGATTCTGTGGTTGACATCTGGTCATATAACGCACAACTCCTCGTT
TGGCTTGAAAATGAGAAACTCTGGATCTCCACGATTCCAATGTTAGGAATCTTCATGA
GAAAGTCAGAAGGATGCTAAAGGACAATGCCAAAGATGAGGGAAATGGATGCTTCACCT
TTTACCACAAGTGTGACAACGAATGCATCGAAAAGGTTAGAAACGGAACATATGATCAC
AAAGAATTCGAAGAAGAATCAAGAATCAATCGCCAGGAGATTGAGGGAGTGAGATTAGA
TTCTAGTGGGAATGTGTATAAAATACTGTCAATTTACAGCTGCATCGCAAGCAGTCTTG
TATTAGCAGCACTCATCATGGGTTTCATCCTATGGGCGTGCAGCAATGGATCATGTAGA
TGTACCATTTGCATTTAGA<u>ATTGTGGCAAAAACACCC</u>-3'

FIG. 23A

MKKALLFAAIFLYAKADEICIGYLSNNSTDKVDTIIENNVTVTSSVELVETEHTGSFCS
INGKQPISLGDCSFAGWILGNPMCDDLIGKTSWSYIVEKPNPTNGICYPGTLEDEEELR
LKFSGVLEFSKFEAFTSNGWGAVNSGAGVTAACKFGSSNSFFRNMVWLIHQSGTYPVIK
RTFNNTKGRDVLIVWGIHHPATLKEHQDLYKKDSSYVAVGSETYNRRFTPEISTRPKVN
GQAGRMTFYWTMVKPGESITFESNGAFLAPRYAFEIVSVGNGKLFRSELSIESCSTKCQ
TEVGGINTNKSFHSVHRNTIGDCPKYVNVKSLKLATGLRNVPAIASRGLFGAIAGFIEG
GWPGLINGWYGFQHRNEEGTGIAADRESTQKAVDQITSKVNNIVDRMNTNFESVQHEFS
EIEERINQLSKHVDDSVVDIWSYNAQLLVWLENEKTLDLHDSNVRNLHEKVRRMLKDNA
KDEGNGCFTFYHKCDNECIEKVRNGTYDHKEFEEESRINRQEIEGVRLDSSGNVYKILS
IYSCIASSLVLAALIMGFILWACSNGSCRCTICI

FIG. 23B

5'-<u>GGTCACA</u>ATGGAAAAATTCATCATTTTGAGCACTGTCCTGGCAGTAAGCTTTGCAT
ATGACAAAATTTGCATTGGATATCAAACAAACAACTCGACTGAGACAGTAAACACACTA
ATCGAGCAAAACGTTCCGGTGACACAGGTGGAAGAACTCGTGCATGGTGGGATCGATCC
GGTCCTATGTGGAACGGAGCTAGGGTCACCATTAGTGCTTGATGACTGTTCACTCGAAG
GTCTCATTCTAGGCAATCCCAAATGTGATCTTTATCTGAATGGCAGGGAATGGTCATAC
ATAGTAGAGAGGCCCAAAGAAATGGAAGGAGTTTGCTACCCAGGATCAATTGAAAATCA
AGAGGAGTTGAGATCTCTGTTTTCTTCCATCAAGAAGTATGAAAGAGTGAAGATGTTTG
ATTTCACCAAATGGAATGTCACGTACACTGGAACCAGCAAGGCCTGCAACAATACATCA
AACCAAGGCTCATTCTATAGGAGCATGAGATGGTTAACCTTAAAATCAGGACAATTCCC
AGTCCAGACAGATGAGTACAAGAACACCAGAGATTCGGACATTGTCTTCACCTGGGCCA
TCCATCACCCACCAACATCTGATGAACAGATAAAGTTATACAAAATCCGGATACCCTC
TCCTCAGTCACCACTGATGAAATCAATAGGAGTTTCAAGCCTAACATAGGACCAAGGCC
ATTAGTGAGAGGACAACAGGGGAGAATGGATTACTACTGGGCTGTCCTCAAACCTGGAC
AAACTGTCAAATACAGACCAATGGTAATCTTATTGCACCTGAATATGGTCACTTAATT
ACAGGGAAATCACATGGCAGGATACTCAAGAATAACTTGCCCATAGGACAGTGTGTGAC
TGAGTGCCAGTTGAATGAAGGGGTGATGAATACAAGTAAACCTTTCCAGAACACTAGTA
AGCACTATATTGGGAAATGTCCCAAATACATACCATCAGGAAGCCTGAAATTGGCGATA
GGGCTCAGAAATGTTCCACAAGTTCAGAACAGAGGACTATTTGGAGCAAAAGCAGGTTT
CATAGAGGGCGGATGGCCAGGACTAGTGGCTGGTTGGTATGGATTTCAGCATCAAAATG
CAGAGGGGACAGGCATAGCCGCAGACAGAGACAGCACTCAGAAGGCAATAGACAATATG
CAAAACAAACTCAACAATGTCATTGACAAAATGAACAAACAATTTGAAGTGGTGAATCA
TGAGTTTTCAGAAGTGGAAAGCAGAATAAACATGATTAATTCCCAAATTGATGATCAAA
TAACTGACATATGGGCATACAATGCTGAACTGCTTGTCCTATTGGAAAATCAGAAGACA
TTAGATGAGCATGATGCTAATGTAAGAAACTTACACGATAGAGTCAGAAGAGTCCTAAG
AGAAAATGCAATTGATACAGGAGATGGTTGCTTTGAAATTCTGCATAAATGTGACAACA
ATTGCATGGACACAATCAGAAATGGGACATACAATCACAAGGAGTATGAGGAAGAAAGC
AAAATCGAACGACAGAAAATTAATGGTGTCAAACTTGAGGAGAATTCTACATATAAAAT
TCTGAGCATCTACAGCAGTGTTGCCTCAAGCTTAGTTCTACTGCTCATGATTATTGGGG
GTTTCATTTTCGGGTGTCAAAATGGAAATGTTCGTTGTACTTTCTGTATTTAA<u>TTAAAA
ACAC</u>-3'

FIG. 24A

MEKFIILSTVLAVSFAYDKICIGYQTNNSTETVNTLIEQNVPVTQVEELVHGGIDPVLC
GTELGSPLVLDDCSLEGLILGNPKCDLYLNGREWSYIVERPKEMEGVCYPGSIENQEEL
RSLFSSIKKYERVKMFDFTKWNVTYTGTSKACNNTSNQGSFYRSMRWLTLKSGQFPVQT
DEYKNTRDSDIVFTWAIHHPPTSDEQIKLYKNPDTLSSVTTDEINRSFKPNIGPRPLVR
GQQGRMDYYWAVLKPGQTVKIQTNGNLIAPEYGHLITGKSHGRILKNNLPIGQCVTECQ
LNEGVMNTSKPFQNTSKHYIGKCPKYIPSGSLKLAIGLRNVPQVQNRGLFGAKAGFIEG
GWPGLVAGWYGFQHQNAEGTGIAADRDSTQKAIDNMQNKLNNVIDKMNKQFEVVNHEFS
EVESRINMINSQIDDQITDIWAYNAELLVLLENQKTLDEHDANVRNLHDRVRRVLRENA
IDTGDGCFEILHKCDNNCMDTIRNGTYNHKEYEEESKIERQKINGVKLEENSTYKILSI
YSSVASSLVLLLMIIGGFIFGCQNGNVRCTFCI

FIG. 24B

5'-agcaaaagcaggggaaaataaaaacaaccaaaATGAAGGCAAACCTACTGGTCCTG
TTAAGTGCACTTGCAGCTGCAGATGCAGACACAATATGTATAGGCTACCATGCGAACAA
TTCAACCGACACTGTTGACACAGTACTCGAGAAGAATGTGACAGTGACACACTCTGTTA
ACCTGCTCGAAGACAGCCACAACGGAAAACTATGTAGATTAAAAGGAATAGCCCCACTA
CAATTGGGGAAATGTAACATCGCCGGATGGCTCTTGGGAAACCCAGAATGCGACCCACT
GCTTCCAGTGAGATCATGGTCCTACATTGTAGAAACACCAAACTCTGAGAATGGAATAT
GTTATCCAGGAGATTTCATCGACTATGAGGAGCTGAGGGAGCAATTGAGCTCAGTGTCA
TCATTCGAAGATTCGAAATATTTCCCAAAGAAAGCTCATGGCCCAACCACAACACAAA
CGGAGTAACGGCAGCATGCTCCCATGAGGGGAAAAGCAGTTTTTACAGAAATTTGCTAT
GGCTGACGGAGAAGGAGGGCTCATACCCAAAGCTGAAAAATTCTTATGTGAACAAAAAA
GGGAAAGAAGTCCTTGTACTGTGGGGTATTCATCACCCGCCTAACAGTAAGGAACAACA
GAATATCTATCAGAATGAAAATGCTTATGTCTCTGTAGTGACTTCAAATTATAACAGGA
GATTTACCCCGGAAATAGCAGAAAGACCCAAAGTAAGAGATCAAGCTGGGAGGATGAAC
TATTACTGGACCTTGCTAAAACCCGGAGACACAATAATATTTGAGGCAAATGGAAATCT
AATAGCACCAATGTATGCTTTCGCACTGAGTAGAGGCTTTGGGTCCGGCATCATCACCT
CAAACGCATCAATGCATGAGTGTAACACGAAGTGTCAAACACCCCTGGGAGCTATAAAC
AGCAGTCTCCCTTACCAGAATATACACCCAGTCACAATAGGAGAGTGCCCAAAATACGT
CAGGAGTGCCAAATTGAGGATGGTTACAGGACTAAGGAACACTCCGTCCATTCAATCCA
GAGGTCTATTTGGAGCCATTGCCGGTTTTATTGAAGGGGGATGGACTGGAATGATAGAT
GGATGGTATGGTTATCATCATCAGAATGAACAGGGATCAGGCTATGCAGCGGATCAAAA
AAGCACACAAAATGCCATTAACGGGATTACAAACAAGGTGAACACTGTTATCGAGAAAA
TGAACATTCAATTCACAGCTGTGGGTAAAGAATTCAACAAATTAGAAAAAGGATGGAA
AATTTAAATAAAAAGTTGATGATGGATTTCTGGACATTTGGACATATAATGCAGAATT
GTTAGTTCTACTGGAAAATGAAAGGACTCTGGATTTCCATGACTCAAATGTGAAGAATC
TGTATGAGAAAGTAAAAAGCCAATTAAAGAATAATGCCAAAGAAATCGGAAATGGATGT
TTTGAGTTCTACCACAAGTGTGACAATGAATGCATGGAAAGTGTAAGAAATGGGACTTA
TGATTATCCCAAATATTCAGAAGAGTCAAAGTTGAACAGGGAAAAGGTAGATGGAGTGA
AATTGGAATCAATGGGGATCTATCAGATTCTGGCGATCTACTCAACTGTCGCCAGTTCA
CTGGTGCTTTTGGTCTCCCTGGGGGCAATCAGTTTCTGGATGTGTTCTAATGGATCTTT
GCAGTGCAGAATATGCATCTGAgattagaatttcagaaatatgaggaaaaacacccttg
tttctact-3'

MKANLLVLLSALAAADADTICIGYHANNSTDTVDTVLEKNVTVTHSVNLLEDSHNGKLC
RLKGIAPLQLGKCNIAGWLLGNPECDPLLPVRSWSYIVETPNSENGICYPGDFIDYEEL
REQLSSVSSFERFEIFPKESSWPNHNTNGVTAACSHEGKSSFYRNLLWLTEKEGSYPKL
KNSYVNKKGKEVLVLWGIHHPPNSKEQQNIYQNENAYVSVVTSNYNRRFTPEIAERPKV
RDQAGRMNYYWTLLKPGDTIIFEANGNLIAPMYAFALSRGFGSGIITSNASMHECNTKC
QTPLGAINSSLPYQNIHPVTIGECPKYVRSAKLRMVTGLRNTPSIQSRGLFGAIAGFIE
GGWTGMIDGWYGYHHQNEQGSGYAADQKSTQNAINGITNKVNTVIEKMNIQFTAVGKEF
NKLEKRMENLNKKVDDGFLDIWTYNAELLVLLENERTLDFHDSNVKNLYEKVKSQLKNN
AKEIGNGCFEFYHKCDNECMESVRNGTYDYPKYSEESKLNREKVDGVKLESMGIYQILA
IYSTVASSLVLLVSLGAISFWMCSNGSLQ

FIG. 25B

5'-agcagaagcagagcattttctaatatccacaaaATGAAGGCAATAATTGTACTACT
CATGGTAGTAACATCCAACGCAGATCGAATCTGCACTGGGATAACATCTTCAAACTCAC
CTCATGTGGTCAAAACAGCTACTCAAGGGGAAGTTAATGTGACTGGTGTGATACCACTG
ACAACAACACCAACAAAATCTCATTTTGCAAATCTCAAAGGAACAAAGACCAGAGGGAA
ACTATGCCCAAACTGTCTCAACTGCACAGATCTGGATGTGGCCTTGGGCAGACCAATGT
GTATGGGGACCATACCTTCGGCAAAAGCTTCAATACTCCACGAAGTCAGACCTGTTACA
TCCGGGTGCTTTCCTATAATGCACGACAGAACAAAAATCAGACAGCTACCCAATCTTCT
CAGAGGATATGAAAATATCAGATTATCAACCCATAACGTTATCAACGCAGAAAGGGCAC
CAGGAGGACCCTACAGACTTGGAACCTCAGAATCTTGCCCTAACGTTACCAGTAGAAAC
GGATTCTTCGCAACAATGGCTTGGGCTGTCCCAAGGGACAACAAAACAGCAACGAATCC
ACTAACAGTAGAAGTACCATACATTTGCACAAAAGGAGAAGACCAAATTACTGTTTGGG
GGTTCCATTCTGATAACAAAAACCAAATGAAAAACCTCTATGGAGACTCAAATCCTCAA
AAGTTCACCTCATCTGCCAATGGAGTAACCACACATTATGTTTCTCAGATTGGTGACTT
CCCAAATCAAACAGAAGACGGAGGGCTACCACAAAGCGGCAGAATTGTTGTTGATTACA
TGGTGCAAAAACCTGGGAAAACAGGAACAATTGTCTATCAAAGAGGTGTTTTGTTGCCT
CAAAAGGTGTGGTGCGCAAGTGGCAGGAGCAAGGTAATAAAAGGGTCCTTGCCTTTAAT
TGGTGAAGCAGATTGCCTTCACGAAAAATACGGTGGATTAAACAAAAGCAAGCCTTACT
ACACAGGAGAACATGCAAAAGCCATAGGAAATTGCCCAATATGGGTGAAAACACCTTTG
AAGCTTGCCAATGGAACCAAATATAGACCTCCTGCAAAACTATTAAAGGAAAGGGGTTT
CTTCGGAGCTATTGCTGGTTTCTTAGAGGGAGGATGGGAAGGAATGATTGCAGGTTGGC
ACGGATACACATCTCATGGAGCACATGGAGTGGCAGTGGCAGCAGACCTTAAGAGCACG
CAAGAAGCCATAAACAAGATAACAAAAAATCTCAATTCTTTGAGTGAGCTAGAAGTAAA
GAATCTTCAAAGACTAAGTGGTGCCATGGATGAACTCCACAACGAAATACTCGAGCTGG
ATGAGAAAGTGGATGATCTCAGAGCTGACACAATAAGCTCGCAAATAGAGCTTGCAGTC
TTGCTTTCCAACGAAGGAATAATAAACAGTGAAGATGAGCATCTATTGGCACTTGAGAG
AAAACTAAAGAAATGCTGGGTCCCTCTGCTGTAGACATAGGGAATGGATGCTTCGAAA
CCAAACACAAGTGCAACCAGACCTGCTTAGACAGGATAGCTGCTGGCACCTTTAATGCA
GGAGAATTTTCTCTTCCCACTTTTGATTCACTGAATATTACTGCTGCATCTTTAAATGA
TGATGGATTGGATAATCATACTATACTGCTCTACTACTCAACTGCTGCTTCTAGTTTGG
CCGTAACATTGATGATAGCTATTTTTATTGTTTATATGGTCTCCAGAGACAATGTTTCT
TGCTCCATCTGTCTATAAggaaaattaagccctgtatttcctttattgtagtgcttgt
ttgcttgttaccattacaaagaaacgttattgaaaatgctcttgttactact-3'

FIG. 26A

MKAIIVLLMVVTSNADRICTGITSSNSPHVVKTATQGEVNVTGVIPLTTTPTKSHFANL
KGTKTRGKLCPNCLNCTDLDVALGRPMCMGTIPSAKASILHEVRPVTSGCFPIMHDRTK
IRQLPNLLRGYENIRLSTHNVINAERAPGGPYRLGTSESCPNVTSRNGFFATMAWAVPR
DNKTATNPLTVEVPYICTKGEDQITVWGFHSDNKNQMKNLYGDSNPQKFTSSANGVTTH
YVSQIGDFPNQTEDGGLPQSGRIVVDYMVQKPGKTGTIVYQRGVLLPQKVWCASGRSKV
IKGSLPLIGEADCLHEKYGGLNKSKPYYTGEHAKAIGNCPIWVKTPLKLANGTKYRPPA
KLLKERGFFGAIAGFLEGGWEGMIAGWHGYTSHGAHGVAVAADLKSTQEAINKITKNLN
SLSELEVKNLQRLSGAMDELHNEILELDEKVDDLRADTISSQIELAVLLSNEGIINSED
EHLLALERKLKKMLGPSAVDIGNGCFETKHKCNQTCLDRIAAGTFNAGEFSLPTFDSLN
ITAASLNDDGLDNHTILLYYSTAASSLAVTLMIAIFIVYMVSRDNVSCSICL

FIG. 26B

3' AGCAGAAGCAGAGCATTTTCTAATATCCACAAAATGAAGGCAATAATTGTACT
ACTCATGGTAGTAACATCCAACGCAGATCGAATCTGCACTGGGATAACATCTTCA
AACTCACCTCATGTGGTCAAAACAGCTACTCAAGGGGAAGTTAATGTGACTGGTG
TGATACCACTGACAACAACACCAACAAAATCTCATTTTGCAAATCTCAAAGGAAC
AAAGACCAGAGGGAAACTATGCCCAAACTGTCTCAACTGCACAGATCTGGATGTG
GCCTTGGGCAGACCAATGTGTATGGGGTTCATACCTTCGGCAAAAGCTTCAATAC
TCCACGAAGTCAGACCTGTTACATCCGGGTGCTTTCCTATAATGCACGACAGAAC
AAAAATCAGACAGCTACCCAATCTTCTCAGAGGATATGAAAAAATCCAGTTATCA
ACCAAAAACGTTATCAACGCAGAACATGCACCAGGAGGACCCTACAGACTTGGAA
CCTCAAAATCTTGCccataccagggaaagtcctccTTCTTCGCAACAATGGCTTG
GGCTGTCCCA*aaaaagaacagtacatac*ACGAATCCACTAACAGTAGAAGTACCA
TACATTTGCACAAAAGGAGAAGACCAAATTACTGTTTGGGGGTTCCATTCTGATA
*ATGATGCGGCAATGCAGACA*CTCTATGGAGACTCAAATCCTCAAAAGTTCACCTC
ATCTGCCAATGGAGTAACCACACATTATGTTTCTCAGATTGGTGACTTCCCAAAT
CAAACAGAAGACGGAGGGCTACCACAAAGCGGCAGAATTGTTGTTGATTACATGG
TGCAAAAACCTGGGAAAACAGGAACAATTGTCTATCAAAGAGGTGTTTTGTTGCC
TCAAAAGGTGTGGTGCGCAAGTGGCAGGAGCAAGGTAATAAAAGGGTCCTTGCCT
TTAATTGGTGAAGCAGATTGCCTTCACGAAAATACGGTGGATTAAACAAAAGCA
AGCCTTACTACACAGGAGAACATGCAAAGCCATAGGAAATTGCCCAATATGGGT
GAAAACACCTTTGAAGCTTGCCAATGGAACCAAATATAGACCTCCTGCAAAACTA
TTAAAGGAAAGGGGTTTCTTCGGAGCTATTGCTGGTTTCTTAGAGGGAGGATGGG
AAGGAATGATTGCAGGTTGGCACGGATACACATCTCATGGAGCACATGGAGTGGC
AGTGGCAGCAGACCTTAAGAGCACGCAAGAAGCCATAAACAAGATAACAAAAAAT
CTCAATTCTTTGAGTGAGCTAGAAGTAAAGAATCTTCAAAGACTAAGTGGTGCCA
TGGATGAACTCCACAACGAAATACTCGAGCTGGATGAGAAAGTGGATGATCTCAG
AGCTGACACAATAAGCTCGCAAATAGAGCTTGCAGTCTTGCTTTCCAACGAAGGA
ATAATAAACAGTGAAGATGAGCATCTATTGGCACTTGAGAGAAACTAAAGAAAA
TGCTGGGTCCCTCTGCTGTAGACATAGGGAATGGATGCTTCGAAACCAAACACAA
GTGCAACCAGACCTGCTTAGACAGGATAGCTGCTGGCACCTTTAATGCAGGAGAA
TTTTCTCTTCCCACTTTTGATTCACTGAATATTACTGCTGCATCTTTAAATGATG
ATGGATTGGATAATCATACTATACTGCTCTACTACTCAACTGCTGCTTCTAGTTT
GGCCGTAACATTGATGATAGCTATTTTATTGTTTATATGGTCTCCAGAGACAAT
GTTTCTTGCTCCATCTGTCTATAAGGAAAATTAAGCCCTGTATTTTCCTTTATTG
TAGTGCTTGTTTGCTTGTTACCATTACAAAGAACGTTATTGAAAAATGCTCTTG
TTACTACT5' (SEQ ID NO: 43)

FIG. 29

MKAIIVLLMVVTSNADRICTGITSSNSPHVVKTATQGEVNVTGVIPLTTTPTKSH
FANLKGTKTRGKLCPNCLNCTDLDVALGRPMCMGFIPSAKASILHEVRPVTSGCF
PIMHDRTKIRQLPNLLRGYE<u>K</u>I<u>Q</u>LST<u>K</u>NVINAE<u>H</u>APGGPYR<u>L</u>GTSKSCpyqgkss
FFATMAWAVP*kknsty*TNPLTVEVPYICTKGEDQITVWGFHSD*NDAAMQT*LYGDS
NPQKFTSSANGVTTHYVSQIGDFPNQTEDGGLPQSGRIVVDYMVQKPGKTGTIVY
QRGVLLPQKVWCASGRSKVIKGSLPLIGEADCLHEKYGGLNKSKPYYTGEHAKAI
GNCPIWVKTPLKLANGTKYRPPAKLLKERGFFGAIAGFLEGGWEGMIAGWHGYTS
HGAHGVAVAADLKSTQEAINKITKNLNSLSELEVKNLQRLSGAMDELHNEILELD
EKVDDLRADTISSQIELAVLLSNEGIINSEDEHLLALERKLKKMLGPSAVDIGNG
CFETKHKCNQTCLDRIAAGTFNAGEFSLPTFDSLNITAASLNDDGLDNHTILLYY
STAASSLAVTLMIAIFIVYMVSRDNVSCSICL (SEQ ID NO: 44)

FIG. 30

3' AGCAGAAGCAGAGCATTTTCTAATATCCACAAAATGAAGGCAATAATTGTACT
ACTCATGGTAGTAACATCCAACGCAGATCGAATCTGCACTGGGATAACATCTTCA
AACTCACCTCATGTGGTCAAAACAGCTACTCAAGGGGAAGTTAATGTGACTGGTG
TGATACCACTGACAACAACACCAACAAAATCTCATTTTGCAAATCTCAAAGGAAC
AAAGACCAGAGGGAAACTATGCCCAAACTGTCTCAACTGCACAGATCTGGATGTG
GCCTTGGGCAGACCAATGTGTATGGGGCACATACCTTCGGCAAAAGCTTCAATAC
TCCACGAAGTCAGACCTGTTACATCCGGGTGCTTTCCTATAATGCACGACAGAAC
AAAAATCAGACAGCTACCCAATCTTCTCAGAGGATATGAAAGGATCAGATTATCA
ACCTACAACGTTATCAACGCAGAAACCGCACCAGGAGGACCCTACAGACTTGGAA
CCTCAAAATCTTGCaatgcttcaacaggaggccaatctTTCTTCGCAACAATGGC
TTGGGCTGTCCCA*aaaaagaaagcagacacctat*ACGAATCCACTAACAGTAGAA
GTACCATACATTTGCACAAAAGGAGAAGACCAAATTACTGTTTGGGGGTTCCATT
CTGAT*GCAGATGCAAAATGCAAACA*CTCTATGGAGACTCAAATCCTCAAAAGTT
CACCTCATCTGCCAATGGAGTAACCACACATTATGTTTCTCAGATTGGTGACTTC
CCAAATCAAACAGAAGACGGAGGGCTACCACAAAGCGGCAGAATTGTTGTTGATT
ACATGGTGCAAAAACCTGGGAAAACAGGAACAATTGTCTATCAAAGAGGTGTTTT
GTTGCCTCAAAAGGTGTGGTGCGCAAGTGGCAGGAGCAAGGTAATAAAAGGGTCC
TTGCCTTTAATTGGTGAAGCAGATTGCCTTCACGAAAAATACGGTGGATTAAACA
AAAGCAAGCCTTACTACACAGGAGAACATGCAAAAGCCATAGGAAATTGCCCAAT
ATGGGTGAAAACACCTTTGAAGCTTGCCAATGGAACCAAATATAGACCTCCTGCA
AAACTATTAAAGGAAGGGGTTTCTTCGGAGCTATTGCTGGTTTCTTAGAGGGAG
GATGGGAAGGAATGATTGCAGGTTGGCACGGATACACATCTCATGGAGCACATGG
AGTGGCAGTGGCAGCAGACCTTAAGAGCACGCAAGAAGCCATAAACAAGATAACA
AAAAATCTCAATTCTTTGAGTGAGCTAGAAGTAAAGAATCTTCAAAGACTAAGTG
GTGCCATGGATGAACTCCACAACGAAATACTCGAGCTGGATGAGAAAGTGGATGA
TCTCAGAGCTGACACAATAAGCTCGCAAATAGAGCTTGCAGTCTTGCTTTCCAAC
GAAGGAATAATAAACAGTGAAGATGAGCATCTATTGGCACTTGAGAGAAAACTAA
AGAAAATGCTGGGTCCCTCTGCTGTAGACATAGGGAATGGATGCTTCGAAACCAA
ACACAAGTGCAACCAGACCTGCTTAGACAGGATAGCTGCTGGCACCTTTAATGCA
GGAGAATTTTCTCTTCCCACTTTTGATTCACTGAATATTACTGCTGCATCTTTAA
ATGATGATGGATTGGATAATCATACTATACTGCTCTACTACTCAACTGCTGCTTC
TAGTTTGGCCGTAACATTGATGATAGCTATTTTATTGTTTATATGGTCTCCAGA
GACAATGTTTCTTGCTCCATCTGTCTATAAGGAAAATTAAGCCCTGTATTTTCCT
TTATTGTAGTGCTTGTTTGCTTGTTACCATTACAAAGAAACGTTATTGAAAATG
CTCTTGTTACTACT5' (SEQ ID NO: 45)

FIG. 31

MKAIIVLLMVVTSNADRICTGITSSNSPHVVKTATQGEVNVTGVIPLTTTPTKSH
FANLKGTKTRGKLCPNCLNCTDLDVALGRPMCMGHIPSAKASILHEVRPVTSGCF
PIMHDRTKIRQLPNLLRGYERIRLSTYNVINAETAPGGPYRLGTSKSCnastggq
sFFATMAWAVP*kkkadty*TNPLTVEVPYICTKGEDQITVWGFHSD*ADAKMQT*LYG
DSNPQKFTSSANGVTTHYVSQIGDFPNQTEDGGLPQSGRIVVDYMVQKPGKTGTI
VYQRGVLLPQKVWCASGRSKVIKGSLPLIGEADCLHEKYGGLNKSKPYYTGEHAK
AIGNCPIWVKTPLKLANGTKYRPPAKLLKERGFFGAIAGFLEGGWEGMIAGWHGY
TSHGAHGVAVAADLKSTQEAINKITKNLNSLSELEVKNLQRLSGAMDELHNEILE
LDEKVDDLRADTISSQIELAVLLSNEGIINSEDEHLLALERKLKKMLGPSAVDIG
NGCFETKHKCNQTCLDRIAAGTFNAGEFSLPTFDSLNITAASLNDDGLDNHTILL
YYSTAASSLAVTLMIAIFIVYMVSRDNVSCSICL (SEQ ID NO: 46)

FIG. 32

3' agcagaagcagagcattttctaatatccacaaaATGAAGGCAATAATTGTACT
ACTCATGGTAGTAACATCCAACGCAGATCGAATCTGCACTGGGATAACATCTTCA
AACTCACCTCATGTGGTCAAAACAGCTACTCAAGGGGAAGTTAATGTGACTGGTG
TGATACCACTGACAACAACACCAACAAAATCTCATTTTGCAAATCTCAAAGGAAC
AAAGACCAGAGGGAAACTATGCCCAAACTGTCTCAACTGCACAGATCTGGATGTG
GCCTTGGGCAGACCAATGTGTATGGGGCTAATACCTTCGGCAAAAGCTTCAATAC
TCCACGAAGTCAGACCTGTTACATCCGGGTGCTTTCCTATAATGCACGACAGAAC
AAAAATCAGACAGCTACCCAATCTTCTCAGAGGATATGAAAAGATCGAATTATCA
ACCTCAAACGTTATCAACGCAGAAGTGGCACCAGGAGGACCCTACAGACTTGGAA
CCTCAGAATCTTGCcctttcggaagctccaattctTTCTTCGCAACAATGGCTTG
GGCTGTCCCA*catcaatcaggaacatat*ACGAATCCACTAACAGTAGAAGTACCA
TACATTTGCACAAAAGGAGAAGACCAAATTACTGTTTGGGGGTTCCATTCTGATA
CCACACTGAAAATGCACCAACTCTATGGAGACTCAAATCCTCAAAAGTTCACCTC
ATCTGCCAATGGAGTAACCACACATTATGTTTCTCAGATTGGTGACTTCCCAAAT
CAAACAGAAGACGAAGGGCTACCACAAAGCGGCAGAATTGTTGTTGATTACATGG
TGCAAAAACCTGGGAAAACAGGAACAATTGTCTATCAAAGAGGTGTTTTGTTGCC
TCAAAAGGTGTGGTGCGCAAGTGGCAGGAGCAAGGTAATAAAAGGGTCCTTGCCT
TTAATTGGTGAAGCAGATTGCCTTCACGAAAATACGGTGGATTAAACAAAAGCA
AGCCTTACTACACAGGAGAACATGCAAAAGCCATAGGAAATTGCCCAATATGGGT
GAAAACACCTTTGAAGCTTGCCAATGGAACCAAATATAGACCTCCTGCAAAACTA
TTAAAGGAAAGGGGTTTCTTCGGAGCTATTGCTGGTTTCTTAGAGGGAGGATGGG
AAGGAATGATTGCAGGTTGGCACGGATACACATCTCATGGAGCACATGGAGTGGC
AGTGGCAGCAGACCTTAAGAGCACGCAAGAAGCCATAAACAAGATAACAAAAAAT
CTCAATTCTTTGAGTGAGCTAGAAGTAAAGAATCTTCAAAGACTAAGTGGTGCCA
TGGATGAACTCCACAACGAAATACTCGAGCTGGATGAGAAGTGGATGATCTCAG
AGCTGACACAATAAGCTCGCAAATAGAGCTTGCAGTCTTGCTTTCCAACGAAGGA
ATAATAAACAGTGAAGATGAGCATCTATTGGCACTTGAGAGAAACTAAAGAAAA
TGCTGGGTCCCTCTGCTGTAGACATAGGGAATGGATGCTTCGAAACCAAACACAA
GTGCAACCAGACCTGCTTAGACAGGATAGCTGCTGGCACCTTTAATGCAGGAGAA
TTTTCTCTTCCCACTTTTGATTCACTGAATATTACTGCTGCATCTTTAAATGATG
ATGGATTGGATAATCATACTATACTGCTCTACTACTCAACTGCTGCTTCTAGTTT
GGCCGTAACATTGATGATAGCTATTTTATTGTTTATATGGTCTCCAGAGACAAT
GTTTCTTGCTCCATCTGTCTATAAGGAAAATTAAGCCCTGTATTTTCCTTTATTG
TAGTGCTTGTTTGCTTGTTACCATTACAAAGAACGTTATTGAAAATGCTCTTG
TTTACTACTAggaaaattaagccctgtatttcctttattgtagtgcttgtttgc
ttgttaccattacaaagaaacgttattgaaaaatgctcttgttactact 5'
(SEQ ID NO: 47)

FIG. 33

MKAIIVLLMVVTSNADRICTGITSSNSPHVVKTATQGEVNVTGVIPLTTTPTKSH
FANLKGTKTRGKLCPNCLNCTDLDVALGRPMCMGLIPSAKASILHEVRPVTSGCF
PIMHDRTKIRQLPNLLRGYEKIELSTSNVINAEVAPGGPYRLGTSESCpfgssns
FFATMAWAVP*hqsgty*TNPLTVEVPYICTKGEDQITVWGFHSD*TTLKMHQ*LYGDS
NPQKFTSSANGVTTHYVSQIGDFPNQTEDEGLPQSGRIVVDYMVQKPGKTGTIVY
QRGVLLPQKVWCASGRSKVIKGSLPLIGEADCLHEKYGGLNKSKPYYTGEHAKAI
GNCPIWVKTPLKLANGTKYRPPAKLLKERGFFGAIAGFLEGGWEGMIAGWHGYTS
HGAHGVAVAADLKSTQEAINKITKNLNSLSELEVKNLQRLSGAMDELHNEILELD
EKVDDLRADTISSQIELAVLLSNEGIINSEDEHLLALERKLKKMLGPSAVDIGNG
CFETKHKCNQTCLDRIAAGTFNAGEFSLPTFDSLNITAASLNDDGLDNHTILLYY
STAASSLAVTLMIAIFIVYMVSRDNVSCSICL (SEQ ID NO: 48)

FIG. 34

3' agcagaagcagagcattttctaatatccacaaaATGAAGGCAATAATTGTACT
ACTCATGGTAGTAACATCCAACGCAGATCGAATCTGCACTGGGATAACATCTTCA
AACTCACCTCATGTGGTCAAAACAGCTACTCAAGGGGAAGTTAATGTGACTGGTG
TGATACCACTGACAACAACACCAACAAAATCTCATTTTGCAAATCTCAAAGGAAC
AAAGACCAGAGGGAAACTATGCCCAAACTGTCTCAACTGCACAGATCTGGATGTG
GCCTTGGGCAGACCAATGTGTATGGGGAACATACCTTCGGCAAAAGCTTCAATAC
TCCACGAAGTCAGACCTGTTACATCCGGGTGCTTTCCTATAATGCACGACAGAAC
AAAAATCAGACAGCTACCCAATCTTCTCAGAGGATATGAAAGAATCGAGTTATCA
ACCCATAACGTTATCAACGCAGAAGTGGCACCAGGAGGACCCTACAGACTTGGAA
CCTCAAAATCTTGCccagataaaggagccagcagcTTCTTCGCAACAATGGCTTG
GGCTGTCCCA*aagagaggaaatcagtat*ACGAATCCACTAACAGTAGAAGTACCA
TACATTTGCACAAAAGGAGAAGACCAAATTACTGTTTGGGGGTTCCATTCTGAT*G*
*TTTCCACAAACATGGCGAAA*CTCTATGGAGACTCAAATCCTCAAAAGTTCACCTC
ATCTGCCAATGGAGTAACCACACATTATGTTTCTCAGATTGGTGACTTCCCAAAT
CAAACAGAAGACGGAGGGCTACCACAAAGCGGCAGAATTGTTGTTGATTACATGG
TGCAAAAACCTGGGAAAACAGGAACAATTGTCTATCAAAGAGGTGTTTTGTTGCC
TCAAAAGGTGTGGTGCGCAAGTGGCAGGAGCAAGGTAATAAAAGGGTCCTTGCCT
TTAATTGGTGAAGCAGATTGCCTTCACGAAAATACGGTGGATTAAACAAAAGCA
AGCCTTACTACACAGGAGAACATGCAAAAGCCATAGGAAATTGCCCAATATGGGT
GAAAACACCTTTGAAGCTTGCCAATGGAACCAAATATAGACCTCCTGCAAAACTA
TTAAAGGAAAGGGGTTTCTTCGGAGCTATTGCTGGTTTCTTAGAGGGAGGATGGG
AAGGAATGATTGCAGGTTGGCACGGATACACATCTCATGGAGCACATGGAGTGGC
AGTGGCAGCAGACCTTAAGAGCACGCAAGAAGCCATAAACAAGATAACAAAAAAT
CTCAATTCTTTGAGTGAGCTAGAAGTAAAGAATCTTCAAAGACTAAGTGGTGCCA
TGGATGAACTCCACAACGAAATACTCGAGCTGGATGAGAAAGTGGATGATCTCAG
AGCTGACACAATAAGCTCGCAAATAGAGCTTGCAGTCTTGCTTTCCAACGAAGGA
ATAATAAACAGTGAAGATGAGCATCTATTGGCACTTGAGAGAAAACTAAAGAAAA
TGCTGGGTCCCTCTGCTGTAGACATAGGGAATGGATGCTTCGAAACCAAACACAA
GTGCAACCAGACCTGCTTAGACAGGATAGCTGCTGGCACCTTTAATGCAGGAGAA
TTTTCTCTTCCCACTTTTGATTCACTGAATATTACTGCTGCATCTTTAAATGATG
ATGGATTGGATAATCATACTATACTGCTCTACTACTCAACTGCTGCTTCTAGTTT
GGCCGTAACATTGATGATAGCTATTTTTATTGTTTATATGGTCTCCAGAGACAAT
GTTTCTTGCTCCATCTGTCTATAAGgaaattaagccctgtattttcctttattg
tagtgcttgtttgcttgttaccattacaaagaaacgttattgaaaaatgctcttg
tt5' (SEQ ID NO: 49)

FIG. 35

MKAIIVLLMVVTSNADRICTGITSSNSPHVVKTATQGEVNVTGVIPLTTTPTKSH
FANLKGTKTRGKLCPNCLNCTDLDVALGRPMCMGNIPSAKASILHEVRPVTSGCF
PIMHDRTKIRQLPNLLRGYERIELSTHNVINAEVAPGGPYRLGTSKSCpdkgass
FFATMAWAVP*krgnqy*TNPLTVEVPYICTKGEDQITVWGFHSD*VSTNMAK*LYGDS
NPQKFTSSANGVTTHYVSQIGDFPNQTEDGGLPQSGRIVVDYMVQKPGKTGTIVY
QRGVLLPQKVWCASGRSKVIKGSLPLIGEADCLHEKYGGLNKSKPYYTGEHAKAI
GNCPIWVKTPLKLANGTKYRPPAKLLKERGFFGAIAGFLEGGWEGMIAGWHGYTS
HGAHGVAVAADLKSTQEAINKITKNLNSLSELEVKNLQRLSGAMDELHNEILELD
EKVDDLRADTISSQIELAVLLSNEGIINSEDEHLLALERKLKKMLGPSAVDIGNG
CFETKHKCNQTCLDRIAAGTFNAGEFSLPTFDSLNITAASLNDDGLDNHTILLYY
STAASSLAVTLMIAIFIVYMVSRDNVSCSICL (SEQ ID NO: 50)

FIG. 36

```
AGCAAAAGCAGGGGAAAATTTCAACAAACTGATACAAGAGAAATGGACATCCCAG
TAGTCGCATTCTTGATATTAACCAGTACATGCGTACAGGCTGATAGGATATGTGT
TGGGTACTTAAGCACCAACTCATCAGAAAAGGTTGACACACTGTTAGAAAACGAT
GTTCCGGTTACAAGCTCTGTTGATCTGGTTGAGACTAACCACACAGGAACATATT
GTTCTTTGGGTGGAATCAGTCCGGTGCACCTGGGAGACTGTAGCTTCGAGGGCTG
GATTGTAGGGAACCCTGCCTGTGCCAGCAACCTGGGGATCAGAGAATGGTCATAC
TTGATTGAAGATCCTTCTGCTCCTCATGGATTGTGCTACCCAGGGGAGTTAGACA
ACAATGGAGAATTGAGGCACTTGTTCAGTGGAATCAGATCTTTCAGTAGAACAGA
GTTGATTGCACCTACTTCTTGGGGGCAGTGAATGATGGAGTATCGTCGGCCTGT
CCAGATAAAGGAGCCAGCAGCTTTTACCGGAACTTGGTATGGTTTGTGAAGAGAG
GAAATCAGTATCCTGTAATCCGCGGGACCTACAACAACACTACTGGCAGAGATGT
TTTGGTTATATGGGGTATACATCACCCTGTTTCCACAGACGAAGCGAAACAACTA
TATGTCAATAACAACCCATACACGTTGGTATCTACCAGTTCATGGAGTAGGAAAT
ACAACTTAGAGACTGGAACCCGGCCTGGATACAATGGCCAAAAGAGTTGGATGAA
GATTTACTGGTATTTGATGCACCCAGGGGAGTCAATCAGTTTCGAAAGCAATGGA
GGATTATTGGCACCCAGATATGGTTATATTATTGAGGAATATGGAAAAGGGCGAA
TTTTCCAAAGCCGCATTCGAATTGCTAAATGCAATACTAAGTGCCAAACATCTGT
CGGTGGGATAAATACCAACAAAACATTTCAAAACATAGAGAGAAATGCACTTGGG
GATTGCCCGAAATACATAAATCTGGACAGCTCAAGTTAGCCACCGGACTTAGGA
ATGTACCTGCCATATCAAACAGAGGGTTGTTCGGGGCTATTGCAGGCTTCATAGA
AGGTGGTTGGCCAGGATTAATAAATGGTTGGTATGGATTCCAACATCAGAACGAA
CAAGGAGTGGGCATGGCTGCAGACAAAGAGTCAACACAAAAGGCTATTGATCAAA
TAACAACCAAGATAAACAATATCATTGAAAAATGAATGGGAATTATGACTCCAT
ACGAGGTGAATTCAATCAGGTGGAACAAAGAATAAATATGCTTGCAGACAGAATA
GATGATGCTGTAACTGATGTATGGTCATACAATGCAAAGCTTCTTGTGTTACTAG
AGAACGATAAAACTCTAGACATGCATGATGCTAATGTTAGAAACCTGCATGATCA
AGTCCGTAGAGCACTAAAGACCAATGCAATTGATGAGGGAAATGGATGTTTCGAA
CTCCTCCATAAATGCAATGACTCTTGCATGGAGACAATAAGAAATGGAACGTACA
ATCATACAGAATATGAGGAAGAATCCAAATTAAAGAGACAGGAAATAGAAGGAAT
AAAGCTGAAGTCAGACGATAGTGTTTATAAAGCACTATCGATTTACAGCTGCATT
GCAAGCAGTATTGTATTGGTAGGACTCATACTTACATTCATCATGTGGGCATGCA
GCAGTGGCAATTGCCGGTTCAATATTTGTATATAAGTAGAAAAAACACCCTTGTT
CTACT (SEQ ID NO: 71)
```

FIG. 41A

MDIPVVAFLILTSTCVQADRICVGYLSTNSSEKVDTLLENDVPVTSSVDLVETNH
TGTYCSLGGISPVHLGDCSFEGWIVGNPACASNLGIREWSYLIEDPSAPHGLCYP
GELDNNGELRHLFSGIRSFSRTELIAPTSWGAVNDGVSSACPDKGASSFYRNLVW
FVKRGNQYPVIRGTYNNTTGRDVLVIWGIHHPVSTDEAKQLYVNNNPYTLVSTSS
WSRKYNLETGTRPGYNGQKSWMKIYWYLMHPGESISFESNGGLLAPRYGYIEEY
GKGRIFQSRIRIAKCNTKCQTSVGGINTNKTFQNIERNALGDCPKYIKSGQLKLA
TGLRNVPAISNRGLFGAIAGFIEGGWPGLINGWYGFQHQNEQGVGMAADKESTQK
AIDQITTKINNIIEKMNGNYDSIRGEFNQVEQRINMLADRIDDAVTDVWSYNAKL
LVLLENDKTLDMHDANVRNLHDQVRRALKTNAIDEGNGCFELLHKCNDSCMETIR
NGTYNHTEYEEESKLKRQEIEGIKLKSDDSVYKALSIYSCIASSIVLVGLILTFI
MWACSSGNCRFNICI (SEQ ID NO: 72)

FIG. 41B

SEQUENCE LISTING

<160> NUMBER OF SEQ ID NOS: 95

<210> SEQ ID NO 1
<211> LENGTH: 22
<212> TYPE: PRT
<213> ORGANISM: Artificial Sequence
<220> FEATURE:
<223> OTHER INFORMATION: B/Yamagata/16/88 120 loop

<400> SEQUENCE: 1

Asn Ile Arg Leu Ser Thr His Asn Val Ile Asn Ala Glu Arg Ala Pro
1               5                   10                  15

Gly Gly Pro Tyr Arg Leu
            20

<210> SEQ ID NO 2
<211> LENGTH: 22
<212> TYPE: PRT
<213> ORGANISM: Artificial Sequence
<220> FEATURE:
<223> OTHER INFORMATION: Exemplary B/Yamagata/16/88 120 loop substituted
      with amino acids from A/Vietnam/1203/04

<400> SEQUENCE: 2

Lys Ile Gln Leu Ser Thr Lys Asn Val Ile Asn Ala Glu His Ala Pro
1               5                   10                  15

Gly Gly Pro Tyr Arg Leu
            20

<210> SEQ ID NO 3
<211> LENGTH: 7
<212> TYPE: PRT
<213> ORGANISM: Artificial Sequence
<220> FEATURE:
<223> OTHER INFORMATION: B/Yamagata/16/88 150 loop

<400> SEQUENCE: 3

Asn Val Thr Ser Arg Asn Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Exemplary B/Yamagata/16/88 150 loop substituted
      with amino acids from A/Vietnam/1203/04

<400> SEQUENCE: 4

Tyr Gln Gly Lys Ser Ser
1               5

<210> SEQ ID NO 5
<211> LENGTH: 6
<212> TYPE: PRT
<213> ORGANISM: Artificial Sequence
<220> FEATURE:
<223> OTHER INFORMATION: B/Yamagata/16/88 160 loop

<400> SEQUENCE: 5

Arg Asp Asn Lys Thr Ala
1               5

<210> SEQ ID NO 6
<211> LENGTH: 6
<212> TYPE: PRT

```
<213> ORGANISM: Artificial Sequence
<220> FEATURE:
<223> OTHER INFORMATION: Exemplary B/Yamagata/16/88 160 loop substituted
      with amino acids from A/Vietnam/1203/04

<400> SEQUENCE: 6

Lys Lys Asn Ser Thr Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: B/Yamagata/16/88 190 helix

<400> SEQUENCE: 7

Asn Lys Asn Gln Met Lys Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/Vietnam/1203/04

<400> SEQUENCE: 8

Asn Asp Ala Ala Met Gln Thr
1               5

<210> SEQ ID NO 9
<211> LENGTH: 15
<212> TYPE: PRT
<213> ORGANISM: Artificial Sequence
<220> FEATURE:
<223> OTHER INFORMATION: B/Hong Kong/8/73 HA signal peptide

<400> SEQUENCE: 9

Met Lys Ala Ile Ile Val Leu Leu Met Val Val Thr Ser Asn Ala
1               5                   10                  15

<210> SEQ ID NO 10
<211> LENGTH: 344
<212> TYPE: PRT
<213> ORGANISM: Artificial Sequence
<220> FEATURE:
<223> OTHER INFORMATION: B/Hong Kong/8/73 HA HA1 polypeptide (no signal
      peptide)

<400> SEQUENCE: 10

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
                20                  25                  30

Thr Thr Thr Pro Thr Lys Ser His Phe Ala Asn Leu Lys Gly Thr Gln
            35                  40                  45

Thr Arg Gly Lys Leu Cys Pro Asn Cys Leu Asn Cys Thr Asp Leu Asp
        50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys Phe Pro
                85                  90                  95
```

```
Ile Met His Asp Arg Thr Lys Ile Arg Gln Leu Pro Asn Leu Leu Arg
            100                 105                 110

Gly Tyr Glu Asn Ile Arg Leu Ser Ala Arg Asn Val Thr Asn Ala Glu
        115                 120                 125

Thr Ala Pro Gly Gly Pro Tyr Ile Val Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Lys Thr Ala Thr Asn Pro Leu Thr Val Glu Val Pro Tyr
                165                 170                 175

Ile Cys Thr Lys Gly Glu Asp Gln Ile Thr Val Trp Gly Phe His Ser
            180                 185                 190

Asp Asp Glu Thr Gln Met Val Lys Leu Tyr Gly Asp Ser Lys Pro Gln
        195                 200                 205

Lys Phe Thr Ser Ser Ala Asn Gly Val Thr Thr His Tyr Val Ser Gln
    210                 215                 220

Ile Gly Gly Phe Pro Asn Gln Ala Glu Asp Glu Gly Leu Pro Gln Ser
225                 230                 235                 240

Gly Arg Ile Val Val Asp Tyr Met Val Gln Lys Pro Gly Lys Thr Gly
                245                 250                 255

Thr Ile Ala Tyr Gln Arg Gly Val Leu Leu Pro Gln Lys Val Trp Cys
            260                 265                 270

Ala Ser Gly Arg Ser Lys Val Ile Lys Gly Ser Leu Pro Leu Ile Gly
        275                 280                 285

Glu Ala Asp Cys Leu His Glu Lys Tyr Gly Gly Leu Asn Lys Ser Lys
    290                 295                 300

Pro Tyr Tyr Thr Gly Glu His Ala Lys Ala Ile Gly Asn Cys Pro Ile
305                 310                 315                 320

Trp Val Lys Thr Pro Leu Lys Leu Ala Asn Gly Thr Lys Tyr Arg Pro
                325                 330                 335

Pro Ala Lys Leu Leu Lys Glu Arg
            340
```

<210> SEQ ID NO 11
<211> LENGTH: 223
<212> TYPE: PRT
<213> ORGANISM: Artificial Sequence
<220> FEATURE:
<223> OTHER INFORMATION: B/Hong Kong/8/73 HA HA2 polypeptide (no stop
      codon)

<400> SEQUENCE: 11

```
Gly Phe Phe Gly Ala Ile Ala Gly Phe Leu Glu Gly Gly Trp Glu Gly
1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110
```

-continued

```
Glu His Leu Leu Ala Leu Glu Arg Lys Leu Lys Lys Met Leu Gly Pro
            115                 120                 125

Ser Ala Val Asp Ile Gly Asn Gly Cys Phe Glu Thr Lys His Lys Cys
        130                 135                 140

Asn Gln Thr Cys Leu Asp Arg Ile Ala Ala Gly Thr Phe Asn Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Ile Ala Ile Phe Ile
        195                 200                 205

Val Tyr Met Val Ser Arg Asp Asn Val Ser Cys Ser Ile Cys Leu
    210                 215                 220
```

<210> SEQ ID NO 12
<211> LENGTH: 530
<212> TYPE: PRT
<213> ORGANISM: Artificial Sequence
<220> FEATURE:
<223> OTHER INFORMATION: B/Hong Kong/8/73 HA

```
                245                 250                 255

Thr Ile Ala Tyr Gln Arg Gly Val Leu Leu Pro Gln Lys Val Trp Cys
            260                 265                 270

Ala Ser Gly Arg Ser Lys Val Ile Lys Gly Ser Leu Pro Leu Ile Gly
        275                 280                 285

Glu Ala Asp Cys Leu His Glu Lys Tyr Gly Gly Leu Asn Lys Ser Lys
    290                 295                 300

Pro Tyr Tyr Thr Gly Glu His Ala Lys Ala Ile Gly Asn Cys Pro Ile
305                 310                 315                 320

Trp Val Lys Thr Pro Leu Lys Leu Ala Asn Gly Thr Lys Tyr Arg Pro
                325                 330                 335

Pro Ala Lys Leu Leu Lys Glu Arg Gly Phe Phe Gly Ala Ile Ala Gly
            340                 345                 350

Phe Leu Glu Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr
    530

<210> SEQ ID NO 13
<211> LENGTH: 27
<212> TYPE: PRT
<213> ORGANISM: Artificial Sequence
<220> FEATURE:
<223> OTHER INFORMATION: B/Hong Kong/8/73 HA Transmembrane domain

<400> SEQUENCE: 13

Ile Leu Leu Tyr Tyr Ser Thr Ala Ala Ser Ser Leu Ala Val Thr Leu
1               5                   10                  15

Met Ile Ala Ile Phe Ile Val Tyr Met Val Ser
            20                  25

<210> SEQ ID NO 14
<211> LENGTH: 10
<212> TYPE: PRT
<213> ORGANISM: Artificial Sequence
<220> FEATURE:
<223> OTHER INFORMATION: B/Hong Kong/8/73 HA Cytoplasmic domain (no stop
``` codon)

<400> SEQUENCE: 14

Arg Asp Asn Val Ser Cys Ser Ile Cys Leu
1               5                   10

<210> SEQ ID NO 15
<211> LENGTH: 42
<212> TYPE: PRT
<213> ORGANISM: Artificial Sequence
<220> FEATURE:
<223> OTHER INFORMATION: B/Hong Kong/8/73 HA Stem domain (encompasses
      alanines at interface; no signal peptide or stop codon) Piece 1:

<400> SEQUENCE: 15

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala
            35                  40

<210> SEQ ID NO 16
<211> LENGTH: 241
<212> TYPE: PRT
<213> ORGANISM: Artificial Sequence
<220> FEATURE:
<223> OTHER INFORMATION: B/Hong Kong/8/73 HA Stem domain (encompasses
      alanines at interface; no signal peptide or stop codon) Piece 2:

<400> SEQUENCE: 16

Ala Asp Cys Leu His Glu Lys Tyr Gly Gly Leu Asn Lys Ser Lys Pro
1               5                   10                  15

Tyr Tyr Thr Gly Glu His Ala Lys Ala Ile Gly Asn Cys Pro Ile Trp
            20                  25                  30

Val Lys Thr Pro Leu Lys Leu Ala Asn Gly Thr Lys Tyr Arg Pro Pro
            35                  40                  45

Ala Lys Leu Leu Lys Glu Arg Gly Phe Phe Gly Ala Ile Ala Gly Phe
        50                  55                  60

Leu Glu Gly Gly Trp Glu Gly Met Ile Ala Gly Trp His Gly Tyr Thr
65                  70                  75                  80

Ser His Gly Ala His Gly Val Ala Val Ala Ala Asp Leu Lys Ser Thr
                85                  90                  95

Gln Glu Ala Ile Asn Lys Ile Thr Lys Asn Leu Asn Ser Leu Ser Glu
            100                 105                 110

Leu Glu Val Lys Asn Leu Gln Arg Leu Ser Gly Ala Met Asp Glu Leu
        115                 120                 125

His Asn Glu Ile Leu Glu Leu Asp Glu Lys Val Asp Asp Leu Arg Ala
    130                 135                 140

Asp Thr Ile Ser Ser Gln Ile Glu Leu Ala Val Leu Leu Ser Asn Glu
145                 150                 155                 160

Gly Ile Ile Asn Ser Glu Asp Glu His Leu Leu Ala Leu Glu Arg Lys
                165                 170                 175

Leu Lys Lys Met Leu Gly Pro Ser Ala Val Asp Ile Gly Asn Gly Cys
            180                 185                 190

Phe Glu Thr Lys His Lys Cys Asn Gln Thr Cys Leu Asp Arg Ile Ala
        195                 200                 205

Ala Gly Thr Phe Asn Ala Gly Glu Phe Ser Leu Pro Thr Phe Asp Ser
    210                 215                 220

```
Leu Asn Ile Thr Ala Ala Ser Leu Asn Asp Asp Gly Leu Asp Asn His
225                 230                 235                 240

Thr

<210> SEQ ID NO 17
<211> LENGTH: 247
<212> TYPE: PRT
<213> ORGANISM: Artificial Sequence
<220> FEATURE:
<223> OTHER INFORMATION: B/Hong Kong/8/73 HA Globular head domain
      (not including alanines)

<400> SEQUENCE: 17

Asn Leu Lys Gly Thr Gln Thr Arg Gly Lys Leu Cys Pro Asn Cys Leu
1               5                   10                  15

Asn Cys Thr Asp Leu Asp Val Ala Leu Gly Arg Pro Lys Cys Met Gly
            20                  25                  30

Thr Ile Pro Ser Ala Lys Ala Ser Ile Leu His Glu Val Lys Pro Val
        35                  40                  45

Thr Ser Gly Cys Phe Pro Ile Met His Asp Arg Thr Lys Ile Arg Gln
    50                  55                  60

Leu Pro Asn Leu Leu Arg Gly Tyr Glu Asn Ile Arg Leu Ser Ala Arg
65                  70                  75                  80

Asn Val Thr Asn Ala Glu Thr Ala Pro Gly Gly Pro Tyr Ile Val Gly
                85                  90                  95

Thr Ser Gly Ser Cys Pro Asn Val Thr Asn Gly Asn Gly Phe Phe Ala
            100                 105                 110

Thr Met Ala Trp Ala Val Pro Lys Asn Lys Thr Ala Thr Asn Pro Leu
        115                 120                 125

Thr Val Glu Val Pro Tyr Ile Cys Thr Lys Gly Glu Asp Gln Ile Thr
    130                 135                 140

Val Trp Gly Phe His Ser Asp Asp Glu Thr Gln Met Val Lys Leu Tyr
145                 150                 155                 160

Gly Asp Ser Lys Pro Gln Lys Phe Thr Ser Ser Ala Asn Gly Val Thr
                165                 170                 175

Thr His Tyr Val Ser Gln Ile Gly Gly Phe Pro Asn Gln Ala Glu Asp
            180                 185                 190

Glu Gly Leu Pro Gln Ser Gly Arg Ile Val Val Asp Tyr Met Val Gln
        195                 200                 205

Lys Pro Gly Lys Thr Gly Thr Ile Ala Tyr Gln Arg Gly Val Leu Leu
    210                 215                 220

Pro Gln Lys Val Trp Cys Ala Ser Gly Arg Ser Lys Val Ile Lys Gly
225                 230                 235                 240

Ser Leu Pro Leu Ile Gly Glu
                245

<210> SEQ ID NO 18
<211> LENGTH: 8
<212> TYPE: PRT
<213> ORGANISM: Artificial Sequence
<220> FEATURE:
<223> OTHER INFORMATION: influenza B/Yamagata/16/88 virus HA 150 loop
      (including N terminal P)

<400> SEQUENCE: 18

Pro Asn Val Thr Ser Arg Asn Gly
1               5
```

<210> SEQ ID NO 19
<211> LENGTH: 7
<212> TYPE: PRT
<213> ORGANISM: Artificial Sequence
<220> FEATURE:
<223> OTHER INFORMATION: Sequence from influenza A/Vietnam/1203/04(HALo) virus globular head domain (including N terminal P)

<400> SEQUENCE: 19

Pro Tyr Gln Gly Lys Ser Ser
1               5

<210> SEQ ID NO 20
<211> LENGTH: 1862
<212> TYPE: DNA
<213> ORGANISM: Artificial Sequence
<220> FEATURE:
<223> OTHER INFORMATION: Nucleic acid sequence encoding H5-4 loop chimeric HA for rescue in PR8

<400> SEQUENCE: 20

```
ccgaagttgg gggggagcaa aagcagggga aaataaaaac aaccaaaatg aaggcaaacc      60
tactggtcct gttaagtgca cttgcagctg cagatgcaga tcgaatctgc actgggataa     120
catcttcaaa ctcacctcat gtggtcaaaa cagctactca aggggaagtt aatgtgactg     180
gtgtgatacc actgacaaca cactccaacaa aatctcattt tgcaaatctc aaaggaacaa     240
agaccagagg gaaactatgc ccaaactgtc tcaactgcac agatctggat gtggccttgg     300
gcagaccaat gtgtatgggg ttcatacctt cggcaaaagc ttcaatactc cacgaagtca     360
gacctgttac atccgggtgc tttcctataa tgcacgacag aacaaaaatc agacagctac     420
ccaatcttct cagaggatat gaaaaaatcc agttatcaac caaaaacgtt atcaacgcag     480
aacatgcacc aggaggaccc tacagacttg gaacctcaga atcttgccca taccaaggaaa     540 agtcctcctt cttcgcaaca atggcttggg ctgtcccaaa aaagaacagt acatacacga     600
atccactaac agtagaagta ccatacattt gcacaaaagg agaagaccaa attactgttt     660
gggggttcca ttctgataat gatgcggcaa tgcagacact ctatgagac tcaaatcctc     720 aaaagttcac ctcatctgcc aatggagtaa ccacacatta tgtttctcag attggtgact     780
tcccaaatca aacagaagac ggagggctac cacaaagcgg cagaattgtt gttgattaca     840
tggtgcaaaa acctggaaaa acaggaacaa ttgtctatca aagaggtgtt ttgttgcctc     900
aaaaggtgtg gtgcgcaagt ggcaggagca aggtaataaa agggtccttg cctttaattg     960
gtgaagcaga ttgccttcac gaaaaatacg gtggattaaa caaaagcaag ccttactaca    1020
caggagaaca tgcaaaagcc ataggaaatt gcccaatatg ggtgaaaaca cctttgaagc    1080
ttgccaatgg aaccaaatat agacctcctg caaaactatt aaaggaaagg gtttcttcg    1140 gagctattgc tggttttctta gagggaggat gggaaggaat gattgcaggt tggcacggat    1200
acacatctca tggagcacat ggagtggcag tggcagcaga ccttaagagc acgcaagaag    1260
ccataaacaa gataacaaaa aatctcaatt ctttgagtga gctagaagta aagaatcttc    1320
aaagactaag tggtgccatg gatgaactcc acaacgaaat actcgagctg gatgagaaag    1380
tggatgatct cagagctgac acaataagct cgcaaataga gcttgcagtc ttgctttcca    1440
acgaaggaat aataaacagt gaagatgagc atctattggc acttgagaga aaactaaaga    1500
aaatgctggg tccctctgct gtagacatag ggaatggatg cttcgaaacc aaacacaagt    1560
gcaaccagac ctgcttagac aggatagctg ctggcaccttt taatgcagga gaattttctc    1620
```

```
ttcccactttt tgattcactg aatattactg ctgcatcttt aaatgatgat ggattggata    1680
attatcagat tctggcgatc tactcaactg tcgccagttc actggtgctt ttggtctccc    1740
tgggggcaat cagtttctgg atgtgttcta atggatcttt gcagtgcaga atatgcatct    1800
gagattagaa tttcagaaat atgaggaaaa acacccttgt ttctactaat aacccggcgg    1860
cc                                                                  1862
```

<210> SEQ ID NO 21
<211> LENGTH: 584
<212> TYPE: PRT
<213> ORGANISM: Artificial Sequence
<220> FEATURE:
<223> OTHER INFORMATION: Amino acid sequence of H5-4 loop chimeric HA
      for rescue in PR8

<400> SEQUENCE: 21

```
Met Lys Ala Asn Leu Leu Val Leu Leu Ser Ala Leu Ala Ala Ala Asp
1               5                   10                  15

Ala Asp Arg Ile Cys Thr Gly Ile Thr Ser Ser Asn Ser Pro His Val
            20                  25                  30

Val Lys Thr Ala Thr Gln Gly Glu Val Asn Val Thr Gly Val Ile Pro
        35                  40                  45

Leu Thr Thr Thr Pro Thr Lys Ser His Phe Ala Asn Leu Lys Gly Thr
    50                  55                  60

Lys Thr Arg Gly Lys Leu Cys Pro Asn Cys Leu Asn Cys Thr Asp Leu
65                  70                  75                  80

Asp Val Ala Leu Gly Arg Pro Met Cys Met Gly Phe Ile Pro Ser Ala
                85                  90                  95

Lys Ala Ser Ile Leu His Glu Val Arg Pro Val Thr Ser Gly Cys Phe
            100                 105                 110

Pro Ile Met His Asp Arg Thr Lys Ile Arg Gln Leu Pro Asn Leu Leu
        115                 120                 125

Arg Gly Tyr Glu Lys Ile Gln Leu Ser Thr Lys Asn Val Ile Asn Ala
    130                 135                 140

Glu His Ala Pro Gly Gly Pro Tyr Arg Leu Gly Thr Ser Glu Ser Cys
145                 150                 155                 160

Pro Tyr Gln Gly Lys Ser Ser Phe Phe Ala Thr Met Ala Trp Ala Val
                165                 170                 175

Pro Lys Lys Asn Ser Thr Tyr Thr Asn Pro Leu Thr Val Glu Val Pro
            180                 185                 190

Tyr Ile Cys Thr Lys Gly Glu Asp Gln Ile Thr Val Trp Gly Phe His
        195                 200                 205

Ser Asp Asn Asp Ala Ala Met Gln Thr Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asn Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
```

-continued

```
305                 310                 315                 320
Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn Tyr Gln Ile Leu Ala Ile Tyr Ser Thr Val Ala Ser Ser Leu Val
545                 550                 555                 560

Leu Leu Val Ser Leu Gly Ala Ile Ser Phe Trp Met Cys Ser Asn Gly
                565                 570                 575

Ser Leu Gln Cys Arg Ile Cys Ile
            580
```

<210> SEQ ID NO 22
<211> LENGTH: 1868
<212> TYPE: DNA
<213> ORGANISM: Artificial Sequence
<220> FEATURE:
<223> OTHER INFORMATION: Nucleic acid sequence encoding H8-4 loop chimeric HA for rescue in PR8

<400> SEQUENCE: 22

```
ccgaagttgg gggggagcaa aagcagggga aaataaaaac aaccaaaatg aaggcaaacc     60
tactggtcct gttaagtgca cttgcagctg cagatgcaga tcgaatctgc actgggataa    120
catcttcaaa ctcacctcat gtggtcaaaa cagctactca aggggaagtt aatgtgactg    180
gtgtgatacc actgacaaca acaccaacaa aatctcattt tgcaaatctc aaaggaacaa    240
agaccagagg gaaactatgc ccaaactgtc tcaactgcac agatctggat gtggccttgg    300
gcagaccaat gtgtatgggg cacatacctt cggcaaaagc ttcaatactc cacgaagtca    360
gacctgttac atccgggtgc tttcctataa tgcacgacag aacaaaaatc agacagctac    420
ccaatcttct cagaggatat gaaaggatca gattatcaac ctacaacgtt atcaacgcag    480
```

```
aaaccgcacc aggaggaccc tacagacttg gaacctcaaa atcttgcaat gcttcaacag    540
gaggccaatc tttcttcgca acaatggctt gggctgtccc aaaaaagaaa cccgacacct    600
atacgaatcc actaacagta gaagtaccat acatttgcac aaaaggagaa gaccaaatta    660
ctgtttgggg gttccattct gatccggatg caaaaatgca acactctat  ggagactcaa    720 atcctcaaaa gttcacctca tctgccaatg gagtaaccac acattatgtt tctcagattg    780
gtgacttccc aaatcaaaca gaagacggag ggctaccaca agcggcaga  attgttgttg    840 attacatggt gcaaaaacct gggaaaacag gaacaattgt ctatcaaaga ggtgttttgt    900
tgcctcaaaa ggtgtggtgc gcaagtggca ggagcaaggt aataaaaggg tccttgcctt    960
taattggtga agcagattgc cttcacgaaa atacggtgg  attaaacaaa agcaagcctt   1020
actacacagg agaacatgca aaagcctag  gaaattgccc aatatgggtg aaaacaccctt  1080 tgaagcttgc caatggaacc aaatatagac ctcctgcaaa actattaaag gaaggggtt   1140 tcttcggagc tattgctggt ttcttagagg gaggatggga aggaatgatt gcaggttggc   1200
acggatacac atctcatgga gcacatggag tggcagtggc agcagacctt aagagcacgc   1260
aagaagccat aaacaagata acaaaaaatc tcaattcttt gagtgagcta aagtaaaga    1320 atcttcaaag actaagtggt gccatggatg aactccacaa cgaaatactc gagctggatg   1380
agaaagtgga tgatctcaga gctgacacaa taagctcgca aatagagctt gcagtcttgc   1440
tttccaacga aggaataata aacagtgaag atgagcatct attggcactt gagagaaaac   1500
taaagaaaat gctgggtccc tctgctgtag acatagggaa tggatgcttc gaaaccaaac   1560
acaagtgcaa ccagacctgc ttagacagga tagctgctgg caccttttaat gcaggagaat  1620 tttctcttcc cactttttgat tcactgaata ttactgctgc atctttaaat gatgatggat   1680
tggataatta tcagattctg gcgatctact caactgtcgc cagttcactg gtgcttttgg   1740
tctccctggg ggcaatcagt ttctggatgt gttctaatgg atctttgcag tgcagaatat   1800
gcatctgaga ttagaatttc agaaatatga ggaaaaacac ccttgtttct actaataacc   1860
cggcggcc                                                            1868
```

<210> SEQ ID NO 23
<211> LENGTH: 586
<212> TYPE: PRT
<213> ORGANISM: Artificial Sequence
<220> FEATURE:
<223> OTHER INFORMATION: Amino acid sequence of H8-4 loop chimeric HA for rescue in PR8

<400> SEQUENCE: 23

Met Lys Ala Asn Leu Leu Val Leu Leu Ser Ala Leu Ala Ala Ala Asp
1               5                   10                  15

Ala Asp Arg Ile Cys Thr Gly Ile Thr Ser Ser Asn Ser Pro His Val
                20                  25                  30

Val Lys Thr Ala Thr Gln Gly Glu Val Asn Val Thr Gly Val Ile Pro
            35                  40                  45

Leu Thr Thr Thr Pro Thr Lys Ser His Phe Ala Asn Leu Lys Gly Thr
        50                  55                  60

Lys Thr Arg Gly Lys Leu Cys Pro Asn Cys Leu Asn Cys Thr Asp Leu
65                  70                  75                  80

Asp Val Ala Leu Gly Arg Pro Met Cys Met Gly His Ile Pro Ser Ala
                85                  90                  95

Lys Ala Ser Ile Leu His Glu Val Arg Pro Val Thr Ser Gly Cys Phe

```
                100                 105                 110
Pro Ile Met His Asp Arg Thr Lys Ile Arg Gln Leu Pro Asn Leu Leu
            115                 120                 125
Arg Gly Tyr Glu Arg Ile Arg Leu Ser Thr Tyr Asn Val Ile Asn Ala
            130                 135                 140
Glu Thr Ala Pro Gly Pro Tyr Arg Leu Gly Thr Ser Lys Ser Cys
145                 150                 155                 160
Asn Ala Ser Thr Gly Gly Gln Ser Phe Phe Ala Thr Met Ala Trp Ala
                165                 170                 175
Val Pro Lys Lys Pro Asp Thr Tyr Thr Asn Pro Leu Thr Val Glu
            180                 185                 190
Val Pro Tyr Ile Cys Thr Lys Gly Glu Asp Gln Ile Thr Val Trp Gly
            195                 200                 205
Phe His Ser Asp Pro Asp Ala Lys Met Gln Thr Leu Tyr Gly Asp Ser
    210                 215                 220
Asn Pro Gln Lys Phe Thr Ser Ser Ala Asn Gly Val Thr Thr His Tyr
225                 230                 235                 240
Val Ser Gln Ile Gly Asp Phe Pro Asn Gln Thr Glu Asp Gly Gly Leu
                245                 250                 255
Pro Gln Ser Gly Arg Ile Val Val Asp Tyr Met Val Gln Lys Pro Gly
                260                 265                 270
Lys Thr Gly Thr Ile Val Tyr Gln Arg Gly Val Leu Leu Pro Gln Lys
            275                 280                 285
Val Trp Cys Ala Ser Gly Arg Ser Lys Val Ile Lys Gly Ser Leu Pro
            290                 295                 300
Leu Ile Gly Glu Ala Asp Cys Leu His Glu Lys Tyr Gly Gly Leu Asn
305                 310                 315                 320
Lys Ser Lys Pro Tyr Tyr Thr Gly Glu His Ala Lys Ala Ile Gly Asn
                325                 330                 335
Cys Pro Ile Trp Val Lys Thr Pro Leu Lys Leu Ala Asn Gly Thr Lys
            340                 345                 350
Tyr Arg Pro Pro Ala Lys Leu Leu Lys Glu Arg Gly Phe Phe Gly Ala
            355                 360                 365
Ile Ala Gly Phe Leu Glu Gly Gly Trp Glu Gly Met Ile Ala Gly Trp
            370                 375                 380
His Gly Tyr Thr Ser His Gly Ala His Gly Val Ala Val Ala Ala Asp
385                 390                 395                 400
Leu Lys Ser Thr Gln Glu Ala Ile Asn Lys Ile Thr Lys Asn Leu Asn
                405                 410                 415
Ser Leu Ser Glu Leu Glu Val Lys Asn Leu Gln Arg Leu Ser Gly Ala
            420                 425                 430
Met Asp Glu Leu His Asn Glu Ile Leu Glu Leu Asp Glu Lys Val Asp
            435                 440                 445
Asp Leu Arg Ala Asp Thr Ile Ser Ser Gln Ile Glu Leu Ala Val Leu
            450                 455                 460
Leu Ser Asn Glu Gly Ile Ile Asn Ser Glu Asp Glu His Leu Leu Ala
465                 470                 475                 480
Leu Glu Arg Lys Leu Lys Lys Met Leu Gly Pro Ser Ala Val Asp Ile
                485                 490                 495
Gly Asn Gly Cys Phe Glu Thr Lys His Lys Cys Asn Gln Thr Cys Leu
                500                 505                 510
Asp Arg Ile Ala Ala Gly Thr Phe Asn Ala Gly Glu Phe Ser Leu Pro
            515                 520                 525
```

```
Thr Phe Asp Ser Leu Asn Ile Thr Ala Ala Ser Leu Asn Asp Asp Gly
        530                 535                 540

Leu Asp Asn Tyr Gln Ile Leu Ala Ile Tyr Ser Thr Val Ala Ser Ser
545                 550                 555                 560

Leu Val Leu Leu Val Ser Leu Gly Ala Ile Ser Phe Trp Met Cys Ser
                565                 570                 575

Asn Gly Ser Leu Gln Cys Arg Ile Cys Ile
            580                 585

<210> SEQ ID NO 24
<211> LENGTH: 1862
<212> TYPE: DNA
<213> ORGANISM: Artificial Sequence
<220> FEATURE:
<223> OTHER INFORMATION: Nucleic acid sequence encoding H11-4 loop
      chimeric HA for rescue in PR8

<400> SEQUENCE: 24
```

| | | | | | |
|---|---|---|---|---|---|
| ccgaagttgg | gggggagcaa | agcagggga | aataaaaac | aaccaaaatg | aaggcaaacc | 60 |
| tactggtcct | gttaagtgca | cttgcagctg | cagatgcaga | tcgaatctgc | actgggataa | 120 |
| catcttcaaa | ctcacctcat | gtggtcaaaa | cagctactca | aggggaagtt | aatgtgactg | 180 |
| gtgtgatacc | actgacaaca | acaccaacaa | aatctcattt | tgcaaatctc | aaaggaacaa | 240 |
| agaccagagg | gaaactatgc | ccaaactgtc | tcaactgcac | agatctggat | gtggccttgg | 300 |
| gcagaccaat | gtgtatgggg | ctaataccct | cggcaaaagc | ttcaatactc | cacgaagtca | 360 |
| gacctgttac | atccgggtgc | tttcctataa | tgcacgacag | aacaaaaatc | agacagctac | 420 |
| ccaatcttct | cagaggatat | gaaaagatcg | aattatcaac | ctcaaacgtt | atcaacgcag | 480 |
| aagtggcacc | aggaggaccc | tacagacttg | aacctcaaa | atcttgcaaa | ttcggaagct | 540 |
| ccaattcttt | cttcgcaaca | atggcttggg | ctgtcccaca | tcaatcagga | acatatacga | 600 |
| atccactaac | agtagaagta | ccatacattt | gcacaaaagg | agaagaccaa | attactgttt | 660 |
| gggggttcca | ttctgatgcc | acactgaaaa | tgcaccaact | ctatggagac | tcaaatcctc | 720 |
| aaaagttcac | ctcatctgcc | aatggagtaa | ccacacatta | tgtttctcag | attggtgact | 780 |
| tcccaaatca | aacagaagac | ggagggctac | acaaagcgg | cagaattgtt | gttgattaca | 840 |
| tggtgcaaaa | acctgggaaa | acaggaacaa | ttgtctatca | aagaggtgtt | ttgttgcctc | 900 |
| aaaaggtgtg | gtgcgcaagt | ggcaggagca | aggtaataaa | agggtccttg | cctttaattg | 960 |
| gtgaagcaga | ttgccttcac | gaaaaatacg | gtggattaaa | caaaagcaag | ccttactaca | 1020 |
| caggagaaca | tgcaaaagcc | ataggaaatt | gcccaatatg | ggtgaaaaca | cctttgaagc | 1080 |
| ttgccaatgg | aaccaaatat | agacctcctg | caaaactatt | aaaggaaagg | ggtttcttcg | 1140 |
| gagctattgc | tggtttctta | gagggaggat | gggaaggaat | gattgcaggt | tggcacggat | 1200 |
| acacatctca | tggagcacat | ggagtggcag | tggcagcaga | ccttaagagc | acgcaagaag | 1260 |
| ccataaacaa | gataacaaaa | aatctcaatt | ctttgagtga | gctagaagta | aagaatcttc | 1320 |
| aaagactaag | tggtgccatg | gatgaactcc | acaacgaaat | actcgagctg | gatgagaaag | 1380 |
| tggatgatct | cagagctgac | acaataagct | cgcaaataga | gcttgcagtc | ttgctttcca | 1440 |
| acgaaggaat | aataaacagt | gaagatgagc | atctattggc | acttgagaga | aaactaaaga | 1500 |
| aaatgctggg | tccctctgct | gtagacatag | ggaatggatg | cttcgaaacc | aaacacaagt | 1560 |
| gcaaccagac | ctgcttagac | aggatagctg | ctggcacctt | taatgcagga | gaattttctc | 1620 |
| ttcccacttt | tgattcactg | aatattactg | ctgcatcttt | aaatgatgat | ggattggata | 1680 |

```
attatcagat tctggcgatc tactcaactg tcgccagttc actggtgctt ttggtctccc   1740 tggggggcaat cagtttctgg atgtgttcta atggatcttt gcagtgcaga atatgcatct   1800
gagattagaa tttcagaaat atgaggaaaa acacccttgt ttctactaat aacccggcgg   1860
cc                                                                  1862
```

<210> SEQ ID NO 25
<211> LENGTH: 584
<212> TYPE: PRT
<213> ORGANISM: Artificial Sequence
<220> FEATURE:
<223> OTHER INFORMATION: Amino acid sequence of H11-4 loop chimeric HA
      for rescue in PR8

<400> SEQUENCE: 25

```
Met Lys Ala Asn Leu Leu Val Leu Leu Ser Ala Leu Ala Ala Ala Asp
1               5                   10                  15

Ala Asp Arg Ile Cys Thr Gly Ile Thr Ser Ser Asn Ser Pro His Val
                20                  25                  30

Val Lys Thr Ala Thr Gln Gly Glu Val Asn Val Thr Gly Val Ile Pro
            35                  40                  45

Leu Thr Thr Thr Pro Thr Lys Ser His Phe Ala Asn Leu Lys Gly Thr
        50                  55                  60

Lys Thr Arg Gly Lys Leu Cys Pro Asn Cys Leu Asn Cys Thr Asp Leu
65                  70                  75                  80

Asp Val Ala Leu Gly Arg Pro Met Cys Met Gly Leu Ile Pro Ser Ala
                85                  90                  95

Lys Ala Ser Ile Leu His Glu Val Arg Pro Val Thr Ser Gly Cys Phe
                100                 105                 110

Pro Ile Met His Asp Arg Thr Lys Ile Arg Gln Leu Pro Asn Leu Leu
            115                 120                 125

Arg Gly Tyr Glu Lys Ile Glu Leu Ser Thr Ser Asn Val Ile Asn Ala
        130                 135                 140

Glu Val Ala Pro Gly Gly Pro Tyr Arg Leu Gly Thr Ser Lys Ser Cys
145                 150                 155                 160

Lys Phe Gly Ser Ser Asn Ser Phe Phe Ala Thr Met Ala Trp Ala Val
                165                 170                 175

Pro His Gln Ser Gly Thr Tyr Thr Asn Pro Leu Thr Val Glu Val Pro
            180                 185                 190

Tyr Ile Cys Thr Lys Gly Glu Asp Gln Ile Thr Val Trp Gly Phe His
        195                 200                 205

Ser Asp Ala Thr Leu Lys Met His Gln Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Asp Phe Pro Asn Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320
```

```
Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn Tyr Gln Ile Leu Ala Ile Tyr Ser Thr Val Ala Ser Ser Leu Val
545                 550                 555                 560

Leu Leu Val Ser Leu Gly Ala Ile Ser Phe Trp Met Cys Ser Asn Gly
                565                 570                 575

Ser Leu Gln Cys Arg Ile Cys Ile
            580
```

<210> SEQ ID NO 26
<211> LENGTH: 1865
<212> TYPE: DNA
<213> ORGANISM: Artificial Sequence
<220> FEATURE:
<223> OTHER INFORMATION: Nucleic acid sequence encoding H12-4 loop chimeric HA for rescue in PR8

<400> SEQUENCE: 26

```
ccgaagttgg gggggagcaa aagcagggga aaataaaaac aaccaaaatg aaggcaaacc     60
tactggtcct gttaagtgca cttgcagctg cagatgcaga tcgaatctgc actgggataa    120
catcttcaaa ctcacctcat gtggtcaaaa cagctactca aggggaagtt aatgtgactg    180
gtgtgatacc actgacaaca acaccaacaa aatctcattt tgcaaatctc aaaggaacaa    240
agaccagagg gaaactatgc ccaaactgtc tcaactgcac agatctggat gtggccttgg    300
gcagaccaat gtgtatgggg tatatacctt cggcaaaagc ttcaatactc cacgaagtca    360
gacctgttac atccgggtgc tttcctataa tgcacgacag aacaaaaatc agacagctac    420
ccaatcttct cagaggatat gaaagaatca agttatcaac cttcaacgtt atcaacgcag    480
```

-continued

```
aaacggcacc aggaggaccc tacagacttg aacctcaaa atcttgcaac aatacatcaa      540
accaaggctc attcttcgca acaatggctt gggctgtccc attaaaatca ggacaattca      600
cgaatccact aacagtagaa gtaccataca tttgcacaaa aggagaagac caaattactg      660
tttgggggtt ccattctgat ccaacatctg atatgcagat actctatgga gactcaaatc      720
ctcaaaagtt cacctcatct gccaatggag taaccacaca ttatgtttct cagattggtg      780
acttcccaaa tcaaacagaa gacggagggc taccacaaag cggcagaatt gttgttgatt      840
acatggtgca aaaacctggg aaaacaggaa caattgtcta tcaagaggt gttttgttgc      900 ctcaaaaggt gtggtgcgca agtggcagga gcaaggtaat aaaagggtcc ttgcctttaa      960
ttggtgaagc agattgcctt cacgaaaaat acggtggatt aaacaaaagc aagccttact     1020
acacaggaga acatgcaaaa gccataggaa attgcccaat atgggtgaaa acacctttga     1080
agcttgccaa tggaaccaaa tatagacctc ctgcaaaact attaaaggaa aggggtttct     1140
tcggagctat tgctggtttc ttagagggag gatgggaagg aatgattgca ggttggcacg     1200
gatacacatc tcatggagca catggagtgg cagtggcagc agaccttaag agcacgcaag     1260
aagccataaa caagataaca aaaaatctca attctttgag tgagctagaa gtaaagaatc     1320
ttcaaagact aagtggtgcc atggatgaac tccacaacga aatactcgag ctggatgaga     1380
aagtggatga tctcagagct gacacaataa gctcgcaaat agagcttgca gtcttgcttt     1440
ccaacgaagg aataataaac agtgaagatg agcatctatt ggcacttgag agaaaactaa     1500
agaaaatgct gggtccctct gctgtagaca tagggaatgg atgcttcgaa accaaacaca     1560
agtgcaacca gacctgctta gacaggatag ctgctggcac cttaatgca ggagaatttt     1620 ctcttcccac ttttgattca ctgaatatta ctgctgcatc tttaaatgat gatggattgg     1680
ataattatca gattctggcg atctactcaa ctgtcgccag ttcactggtg cttttggtct     1740
ccctgggggc aatcagtttc tggatgtgtt ctaatggatc tttgcagtgc agaatatgca     1800
tctgagatta gaattcaga aatatgagga aaaacaccct tgtttctact aataacccgg     1860
cggcc                                                                 1865
```

<210> SEQ ID NO 27
<211> LENGTH: 585
<212> TYPE: PRT
<213> ORGANISM: Artificial Sequence
<220> FEATURE:
<223> OTHER INFORMATION: Amino acid sequence of H12-4 loop chimeric HA for rescue in PR8

<400> SEQUENCE: 27

```
Met Lys Ala Asn Leu Leu Val Leu Leu Ser Ala Leu Ala Ala Ala Asp
1               5                   10                  15

Ala Asp Arg Ile Cys Thr Gly Ile Thr Ser Ser Asn Ser Pro His Val
            20                  25                  30

Val Lys Thr Ala Thr Gln Gly Glu Val Asn Val Thr Gly Val Ile Pro
        35                  40                  45

Leu Thr Thr Thr Pro Thr Lys Ser His Phe Ala Asn Leu Lys Gly Thr
    50                  55                  60

Lys Thr Arg Gly Lys Leu Cys Pro Asn Cys Leu Asn Cys Thr Asp Leu
65                  70                  75                  80

Asp Val Ala Leu Gly Arg Pro Met Cys Met Gly Tyr Ile Pro Ser Ala
                85                  90                  95

Lys Ala Ser Ile Leu His Glu Val Arg Pro Val Thr Ser Gly Cys Phe
            100                 105                 110
```

```
Pro Ile Met His Asp Arg Thr Lys Ile Arg Gln Leu Pro Asn Leu Leu
            115                 120                 125

Arg Gly Tyr Glu Arg Ile Lys Leu Ser Thr Phe Asn Val Ile Asn Ala
130                 135                 140

Glu Thr Ala Pro Gly Pro Tyr Arg Leu Gly Thr Ser Lys Ser Cys
145                 150                 155                 160

Asn Asn Thr Ser Asn Gln Gly Ser Phe Phe Ala Thr Met Ala Trp Ala
                165                 170                 175

Val Pro Leu Lys Ser Gly Gln Phe Thr Asn Pro Leu Thr Val Glu Val
            180                 185                 190

Pro Tyr Ile Cys Thr Lys Gly Asp Gln Ile Thr Val Trp Gly Phe
195                 200                 205

His Ser Asp Pro Thr Ser Asp Met Gln Ile Leu Tyr Gly Asp Ser Asn
    210                 215                 220

Pro Gln Lys Phe Thr Ser Ser Ala Asn Gly Val Thr Thr His Tyr Val
225                 230                 235                 240

Ser Gln Ile Gly Asp Phe Pro Asn Gln Thr Glu Asp Gly Gly Leu Pro
                245                 250                 255

Gln Ser Gly Arg Ile Val Val Asp Tyr Met Val Gln Lys Pro Gly Lys
            260                 265                 270

Thr Gly Thr Ile Val Tyr Gln Arg Gly Val Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Asp Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
            515                 520                 525
```

```
Phe Asp Ser Leu Asn Ile Thr Ala Ala Ser Leu Asn Asp Asp Gly Leu
        530                 535                 540

Asp Asn Tyr Gln Ile Leu Ala Ile Tyr Ser Thr Val Ala Ser Ser Leu
545                 550                 555                 560

Val Leu Leu Val Ser Leu Gly Ala Ile Ser Phe Trp Met Cys Ser Asn
                565                 570                 575

Gly Ser Leu Gln Cys Arg Ile Cys Ile
            580                 585

<210> SEQ ID NO 28
<211> LENGTH: 582
<212> TYPE: PRT
<213> ORGANISM: Artificial Sequence
<220> FEATURE:
<223> OTHER INFORMATION: Influenza B/Hong Kong/8/73 virus HA

<400> SEQUENCE: 28

Met Lys Ala Ile Ile Val Leu Leu Met Val Val Thr Ser Asn Ala Asp
1               5

```
Ala Asp Cys Leu His Glu Lys Tyr Gly Gly Leu Asn Lys Ser Lys Pro
305                 310                 315                 320

Tyr Tyr Thr Gly Glu His Ala Lys Ala Ile Gly Asn Cys Pro Ile Trp
            325                 330                 335

Val Lys Thr Pro Leu Lys Leu Ala Asn Gly Thr Lys Tyr Arg Pro Pro
            340                 345                 350

Ala Lys Leu Leu Lys Glu Arg Gly Phe Phe Gly Ala Ile Ala Gly Phe
        355                 360                 365

Leu Glu Gly Gly Trp Glu Gly Met Ile Ala Gly Trp His Gly Tyr Thr
        370                 375                 380

Ser His Gly Ala His Gly Val Ala Val Ala Ala Asp Leu Lys Ser Thr
385                 390                 395                 400

Gln Glu Ala Ile Asn Lys Ile Thr Lys Asn Leu Asn Ser Leu Ser Glu
                405                 410                 415

Leu Glu Val Lys Asn Leu Gln Arg Leu Ser Gly Ala Met Asp Glu Leu
            420                 425                 430

His Asn Glu Ile Leu Glu Leu Asp Glu Lys Val Asp Asp Leu Arg Ala
                435                 440                 445

Asp Thr Ile Ser Ser Gln Ile Glu Leu Ala Val Leu Leu Ser Asn Glu
    450                 455                 460

Gly Ile Ile Asn Ser Glu Asp Glu His Leu Leu Ala Leu Glu Arg Lys
465                 470                 475                 480

Leu Lys Lys Met Leu Gly Pro Ser Ala Val Asp Ile Gly Asn Gly Cys
                485                 490                 495

Phe Glu Thr Lys His Lys Cys Asn Gln Thr Cys Leu Asp Arg Ile Ala
            500                 505                 510

Ala Gly Thr Phe Asn Ala Gly Glu Phe Ser Leu Pro Thr Phe Asp Ser
        515                 520                 525

Leu Asn Ile Thr Ala Ala Ser Leu Asn Asp Asp Gly Leu Asp Asn His
        530                 535                 540

Thr Ile Leu Leu Tyr Tyr Ser Thr Ala Ala Ser Ser Leu Ala Val Thr
545                 550                 555                 560

Leu Met Ile Ala Ile Phe Ile Val Tyr Met Val Ser Arg Asp Asn Val
                565                 570                 575

Ser Cys Ser Ile Cys Leu
            580

<210> SEQ ID NO 29
<211> LENGTH: 565
<212> TYPE: PRT
<213> ORGANISM: Artificial Sequence
<220> FEATURE:
<223> OTHER INFORMATION: Influenza A/Puerto Rico/8/34 virus HA

<400> SEQUENCE: 29

Met

```
Asn Pro Glu Cys Asp Pro Leu Leu Pro Val Arg Ser Trp Ser Tyr Ile
                85                  90                  95
Val Glu Thr Pro Asn Ser Glu Asn Gly Ile Cys Tyr Pro Gly Asp Phe
            100                 105                 110
Ile Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Asn His Asn
    130                 135                 140
Thr Asn Gly Val Thr Ala Ala Cys Ser His Glu Gly Lys Ser Ser Phe
145                 150                 155                 160
Tyr Arg Asn Leu Leu Trp Leu Thr Glu Lys Glu Gly Ser Tyr Pro Lys
                165                 170                 175
Leu Lys Asn Ser Tyr Val Asn Lys Lys Gly Lys Glu Val Leu Val Leu
            180                 185                 190
Trp Gly Ile His His Pro Pro Asn Ser Lys Glu Gln Gln Asn Ile Tyr
        195                 200                 205
Gln Asn Glu Asn Ala Tyr Val Ser Val Val Thr Ser Asn Tyr Asn Arg
    210                 215                 220
Arg Phe Thr Pro Glu Ile Ala Glu Arg Pro Lys Val Arg Asp Gln Ala
225                 230                 235                 240
Gly Arg Met Asn Tyr Tyr Trp Thr Leu Leu Lys Pro Gly Asp Thr Ile
                245                 250                 255
Ile Phe Glu Ala Asn Gly Asn Leu Ile Ala Pro Met Tyr Ala Phe Ala
            260                 265                 270
Leu Ser Arg Gly Phe Gly Ser Gly Ile Ile Thr Ser Asn Ala Ser Met
        275                 280                 285
His Glu Cys Asn Thr Lys Cys Gln Thr Pro Leu Gly Ala Ile Asn Ser
    290                 295                 300
Ser Leu Pro Tyr Gln Asn Ile His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Thr Pro Ser Ile Gln Ser Arg Gly Leu Phe Gly Ala Ile Ala Gly Phe
            340                 345                 350
Ile Glu Gly Gly Trp Thr Gly Met Ile Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Thr Val Ile Glu
385                 390                 395                 400
Lys Met Asn Ile Gln Phe Thr Ala Val Gly Lys Glu Phe Asn Lys Leu
                405                 410                 415
Glu Lys Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asp Asn Glu Cys Met Glu Ser Val Arg
                485                 490                 495
Asn Gly Thr Tyr Asp Tyr Pro Lys Tyr Ser Glu Glu Ser Lys Leu Asn
```

```
                    500                 505                 510
Arg Glu Lys Val Asp Gly Val Lys Leu Glu Ser Met Gly Ile Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 30
<211> LENGTH: 583
<212> TYPE: PRT
<213> ORGANISM: Artificial Sequence
<220> FEATURE:
<223> OTHER INFORMATION: Influenza B/Yamagata/16/88 virus HA

<400> SEQUENCE: 30

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Thr Ile Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr His Asn Val Ile Asn Ala Glu Arg
    130                 135                 140

Ala Pro Gly Gly Pro Tyr Arg Leu Gly Thr Ser Glu Ser Cys Pro Asn
145                 150                 155                 160

Val Thr Ser Arg Asn Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
        195                 200                 205

Asp Asn Lys Asn Gln Met Lys Asn Leu Tyr Gly Asp Ser Asn Pro Gln
    210                 215                 220

Lys Phe Thr Ser Ser Ala Asn Gly Val Thr Thr His Tyr Val Ser Gln
225                 230                 235                 240

Ile Gly Asp Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
        275                 280                 285

Ala Ser Gly Arg Ser Lys Val Ile Lys Gly Ser Leu Pro Leu Ile Gly
```

```
                290                 295                 300
Glu Ala Asp Cys Leu His Glu Lys Tyr Gly Gly Leu Asn Lys Ser Lys
305                 310                 315                 320
Pro Tyr Tyr Thr Gly Glu His Ala Lys Ala Ile Gly Asn Cys Pro Ile
            325                 330                 335
Trp Val Lys Thr Pro Leu Lys Leu Ala Asn Gly Thr Lys Tyr Arg Pro
                340                 345                 350
Pro Ala Lys Leu Leu Lys Glu Arg Gly Phe Phe Gly Ala Ile Ala Gly
            355                 360                 365
Phe Leu Glu Gly Gly Trp Glu Gly Met Ile Ala Gly Trp His Gly Tyr
370                 375                 380
Thr Ser His Gly Ala His Gly Val Ala Val Ala Ala Asp Leu Lys Ser
385                 390                 395                 400
Thr Gln Glu Ala Ile Asn Lys Ile Thr Lys Asn Leu Asn Ser Leu Ser
                405                 410                 415
Glu Leu Glu Val Lys Asn Leu Gln Arg Leu Ser Gly Ala Met Asp Glu
            420                 425                 430
Leu His Asn Glu Ile Leu Glu Leu Asp Glu Lys Val Asp Asp Leu Arg
        435                 440                 445
Ala Asp Thr Ile Ser Ser Gln Ile Glu Leu Ala Val Leu Leu Ser Asn
    450                 455                 460
Glu Gly Ile Ile Asn Ser Glu Asp Glu His Leu Leu Ala Leu Glu Arg
465                 470                 475                 480
Lys Leu Lys Lys Met Leu Gly Pro Ser Ala Val Asp Ile Gly Asn Gly
                485                 490                 495
Cys Phe Glu Thr Lys His Lys Cys Asn Gln Thr Cys Leu Asp Arg Ile
            500                 505                 510
Ala Ala Gly Thr Phe Asn Ala Gly Glu Phe Ser Leu Pro Thr Phe Asp
            515                 520                 525
Ser Leu Asn Ile Thr Ala Ala Ser Leu Asn Asp Asp Gly Leu Asp Asn
530                 535                 540
His Thr Ile Leu Leu Tyr Tyr Ser Thr Ala Ala Ser Ser Leu Ala Val
545                 550                 555                 560
Thr Leu Met Ile Ala Ile Phe Ile Val Tyr Met Val Ser Arg Asp Asn
                565                 570                 575
Val Ser Cys Ser Ile Cys Leu
            580

<210> SEQ ID NO 31
<211> LENGTH: 1742
<212> TYPE: DNA
<213> ORGANISM: Artificial Sequence
<220> FEATURE:
<223> OTHER INFORMATION: Nucleic acid sequence encoding influenza
      A/mallard/Sweden/24/2002 virus HA

<400> SEQUENCE: 31
gcaaaagcag gggtcacaat ggagaagttc atcataatgg caatgctctt ggtgagcaca    60
aatgcatatg ataggatatg cattggatac caatcaaaca actccactga cacagtaaac   120
acactcatag agcaaaatgt gccagtcacc cagacaatgg aactagtgga aaccgagaaa   180
catcctgcct attgcaatac tgatttgggt gctccactag agttgcgtga ttgcaagatt   240
gaggcggtga tctatgggaa cccaaaatgt gacatccact tgaaagacca aggttggtca   300
tacatagtgg agagacccag tgcaccagag gggatgtgct accctggatc agtggagaat   360
```

-continued

```
ctcgaagagt tgaggtttgt tttctccagt gctgcttcct acaaaaggat aagattgttt    420
gattactcca gatggaatgt taccagatct gggacaagca aggcatgcaa tgcttcaaca    480
ggaggccaat ctttctatcg gagcatcaat tggctaacta aaaagaaacc cgacacctat    540
gacttcaatg aggggactta tatcaataat gaagatgggg acataatttt cttatggggg    600
attcatcacc caccggatgc aaaagagcaa acaacactgt acaagaatgc aaatactttg    660
agtagtgtta ctaccaacac tataaacagg agcttccaac ccaatatcgg gcccaggcca    720
ctggtgagag ggcaacaagg gcggatggac tattattggg gcattttgaa gaggggagaa    780
actttaaaaa ttagaaccaa tgggaacctg atcgcgcctg aattcggtta tctgctcaaa    840
ggggagagcc atggcagaat aattcaaaat gaggacatac caattgggag ttgtcacacg    900
aaatgtcaga catacgcagg agcaattaat agcagcaaac cctttcagaa trcaagcagg    960
cactacatgg gagaatgtcc caagtatgtg aagaaggaaa gcttacggct ggcagttgga   1020
cttagaaaca ctccttctat tgaacccaga ggcttgtttg gagccattgc tggttttatt   1080
gaagggggat ggtctgggat gattgatgga tggtatgggt ttcaccatag taattcagaa   1140
ggaacaggaa tggcggccga tcagaaatcg acacaagaag caattgacaa aatcaccaat   1200
aaggtcaata atatagttga taaaatgaac agggaatttg aagtagtgaa ccatgagttt   1260
tccgaagtcg aaaaaagaat aaacatgata aatgacaaaa ttgatgacca gattgaagat   1320
ctttgggcct acaatgcaga gcttctggtc ctcctagaga accagaaaac actggatgaa   1380
cacgactcca atgtcaaaaa tctctttgat gaagtaagaa ggagactttc agccaatgca   1440
atagatactg ggaatggctg cttcgacata ctccacaaat gtgacaacga gtgcatggag   1500
accataaaga atgggactta taaccataaa gagtatgagg aagaggccaa gctggaaagg   1560
agcaagatta acggagtaaa gctagaggaa aataccacct ataaaattct cagcatttac   1620
agtacggtgg cggccagtct ttgcttggca atcctgattg ctggaggtct aatcctgggc   1680
atgcaaaatg gatcttgtag atgcatgttc tgtatttaag aaaaaacacc cttgtttcta   1740
ct                                                                  1742

<210> SEQ ID NO 32
<211> LENGTH: 566
<212> TYPE: PRT
<213> ORGANISM: Artificial Sequence
<220> FEATURE:
<223> OTHER INFORMATION: Amino acid sequence of influenza
      A/mallard/Sweden/24/2002 virus HA
<220> FEATURE:
<221> NAME/KEY: misc_feature
<222> LOCATION: (312)..(312)
<223> OTHER INFORMATION: Xaa can be any naturally occurring amino acid
<400> SEQUENCE: 32

Met Glu Lys Phe Ile Ile Met Ala Met Leu Leu Val Ser Thr Asn Ala
1               5                   10                  15

Tyr Asp Arg Ile Cys Ile Gly Tyr Gln Ser Asn Asn Ser Thr Asp Thr
            20                  25                  30

Val Asn Thr Leu Ile Glu Gln Asn Val Pro Val Thr Gln Thr Met Glu
        35                  40                  45

Leu Val Glu Thr Glu Lys His Pro Ala Tyr Cys Asn Thr Asp Leu Gly
    50                  55                  60

Ala Pro Leu Glu Leu Arg Asp Cys Lys Ile Glu Ala Val Ile Tyr Gly
65                  70                  75                  80

Asn Pro Lys Cys Asp Ile His Leu Lys Asp Gln Gly Trp Ser Tyr Ile
```

```
                    85                  90                  95
Val Glu Arg Pro Ser Ala Pro Glu Gly Met Cys Tyr Pro Gly Ser Val
                100                 105                 110
Glu Asn Leu Glu Glu Leu Arg Phe Val Phe Ser Ser Ala Ala Ser Tyr
                115                 120                 125
Lys Arg Ile Arg Leu Phe Asp Tyr Ser Arg Trp Asn Val Thr Arg Ser
130                 135                 140
Gly Thr Ser Lys Ala Cys Asn Ala Ser Thr Gly Gly Gln Ser Phe Tyr
145                 150                 155                 160
Arg Ser Ile Asn Trp Leu Thr Lys Lys Pro Asp Thr Tyr Asp Phe
                165                 170                 175
Asn Glu Gly Thr Tyr Ile Asn Asn Glu Asp Gly Asp Ile Ile Phe Leu
                180                 185                 190
Trp Gly Ile His His Pro Pro Asp Ala Lys Glu Gln Thr Thr Leu Tyr
                195                 200                 205
Lys Asn Ala Asn Thr Leu Ser Ser Val Thr Thr Asn Thr Ile Asn Arg
                210                 215                 220
Ser Phe Gln Pro Asn Ile Gly Pro Arg Pro Leu Val Arg Gly Gln Gln
225                 230                 235                 240
Gly Arg Met Asp Tyr Tyr Trp Gly Ile Leu Lys Arg Gly Glu Thr Leu
                245                 250                 255
Lys Ile Arg Thr Asn Gly Asn Leu Ile Ala Pro Glu Phe Gly Tyr Leu
                260                 265                 270
Leu Lys Gly Glu Ser His Gly Arg Ile Ile Gln Asn Glu Asp Ile Pro
                275                 280                 285
Ile Gly Ser Cys His Thr Lys Cys Gln Thr Tyr Ala Gly Ala Ile Asn
                290                 295                 300
Ser Ser Lys Pro Phe Gln Asn Xaa Ser Arg His Tyr Met Gly Glu Cys
305                 310                 315                 320
Pro Lys Tyr Val Lys Lys Glu Ser Leu Arg Leu Ala Val Gly Leu Arg
                325                 330                 335
Asn Thr Pro Ser Ile Glu Pro Arg Gly Leu Phe Gly Ala Ile Ala Gly
                340                 345                 350
Phe Ile Glu Gly Gly Trp Ser Gly Met Ile Asp Gly Trp Tyr Gly Phe
                355                 360                 365
His His Ser Asn Ser Glu Gly Thr Gly Met Ala Ala Asp Gln Lys Ser
                370                 375                 380
Thr Gln Glu Ala Ile Asp Lys Ile Thr Asn Lys Val Asn Asn Ile Val
385                 390                 395                 400
Asp Lys Met Asn Arg Glu Phe Glu Val Val Asn His Glu Phe Ser Glu
                405                 410                 415
Val Glu Lys Arg Ile Asn Met Ile Asn Asp Lys Ile Asp Gln Ile
                420                 425                 430
Glu Asp Leu Trp Ala Tyr Asn Ala Glu Leu Leu Val Leu Leu Glu Asn
                435                 440                 445
Gln Lys Thr Leu Asp Glu His Asp Ser Asn Val Lys Asn Leu Phe Asp
450                 455                 460
Glu Val Arg Arg Leu Ser Ala Asn Ala Ile Asp Thr Gly Asn Gly
465                 470                 475                 480
Cys Phe Asp Ile Leu His Lys Cys Asp Asn Glu Cys Met Glu Thr Ile
                485                 490                 495
Lys Asn Gly Thr Tyr Asn His Lys Glu Tyr Glu Glu Glu Ala Lys Leu
                500                 505                 510
```

-continued

```
Glu Arg Ser Lys Ile Asn Gly Val Lys Leu Glu Glu Asn Thr Thr Tyr
        515                 520                 525

Lys Ile Leu Ser Ile Tyr Ser Thr Val Ala Ala Ser Leu Cys Leu Ala
    530                 535                 540

Ile Leu Ile Ala Gly Gly Leu Ile Leu Gly Met Gln Asn Gly Ser Cys
545                 550                 555                 560

Arg Cys Met Phe Cys Ile
            565
```

```
<210> SEQ ID NO 33
<211> LENGTH: 1840
<212> TYPE: DNA
<213> ORGANISM: Artificial Sequence
<220> FEATURE:
<223> OTHER INFORMATION: DNA sequence encoding influenza
      A/Vietnam/1203/04 (HALo) virus HA

<400> SEQUENCE: 33
```

| | | | | | |
|---|---|---|---|---|---|
| cggatgttgc | ccagccggcg | ccagcgagga | ggctgggacc | atgccggcca | gcaaaagcag | 60 |
| gggttcaatc | tgtcaaaatg | gagaaaatag | tgcttctttt | tgcaatagtc | agtcttgtta | 120 |
| aaagtgatca | gatttgcatt | ggttaccatg | caaacaactc | gacagagcag | gttgacacaa | 180 |
| taatggaaaa | gaacgttact | gttacacatg | cccaagacat | actggaaaag | aaacacaacg | 240 |
| ggaagctctg | cgatctagat | ggagtgaagc | ctctaatttt | gagagattgt | agcgtagctg | 300 |
| gatggctcct | cggaaaccca | atgtgtgacg | aattcatcaa | tgtgccggaa | tggtcttaca | 360 |
| tagtggagaa | ggccaatcca | gtcaatgacc | tctgttaccc | aggggatttc | aatgactatg | 420 |
| aagaattgaa | acacctattg | agcagaataa | ccatttttga | gaaaattcag | atcatcccca | 480 |
| aaagttcttg | gtccagtcat | gaagcctcat | taggggtgag | ctcagcatgt | ccataccagg | 540 |
| gaaagtcctc | cttttttcaga | aatgtggtat | ggcttatcaa | aagaacagt | acatacccaa | 600 |
| caataaagag | gagctacaat | aataccaacc | aagaagatct | tttggtactg | tggggattc | 660 |
| accatcctaa | tgatgcggca | gagcagacaa | agctctatca | aaacccaacc | acctatattt | 720 |
| ccgttgggac | atcaacacta | aaccagagat | tggtaccaag | aatagctact | agatccaaag | 780 |
| taaacgggca | agtggaagg | atggagttct | tctggacaat | tttaaagccg | aatgatgcaa | 840 |
| tcaacttcga | gagtaatgga | aatttcattg | ctccagaata | tgcatacaaa | attgtcaaga | 900 |
| aaggggactc | aacaattatg | aaaagtgaat | tggaatatgg | taactgcaac | accaagtgtc | 960 |
| aaactccaat | ggggcgata | aactctagca | tgccattcca | caatatacac | cctctcacca | 1020 |
| ttggggaatg | ccccaaatat | gtgaaatcaa | acagattagt | ccttgcgact | gggctcagaa | 1080 |
| atagccctca | gcgggagacg | cggggattat | tggagctat | agcaggtttt | atagagggag | 1140 |
| gatggcaggg | aatggtagat | ggttggtatg | gtaccacca | tagcaatgag | cagggggagtg | 1200 |
| ggtacgctgc | agacaaagaa | tccactcaaa | aggcaataga | tggagtcacc | aataaggtca | 1260 |
| actcgatcat | tgacaaaatg | aacactcagt | ttgaggccgt | tggaagggaa | tttaacaact | 1320 |
| tagaaaggag | aatagagaat | ttaaacaaga | agatggaaga | cgggttccta | gatgtctgga | 1380 |
| cttataatgc | tgaacttctg | gttctcatgg | aaaatgagag | aactctagac | tttcatgact | 1440 |
| caaatgtcaa | gaacctttac | gacaaggtcc | gactacagct | tagggataat | gcaaaggagc | 1500 |
| tgggtaacgg | ttgtttcgag | ttctatcata | aatgtgataa | tgaatgtatg | gaaagtgtaa | 1560 |
| gaaatggaac | gtatgactac | ccgcagtatt | cagaagaagc | gagactaaaa | agagaggaaa | 1620 |
| taagtggagt | aaaattggaa | tcaataggaa | tttaccaaat | actgtcaatt | tattctacag | 1680 |

-continued

```
tggcgagttc cctagcactg gcaatcatgg tagctggtct atccttatgg atgtgctcca   1740
atgggtcgtt acaatgcaga atttgcattt aaatttgtga gttcagattg tagttaaaaa   1800 caccccttgtt tctactaata acccggcggc caaaatgcc                         1840
```

<210> SEQ ID NO 34
<211> LENGTH: 585
<212> TYPE: PRT
<213> ORGANISM: Artificial Sequence
<220> FEATURE:
<223> OTHER INFORMATION: aa sequence of influenza A/Vietnam/1203/04 (HALo) virus HA

<400> SEQUENCE: 34

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
```

```
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Val Arg Asn
                485                 490                 495
Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525
Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560
Arg Ile Cys Ile Ile Cys Glu Phe Arg Leu Leu Lys Thr Pro Leu Phe
                565                 570                 575
Leu Leu Ile Thr Arg Arg Pro Lys Met
            580                 585

<210> SEQ ID NO 35
<211> LENGTH: 1745
<212> TYPE: DNA
<213> ORGANISM: Artificial Sequence
<220> FEATURE:
<223> OTHER INFORMATION: sequence encoding influenza A/northern shoveler/Netherlands/18/99 virus HA

<400> SEQUENCE: 35

```
aaagcagggg ttctattaag aaatcaaaat gaagaaagca ctgctatttg cagctatttt     60
cctttatgca aaggcagatg aaatctgtat cggctactta agcaacaact caacagacaa    120
agttgacaca ataatcgaga acaatgtcac agtgactagc tcagtggaac tagtcgaaac    180
agaacacact gggtcattct gctcaatcaa tggaaaacaa ccgataagtc ttggagactg    240
ctcttttgct gggtggatat taggtaatcc catgtgtgat gatctaattg gtaagacttc    300
atggtcctac attgtggaga agcccaaccc aacaaatgga atttgttacc ctggaacttt    360
ggaggatgaa gaagaactga gactgaaatt cagtggagtc ctggaattca gcaagttcga    420
agcattcaca tcaaatggat ggggtgctgt gaattcggga gcaggagtga ctgctgcatg    480
caaattcgga agctccaatt ctttcttccg aaacatggta tggcttatac atcaatcagg    540
```

```
aacatatcct gtaataaaga ggacttttaa caataccaaa ggaagagatg tgttgatcgt    600
ttggggaatt catcaccctg ccacactgaa agagcaccaa gacctataca agaaagacag    660
ttcctatgta gcagtgggtt cagaaactta acacagaaga ttcaccccag aaatcagcac    720
taggcccaaa gtcaatggac aggctggacg gatgacattt tattggacaa tggtcaaacc    780
aggagagtca ataacatttg agtctaatgg tgcattcttg gctcctagat atgcttttga    840
gattgtctct gttggaaatg ggaaattatt cagaagcgaa ctgagtattg aatcatgctc    900
taccaaatgc caaacagaag taggagggat taatacaaac aaaagtttcc acagtgttca    960
taggaacact attggagact gtcccaaata tgtgaatgtc aaatccctaa agcttgccac   1020
aggacttaga aatgttccag caatagcatc aagaggattg tttggagcaa tagccggatt   1080
tatagaaggt gggtggccag ggcttatcaa tggatggtac ggttttcaac acagaaatga   1140
ggaaggaaca ggcatagcag cagacaggga gtcaactcaa aaggcagtag accagataac   1200
atccaaagta acaacatcg tcgacagaat gaatacaaat ttcgagtctg tgcaacacga   1260
attcagtgaa atagaggaga ggataaacca attgtcgaaa cacgtagatg attctgtggt   1320
tgacatctgg tcatataacg cacaactcct cgtttggctt gaaaatgaga aaactctgga   1380
tctccacgat tccaatgtta ggaatcttca tgagaaagtc agaaggatgc taaggacaa    1440 tgccaaagat gagggaaatg gatgcttcac cttttaccac aagtgtgaca acgaatgcat   1500
cgaaaaggtt agaaacggaa catatgatca aaagaattc gaagaagaat caagaatcaa    1560
tcgccaggag attgagggag tgagattaga ttctagtggg aatgtgtata aaatactgtc   1620
aatttacagc tgcatcgcaa gcagtcttgt attagcagca ctcatcatgg gtttcatcct   1680
atgggcgtgc agcaatggat catgtagatg taccatttgc atttagaatt gtggcaaaaa   1740
caccc                                                              1745
```

<210> SEQ ID NO 36
<211> LENGTH: 565
<212> TYPE: PRT
<213> ORGANISM: Artificial Sequence
<220> FEATURE:
<223> OTHER INFORMATION: sequence of influenza A/northern
      shoveler/Netherlands/18/99 virus HA

<400> SEQUENCE: 36

```
Met Lys Lys Ala Leu Leu Phe Ala Ala Ile Phe Leu Tyr Ala Lys Ala
1               5                   10                  15

Asp Glu Ile Cys Ile Gly Tyr Leu Ser Asn Asn Ser Thr Asp Lys Val
            20                  25                  30

Asp Thr Ile Ile Glu Asn Asn Val Thr Val Thr Ser Ser Val Glu Leu
        35                  40                  45

Val Glu Thr Glu His Thr Gly Ser Phe Cys Ser Ile Asn Gly Lys Gln
    50                  55                  60

Pro Ile Ser Leu Gly Asp Cys Ser Phe Ala Gly Trp Ile Leu Gly Asn
65                  70                  75                  80

Pro Met Cys Asp Asp Leu Ile Gly Lys Thr Ser Trp Ser Tyr Ile Val
                85                  90                  95

Glu Lys Pro Asn Pro Thr Asn Gly Ile Cys Tyr Pro Gly Thr Leu Glu
            100                 105                 110

Asp Glu Glu Glu Leu Arg Leu Lys Phe Ser Gly Val Leu Glu Phe Ser
        115                 120                 125

Lys Phe Glu Ala Phe Thr Ser Asn Gly Trp Gly Ala Val Asn Ser Gly
    130                 135                 140
```

```
Ala Gly Val Thr Ala Ala Cys Lys Phe Gly Ser Ser Asn Ser Phe Phe
145                 150                 155                 160

Arg Asn Met Val Trp Leu Ile His Gln Ser Gly Thr Tyr Pro Val Ile
            165                 170                 175

Lys Arg Thr Phe Asn Asn Thr Lys Gly Arg Asp Val Leu Ile Val Trp
        180                 185                 190

Gly Ile His His Pro Ala Thr Leu Lys Glu His Gln Asp Leu Tyr Lys
    195                 200                 205

Lys Asp Ser Ser Tyr Val Ala Val Gly Ser Glu Thr Tyr Asn Arg Arg
210                 215                 220

Phe Thr Pro Glu Ile Ser Thr Arg Pro Lys Val Asn Gly Gln Ala Gly
225                 230                 235                 240

Arg Met Thr Phe Tyr Trp Thr Met Val Lys Pro Gly Glu Ser Ile Thr
            245                 250                 255

Phe Glu Ser Asn Gly Ala Phe Leu Ala Pro Arg Tyr Ala Phe Glu Ile
        260                 265                 270

Val Ser Val Gly Asn Gly Lys Leu Phe Arg Ser Glu Leu Ser Ile Glu
    275                 280                 285

Ser Cys Ser Thr Lys Cys Gln Thr Glu Val Gly Gly Ile Asn Thr Asn
290                 295                 300

Lys Ser Phe His Ser Val His Arg Asn Thr Ile Gly Asp Cys Pro Lys
305                 310                 315                 320

Tyr Val Asn Val Lys Ser Leu Lys Leu Ala Thr Gly Leu Arg Asn Val
            325                 330                 335

Pro Ala Ile Ala Ser Arg Gly Leu Phe Gly Ala Ile Ala Gly Phe Ile
        340                 345                 350

Glu Gly Gly Trp Pro Gly Leu Ile Asn Gly Trp Tyr Gly Phe Gln His
    355                 360                 365

Arg Asn Glu Glu Gly Thr Gly Ile Ala Ala Asp Arg Glu Ser Thr Gln
370                 375                 380

Lys Ala Val Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
            405                 410                 415

Glu Arg Ile Asn Gln Leu Ser Lys His Val Asp Asp Ser Val Val Asp
        420                 425                 430

Ile Trp Ser Tyr Asn Ala Gln Leu Leu Val Trp Leu Glu Asn Glu Lys
    435                 440                 445

Thr Leu Asp Leu His Asp Ser Asn Val Arg Asn Leu His Glu Lys Val
450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Glu Cys Ile Glu Lys Val Arg Asn
            485                 490                 495

Gly Thr Tyr Asp His Lys Glu Phe Glu Glu Ser Arg Ile Asn Arg
        500                 505                 510

Gln Glu Ile Glu Gly Val Arg Leu Asp Ser Ser Gly Asn Val Tyr Lys
    515                 520                 525

Ile Leu Ser Ile Tyr Ser Cys Ile Ala Ser Ser Leu Val Leu Ala Ala
530                 535                 540

Leu Ile Met Gly Phe Ile Leu Trp Ala Cys Ser Asn Gly Ser Cys Arg
545                 550                 555                 560
```

Cys Thr Ile Cys Ile
             565

<210> SEQ ID NO 37
<211> LENGTH: 1712
<212> TYPE: DNA
<213> ORGANISM: Artificial Sequence
<220> FEATURE:
<223> OTHER INFORMATION: sequence encoding A_mallard_interior
      Alaska_7MP0167_2007 virus HA

<400> SEQUENCE: 37

| | | | | | |
|---|---|---|---|---|---|
| ggtcacaatg | gaaaaattca | tcattttgag | cactgtcctg | gcagtaagct | ttgcatatga | 60 |
| caaaatttgc | attggatatc | aaacaaacaa | ctcgactgag | acagtaaaca | cactaatcga | 120 |
| gcaaaacgtt | ccggtgacac | aggtggaaga | actcgtgcat | ggtgggatcg | atccggtcct | 180 |
| atgtggaacg | gagctagggt | caccattagt | gcttgatgac | tgttcactcg | aaggtctcat | 240 |
| tctaggcaat | cccaaatgtg | atctttatct | gaatggcagg | gaatggtcat | acatagtaga | 300 |
| gaggcccaaa | gaaatggaag | gagtttgcta | cccaggatca | attgaaaatc | aagaggagtt | 360 |
| gagatctctg | ttttcttcca | tcaagaagta | tgaaagagtg | aagatgtttg | atttcaccaa | 420 |
| atggaatgtc | acgtacactg | gaaccagcaa | ggcctgcaac | aatacatcaa | ccaaggctc  | 480 |
| attctatagg | agcatgagat | ggttaacctt | aaaatcagga | caattcccag | tccagacaga | 540 |
| tgagtacaag | aacaccagag | attcggacat | tgtcttcacc | tgggccatcc | atcacccacc | 600 |
| aacatctgat | gaacagataa | agttatacaa | aaatccggat | accctctcct | cagtcaccac | 660 |
| tgatgaaatc | aataggagtt | tcaagcctaa | cataggacca | aggccattag | tgagaggaca | 720 |
| acagggagga | atggattact | actgggctgt | cctcaaacct | ggacaaactg | tcaaaataca | 780 |
| gaccaatggt | aatcttattg | cacctgaata | tggtcactta | attacaggga | aatcacatgg | 840 |
| caggatactc | aagaataact | tgcccatagg | acagtgtgtg | actgagtgcc | agttgaatga | 900 |
| agggtgatg  | aatacaagta | aaccttccca | gaacactagt | aagcactata | ttgggaaatg | 960 |
| tcccaaatac | ataccatcag | gaagcctgaa | attggcgata | gggctcagaa | atgttccaca | 1020 |
| agttcagaac | agaggactat | ttggagcaaa | agcaggtttc | atagagggcg | gatggccagg | 1080 |
| actagtggct | ggttggtatg | gatttcagca | tcaaaatgca | gaggggacag | gcatagccgc | 1140 |
| agacagagac | agcactcaga | aggcaataga | caatatgcaa | aacaaactca | acaatgtcat | 1200 |
| tgacaaaatg | aacaaacaat | tgaagtggt  | gaatcatgag | ttttcagaag | tggaaagcag | 1260 |
| aataaacatg | attaattccc | aaattgatga | tcaaataact | gacatatggg | catacaatgc | 1320 |
| tgaactgctt | gtcctattgg | aaaatcagaa | gacattagat | gagcatgatg | ctaatgtaag | 1380 |
| aaacttacac | gatagagtca | gaagagtcct | aagagaaaat | gcaattgata | caggagatgg | 1440 |
| ttgctttgaa | attctgcata | aatgtgacaa | caattgcatg | gacacaatca | gaaatgggac | 1500 |
| atacaatcac | aaggagtatg | aggaagaaag | caaaatcgaa | cgacagaaaa | ttaatggtgt | 1560 |
| caaacttgag | gagaattcta | catataaaat | tctgagcatc | tacagcagtg | ttgcctcaag | 1620 |
| cttagttcta | ctgctcatga | ttattggggg | tttcattttc | gggtgtcaaa | atggaaatgt | 1680 |
| tcgttgtact | ttctgtattt | aattaaaaac | ac | | | 1712 |

<210> SEQ ID NO 38
<211> LENGTH: 564
<212> TYPE: PRT
<213> ORGANISM: Artificial Sequence
<220> FEATURE:
<223> OTHER INFORMATION: sequence of A_mallard_interior Alaska_7MP0167_2007 virus HA

<400> SEQUENCE: 38

```
Met Glu Lys Phe Ile Ile Leu Ser Thr Val Leu Ala Val Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ile Glu Gln Asn Val Pro Val Thr Gln Val Glu Glu
        35                  40                  45

Leu Val His Gly Gly Ile Asp Pro Val Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

Val Glu Arg Pro Lys Glu Met Glu Gly Val Cys Tyr Pro Gly Ser Ile
            100                 105                 110

Glu Asn Gln Glu Glu Leu Arg Ser Leu Phe Ser Ser Ile Lys Lys Tyr
        115                 120                 125

Glu Arg Val Lys Met Phe Asp Phe Thr Lys Trp Asn Val Thr Tyr Thr
    130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Ile Lys Leu Tyr Lys
        195                 200                 205

Asn Pro Asp Thr Leu Ser Ser Val Thr Thr Asp Glu Ile Asn Arg Ser
    210                 215                 220

Phe Lys Pro Asn Ile Gly Pro Arg Pro Leu Val Arg Gly Gln Gln Gly
225                 230                 235                 240

Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
            260                 265                 270

Thr Gly Lys Ser His Gly Arg Ile Leu Lys Asn Asn Leu Pro Ile Gly
        275                 280                 285

Gln Cys Val Thr Glu Cys Gln Leu Asn Glu Gly Val Met Asn Thr Ser
    290                 295                 300

Lys Pro Phe Gln Asn Thr Ser Lys His Tyr Ile Gly Lys Cys Pro Lys
305                 310                 315                 320

Tyr Ile Pro Ser Gly Ser Leu Lys Leu Ala Ile Gly Leu Arg Asn Val
                325                 330                 335

Pro Gln Val Gln Asn Arg Gly Leu Phe Gly Ala Lys Ala Gly Phe Ile
            340                 345                 350

Glu Gly Gly Trp Pro Gly Leu Val Ala Gly Trp Tyr Gly Phe Gln His
        355                 360                 365

Gln Asn Ala Glu Gly Thr Gly Ile Ala Ala Asp Arg Asp Ser Thr Gln
    370                 375                 380

Lys Ala Ile Asp Asn Met Gln Asn Lys Leu Asn Asn Val Ile Asp Lys
385                 390                 395                 400
```

```
Met Asn Lys Gln Phe Glu Val Val Asn His Glu Phe Ser Glu Val Glu
                405                 410                 415

Ser Arg Ile Asn Met Ile Asn Ser Gln Ile Asp Asp Gln Ile Thr Asp
            420                 425                 430

Ile Trp Ala Tyr Asn Ala Glu Leu Leu Val Leu Leu Glu Asn Gln Lys
        435                 440                 445

Thr Leu Asp Glu His Asp Ala Asn Val Arg Asn Leu His Asp Arg Val
    450                 455                 460

Arg Arg Val Leu Arg Glu Asn Ala Ile Asp Thr Gly Asp Gly Cys Phe
465                 470                 475                 480

Glu Ile Leu His Lys Cys Asp Asn Asn Cys Met Asp Thr Ile Arg Asn
                485                 490                 495

Gly Thr Tyr Asn His Lys Glu Tyr Glu Glu Glu Ser Lys Ile Glu Arg
            500                 505                 510

Gln Lys Ile Asn Gly Val Lys Leu Glu Glu Asn Ser Thr Tyr Lys Ile
        515                 520                 525

Leu Ser Ile Tyr Ser Ser Val Ala Ser Ser Leu Val Leu Leu Leu Met
    530                 535                 540

Ile Ile Gly Gly Phe Ile Phe Gly Cys Gln Asn Gly Asn Val Arg Cys
545                 550                 555                 560

Thr Phe Cys Ile

<210> SEQ ID NO 39
<211> LENGTH: 1775
<212> TYPE: DNA
<213> ORGANISM: Artificial Sequence
<220> FEATURE:
<223> OTHER INFORMATION: sequence encoding influenza A/Puerto Rico/8/34
      virus HA

<400> SEQUENCE: 39
agcaaaagca ggggaaaata aaaacaacca aaatgaaggc aaacctactg gtcctgttaa      60
gtgcacttgc agctgcagat gcagacacaa tatgtatagg ctaccatgcg aacaattcaa     120
ccgacactgt tgacacagta ctcgagaaga atgtgacagt gacacactct gttaacctgc     180
tcgaagacag ccacaacgga aaactatgta gattaaaagg aatagcccca ctacaattgg     240
ggaaatgtaa catcgccgga tggctcttgg gaaacccaga atgcgaccca ctgcttccag     300
tgagatcatg gtcctacatt gtagaaacac caaactctga gaatggaata tgttatccag     360
gagatttcat cgactatgag gagctgaggg agcaattgag ctcagtgtca tcattcgaaa     420
gattcgaaat atttcccaaa gaaagctcat ggcccaacca caacacaaac ggagtaacgg     480
cagcatgctc ccatgagggg aaaagcagtt tttacagaaa tttgctatgg ctgacggaga     540
aggagggctc atacccaaag ctgaaaaatt cttatgtgaa caaaaaaggg aaagaagtcc     600
ttgtactgtg gggtattcat cacccgccta acagtaagga acaacagaat atctatcaga     660
atgaaaatgc ttatgtctct gtagtgactt caaattataa caggagattt accccggaaa     720
tagcagaaag acccaaagta agagatcaag ctgggaggat gaactattac tggaccttgc     780
taaaacccgg agacacaata atatttgagg caaatggaaa tctaatagca ccaatgtatg     840
ctttcgcact gagtagaggc tttgggtccg gcatcatcac ctcaaacgca tcaatgcatg     900
agtgtaacac gaagtgtcaa acacccctgg gagctataaa cagcagtctc ccttaccaga     960
atatacaccc agtcacaata ggagagtgcc caaaatacgt caggagtgcc aaattgagga    1020
tggttacagg actaaggaac actccgtcca ttcaatccag aggtctattt ggagccattg    1080
```

-continued

```
ccggttttat tgaagggga tggactggaa tgatagatgg atggtatggt tatcatcatc    1140
agaatgaaca gggatcaggc tatgcagcgg atcaaaaaag cacacaaaat gccattaacg    1200
ggattacaaa caaggtgaac actgttatcg agaaaatgaa cattcaattc acagctgtgg    1260
gtaaagaatt caacaaatta gaaaaaagga tggaaaattt aaataaaaaa gttgatgatg    1320
gatttctgga catttggaca tataatgcag aattgttagt tctactggaa aatgaaagga    1380
ctctggattt ccatgactca aatgtgaaga atctgtatga aaagtaaaaa agccaattaa    1440
agaataatgc caagaaatc ggaaatggat gttttgagtt ctaccacaag tgtgacaatg     1500
aatgcatgga aagtgtaaga aatgggactt atgattatcc caaatattca gaagagtcaa    1560
agttgaacag ggaaaaggta gatggagtga aattggaatc aatggggatc tatcagattc    1620
tggcgatcta ctcaactgtc gccagttcac tggtgctttt ggtctccctg ggggcaatca    1680
gtttctggat gtgttctaat ggatctttgc agtgcagaat atgcatctga gattagaatt    1740
tcagaaatat gaggaaaaac acccttgttt ctact                                1775
```

<210> SEQ ID NO 40
<211> LENGTH: 560
<212> TYPE: PRT
<213> ORGANISM: Artificial Sequence
<220> FEATURE:
<223> OTHER INFORMATION: sequence of influenza A/Puerto Rico/8/34 virus HA

<400> SEQUENCE: 40

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240
```

```
Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

<210> SEQ ID NO 41
<211> LENGTH: 1879
<212> TYPE: DNA
<213> ORGANISM: Artificial Sequence
<220> FEATURE:
<223> OTHER INFORMATION: sequence encoding influenza B/Yamagata/16/88
      virus HA

<400> SEQUENCE: 41
agcagaagca gagcattttc taatatccac aaaatgaagg caataattgt actactcatg      60
gtagtaacat ccaacgcaga tcgaatctgc actgggataa catcttcaaa ctcacctcat     120
gtggtcaaaa cagctactca aggggaagtt aatgtgactg gtgtgatacc actgacaaca     180
acaccaacaa aatctcattt tgcaaatctc aaaggaacaa agaccagagg gaaactatgc     240
```

```
ccaaactgtc tcaactgcac agatctggat gtggccttgg gcagaccaat gtgtatgggg    300
accatacctt cggcaaaagc ttcaatactc cacgaagtca gacctgttac atccgggtgc    360
tttcctataa tgcacgacag aacaaaaatc agacagctac ccaatcttct cagaggatat    420
gaaaatatca gattatcaac ccataacgtt atcaacgcag aaagggcacc aggaggaccc    480

tacagacttg gaacctcaga atcttgccct aacgttacca gtagaaacgg attcttcgca    540
acaatggctt gggctgtccc aagggacaac aaaacagcaa cgaatccact aacagtagaa    600
gtaccataca tttgcacaaa aggagaagac caaattactg tttggggtt ccattctgat    660 aacaaaaacc aaatgaaaaa cctctatgga gactcaaatc ctcaaaagtt cacctcatct    720
gccaatggag taaccacaca ttatgtttct cagattggtg acttcccaaa tcaaacagaa    780
gacggagggc taccacaaag cggcagaatt gttgttgatt acatggtgca aaaacctggg    840
aaaacaggaa caattgtcta tcaaagaggt gttttgttgc ctcaaaaggt gtggtgcgca    900
agtggcagga gcaaggtaat aaaagggtcc ttgcctttaa ttggtgaagc agattgcctt    960
cacgaaaaat acggtggatt aaacaaaagc aagccttact acacaggaga acatgcaaaa   1020
gccataggaa attgcccaat atgggtgaaa acaccттттga agcttgccaa tggaaccaaa   1080

tatagacctc ctgcaaaact attaaaggaa aggggtttct tcggagctat tgctggtttc   1140

ttagagggag gatgggaagg aatgattgca ggttggcacg gatacacatc tcatggagca   1200
catggagtgg cagtggcagc agaccttaag agcacgcaag aagccataaa caagataaca   1260
aaaaatctca attctttgag tgagctagaa gtaaagaatc ttcaaagact aagtggtgcc   1320
atggatgaac tccacaacga aatactcgag ctggatgaga agtggatga tctcagagct   1380 gacacaataa gctcgcaaat agagcttgca gtcttgcttt ccaacgaagg aataataaac   1440
agtgaagatg agcatctatt ggcacttgag agaaaactaa agaaaatgct gggtccctct   1500
gctgtagaca tagggaatgg atgcttcgaa accaaacaca gtgcaacca gacctgctta   1560 gacaggatag ctgctggcac ctttaatgca ggagaatttt ctcttcccac ttttgattca   1620

ctgaatatta ctgctgcatc ttaaatgat gatggattgg ataatcatac tatactgctc   1680

tactactcaa ctgctgcttc tagtttggcc gtaacattga tgatagctat tttattgtt   1740

tatatggtct ccagagacaa tgtttcttgc тccaтсstgтc taaaggaaa attaagccct   1800 gtattttcct ttattgtagt gcttgtttgc ttgttaccat acaaagaaa cgttattgaa   1860 aaatgctctt gttactact                                                1879
```

<210> SEQ ID NO 42
<211> LENGTH: 583
<212> TYPE: PRT
<213> ORGANISM: Artificial Sequence
<220> FEATURE:
<223> OTHER INFORMATION: sequence of influenza B/Yamagata/16/88 virus HA

<400> SEQUENCE: 42

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Thr Ile Pro Ser Ala Lys Ala
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu Asn Ile Arg Leu Ser Thr His Asn Val Ile Asn Ala Glu Arg
            130                 135                 140

Ala Pro Gly Gly Pro Tyr Arg Leu Gly Thr Ser Glu Ser Cys Pro Asn
145                 150                 155                 160

Val Thr Ser Arg Asn Gly Phe Phe Ala Thr Met Ala Trp Ala Val Pro
            165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
            195                 200                 205

Asp Asn Lys Asn Gln Met Lys Asn Leu Tyr Gly Asp Ser Asn Pro Gln
210                 215                 220

Lys Phe Thr Ser Ser Ala Asn Gly Val Thr Thr His Tyr Val Ser Gln
225                 230                 235                 240

Ile Gly Asp Phe Pro Asn Gln Thr Glu Asp Gly Gly Leu Pro Gln Ser
            245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
            275                 280                 285

Ala Ser Gly Arg Ser Lys Val Ile Lys Gly Ser Leu Pro Leu Ile Gly
            290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
            325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
            355                 360                 365

Phe Leu Glu Gly Gly Trp Glu Gly Met Ile Ala Gly Trp His Gly Tyr
            370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
            405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
            435                 440                 445

Ala Asp Thr Ile Ser Ser Gln Ile Glu Leu Ala Val Leu Leu Ser Asn
            450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly

```
                485                 490                 495
Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
            515                 520                 525

Ser Leu Asn Ile Thr Ala Ala Ser Leu Asn Asp Asp Gly Leu Asp Asn
        530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580

<210> SEQ ID NO 43
<211> LENGTH: 1876
<212> TYPE: DNA
<213> ORGANISM: Artificial Sequence
<220> FEATURE:
<223> OTHER INFORMATION: sequence encoding mH5/B chimeric HA for rescue
      in B/Yamagata/16/88

<400> SEQUENCE: 43
agcagaagca gagcattttc taatatccac aaaatgaagg caataattgt actactcatg      60
gtagtaacat ccaacgcaga tcgaatctgc actgggataa catcttcaaa ctcacctcat     120
gtggtcaaaa cagctactca agggaagtt aatgtgactg tgtgatacc actgacaaca      180 acaccaacaa atctcattt tgcaaatctc aaaggaacaa agaccagagg gaaactatgc     240
ccaaactgtc tcaactgcac agatctggat gtggccttgg gcagaccaat gtgtatgggg     300 ttcataccctt cggcaaaagc ttcaatactc cacgaagtca gacctgttac atccgggtgc     360
tttcctataa tgcacgacag aacaaaatc agacagctac ccaatcttct cagaggatat     420
gaaaaaatcc agttatcaac caaaaacgtt atcaacgcag aacatgcacc aggaggaccc     480
tacagacttg aacctcaaa atcttgccca taccagggaa agtcctcctt cttcgcaaca     540
atggcttggg ctgtcccaaa aaagaacagt acatacacga atccactaac agtagaagta     600
ccatacattt gcacaaaagg agaagaccaa attactgttt gggggttcca ttctgataat     660
gatgcggcaa tgcagacact ctatgagac tcaaatcctc aaaagttcac ctcatctgcc     720 aatgagtaa ccacacatta tgtttctcag attggtgact tcccaaatca acagaagac      780 ggagggctac cacaaagcgg cagaattgtt gttgattaca tggtgcaaaa acctgggaaa     840
acaggaacaa ttgtctatca aagaggtgtt ttgttgcctc aaaaggtgtg gtgcgcaagt     900
ggcaggagca agtaataaa agggtccttg cctttaattg tgaagcaga ttgccttcac      960 gaaaaatacg gtggattaaa caaaagcaag ccttactaca caggagaaca tgcaaaagcc    1020
ataggaaatt gcccaatatg ggtgaaaaca cctttgaagc ttgccaatgg aaccaaatat    1080
agacctcctg caaaactatt aaaggaaagg ggtttcttcg agctattgc tggttttctta    1140 gagggaggat gggaaggaat gattgcaggt tggcacggat acacatctca tggagcacat    1200
ggagtggcag tggcagcaga ccttaagagc acgcaagaag ccataaacaa gataacaaaa    1260
aatctcaatt ctttgagtga gctagaagta aagaatcttc aaagactaag tggtgccatg    1320
gatgaactcc acaacgaaat actcgagctg atgagaaag tggatgatct cagagctgac    1380
acaataagct cgcaaataga gcttgcagtc ttgctttcca acgaaggaat aataaacagt    1440
```

```
gaagatgagc atctattggc acttgagaga aaactaaaga aaatgctggg tccctctgct   1500
gtagacatag ggaatggatg cttcgaaacc aaacacaagt gcaaccagac ctgcttagac   1560
aggatagctg ctggcacctt taatgcagga gaatttctc ttcccacttt tgattcactg    1620
aatattactg ctgcatcttt aaatgatgat ggattggata atcatactat actgctctac   1680
tactcaactg ctgcttctag tttggccgta acattgatga tagctatttt tattgtttat   1740
atggtctcca gagacaatgt ttcttgctcc atctgtctat aaggaaaatt aagccctgta   1800 ttttcctta ttgtagtgct tgtttgcttg ttaccattac aaagaaacgt tattgaaaaa    1860
tgctcttgtt actact                                                    1876
```

<210> SEQ ID NO 44
<211> LENGTH: 582
<212> TYPE: PRT
<213> ORGANISM: Artificial Sequence
<220> FEATURE:
<223> OTHER INFORMATION: sequence of mH5/B chimeric HA for rescue in
      B/Yamagata/16/88

<400> SEQUENCE: 44

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Lys Thr
        50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Phe Ile Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu Lys Ile Gln Leu Ser Thr Lys Asn Val Ile Asn Ala Glu His
        130                 135                 140

Ala Pro Gly Gly Pro Tyr Arg Leu Gly Thr Ser Lys Ser Cys Pro Tyr
145                 150                 155                 160

Gln Gly Lys Ser Ser Phe Phe Ala Thr Met Ala Trp Ala Val Pro Lys
                165                 170                 175

Lys Asn Ser Thr Tyr Thr Asn Pro Leu Thr Val Glu Val Pro Tyr Ile
            180                 185                 190

Cys Thr Lys Gly Glu Asp Gln Ile Thr Val Trp Gly Phe His Ser Asp
        195                 200                 205

Asn Asp Ala Ala Met Gln Thr Leu Tyr Gly Asp Ser Asn Pro Gln Lys
    210                 215                 220

Phe Thr Ser Ser Ala Asn Gly Val Thr Thr His Tyr Val Ser Gln Ile
225                 230                 235                 240

Gly Asp Phe Pro Asn Gln Thr Glu Asp Gly Gly Leu Pro Gln Ser Gly
                245                 250                 255

Arg Ile Val Val Asp Tyr Met Val Gln Lys Pro Gly Lys Thr Gly Thr
            260                 265                 270

Ile Val Tyr Gln Arg Gly Val Leu Leu Pro Gln Lys Val Trp Cys Ala

```
            275                 280                 285
Ser Gly Arg Ser Lys Val Ile Lys Gly Ser Leu Pro Leu Ile Gly Glu
            290                 295                 300
Ala Asp Cys Leu His Glu Lys Tyr Gly Gly Leu Asn Lys Ser Lys Pro
305                 310                 315                 320
Tyr Tyr Thr Gly Glu His Ala Lys Ala Ile Gly Asn Cys Pro Ile Trp
                325                 330                 335
Val Lys Thr Pro Leu Lys Leu Ala Asn Gly Thr Lys Tyr Arg Pro Pro
            340                 345                 350
Ala Lys Leu Leu Lys Glu Arg Gly Phe Phe Gly Ala Ile Ala Gly Phe
                355                 360                 365
Leu Glu Gly Gly Trp Glu Gly Met Ile Ala Gly Trp His Gly Tyr Thr
            370                 375                 380
Ser His Gly Ala His Gly Val Ala Val Ala Ala Asp Leu Lys Ser Thr
385                 390                 395                 400
Gln Glu Ala Ile Asn Lys Ile Thr Lys Asn Leu Asn Ser Leu Ser Glu
                405                 410                 415
Leu Glu Val Lys Asn Leu Gln Arg Leu Ser Gly Ala Met Asp Glu Leu
            420                 425                 430
His Asn Glu Ile Leu Glu Leu Asp Glu Lys Val Asp Asp Leu Arg Ala
                435                 440                 445
Asp Thr Ile Ser Ser Gln Ile Glu Leu Ala Val Leu Leu Ser Asn Glu
450                 455                 460
Gly Ile Ile Asn Ser Glu Asp Glu His Leu Leu Ala Leu Glu Arg Lys
465                 470                 475                 480
Leu Lys Lys Met Leu Gly Pro Ser Ala Val Asp Ile Gly Asn Gly Cys
                485                 490                 495
Phe Glu Thr Lys His Lys Cys Asn Gln Thr Cys Leu Asp Arg Ile Ala
                500                 505                 510
Ala Gly Thr Phe Asn Ala Gly Glu Phe Ser Leu Pro Thr Phe Asp Ser
            515                 520                 525
Leu Asn Ile Thr Ala Ala Ser Leu Asn Asp Asp Gly Leu Asp Asn His
            530                 535                 540
Thr Ile Leu Leu Tyr Tyr Ser Thr Ala Ala Ser Ser Leu Ala Val Thr
545                 550                 555                 560
Leu Met Ile Ala Ile Phe Ile Val Tyr Met Val Ser Arg Asp Asn Val
                565                 570                 575
Ser Cys Ser Ile Cys Leu
            580

<210> SEQ ID NO 45
<211> LENGTH: 1882
<212> TYPE: DNA
<213> ORGANISM: Artificial Sequence
<220> FEATURE:
<223> OTHER INFORMATION: sequence encoding mH8/B chimeric HA for rescue
      in B/Yamagata/16/88

<400> SEQUENCE: 45
agcagaagca gagcattttc taatatccac aaaatgaagg caataattgt actactcatg      60
gtagtaacat ccaacgcaga tcgaatctgc actgggataa catcttcaaa ctcacctcat     120
gtggtcaaaa cagctactca agggaagtt aatgtgactg gtgtgatacc actgacaaca     180
acaccaacaa aatctcattt tgcaaatctc aaaggaacaa agaccagagg gaaactatgc     240
ccaaactgtc tcaactgcac agatctggat gtggccttgg gcagaccaat gtgtatgggg     300
```

```
cacataccttc ggcaaaagct tcaatactcc acgaagtcag acctgttaca tccgggtgc    360
tttcctataa tgcacgacag aacaaaaatc agacagctac ccaatcttct cagaggatat    420
gaaaggatca gattatcaac ctacaacgtt atcaacgcag aaaccgcacc aggaggaccc    480
tacagacttg aacctcaaa  atcttgcaat gcttcaacag gaggccaatc tttcttcgca    540
acaatggctt gggctgtccc aaaaaagaaa gcagacacct atacgaatcc actaacagta    600
gaagtaccat acatttgcac aaaaggagaa gaccaaatta ctgtttgggg gttccattct    660
gatgcagatg caaaaatgca aacactctat ggagactcaa atcctcaaaa gttcacctca    720
tctgccaatg gagtaaccac acattatgtt tctcagattg tgacttcccc aaatcaaaca    780
gaagacggag ggctaccaca aagcggcaga attgttgttg attacatggt gcaaaaacct    840
gggaaaacag aacaattgt  ctatcaaaga ggtgttttgt tgcctcaaaa ggtgtggtgc    900
gcaagtggca ggagcaaggt aataaaaggg tccttgcctt taattggtga agcagattgc    960
cttcacgaaa aataccggtgg attaaacaaa agcaagcctt actacacagg agaacatgca   1020
aaagccatag gaaattgccc aatatgggtg aaaacaccct tgaagcttgc caatggaacc   1080
aaatatagac tccctgcaaa actattaaag gaaagggggtt cttcggagc  tattgctggt   1140
ttcttagagg gaggatggga aggaatgatt gcaggttggc acggatacac atctcatgga   1200
gcacatggag tggcagtggc agcagaccct aagagcacgc aagaagccat aaacaagata   1260
acaaaaaatc tcaattcttt gagtgagcta gaagtaaaga atcttcaaag actaagtggt   1320
gccatggatg aactccacaa cgaaatactc gagctggatg agaaagtgga tgatctcaga   1380
gctgacacaa taagctcgca aatagagctt gcagtcttgc tttccaacga aggaataata   1440
aacagtgaag atgagcatct attggcactt gagagaaaac taagaaaat  gctgggtccc   1500
tctgctgtag acatagggaa tggatgcttc gaaaccaaac acaagtgcaa ccagacctgc   1560
ttagacagga tagctgctgg caccttttaat gcaggagaat tttctcttcc cacttttgat   1620
tcactgaata ttactgctgc atcttttaaat gatgatggat tggataatca tactatactg   1680
ctctactact caactgctgc ttctagtttg gccgtaacat tgatgatagc tatttttatt   1740
gtttatatgg tctccagaga caatgtttct tgctccatct gtctataagg aaaattaagc   1800
cctgtatttt cctttattgt agtgcttgtt tgcttgttac cattacaaag aaacgttatt   1860
gaaaaatgct cttgttacta ct                                            1882
```

<210> SEQ ID NO 46
<211> LENGTH: 584
<212> TYPE: PRT
<213> ORGANISM: Artificial Sequence
<220> FEATURE:
<223> OTHER INFORMATION: sequence of mH8/B chimeric HA for rescue in
      B/Yamagata/16/88

<400> SEQUENCE: 46

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
```

```
                65                  70                  75                  80
Ala Leu Gly Arg Pro Met Cys Met Gly His Ile Pro Ser Ala Lys Ala
                    85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu Arg Ile Arg Leu Ser Thr Tyr Asn Val Ile Asn Ala Glu Thr
                130                 135                 140

Ala Pro Gly Gly Pro Tyr Arg Leu Gly Thr Ser Lys Ser Cys Asn Ala
145                 150                 155                 160

Ser Thr Gly Gly Gln Ser Phe Phe Ala Thr Met Ala Trp Ala Val Pro
                    165                 170                 175

Lys Lys Lys Ala Asp Thr Tyr Thr Asn Pro Leu Thr Val Glu Val Pro
                180                 185                 190

Tyr Ile Cys Thr Lys Gly Glu Asp Gln Ile Thr Val Trp Gly Phe His
                195                 200                 205

Ser Asp Ala Asp Ala Lys Met Gln Thr Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Asp Phe Pro Asn Gln Thr Glu Asp Gly Gly Leu Pro Gln
                245                 250                 255

Ser Gly Arg Ile Val Val Asp Tyr Met Val Gln Lys Pro Gly Lys Thr
                260                 265                 270

Gly Thr Ile Val Tyr Gln Arg Gly Val Leu Leu Pro Gln Lys Val Trp
                275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495
```

```
Gly Cys Phe Glu Thr Lys His Lys Cys Asn Gln Thr Cys Leu Asp Arg
            500                 505                 510
Ile Ala Ala Gly Thr Phe Asn Ala Gly Glu Phe Ser Leu Pro Thr Phe
            515                 520                 525
Asp Ser Leu Asn Ile Thr Ala Ala Ser Leu Asn Asp Asp Gly Leu Asp
            530                 535                 540
Asn His Thr Ile Leu Leu Tyr Tyr Ser Thr Ala Ala Ser Ser Leu Ala
545                 550                 555                 560
Val Thr Leu Met Ile Ala Ile Phe Ile Val Tyr Met Val Ser Arg Asp
                565                 570                 575
Asn Val Ser Cys Ser Ile Cys Leu
            580
```

<210> SEQ ID NO 47
<211> LENGTH: 1972
<212> TYPE: DNA
<213> ORGANISM: Artificial Sequence
<220> FEATURE:
<223> OTHER INFORMATION: sequence encoding mH11/B chimeric HA for rescue
    in B/Yamagata/16/88

<400> SEQUENCE: 47

```
agcagaagca gagcattttc taatatccac aaaatgaagg caataattgt actactcatg      60
gtagtaacat ccaacgcaga tcgaatctgc actgggataa catcttcaaa ctcacctcat     120
gtggtcaaaa cagctactca aggggaagtt aatgtgactg gtgtgatacc actgacaaca     180
acaccaacaa aatctcattt tgcaaatctc aaaggaacaa agaccagagg gaaactatgc     240
ccaaactgtc tcaactgcac agatctggat gtggccttgg gcagaccaat gtgtatgggg     300
ctaatacctt cggcaaaagc ttcaatactc acgaagtca gacctgttac atccgggtgc     360
tttcctataa tgcacgacag aacaaaaatc agacagctac ccaatcttct cagaggatat     420
gaaaagatcg aattatcaac ctcaaacgtt atcaacgcag aagtggcacc aggaggaccc     480
tacagacttg aacctcaga atcttgccct tcggaagct ccaattcttt cttcgcaaca     540
atggcttggg ctgtcccaca tcaatcagga acatatacga atccactaac agtagaagta     600
ccatacattt gcacaaaagg agaagaccaa attactgttt gggggttcca ttctgatacc     660
acactgaaaa tgcaccaact ctatggagac tcaaatcctc aaaagttcac ctcatctgcc     720
aatggagtaa ccacacatta tgtttctcag attggtgact cccaaatca acagaagac     780
gaagggctac cacaaagcgg cagaattgtt gttgattaca tggtgcaaaa acctgggaaa     840
acaggaacaa ttgtctatca agaggtgtt ttgttgcctc aaaaggtgtg gtgcgcaagt     900
ggcaggagca aggtaataaa agggtccttg cctttaattg gtgaagcaga ttgccttcac     960
gaaaaatacg gtggattaaa caaaagcaag cctactaca caggagaaca tgcaaaagcc    1020
ataggaaatt gcccaatatg ggtgaaaaca cctttgaagc ttgccaatgg aaccaaatat    1080
agacctcctg caaaactatt aaaggaaagg ggtttcttcg gagctattgc tggtttctta    1140
gagggaggat gggaaggaat gattgcaggt tggcacggat acacatctca tggagcacat    1200
ggagtggcag tggcagcaga ccttaagagc acgcaagaag ccataaacaa gataacaaaa    1260
aatctcaatt ctttgagtga gctagaagta aagaatcttc aaagactaag tggtgccatg    1320
gatgaactcc acaacgaaat actcgagctg gatgagaaag tggatgatct cagagctgac    1380
acaataagct cgcaaataga gcttgcagtc ttgctttcca acgaaggaat aataaacagt    1440
gaagatgagc atctattggc acttgagaga aaactaaaga aatgctggg tccctctgct    1500
```

```
gtagacatag ggaatggatg cttcgaaacc aaacacaagt gcaaccagac ctgcttagac   1560
aggatagctg ctggcacctt taatgcagga gaattttctc ttcccacttt tgattcactg   1620
aatattactg ctgcatcttt aaatgatgat ggattggata atcatactat actgctctac   1680
tactcaactg ctgcttctag tttggccgta acattgatga tagctatttt tattgtttat   1740
atggtctcca gagacaatgt ttcttgctcc atctgtctat aaggaaaatt aagccctgta   1800
ttttccttta ttgtagtgct tgtttgcttg ttaccattac aaagaaacgt tattgaaaaa   1860
tgctcttgtt tactactagg aaaattaagc cctgtatttt cctttattgt agtgcttgtt   1920
tgcttgttac cattacaaag aaacgttatt gaaaatgct cttgttacta ct            1972
```

<210> SEQ ID NO 48
<211> LENGTH: 582
<212> TYPE: PRT
<213> ORGANISM: Artificial Sequence
<220> FEATURE:
<223> OTHER INFORMATION: sequence of mH11/B chimeric HA for rescue in B/Yamagata/16/88

<400> SEQUENCE: 48

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Leu Ile Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Glu Leu Ser Thr Ser Asn Val Ile Asn Ala Glu Val
    130                 135                 140

Ala Pro Gly Gly Pro Tyr Arg Leu Gly Thr Ser Glu Ser Cys Pro Phe
145                 150                 155                 160

Gly Ser Ser Asn Ser Phe Phe Ala Thr Met Ala Trp Ala Val Pro His
                165                 170                 175

Gln Ser Gly Thr Tyr Thr Asn Pro Leu Thr Val Glu Val Pro Tyr Ile
            180                 185                 190

Cys Thr Lys Gly Glu Asp Gln Ile Thr Val Trp Gly Phe His Ser Asp
        195                 200                 205

Thr Thr Leu Lys Met His Gln Leu Tyr Gly Asp Ser Asn Pro Gln Lys
    210                 215                 220

Phe Thr Ser Ser Ala Asn Gly Val Thr Thr His Tyr Val Ser Gln Ile
225                 230                 235                 240

Gly Asp Phe Pro Asn Gln Thr Glu Asp Glu Gly Leu Pro Gln Ser Gly
                245                 250                 255

Arg Ile Val Val Asp Tyr Met Val Gln Lys Pro Gly Lys Thr Gly Thr
            260                 265                 270
```

Ile Val Tyr Gln Arg Gly Val Leu Leu Pro Gln Lys Val Trp Cys Ala
            275                 280                 285

Ser Gly Arg Ser Lys Val Ile Lys Gly Ser Leu Pro Leu Ile Gly Glu
    290                 295                 300

Ala Asp Cys Leu His Glu Lys Tyr Gly Gly Leu Asn Lys Ser Lys Pro
305                 310                 315                 320

Tyr Tyr Thr Gly Glu His Ala Lys Ala Ile Gly Asn Cys Pro Ile Trp
                325                 330                 335

Val Lys Thr Pro Leu Lys Leu Ala Asn Gly Thr Lys Tyr Arg Pro Pro
            340                 345                 350

Ala Lys Leu Leu Lys Glu Arg Gly Phe Phe Gly Ala Ile Ala Gly Phe
    355                 360                 365

Leu Glu Gly Gly Trp Glu Gly Met Ile Ala Gly Trp His Gly Tyr Thr
370                 375                 380

Ser His Gly Ala His Gly Val Ala Val Ala Ala Asp Leu Lys Ser Thr
385                 390                 395                 400

Gln Glu Ala Ile Asn Lys Ile Thr Lys Asn Leu Asn Ser Leu Ser Glu
                405                 410                 415

Leu Glu Val Lys Asn Leu Gln Arg Leu Ser Gly Ala Met Asp Glu Leu
            420                 425                 430

His Asn Glu Ile Leu Glu Leu Asp Glu Lys Val Asp Asp Leu Arg Ala
    435                 440                 445

Asp Thr Ile Ser Ser Gln Ile Glu Leu Ala Val Leu Leu Ser Asn Glu
450                 455                 460

Gly Ile Ile Asn Ser Glu Asp Glu His Leu Leu Ala Leu Glu Arg Lys
465                 470                 475                 480

Leu Lys Lys Met Leu Gly Pro Ser Ala Val Asp Ile Gly Asn Gly Cys
                485                 490                 495

Phe Glu Thr Lys His Lys Cys Asn Gln Thr Cys Leu Asp Arg Ile Ala
            500                 505                 510

Ala Gly Thr Phe Asn Ala Gly Glu Phe Ser Leu Pro Thr Phe Asp Ser
    515                 520                 525

Leu Asn Ile Thr Ala Ala Ser Leu Asn Asp Asp Gly Leu Asp Asn His
530                 535                 540

Thr Ile Leu Leu Tyr Tyr Ser Thr Ala Ala Ser Ser Leu Ala Val Thr
545                 550                 555                 560

Leu Met Ile Ala Ile Phe Ile Val Tyr Met Val Ser Arg Asp Asn Val
                565                 570                 575

Ser Cys Ser Ile Cys Leu
            580

<210> SEQ ID NO 49
<211> LENGTH: 1870
<212> TYPE: DNA
<213> ORGANISM: Artificial Sequence
<220> FEATURE:
<223> OTHER INFORMATION: sequence encoding mH13/B chimeric HA for rescue
      in B/Yamagata/16/88

<400> SEQUENCE: 49
agcagaagca gagcattttc taatatccac aaaatgaagg caataattgt actactcatg        60
gtagtaacat ccaacgcaga tcgaatctgc actgggataa catcttcaaa ctcacctcat       120
gtggtcaaaa cagctactca agggaagtt aatgtgactg gtgtgatacc actgacaaca       180
acaccaacaa atctcatttt tgcaaatctc aaaggaacaa agaccagagg gaaactatgc       240

```
ccaaactgtc tcaactgcac agatctggat gtggccttgg gcagaccaat gtgtatgggg    300
aacataccct cggcaaaagc ttcaatactc cacgaagtca gacctgttac atccgggtgc    360
tttcctataa tgcacgacag aacaaaaatc agacagctac ccaatcttct cagaggatat    420
gaaagaatcg agttatcaac ccataacgtt atcaacgcag aagtggcacc aggaggaccc    480
tacagacttg aacctcaaa atcttgccca gataaaggag ccagcagctt cttcgcaaca    540
atggcttggg ctgtcccaaa gagaggaaat cagtatacga atccactaac agtagaagta    600
ccatacattt gcacaaaagg agaagaccaa attactgttt gggggttcca ttctgatgtt    660
tccacaaaca tggcgaaact ctatggagac tcaaatcctc aaaagttcac ctcatctgcc    720
aatggagtaa ccacacatta tgtttctcag attggtgact ccccaaatca aacagaagac    780
ggagggctac cacaaagcgg cagaattgtt gttgattaca tggtgcaaaa acctgggaaa    840
acaggaacaa ttgtctatca agaggtgtt ttgttgcctc aaaaggtgtg gtgcgcaagt    900
ggcaggagca agtaataaaa agggtccttg cctttaattg gtgaagcaga ttgccttcac    960
gaaaaatacg gtggattaaa caaaagcaag ccttactaca caggagaaca tgcaaaagcc   1020
ataggaaatt gcccaatatg ggtgaaaaca cctttgaagc ttgccaatgg aaccaaatat   1080
agacctcctg caaaactatt aaaggaaagg ggttcttcg gagctattgc tggtttctta   1140
gagggaggat gggaaggaat gattgcaggt tggcacggat acacatctca tggagcacat   1200
ggagtggcag tggcagcaga ccttaagagc acgcaagaag ccataaacaa gataacaaaa   1260
aatctcaatt ctttgagtga gctagaagta aagaatcttc aaagactaag tggtgccatg   1320
gatgaactcc acaacgaaat actcgagctg gatgagaaag tggatgatct cagagctgac   1380
acaataagct cgcaaataga gcttgcagtc ttgctttcca acgaaggaat aataaacagt   1440
gaagatgagc atctattggc acttgagaga aaactaaaga aaatgctggg tcctctgct   1500
gtagacatag ggatggatg cttcgaaacc aaacacaagt gcaaccagac ctgcttagac   1560
aggatagctg ctggcacctt taatgcagga gaatttctc ttcccacttt tgattcactg   1620
aatattactg ctgcatcttt aaatgatgat ggattggata atcatactat actgctctac   1680
tactcaactg ctgcttctag tttggccgta acattgatga tagctatttt tattgtttat   1740
atggtctcca gagacaatgt ttcttgctcc atctgtctat aaggaaaatt aagccctgta   1800
ttttcctta ttgtagtgct tgtttgcttg ttaccattac aaagaaacgt tattgaaaaa   1860
tgctcttgtt                                                          1870
```

<210> SEQ ID NO 50
<211> LENGTH: 582
<212> TYPE: PRT
<213> ORGANISM: Artificial Sequence
<220> FEATURE:
<223> OTHER INFORMATION: sequence of mH13/B chimeric HA for rescue in
      amino acids from B/Yamagata/16/88

<400> SEQUENCE: 50

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60
```

```
Arg Gly Lys Leu Cys Pro Asn Cys Leu Asn Cys Thr Asp Leu Asp Val
 65                  70                  75                  80

Ala Leu Gly Arg Pro Met Cys Met Gly Asn Ile Pro Ser Ala Lys Ala
                 85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu Arg Ile Glu Leu Ser Thr His Asn Val Ile Asn Ala Glu Val
                130                 135                 140

Ala Pro Gly Gly Pro Tyr Arg Leu Gly Thr Ser Lys Ser Cys Pro Asp
145                 150                 155                 160

Lys Gly Ala Ser Ser Phe Phe Ala Thr Met Ala Trp Ala Val Pro Lys
                165                 170                 175

Arg Gly Asn Gln Tyr Thr Asn Pro Leu Thr Val Glu Val Pro Tyr Ile
                180                 185                 190

Cys Thr Lys Gly Glu Asp Gln Ile Thr Val Trp Gly Phe His Ser Asp
                195                 200                 205

Val Ser Thr Asn Met Ala Lys Leu Tyr Gly Asp Ser Asn Pro Gln Lys
210                 215                 220

Phe Thr Ser Ser Ala Asn Gly Val Thr Thr His Tyr Val Ser Gln Ile
225                 230                 235                 240

Gly Asp Phe Pro Asn Gln Thr Glu Asp Gly Gly Leu Pro Gln Ser Gly
                245                 250                 255

Arg Ile Val Val Asp Tyr Met Val Gln Lys Pro Gly Lys Thr Gly Thr
                260                 265                 270

Ile Val Tyr Gln Arg Gly Val Leu Leu Pro Gln Lys Val Trp Cys Ala
                275                 280                 285

Ser Gly Arg Ser Lys Val Ile Lys Gly Ser Leu Pro Leu Ile Gly Glu
                290                 295                 300

Ala Asp Cys Leu His Glu Lys Tyr Gly Gly Leu Asn Lys Ser Lys Pro
305                 310                 315                 320

Tyr Tyr Thr Gly Glu His Ala Lys Ala Ile Gly Asn Cys Pro Ile Trp
                325                 330                 335

Val Lys Thr Pro Leu Lys Leu Ala Asn Gly Thr Lys Tyr Arg Pro Pro
                340                 345                 350

Ala Lys Leu Leu Lys Glu Arg Gly Phe Phe Gly Ala Ile Ala Gly Phe
                355                 360                 365

Leu Glu Gly Gly Trp Glu Gly Met Ile Ala Gly Trp His Gly Tyr Thr
                370                 375                 380

Ser His Gly Ala His Gly Val Ala Val Ala Ala Asp Leu Lys Ser Thr
385                 390                 395                 400

Gln Glu Ala Ile Asn Lys Ile Thr Lys Asn Leu Asn Ser Leu Ser Glu
                405                 410                 415

Leu Glu Val Lys Asn Leu Gln Arg Leu Ser Gly Ala Met Asp Glu Leu
                420                 425                 430

His Asn Glu Ile Leu Glu Leu Asp Glu Lys Val Asp Asp Leu Arg Ala
                435                 440                 445

Asp Thr Ile Ser Ser Gln Ile Glu Leu Ala Val Leu Leu Ser Asn Glu
                450                 455                 460

Gly Ile Ile Asn Ser Glu Asp Glu His Leu Leu Ala Leu Glu Arg Lys
465                 470                 475                 480

Leu Lys Lys Met Leu Gly Pro Ser Ala Val Asp Ile Gly Asn Gly Cys
```

```
                    485                 490                 495
Phe Glu Thr Lys His Lys Cys Asn Gln Thr Cys Leu Asp Arg Ile Ala
                500                 505                 510

Ala Gly Thr Phe Asn Ala Gly Glu Phe Ser Leu Pro Thr Phe Asp Ser
            515                 520                 525

Leu Asn Ile Thr Ala Ala Ser Leu Asn Asp Asp Gly Leu Asp Asn His
        530                 535                 540

Thr Ile Leu Leu Tyr Tyr Ser Thr Ala Ala Ser Ser Leu Ala Val Thr
545                 550                 555                 560

Leu Met Ile Ala Ile Phe Ile Val Tyr Met Val Ser Arg Asp Asn Val
                565                 570                 575

Ser Cys Ser Ile Cys Leu
            580

<210> SEQ ID NO 51
<211> LENGTH: 22
<212> TYPE: PRT
<213> ORGANISM: Artificial Sequence
<220> FEATURE:
<223> OTHER INFORMATION: Exemplary B/Yamagata/16/88 120 loop substituted
      with amino acids from A/Mallard/Sweden/24/2002 virus (H8)

<400> SEQUENCE: 51

Arg Ile Arg Leu Ser Thr Tyr Asn Val Ile Asn Ala Glu Thr Ala Pro
1               5                   10                  15

Gly Gly Pro Tyr Arg Leu
            20

<210> SEQ ID NO 52
<211> LENGTH: 8
<212> TYPE: PRT
<213> ORGANISM: Artificial Sequence
<220> FEATURE:
<223> OTHER INFORMATION: Exemplary B/Yamagata/16/88 150 loop substituted
      with amino acids from A/Mallard/Sweden/24/2002 virus (H8)

<400> SEQUENCE: 52

Asn Ala Ser Thr Gly Gly Gln Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Exemplary B/Yamagata/16/88 160 loop substituted
      with amino acids from A/Mallard/Sweden/24/2002 virus (H8)

<400> SEQUENCE: 53

Lys Lys Lys Ala Asp Thr Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/Mallard/Sweden/24/2002 virus
      (H8)

<400> SEQUENCE: 54

Ala Asp Ala Lys Met Gln Thr
1               5
```

```
<210> SEQ ID NO 55
<211> LENGTH: 22
<212> TYPE: PRT
<213> ORGANISM: Artificial Sequence
<220> FEATURE:
<223> OTHER INFORMATION: Exemplary B/Yamagata/16/88 120 loop substituted
      with amino acids from A/northern shoveler/Netherlands/18/99

<400> SEQUENCE: 55

Lys Ile Glu Leu Ser Thr Ser Asn Val Ile Asn Ala Glu Val Ala Pro
1               5                   10                  15

Gly Gly Pro Tyr Arg Leu
            20

<210> SEQ ID NO 56
<211> LENGTH: 7
<212> TYPE: PRT
<213> ORGANISM: Artificial Sequence
<220> FEATURE:
<223> OTHER INFORMATION: Exemplary B/Yamagata/16/88 150 loop substituted
      with amino acids from A/northern shoveler/Netherlands/18/99

<400> SEQUENCE: 56

Pro Phe Gly Ser Ser Asn Ser
1               5

<210> SEQ ID NO 57
<211> LENGTH: 6
<212> TYPE: PRT
<213> ORGANISM: Artificial Sequence
<220> FEATURE:
<223> OTHER INFORMATION: Exemplary B/Yamagata/16/88 160 loop substituted
      with amino acids from A/northern shoveler/Netherlands/18/99

<400> SEQUENCE: 57

His Gln Ser Gly Thr Tyr
1               5

<210> SEQ ID NO 58
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/northern
      shoveler/Netherlands/18/99

<400> SEQUENCE: 58

Thr Thr Leu Lys Met His Gln
1               5

<210> SEQ ID NO 59
<211> LENGTH: 22
<212> TYPE: PRT
<213> ORGANISM: Artificial Sequence
<220> FEATURE:
<223> OTHER INFORMATION: Exemplary B/Yamagata/16/88 120 loop substituted
      with amino acids from A/black headed gull/Sweden/1/99

<400> SEQUENCE: 59

Arg Ile Glu Leu Ser Thr His Asn Val Ile Asn Ala Glu Val Ala Pro
1               5                   10                  15

Gly Gly Pro Tyr Arg Leu
            20
```

```
<210> SEQ ID NO 60
<211> LENGTH: 7
<212> TYPE: PRT
<213> ORGANISM: Artificial Sequence
<220> FEATURE:
<223> OTHER INFORMATION: Exemplary B/Yamagata/16/88 150 loop substituted
      with amino acids from A/black headed gull/Sweden/1/99

<400> SEQUENCE: 60

Pro Asp Lys Gly Ala Ser Ser
1               5

<210> SEQ ID NO 61
<211> LENGTH: 6
<212> TYPE: PRT
<213> ORGANISM: Artificial Sequence
<220> FEATURE:
<223> OTHER INFORMATION: Exemplary B/Yamagata/16/88 160 loop substituted
      with amino acids from A/black headed gull/Sweden/1/99

<400> SEQUENCE: 61

Lys Arg Gly Asn Gln Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/black headed gull/Sweden/1/99

<400> SEQUENCE: 62

Val Ser Thr Asn Met Ala Lys
1               5

<210> SEQ ID NO 63
<211> LENGTH: 22
<212> TYPE: PRT
<213> ORGANISM: Artificial Sequence
<220> FEATURE:
<223> OTHER INFORMATION: Exemplary B/Yamagata/16/88 120 loop substituted
      with amino acids from A/mallard/interior Alaska/7MP0167/2007

<400> SEQUENCE: 63

Arg Ile Lys Leu Ser Thr Phe Asn Val Ile Asn Ala Glu Thr Ala Pro
1               5                   10                  15

Gly Gly Pro Tyr Arg Leu
            20

<210> SEQ ID NO 64
<211> LENGTH: 8
<212> TYPE: PRT
<213> ORGANISM: Artificial Sequence
<220> FEATURE:
<223> OTHER INFORMATION: Exemplary B/Yamagata/16/88 150 loop substituted
      with amino acids from A/mallard/interior Alaska/7MP0167/2007

<400> SEQUENCE: 64

Asn Asn Thr Ser Asn Gln Gly Ser
1               5

<210> SEQ ID NO 65
<211> LENGTH: 6
<212> TYPE: PRT
<213> ORGANISM: Artificial Sequence
<220> FEATURE:
<223> OTHER INFORMATION: Exemplary B/Yamagata/16/88 160 loop substituted
``` with amino acids from A/mallard/interior Alaska/7MP0167/2007

<400> SEQUENCE: 65

Leu Lys Ser Gly Gln Phe
1               5

<210> SEQ ID NO 66
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/mallard/interior
      Alaska/7MP0167/2007

<400> SEQUENCE: 66

Pro Thr Ser Asp Met Gln Ile
1               5

<210> SEQ ID NO 67
<211> LENGTH: 7
<212> TYPE: PRT
<213> ORGANISM: Artificial Sequence
<220> FEATURE:
<223> OTHER INFORMATION: Exemplary B/Yamagata/16/88 150 loop substituted
      with amino acids from A/northern shoveler/Netherlands/18/99

<400> SEQUENCE: 67

Lys Phe Gly Ser Ser Asn Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Exemplary B/Yamagata/16/88 160 loop substituted
      with amino acids from A/mallard/Sweden/24/2002

<400> SEQUENCE: 68

Lys Lys Lys Pro Asp Thr Tyr
1               5

<210> SEQ ID NO 69
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/mallard/Sweden/24/2002

<400> SEQUENCE: 69

Pro Asp Ala Lys Met Gln Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Exemplary B/Yamagata/16/88 190 helix
      substituted with amino acids from A/northern
      shoveler/Netherlands/18/99

<400> SEQUENCE: 70

Ala Thr Leu Lys Met His Gln
1               5

<210> SEQ ID NO 71
<211> LENGTH: 1765
<212> TYPE: DNA
<213> ORGANISM: Artificial Sequence
<220> FEATURE:
<223> OTHER INFORMATION: Nucleic acid sequence encoding influenza A/black headed gull/Sweden/1/99 virus HA

<400> SEQUENCE: 71

| | | | | | |
|---|---|---|---|---|---|
| agcaaaagca | ggggaaaatt | tcaacaaact | gatacaagag | aaatggacat | cccagtagtc | 60 |
| gcattcttga | tattaaccag | tacatgcgta | caggctgata | ggatatgtgt | tgggtactta | 120 |
| agcaccaact | catcagaaaa | ggttgacaca | ctgttagaaa | acgatgttcc | ggttacaagc | 180 |
| tctgttgatc | tggttgagac | taaccacaca | ggaacatatt | gttctttggg | tggaatcagt | 240 |
| ccggtgcacc | tggagactg | tagcttcgag | ggctggattg | tagggaaccc | tgcctgtgcc | 300 |
| agcaacctgg | ggatcagaga | atggtcatac | ttgattgaag | atccttctgc | tcctcatgga | 360 |
| ttgtgctacc | caggggagtt | agacaacaat | ggagaattga | ggcacttgtt | cagtggaatc | 420 |
| agatctttca | gtagaacaga | gttgattgca | cctacttctt | gggggggcagt | gaatgatgga | 480 |
| gtatcgtcgg | cctgtccaga | taaaggagcc | agcagctttt | accggaactt | ggtatggttt | 540 |
| gtgaagagag | gaaatcagta | tcctgtaatc | cgcgggacct | acaacaacac | tactggcaga | 600 |
| gatgttttgg | ttatatgggg | gtatacatcac | cctgtttcca | cagacgaagc | gaaacaacta | 660 |
| tatgtcaata | acaacccata | cacgttggta | tctaccagtt | catggagtag | gaaatacaac | 720 |
| ttagagactg | gaacccggcc | tggatacaat | ggccaaaaga | gttggatgaa | gatttactgg | 780 |
| tatttgatgc | acccagggga | gtcaatcagt | ttcgaaagca | atggaggatt | attggcaccc | 840 |
| agatatggtt | atattattga | ggaatatgga | aaagggcgaa | ttttccaaag | ccgcattcga | 900 |
| attgctaaat | gcaatactaa | gtgccaaaca | tctgtcggtg | gataaatac | caacaaaaca | 960 |
| tttcaaaaca | tagagagaaa | tgcacttggg | gattgcccga | aatacataaa | atctggacag | 1020 |
| ctcaagttag | ccaccggact | taggaatgta | cctgccatat | caaacagagg | gttgttcggg | 1080 |
| gctattgcag | gcttcataga | aggtggttgg | ccaggattaa | taaatggttg | gtatggattc | 1140 |
| caacatcaga | acgaacaagg | agtgggcatg | gctgcagaca | aagagtcaac | acaaaaggct | 1200 |
| attgatcaaa | taacaaccaa | gataaacaat | atcattgaaa | aaatgaatgg | gaattatgac | 1260 |
| tccatacgag | gtgaattcaa | tcaggtggaa | caaagaataa | atatgcttgc | agacagaata | 1320 |
| gatgatgctg | taactgatgt | atggtcatac | aatgcaaagc | ttcttgtgtt | actagagaac | 1380 |
| gataaaactc | tagacatgca | tgatgctaat | gttagaaacc | tgcatgatca | agtccgtaga | 1440 |
| gcactaaaga | ccaatgcaat | tgatgaggga | aatggatgtt | tcgaactcct | ccataaatgc | 1500 |
| aatgactctt | gcatggagac | aataagaaat | ggaacgtaca | atcatacaga | atatgaggaa | 1560 |
| gaatccaaat | taaagagaca | ggaaatagaa | ggaataaagc | tgaagtcaga | cgatagtgtt | 1620 |
| tataaagcac | tatcgattta | cagctgcatt | gcaagcagta | ttgtattggt | aggactcata | 1680 |
| cttacattca | tcatgtgggc | atgcagcagt | ggcaattgcc | ggttcaatat | ttgtatataa | 1740 |
| gtagaaaaaa | caccctttgtt | ctact | | | | 1765 |

<210> SEQ ID NO 72
<211> LENGTH: 565
<212> TYPE: PRT
<213> ORGANISM: Artificial Sequence
<220> FEATURE:
<223> OTHER INFORMATION: sequence of influenza A/black headed gull/Sweden/1/99 virus HA

<400> SEQUENCE: 72

```
Met Asp Ile Pro Val Val Ala Phe Leu Ile Leu Thr Ser Thr Cys Val
1               5                   10                  15

Gln Ala Asp Arg Ile Cys Val Gly Tyr Leu Ser Thr Asn Ser Ser Glu
            20                  25                  30

Lys Val Asp Thr Leu Leu Glu Asn Asp Val Pro Val Thr Ser Ser Val
        35                  40                  45

Asp Leu Val Glu Thr Asn His Thr Gly Thr Tyr Cys Ser Leu Gly Gly
    50                  55                  60

Ile Ser Pro Val His Leu Gly Asp Cys Ser Phe Glu Gly Trp Ile Val
65                  70                  75                  80

Gly Asn Pro Ala Cys Ala Ser Asn Leu Gly Ile Arg Glu Trp Ser Tyr
            85                  90                  95

Leu Ile Glu Asp Pro Ser Ala Pro His Gly Leu Cys Tyr Pro Gly Glu
            100                 105                 110

Leu Asp Asn Asn Gly Glu Leu Arg His Leu Phe Ser Gly Ile Arg Ser
            115                 120                 125

Phe Ser Arg Thr Glu Leu Ile Ala Pro Thr Ser Trp Gly Ala Val Asn
130                 135                 140

Asp Gly Val Ser Ser Ala Cys Pro Asp Lys Gly Ala Ser Ser Phe Tyr
145                 150                 155                 160

Arg Asn Leu Val Trp Phe Val Lys Arg Gly Asn Gln Tyr Pro Val Ile
                165                 170                 175

Arg Gly Thr Tyr Asn Asn Thr Thr Gly Arg Asp Val Leu Val Ile Trp
            180                 185                 190

Gly Ile His His Pro Val Ser Thr Asp Glu Ala Lys Gln Leu Tyr Val
        195                 200                 205

Asn Asn Asn Pro Tyr Thr Leu Val Ser Thr Ser Ser Trp Ser Arg Lys
210                 215                 220

Tyr Asn Leu Glu Thr Gly Thr Arg Pro Gly Tyr Asn Gly Gln Lys Ser
225                 230                 235                 240

Trp Met Lys Ile Tyr Trp Tyr Leu Met His Pro Gly Glu Ser Ile Ser
                245                 250                 255

Phe Glu Ser Asn Gly Gly Leu Leu Ala Pro Arg Tyr Gly Tyr Ile Ile
            260                 265                 270

Glu Glu Tyr Gly Lys Gly Arg Ile Phe Gln Ser Arg Ile Arg Ile Ala
        275                 280                 285

Lys Cys Asn Thr Lys Cys Gln Thr Ser Val Gly Gly Ile Asn Thr Asn
290                 295                 300

Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ala Ile Ser Asn Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Gln Asn Glu Gln Gly Val Gly Met Ala Ala Asp Lys Glu Ser Thr Gln
370                 375                 380

Lys Ala Ile Asp Gln Ile Thr Thr Lys Ile Asn Asn Ile Ile Glu Lys
385                 390                 395                 400

Met Asn Gly Asn Tyr Asp Ser Ile Arg Gly Glu Phe Asn Gln Val Glu
```

405                 410                 415
Gln Arg Ile Asn Met Leu Ala Asp Arg Ile Asp Asp Ala Val Thr Asp
                420                 425                 430

Val Trp Ser Tyr Asn Ala Lys Leu Leu Val Leu Leu Glu Asn Asp Lys
            435                 440                 445

Thr Leu Asp Met His Asp Ala Asn Val Arg Asn Leu His Asp Gln Val
        450                 455                 460

Arg Arg Ala Leu Lys Thr Asn Ala Ile Asp Glu Gly Asn Gly Cys Phe
465                 470                 475                 480

Glu Leu Leu His Lys Cys Asn Asp Ser Cys Met Glu Thr Ile Arg Asn
                485                 490                 495

Gly Thr Tyr Asn His Thr Glu Tyr Glu Glu Ser Lys Leu Lys Arg
            500                 505                 510

Gln Glu Ile Glu Gly Ile Lys Leu Lys Ser Asp Ser Val Tyr Lys
        515                 520                 525

Ala Leu Ser Ile Tyr Ser Cys Ile Ala Ser Ser Ile Val Leu Val Gly
530                 535                 540

Leu Ile Leu Thr Phe Ile Met Trp Ala Cys Ser Ser Gly Asn Cys Arg
545                 550                 555                 560

Phe Asn Ile Cys Ile
            565

<210> SEQ ID NO 73
<211> LENGTH: 585
<212> TYPE: PRT
<213> ORGANISM: Artificial Sequence
<220> FEATURE:
<223> OTHER INFORMATION: Amino acid sequence of mouse adapted Influenza
      B/Malaysia/2506/2004 virus HA
<220> FEATURE:
<221> NAME/KEY: misc_feature
<222> LOCATION: (212)..(212)
<223> OTHER INFORMATION: Xaa = Asn or Ser
<220> FEATURE:
<221> NAME/KEY: misc_feature
<222> LOCATION: (214)..(214)
<223> OTHER INFORMATION: Xaa = Asn, Ile, Thr or Ser

<400> SEQUENCE: 73

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn

-continued

```
            145                 150                 155                 160
        Val Thr Asn Gly Asn Gly Phe Phe Ala Thr Met Ala Trp Ala Val Pro
                        165                 170                 175

Lys Asn Asp Asn Asn Lys Thr Ala Thr Asn Ser Leu Thr Ile Glu Val
                        180                 185                 190

Pro Tyr Ile Cys Thr Glu Gly Glu Asp Gln Ile Thr Val Trp Gly Phe
                        195                 200                 205

His Ser Asp Xaa Glu Xaa Gln Met Ala Lys Leu Tyr Gly Asp Ser Lys
                        210                 215                 220

Pro Gln Lys Phe Thr Ser Ser Ala Asn Gly Val Thr Thr His Tyr Val
        225                 230                 235                 240

Ser Gln Ile Gly Gly Phe Pro Asn Gln Thr Glu Asp Gly Gly Leu Pro
                        245                 250                 255

Gln Ser Gly Arg Ile Val Val Asp Tyr Met Val Gln Lys Ser Gly Lys
                        260                 265                 270

Thr Gly Thr Ile Thr Tyr Gln Arg Gly Ile Leu Leu Pro Gln Lys Val
                        275                 280                 285

Trp Cys Ala Ser Gly Arg Ser Lys Val Ile Lys Gly Ser Leu Pro Leu
                        290                 295                 300

Ile Gly Glu Ala Asp Cys Leu His Glu Lys Tyr Gly Gly Leu Asn Lys
        305                 310                 315                 320

Ser Lys Pro Tyr Tyr Thr Gly Glu His Ala Lys Ala Ile Gly Asn Cys
                        325                 330                 335

Pro Ile Trp Val Lys Thr Pro Leu Lys Leu Ala Asn Gly Thr Lys Tyr
                        340                 345                 350

Arg Pro Pro Ala Lys Leu Leu Lys Glu Arg Gly Phe Phe Gly Ala Ile
                        355                 360                 365

Ala Gly Phe Leu Glu Gly Gly Trp Glu Gly Met Ile Ala Gly Trp His
                        370                 375                 380

Gly Tyr Thr Ser His Gly Ala His Gly Val Ala Val Ala Ala Asp Leu
        385                 390                 395                 400

Lys Ser Thr Gln Glu Ala Ile Asn Lys Ile Thr Lys Asn Leu Asn Ser
                        405                 410                 415

Leu Ser Glu Leu Glu Val Lys Asn Leu Gln Arg Leu Ser Gly Ala Met
                        420                 425                 430

Asp Glu Leu His Asn Glu Ile Leu Glu Leu Asp Glu Lys Val Asp Asp
                        435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu His Leu Leu Ala Leu
        465                 470                 475                 480

Glu Arg Lys Leu Lys Lys Met Leu Gly Pro Ser Ala Val Glu Ile Gly
                        485                 490                 495

Asn Gly Cys Phe Glu Thr Lys His Lys Cys Asn Gln Thr Cys Leu Asp
                        500                 505                 510

Arg Ile Ala Ala Gly Thr Phe Asp Ala Gly Glu Phe Ser Leu Pro Thr
                        515                 520                 525

Phe Asp Ser Leu Asn Ile Thr Ala Ala Ser Leu Asn Asp Asp Gly Leu
                        530                 535                 540

Asp Asn His Thr Ile Leu Leu Tyr Tyr Ser Thr Ala Ala Ser Ser Leu
        545                 550                 555                 560

Ala Val Thr Leu Met Ile Ala Ile Phe Val Val Tyr Met Val Ser Arg
                        565                 570                 575
```

```
Asp Asn Val Ser Cys Ser Ile Cys Leu
        580                 585

<210> SEQ ID NO 74
<211> LENGTH: 15
<212> TYPE: PRT
<213> ORGANISM: Artificial Sequence
<220> FEATURE:
<223> OTHER INFORMATION: Signal peptide of mouse adapted Influenza
      B/Malaysia/2506/2004 virus HA

<400> SEQUENCE: 74

Met Lys Ala Ile Ile Val Leu Leu Met Val Val Thr Ser Asn Ala
1               5                   10                  15

<210> SEQ ID NO 75
<211> LENGTH: 347
<212> TYPE: PRT
<213> ORGANISM: Artificial Sequence
<220> FEATURE:
<223> OTHER INFORMATION: HA1 of mouse adapted Influenza
      B/Malaysia/2506/2004 virus HA
<220> FEATURE:
<221> NAME/KEY: misc_feature
<222> LOCATION: (197)..(197)
<223> OTHER INFORMATION: Xaa = Asn or Ser
<220> FEATURE:
<221> NAME/KEY: misc_feature
<222> LOCATION: (199)..(199)
<223> OTHER INFORMATION: Xaa = Asn, Ile, Thr or Ser

<400> SEQUENCE: 75

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Asn Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Asp Asn Asn Lys Thr Ala Thr Asn Ser Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Xaa Glu Xaa Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220
```

```
Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
            245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
            275                 280                 285

Leu Ile Gly Glu Ala Asp Cys Leu His Glu Lys Tyr Gly Gly Leu Asn
            290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg
            340                 345

<210> SEQ ID NO 76
<211> LENGTH: 223
<212> TYPE: PRT
<213> ORGANISM: Artificial Sequence
<220> FEATURE:
<223> OTHER INFORMATION: HA2 of mouse adapted Influenza
      B/Malaysia/2506/2004 virus HA

<400> SEQUENCE: 76

Gly Phe Phe Gly Ala Ile Ala Gly Phe Leu Glu Gly Gly Trp Glu Gly
1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Glu Ile Gly Asn Gly Cys Phe Glu Thr Lys His Lys Cys
    130                 135                 140

Asn Gln Thr Cys Leu Asp Arg Ile Ala Ala Gly Thr Phe Asp Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Ile Ala Ile Phe Val
        195                 200                 205

Val Tyr Met Val Ser Arg Asp Asn Val Ser Cys Ser Ile Cys Leu
    210                 215                 220

<210> SEQ ID NO 77
```

<211> LENGTH: 250
<212> TYPE: PRT
<213> ORGANISM: Artificial Sequence
<220> FEATURE:
<223> OTHER INFORMATION: Head Sequence of mouse adapted Influenza
      B/Malaysia/2506/2004 virus HA
<220> FEATURE:
<221> NAME/KEY: misc_feature
<222> LOCATION: (155)..(155)
<223> OTHER INFORMATION: Xaa = Asn or Ser
<220> FEATURE:
<221> NAME/KEY: misc_feature
<222> LOCATION: (157)..(157)
<223> OTHER INFORMATION: Xaa = Asn, Ile, Thr or Ser

<400> SEQUENCE: 77

Asn Leu Lys Gly Thr Glu Thr Arg Gly Lys Leu Cys Pro Lys Cys Leu
1               5                   10                  15

Asn Cys Thr Asp Leu Asp Val Ala Leu Gly Arg Pro Lys Cys Thr Gly
            20                  25                  30

Asn Ile Pro Ser Ala Arg Val Ser Ile Leu His Glu Val Arg Pro Val
        35                  40                  45

Thr Ser Gly Cys Phe Pro Ile Met His Asp Arg Thr Lys Ile Arg Gln
    50                  55                  60

Leu Pro Asn Leu Leu Arg Gly Tyr Glu His Ile Arg Leu Ser Thr His
65                  70                  75                  80

Asn Val Ile Asn Ala Glu Asn Ala Pro Gly Gly Pro Tyr Lys Ile Gly
                85                  90                  95

Thr Ser Gly Ser Cys Pro Asn Val Thr Asn Gly Asn Gly Phe Phe Ala
            100                 105                 110

Thr Met Ala Trp Ala Val Pro Lys Asn Asp Asn Asn Lys Thr Ala Thr
        115                 120                 125

Asn Ser Leu Thr Ile Glu Val Pro Tyr Ile Cys Thr Glu Gly Glu Asp
    130                 135                 140

Gln Ile Thr Val Trp Gly Phe His Ser Asp Xaa Glu Xaa Gln Met Ala
145                 150                 155                 160

Lys Leu Tyr Gly Asp Ser Lys Pro Gln Lys Phe Thr Ser Ser Ala Asn
                165                 170                 175

Gly Val Thr Thr His Tyr Val Ser Gln Ile Gly Gly Phe Pro Asn Gln
            180                 185                 190

Thr Glu Asp Gly Gly Leu Pro Gln Ser Gly Arg Ile Val Val Asp Tyr
        195                 200                 205

Met Val Gln Lys Ser Gly Lys Thr Gly Thr Ile Thr Tyr Gln Arg Gly
    210                 215                 220

Ile Leu Leu Pro Gln Lys Val Trp Cys Ala Ser Gly Arg Ser Lys Val
225                 230                 235                 240

Ile Lys Gly Ser Leu Pro Leu Ile Gly Glu
                245                 250

<210> SEQ ID NO 78
<211> LENGTH: 42
<212> TYPE: PRT
<213> ORGANISM: Artificial Sequence
<220> FEATURE:
<223> OTHER INFORMATION: N-terminal segment of Stalk of mouse adapted
      Influenza B/Malaysia/2506/2004 virus HA

<400> SEQUENCE: 78

Asp Arg Ile Cys Thr Gly Ile Thr Ser Ser Asn Ser Pro His Val Val
1               5                   10                  15

```
Lys Thr Ala Thr Gln Gly Glu Val Asn Val Thr Gly Val Ile Pro Leu
                20                  25                  30

Thr Thr Thr Pro Thr Lys Ser His Phe Ala
        35                  40

<210> SEQ ID NO 79
<211> LENGTH: 241
<212> TYPE: PRT
<213> ORGANISM: Artificial Sequence
<220> FEATURE:
<223> OTHER INFORMATION: C-terminal segment of Stalk of mouse adapted
      Influenza B/Malaysia/2506/2004 virus HA

<400> SEQUENCE: 79

Ala Asp Cys Leu His Glu Lys Tyr Gly Gly Leu Asn Lys Ser Lys Pro
1               5                   10                  15

Tyr Tyr Thr Gly Glu His Ala Lys Ala Ile Gly Asn Cys Pro Ile Trp
                20                  25                  30

Val Lys Thr Pro Leu Lys Leu Ala Asn Gly Thr Lys Tyr Arg Pro Pro
            35                  40                  45

Ala Lys Leu Leu Lys Glu Arg Gly Phe Phe Gly Ala Ile Ala Gly Phe
        50                  55                  60

Leu Glu Gly Gly Trp Glu Gly Met Ile Ala Gly Trp His Gly Tyr Thr
65                  70                  75                  80

Ser His Gly Ala His Gly Val Ala Val Ala Ala Asp Leu Lys Ser Thr
                85                  90                  95

Gln Glu Ala Ile Asn Lys Ile Thr Lys Asn Leu Asn Ser Leu Ser Glu
                100                 105                 110

Leu Glu Val Lys Asn Leu Gln Arg Leu Ser Gly Ala Met Asp Glu Leu
            115                 120                 125

His Asn Glu Ile Leu Glu Leu Asp Glu Lys Val Asp Asp Leu Arg Ala
        130                 135                 140

Asp Thr Ile Ser Ser Gln Ile Glu Leu Ala Val Leu Leu Ser Asn Glu
145                 150                 155                 160

Gly Ile Ile Asn Ser Glu Asp Glu His Leu Leu Ala Leu Glu Arg Lys
                165                 170                 175

Leu Lys Lys Met Leu Gly Pro Ser Ala Val Glu Ile Gly Asn Gly Cys
            180                 185                 190

Phe Glu Thr Lys His Lys Cys Asn Gln Thr Cys Leu Asp Arg Ile Ala
        195                 200                 205

Ala Gly Thr Phe Asp Ala Gly Glu Phe Ser Leu Pro Thr Phe Asp Ser
    210                 215                 220

Leu Asn Ile Thr Ala Ala Ser Leu Asn Asp Asp Gly Leu Asp Asn His
225                 230                 235                 240

Thr

<210> SEQ ID NO 80
<211> LENGTH: 2312
<212> TYPE: DNA
<213> ORGANISM: Artificial Sequence
<220> FEATURE:
<223> OTHER INFORMATION: Nucleotide sequence of mouse adapted Influenza
      B/Malaysia/2506/2004 virus PB1

<400> SEQUENCE: 80
aatataaatc cttatttcct cttcatagat gtgcccatac aggcagcaat ttcaacaaca    60
ttcccataca ctggtgttcc cccttattcc catggaacgg gaacaggcta cacaatagac   120
```

| | |
|---|---|
| accgtgatca gaacacatga gtactcaarc aaggggaaac agtacatttc tgatgttaca | 180 |
| ggatgcacaa tggtagatcc aacaaatggc ccattacccg aagataatga gccgagtgcc | 240 |
| tatgcgcaat tagattgcgt tttagaggct ttggatagaa tggatgaaga cacccaggt | 300 |
| ctgtttcaag cagcctcaca gaatgctatg gaggccctaa tggtcacaac tgtagacaaa | 360 |
| ttaacccagg ggagacagac ttttgattgg acagtatgca gaaaccaacc tgctgcaacg | 420 |
| gcactgaaca caacaataac ctcttttagg ttgaatgatt taaatggagc cgacaaaggt | 480 |
| ggattagtac cttttttgcca ggatatcatt gattcattag acagacctga aatgactttc | 540 |
| ttctcagtaa agaatataaa gaaaaaattg cctgccaaaa acagaaaggg tttcctcata | 600 |
| aagaggatac caatgaaggt aaaggacaaa ataaccaaag tggaatacat caaaagagca | 660 |
| ttatcattaa acacaatgac aaaagacgct gaaagaggca aactaaaaag aagagcgatt | 720 |
| gccaccgctg gaatacaaat cagagggttt gtattagtag ttgaaaactt ggctaaaaat | 780 |
| atatgtgaaa atctagaaca aagtggttta ccagtaggtg gaaacgagaa gaaagccaaa | 840 |
| ctgtcaaacg cagtggcaaa aatgctcagt aactgcccac ctggagggat cagcatgaca | 900 |
| gtaacaggag acaatactaa atggaatgaa tgtttaaacc caagaatctt tttggctatg | 960 |
| actgaaagaa taaccagaga cagcccaatt tggttcaggg attttttgtag tatagcaccg | 1020 |
| gtcctgttct ccaataagat agccagattg gggaaagggt ttatgataac aagcaaaaca | 1080 |
| aagagactga aggctcaaat accttgtcct gatctgttta gtatatcatt agaaagatat | 1140 |
| aatgaagaaa caagggcaaa attgaaaaag ctaaaaccat tcttcaatga agaaggaact | 1200 |
| gcatctttgt cacctgggat gatgatggga atgtttaata tgctatctac cgtgttgggg | 1260 |
| gtagctgcac taggtatcaa gaacattgga acaaagaat acttatggga tggactgcaa | 1320 |
| tcttctgatg atttttgctct atttgttaat gcaaaggatg aagaaacatg tatggaagga | 1380 |
| ataaacgact tttaccgaac atgtaaatta ttgggaataa acatgagcaa aaagaaaagt | 1440 |
| tactgtaatg agactggaat gttttgaattt acaagcatgt tctacagaga tggatttgta | 1500 |
| tctaattttg caatggaact cccttcattt ggggttgctg gagtaaatga atcagcagat | 1560 |
| atggcaatag gatgacaat aataaagaac aacatgatca acaatggaat gggtccggca | 1620 |
| acagcacaaa cagccataca gttattcata gctgattata gatacaccta caaatgccac | 1680 |
| aggggagatt ccaaagtaga gggaagagag atgaaaatca taaggagtt atgggaaaac | 1740 |
| actaaaggaa gagatggtct attagtagca gatggtgggc ccaacattta caatttgaga | 1800 |
| aacttgcata ttccagaaat agtattaaag tataacttaa tggaccctga atacaaaggg | 1860 |
| cggttacttc atcctcaaaa tccctttgtg ggacatttgt ctattgaggg catcaaagag | 1920 |
| gcagatataa ccccagcaca tggtccagta aagaaaatgg actacgatgc ggtgtctgga | 1980 |
| actcatagtt ggagaaccaa agaaacaga tctatactaa acactgatca gaggaacatg | 2040 |
| attcttgagg aacaatgcta cgctaagtgt tgcaacctat ttgaggcctg ttttaacagt | 2100 |
| gcatcataca ggaagccagt gggtcaacat agcatgcttg aggctatggc ccacagatta | 2160 |
| agaatggatg cacgattaga ttatgaatca ggaagaatgt caaggatga ttttgagaaa | 2220 |
| gcaatggctc accttggtga gattgggtac atataagctt cgaagatgtc tatggggtta | 2280 |
| ttggtcatca ttgaatacat gcgatacaca aa | 2312 |

<210> SEQ ID NO 81
<211> LENGTH: 2358
<212> TYPE: DNA
<213> ORGANISM: Artificial Sequence
<220> FEATURE:
<223> OTHER INFORMATION: Nucleotide sequence of mouse adapted Influenza
     B/Malaysia/2506/2004 virus PB2

<400> SEQUENCE: 81

```
ttcaagatga cattggccaa aattgaattg ttaaaacaac tgctaaggga caatgaagcc      60
aaaacagttt tgaagcaaac aacggtagac caatataaca taataagaaa attcaataca     120
tcaaggattg aaaagaatcc ttcactaagg atgaaatggg ccatgtgttc taattttccc     180
ttggctctaa ccaagggcga catggcaaat agaatcccct tggaatacaa aggaatacaa     240
cttaaaacaa atgctgaaga cataggaacc aaaggccaaa tgtgctcaat agcagcagtt     300
acttggtgga atacatatgg accaatagga gatactgaag gtttcgaaag ggtctacgaa     360
agcttttttc tcagaaaaat gagacttgac aatgccactt ggggccgaat aactttggc      420
ccagttgaaa gagtgagaaa aagggtactg ctaaaccctc tcaccaagga aatgcctcca     480
gatgaggcga gcaatgtgat aatggaaata ttgttcccta agaagcagg aataccaaga      540
gaatccactt ggatacatag rgaactgata aagaaaaaa gagaaaaatt gaaaggaaca      600
atgataactc caatcgtact ggcatacatg cttgaaagag aactggttgc tcgaagaaga     660
ttcttgccag tggcaggagc aacatcagct gagttcatag aaatgctaca ctgcttacaa     720
ggtgaaaatt ggagacaaat atatcaccca ggagggaata attaactga gtctaggtct      780
caatcaatga tagtagcttg tagaaaaata atcagaagat caatagtcgc ttcaaaccca     840
ctggagctag ctgtagaaat tgcaaacaag actgtgatag atactgaacc tttaaagtca     900
tgtctggcag ccatagacgg aggtgatgta gcttgtgaca taataagagc tgcattagga     960
ctaaagatca gacaaagaca agatttggaa cggcttgagt taaaaagaat atcaggaaga    1020
ggattcaaaa atgatgaaga atattaata gggaacggaa caatacagaa gattggaata    1080
tgggacgggg aagaggagtt ccatgtaaga tgtggtgaat gcagggaat attaaaaaag     1140
agtaaaatga aactggaaaa actactaata aattcagcca aaaaggagga catgagagat    1200
ttaataatct tatgcatggt attttctcaa gacactagga tgttccaagg ggtgagagga    1260
gaaataaatt ttcttaatcg agcaggccaa ctttttatctc caatgtacca actccaacga    1320
tattttttga atagaagcaa cgacctttt gatcaatggg ggtatgagga atcacccaaa     1380
gcaagtgaac tatatgggat aaatgaatca atgaatgcat ctgactatac attgaaaggg    1440
gttgtagtga caagaaatgt aattgacgac tttagctcta ctgaaacaga aaaagtatcc    1500
ataacaaaaa atcttagttt aataaaaagg actggggaag tcataatggg agctaatgac     1560
gtgagtgaat tagaatcaca agcacagctg atgataacat atgatacacc taagatgtgg    1620
gaaatgggaa caaccaaaga actggtcaa acacttatc aatgggtgct aaaaacttg        1680
gtaacactga aggctcagtt tcttctagga aaagaggaca tgttccaatg ggatgcattt    1740
gaagcatttg agagcataat tcctcagaag atggctggtc agtacagtgg attgcaaga     1800
gcagtgctca acaaatgag agaccaggag gttatgaaaa ctgaccagtt cataaagttg    1860
ttgccttttt gtttctcacc accaaaatta aggagcaatg gggagcctta tcaattctta    1920
aaacttgtat tgaaaggagg aggggaaaat ttcatcgaag taaggaaagg gtcccctcta    1980
ttttcctata atccacaaac agaagtccta accatatgcg gcagaatgat gtcattaaaa    2040
gggaaaattg aagatgaaga aaggaataga tcaatgggga atgcagtatt agcaggcttt    2100
ctcgttagtg gcaagtatga cccagatctt ggagatttca aaactattga gaacttgaa     2160
aggctgaaac cggggaaaa ggcaaatatc ttactttatc aaggaaagcc agttaaagta    2220
```

```
gttaaaagga aaaggtatag tgctttgtcc aatgacattt cacaaggaat taagagacaa    2280
agaatgacag ttgagtccat ggggtgggcc ttgagctaat ataaatttat ccattaattc    2340
aatgaacgca attgagtg                                                  2358

<210> SEQ ID NO 82
<211> LENGTH: 2248
<212> TYPE: DNA
<213> ORGANISM: Artificial Sequence
<220> FEATURE:
<223> OTHER INFORMATION: Nucleotide sequence of mouse adapted Influenza
      B/Malaysia/2506/2004 virus PA

<400> SEQUENCE: 82
atacttttat tacaagaaac ttccaaacta caataataca aaaggccaga aacacaatgg      60
cagaatttag tgaagatcct gaattacaac cagcaatgct attcaatatc tgcgtccatc    120
tagaggtttg ctatgtaata agtgacatga attttcttga cgaagaagga aaagcatata    180
cagcattaga aggacaaggg aaagaacaaa atttgagacc acaatatgaa gtaattgagg    240
gaatgccaag aaccatagca tggatggtcc aaagatcctt agctcaagag catggaatag    300
agactcccaa gtatctggct gatttgtttg attataaaac caagagattt atagaagttg    360
gaataacaaa aggattggct gatgattact tttggaaaaa gaaagaaaag ttgggaaata    420
gcatggaact gatgatattc agctacaatc aagactactc gttaagtaat gaatcctcat    480
tggatgagga agggaaaggg agagtgctaa gcagactcac agaacttcag gctgaattaa    540
gtctgaaaaa cctatggcaa gttctcatag agaagaagaa tgttgaaaag ggaattgact    600
ttaaacttgg acaaacaata tctagactaa gggatatatc tgttcccgct ggtttctcca    660
attttgaagg aatgaggagc tacatagaca atatagaccc aaaaggagca atagagagaa    720
atctagcaag gatgtctccc ttagtatcag tcacacctaa aaagttgaca tgggaggacc    780
taagaccaat agggcctcac atttacaacc atgagctacc agaagttcca tataatgcct    840
ttcttctaat gtctgatgaa ctggggctgg ccaatatgac tgagggaaag tccaaaaaac    900
cgaagacatt agccaaagaa tgtctagaaa agtactcaac actacgggat caaactracc    960
caatattaat aatgaaaagc gaaaaagcta atgaaaattt cctatggaag ctttggagag   1020
actgtgtaaa tacaataagt aatgaggaaa tgagtaacga gttacagaaa accaattatg   1080
ccaagtgggc cacaggggat ggattaacat accagaaaat aatgaaagaa gtagcaatag   1140
atgacgaaac aatgtgccaa gaagagccta aaatccctaa taaatgtaga gtggctgctt   1200
gggttcaaac agagatgaat ctattgagca ctctgacaag taaaagagct ctggacctac   1260
cagaaatagg gccagacgta gcacccgtgg agcatgtagg gagtgaaaga aggaaatact   1320
ttgttaatga aatcaactac tgtaaggcct ctacagttat gatgaagtat gtgcttttc    1380 acacttcatt gttgaatgaa agcaatgcca gcatgggaaa atacaaagta ataccaataa   1440
ccaatagagt agtaaatgaa acaggagaaa gtttcgacat gctttatggt ctggcggtta   1500
aaggacaatc tcatctgagg ggagatactg atgttgtaac agttgtaact ttcgaattta   1560
gtagtacaga cccaagagtg gactcaggaa agtggccaaa atatactgtg tttaggattg   1620
gctccctatt tgtgagtggg agggaaaaat ctgtgtacct gtattgccga gtgaatggca   1680
caaataagat ccaaatgaaa tgggggatgg aagctagaag atgtctgctt caatcaatgc   1740
aacaaatgga agcaattgtt gaacaggaat catcgataca gggatatgac atgaccaagg   1800
cttgtttcaa gggagacaga gtaaatagcc ccaaaacttt cagtattgga actcaagaag   1860
```

```
ggaaactagt aaaaggatcc tttggaaaag cactaagagt aatatttact aaatgtttga   1920
tgcactatgt atttggaaat gcccaattgg aggggtttag tgccgagtct aggagacttc   1980
tactgttgat ccaagcatta aaggacagaa agggcccttg ggtgttcgac ttagagggaa   2040
tgtattctgg aatagaagaa tgtattagca acaacccttg ggtaatacag agtgcatact   2100
ggtttaatga atggttgggc tttgaaaagg aggggagtaa agtgttagaa tcagtggatg   2160
aaataatgga tgaataaaag acatggtac tcaatttggt actattttgt tcattatgta    2220
tctaaacatc aataaaaag aaccaaga                                       2248
```

<210> SEQ ID NO 83
<211> LENGTH: 1824
<212> TYPE: DNA
<213> ORGANISM: Artificial Sequence
<220> FEATURE:
<223> OTHER INFORMATION: Nucleotide sequence of mouse adapted Influenza B/Malaysia/2506/2004 virus HA
<220> FEATURE:
<221> NAME/KEY: misc_feature
<222> LOCATION: (641)..(641)
<223> OTHER INFORMATION: n is a, c, g, or t

<400> SEQUENCE: 83

```
atgaaggcaa taattgtact actcatggta gtaacatcca atgcagatcg aatctgcact   60
gggataacat cgtcaaactc accacatgtt gtcaaaactg ctactcaagg ggaggtcaat   120
gtgactggtg taataccact gacaacaaca cccaccaaat ctcattttgc aaatctcaaa   180
ggaacagaaa ccagagggaa actatgccca aaatgcctca actgcacaga tctggacgtg   240
gccttgggca gaccaaaatg cacggggaac ataccctcgg caagagtttc aatactccat   300
gaagtcagac ctgttacatc tgggtgcttt cctataatgc acgacagaac aaaaattaga   360
cagctgccta accttctcag aggatacgaa catatcaggt tatcaactca taacgttatc   420
aatgcagaaa atgcaccagg aggaccctac aaaattggaa cctcagggtc ttgccctaac   480
gttaccaatg gaaacggatt tttcgcaaca atggcttggg ccgtcccaaa aaacgacaac   540
aacaaaacag caacaaattc attaacaata gaagtaccat acatttgtac agaaggagaa   600
gaccaaatta ccgtttgggg gttccactct gatarcgaaa nccaaatggc aaagctctat   660
ggggactcaa agccccagaa gttcacctca tctgccaacg gagtgaccac acattacgtt   720
tcacagattg gtggcttccc aaatcaaaca gaagacggag gactaccaca agtggtagaa   780
attgttgttg attacatggt gcaaaaatct gggaaaacag gaacaattac ctatcaaaga   840
ggtattttat tgcctcaaaa agtgtggtgc gcaagtggca ggagcaaggt aataaaagga   900
tccttgcctt taattggaga gcagattgc ctccacgaaa aatacggtgg attaaacaaa   960
agcaagcctt actacacagg ggaacatgca aaggccatag gaaattgccc aatatgggtg   1020
aaaacaccct tgaagctggc caatggaacc aaatatagac ctcctgcaaa actattaaag   1080
gaaaggggtt tcttcggagc tattgctggt ttccttagaa gaggatggga aggaatgatt   1140
gcaggttggc acggatacac atcccatggg gcacatggag tagcggtggc agcagacctt   1200
aagagcactc aagaggccat aaacaagata acaaaaatc tcaactcttt gagtgagctg   1260
gaagtaaaga atcttcaaag actaagcggt gccatggatg aactccacaa cgaaatacta   1320
gaactagacg agaaagtgga tgatctcaga gctgatacaa taagctcaca aatagaactc   1380
gcagtcctgc tttccaatga aggaataata acagtgaaga tgagcatct cttggcgctt   1440 gaaagaaagc tgaagaaaat gctgggcccc tctgctgtag agatagggaa tggatgcttt   1500
```

-continued

```
gaaaccaaac acaagtgcaa ccagacctgt ctcgacagaa tagctgctgg tacctttgat    1560
gcaggagaat tttctctccc cacttttgat tcactgaata ttactgctgc atctttaaat    1620
gacgatggat tggataatca tactatactg ctttactact caactgctgc ctccagtttg    1680
gctgtaacat tgatgatagc tatctttgtt gtttatatgg tctccagaga caatgtttct    1740
tgctccatct gtctataagg aaagttaaac cctgtatttt cctttattgt agtgcttgtt    1800
tgcttgttac cattacaaaa aacg                                           1824
```

<210> SEQ ID NO 84
<211> LENGTH: 1772
<212> TYPE: DNA
<213> ORGANISM: Artificial Sequence
<220> FEATURE:
<223> OTHER INFORMATION: Nucleotide sequence of mouse adapted Influenza
      B/Malaysia/2506/2004 virus NP

<400> SEQUENCE: 84

```
caacaaaaga actgaaaatc aaaatgtcca acatggatat tgacggtatc aacactggga      60
caattgacaa agcaccggaa gaaataactt ctggaaccag tgggacaacc agaccaatca     120
tcagaccagc aacccttgcc ccaccaagca acaaacgaac ccggaaccca tccccggaaa     180
gagcaaccac aatcagtgaa gctgatgtcg gaggaaaaac ccaaagaaa cagaccccga     240 cagagataaa gaagagcgtc tacaatatgg tagtgaaact gggtgaattc tataaccaga     300
tgatggtcaa agctggactt aacgatgaca tggagagaaa cctaattcaa aatgcgcatg     360
ctgtggaaag aattctattg gctgccactg atgacaagaa actgaattc cagaagaaaa     420 agaatgccag agatgtcaaa gaagggaaag aagaaataga tcacaacaaa acaggggca     480 ccttttacaa gatggtaaga gatgataaaa ccatctactt cagccctata agagtcacct     540
ttttaaaaga agaagtaaaa acaatgtaca aaccaccat ggggagtgat ggcttcagcg     600
gactaaatca cataatgatt gggcattcac agatgaatga tgtctgtttc caaagatcaa     660
aggcactaaa aagagttgga cttgacccctt cattaatcag tacctttgca ggaagcacac     720
tccccagaag atcaggtgca actggtgttg cgatcaaagg aggtggaact ctagtggctg     780
aagccattcg atttatagga agagcaatgg cagacagagg gctattgaga gacatcaaag     840
ccaagactgc gtatgaaaag attcttctga acctaaaaaa caaatgctct gcgccccaac     900
agaaggctct agttgatcaa gtgatcggaa gtagaaatcc agggattgca gacattgaag     960
acctaaccct acttgctcgt agtatggtcg ttgttaggcc ctctgtggcg agcaaagtag    1020
tgcttcccat aagcatttac gccaaaatac ctcaactagg gttcaacgtt gaagagtact    1080
ctatggttgg gtatgaagcc atggctcttt acaatatggc aacacctgtt tccatattaa    1140
gagtgggaga tgatgcaaag gacaaatcac aattattctt catgtcttgc ttcggagctg    1200
cctatgaaga cctgagagtt ttgtctgcat taacaggcac agaattcaag cctagatcag    1260
cattaaaatg caagggtttc catgttccag caaaggaaca ggtggaagga atgggggcag    1320
ctctgatgtc catcaagctc cagttttggg ctccaatgac cagatctggg ggaaacgaag    1380
taggtggaga cggggggtct ggccaaataa gttcagccc agtgtttgca gtagaaagac    1440
ctattgctct aagcaagcaa gctgtaagaa gaatgctgtc aatgaatatt gagggacgtg    1500
atgcagatgt caaaggaaat ctactcaaga tgatgaatga ctcaatggct aagaaaacca    1560
atggaaatgc tttcattggg aagaaaatgt ttcaaatatc agacaaaaac aaaaccaatc    1620
ccgttgaaat tccaattaag caaaccatcc ccaatttctt ctttgggagg gacacagcag    1680
```

```
aggattatga tgacctcgat tattaaagca acaaaataga cactatgact gtgattgttt   1740
caatacgttt ggaatgtggg tgtttactct ta                                 1772

<210> SEQ ID NO 85
<211> LENGTH: 1483
<212> TYPE: DNA
<213> ORGANISM: Artificial Sequence
<220> FEATURE:
<223> OTHER INFORMATION: Nucleotide sequence of mouse adapted Influenza
      B/Malaysia/2506/2004 virus NA

<400> SEQUENCE: 85
aaatgaacaa tgctaccttc aactatacaa acgttaaccc tatttctcac atcaggggga    60
gtattattat cactatatgt gtcagcttca ttgtcatact tactatattc ggatatattg   120
ctaaaattcc catcaacaga aattactgca ccaacaatgc cattggattg tgcaaacgca   180
tcaaatgttc aggctgtgaa ccgttctgca acaaaagggg tgacacttct tctcccagaa   240
ccggagtgga catacccgcg tttatcttgc ccgggctcaa cctttcagaa agcactccta   300
attagccctc atagattcgg agaaaccaaa ggaaactcag ctcccttgat aataagggaa   360 cctttattg cttgtggacc aaaggaatgc aaacactttg ctctaaccca ctatgcagcc   420
caaccagggg gatactacaa tggaacaaga ggagacagaa acaagctgag gcatctaatt   480
tcagtcaaat tgggcaaaat cccaacagta gaaaactcca ttttccacat ggcagcatgg   540
agcgggtccg catgccatga tggtaaggaa tggacatata tcggagttga tggccctgac   600
aataatgcat tgctcaaaat aaaatatgga gaagcatata ctgacacata ccattcctat   660
gcaaacaaca tcctaagaac acaagaaagt gcctgcaatt gcatcggggg aaattgttat   720
cttatgataa ctgatggctc agcttcaggt gttagtgaat gcagatttct taagattcga   780
gagggccgaa taataaaaga atatttcca acaggaagaa taaaacatac tgaagaatgc   840
acatgcggat ttgctagcaa taaaaccata gaatgtgcct gtagagataa cagttacaca   900
gcaaaaagac cctttgtcaa attaaacgtg gagactgata cagcagaaat aagattgatg   960
tgcacagaga cttatttgga caccccccaga ccagatgatg aagcataac agggccttgt  1020 gaatctaatg gggacaaagg gagtggaggc atcaagggag gatttgtcca tcaaagaatg  1080
gcatccaaga ttggaaggtg gtactctcga acgatgtcta aaactaaaag gatggggatg  1140
gggctgtatg tcaartatga tggagaccca tgggctgaca gtgatgccct tgcttttagt  1200
ggagtaatgg ttccaatgga agaacctggt tggtactcct ttggcttcga aataaaagac  1260
aagaaatgtg atgtcccctg tattgggata gagatggtac atgatggtgg aaaagagact  1320
tggcactcag cagctacagc catttactgt ttaatgggct caggacagct gctgtgggac  1380
actgtcacag gtgttaatat ggctctgtaa tggaggaatg gttgagtctg ttctaaaccc  1440
tttgttccta ttttgtttga acaattgtcc ttactgaact taa                    1483

<210> SEQ ID NO 86
<211> LENGTH: 1140
<212> TYPE: DNA
<213> ORGANISM: Artificial Sequence
<220> FEATURE:
<223> OTHER INFORMATION: Nucleotide sequence of mouse adapted Influenza
      B/Malaysia/2506/2004 virus M

<400> SEQUENCE: 86
cgctgtttgg agacacaatt gcctacctgc tttcattgac agaagatgga gaaggcaaag    60
```

-continued

```
cagaactagc agaaaaatta cactgttggt ttggtgggaa agaatttgac ctagactctg    120
ccttggaatg gataaaaaac aaaagatgct taactgatat acaaaaagca ctaattggtg    180
cctctatatg ctttttaaaa cccaaagacc aggaaagaaa aagaagattc atcacagaac    240
ccttatcagg aatgggaaca acagcaacaa aaaagaaagg cctgattctg gctgagagaa    300
aaatgagaag atgtgtgagc tttcatgaag catttgaaat agcagaaggc catgaaagct    360
cagcgctact atactgtctc atggtcatgt acctgaatcc tggaaattat tcaatgcaag    420
taaaactagg aacgctctgt gctttatgcg agaaacaagc atcacattca cacagggctc    480
atagcagagc agcgagatct tcagtgcctg gagtgagacg agaaatgcag atggtctcag    540
ctatgaacac agcgaaaaca atgaatggaa tgggaaaagg agaagacgtc caaaagctgg    600
cagaagagct gcaaagcaac attggagtgc tgagatctct tggggcaagt caaaagaatg    660
gggaaggaat tgcaaargat gtaatggaag tgctaaagca gagctctatg ggaaattcag    720
ctcttgtgaa gaaatatcta taatgctcga accatttcag attctttcaa tttgttcttt    780
tatcttatca gctctccatt tcatggcttg gacaataggg catttgaatc aaataaaaag    840
aggaataaac atgaaaatac gaataaaagg tccaaacaaa gagacaataa acagagaggt    900
atcaattttg agacacagtt accaaaaaga aatccaggcc aaagaaacaa tgaaggaagt    960
actctctgac aacatggagg tattgagtga ccacataata attgaggggc tttctgccga   1020
agagataata aaaatgggtg aaacagtttt ggagatagaa gaattgcatt aaattcaatt   1080
tttactgtat ttcttactat gcatttaagc aaattgtaat caatgtcagc aaataaactg   1140
```

<210> SEQ ID NO 87
<211> LENGTH: 1033
<212> TYPE: DNA
<213> ORGANISM: Artificial Sequence
<220> FEATURE:
<223> OTHER INFORMATION: Nucleotide sequence of mouse adapted Influenza B/Malaysia/2506/2004 virus NS

<400> SEQUENCE: 87

```
cgaacaacat gaccacaaca caaattgagg tgggtccggg agcaaccaat gccaccataa     60
actttgaagc aggaattctg gagtgctatg aaaggctttc atggcaaaga gcccttgact    120
accctggtca agaccgccta aacagactaa agagaaaatt agagtcaaga ataaagactc    180
acaacaaaag tgagcctgaa agtaaaagga tgtcccttga agagagaaaa gcaattggag    240
taaaaatgat gaaagtactc ctatttatgg atccgtctgc tggaattgaa gggtttgagc    300
catactgtat gaaaagttcc tcaaatagca actgtacgaa atacaattgg accgattacc    360
cttcaacacc agggaggtgc cttgatgaca tagaagaaga accagaggat gttgatggcc    420
caactgaaat agtattaagg gacatgaaca acaaagatgc aaggcaaaag ataaaggagg    480
aagtaaacac tcagaaagaa gggaagttcc gtttgacaat aaaaagggat atgcgtaatg    540
tattgtcctt gagagtgttg gtaaacggaa cattcctcaa acatcccaat ggatacaagt    600
ccttatcaac tctgcataga ttgaatgcat atgaccagag tggaaggctt gttgctaaac    660
ttgttgctac tgatgatctt acagtggagg atgaagaaga tggccatcgg atcctcaact    720
cactcttcga gcgtcttaat gaaggacatt caaagccaat tcgagcagct gaaactgcgg    780
tgggagtctt atcccaattt ggtcaagagc accgattatc accagaagag ggagacaatt    840
agactggtca cggaagaact ttatctttta agtaaaagaa ttgatgataa catattgttc    900
cacaaaacag taatagctaa cagctccata atagctgaca tggttgtatc attatcatta    960
```
ttagaaacat tgtatgaaat gaaggatgta gttgaagtgt acagcaggca gtgcttgtga    1020
atttaaaata aaa                                                      1033

<210> SEQ ID NO 88
<211> LENGTH: 585
<212> TYPE: PRT
<213> ORGANISM: influenza B/Malaysia/2506/20/03
<220> FEATURE:
<223> OTHER INFORMATION: full length amino acid sequence for influenza
      B/Malaysia/2506/20/03 HA
<220> FEATURE:
<221> NAME/KEY: misc_feature
<222> LOCATION: (214)..(214)
<223> OTHER INFORMATION: Xaa = Ile or Thr

<400> SEQUENCE: 88

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Xaa Gln Met Ala Lys Leu Tyr Gly Asp Ser Lys
210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

```
Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
            565                 570                 575

Asp Asn Val Ser Cys Ser Ile Cys Leu
            580                 585

<210> SEQ ID NO 89
<211> LENGTH: 15
<212> TYPE: PRT
<213> ORGANISM: influenza B/Malaysia/2506/20/03
<220> FEATURE:
<223> OTHER INFORMATION: Signal Peptide

<400> SEQUENCE: 89

Met Lys Ala Ile Ile Val Leu Leu Met Val Val Thr Ser Asn Ala
1               5                   10                  15

<210> SEQ ID NO 90
<211> LENGTH: 347
<212> TYPE: PRT
<213> ORGANISM: influenza B/Malaysia/2506/20/03
<220> FEATURE:
<223> OTHER INFORMATION: HA1 Domain
<220> FEATURE:
<221> NAME/KEY: misc_feature
<222> LOCATION: (199)..(199)
<223> OTHER INFORMATION: Xaa = Ile or Thr

<400> SEQUENCE: 90

Asp Arg Ile Cys Thr Gly Ile Thr Ser Ser Asn Ser Pro His Val Val
```

```
  1               5                  10                 15
Lys Thr Ala Thr Gln Gly Glu Val Asn Val Thr Gly Val Ile Pro Leu
                20                 25                 30

Thr Thr Thr Pro Thr Lys Ser His Phe Ala Asn Leu Lys Gly Thr Glu
                35                 40                 45

Thr Arg Gly Lys Leu Cys Pro Lys Cys Leu Asn Cys Thr Asp Leu Asp
             50                 55                 60

Val Ala Leu Gly Arg Pro Lys Cys Thr Gly Asn Ile Pro Ser Ala Arg
 65                 70                 75                 80

Val Ser Ile Leu His Glu Val Arg Pro Val Thr Ser Gly Cys Phe Pro
                85                 90                 95

Ile Met His Asp Arg Thr Lys Ile Arg Gln Leu Pro Asn Leu Leu Arg
                100                105                110

Gly Tyr Glu His Ile Arg Leu Ser Thr His Asn Val Ile Asn Ala Glu
                115                120                125

Asn Ala Pro Gly Gly Pro Tyr Lys Ile Gly Thr Ser Gly Ser Cys Pro
130                135                140

Asn Val Thr Asn Gly Asn Gly Phe Phe Ala Thr Met Ala Trp Ala Val
145                150                155                160

Pro Lys Asn Asp Asn Asn Lys Thr Ala Thr Asn Ser Leu Thr Ile Glu
                165                170                175

Val Pro Tyr Ile Cys Thr Glu Gly Glu Asp Gln Ile Thr Val Trp Gly
                180                185                190

Phe His Ser Asp Asn Glu Xaa Gln Met Ala Lys Leu Tyr Gly Asp Ser
                195                200                205

Lys Pro Gln Lys Phe Thr Ser Ser Ala Asn Gly Val Thr Thr His Tyr
                210                215                220

Val Ser Gln Ile Gly Gly Phe Pro Asn Gln Thr Glu Asp Gly Gly Leu
225                230                235                240

Pro Gln Ser Gly Arg Ile Val Val Asp Tyr Met Val Gln Lys Ser Gly
                245                250                255

Lys Thr Gly Thr Ile Thr Tyr Gln Arg Gly Ile Leu Leu Pro Gln Lys
                260                265                270

Val Trp Cys Ala Ser Gly Arg Ser Lys Val Ile Lys Gly Ser Leu Pro
                275                280                285

Leu Ile Gly Glu Ala Asp Cys Leu His Glu Lys Tyr Gly Gly Leu Asn
                290                295                300

Lys Ser Lys Pro Tyr Tyr Thr Gly Glu His Ala Lys Ala Ile Gly Asn
305                310                315                320

Cys Pro Ile Trp Val Lys Thr Pro Leu Lys Leu Ala Asn Gly Thr Lys
                325                330                335

Tyr Arg Pro Pro Ala Lys Leu Leu Lys Glu Arg
                340                345
```

<210> SEQ ID NO 91
<211> LENGTH: 223
<212> TYPE: PRT
<213> ORGANISM: influenza B/Malaysia/2506/20/03
<220> FEATURE:
<223> OTHER INFORMATION: HA2 Domain

<400> SEQUENCE: 91

```
Gly Phe Phe Gly Ala Ile Ala Gly Phe Leu Glu Gly Gly Trp Glu Gly
1               5                  10                 15

Met Ile Ala Gly Trp His Gly Tyr Thr Ser His Gly Ala His Gly Val
```

```
                    20                  25                  30
Ala Val Ala Ala Asp Leu Lys Ser Thr Gln Glu Ala Ile Asn Lys Ile
                35

```
            50                  55                  60
Leu Glu Gly Gly Trp Glu Gly Met Ile Ala Gly Trp His Gly Tyr Thr
 65                  70                  75                  80

Ser His Gly Ala His Gly Val Ala Val Ala Ala Asp Leu Lys Ser Thr
                     85                  90                  95

Gln Glu Ala Ile Asn Lys Ile Thr Lys Asn Leu Asn Ser Leu Ser Glu
                100                 105                 110

Leu Glu Val Lys Asn Leu Gln Arg Leu Ser Gly Ala Met Asp Glu Leu
                115                 120                 125

His Asn Glu Ile Leu Glu Leu Asp Glu Lys Val Asp Asp Leu Arg Ala
                130                 135                 140

Asp Thr Ile Ser Ser Gln Ile Glu Leu Ala Val Leu Leu Ser Asn Glu
145                 150                 155                 160

Gly Ile Ile Asn Ser Glu Asp Glu His Leu Leu Ala Leu Glu Arg Lys
                165                 170                 175

Leu Lys Lys Met Leu Gly Pro Ser Ala Val Glu Ile Gly Asn Gly Cys
                180                 185                 190

Phe Glu Thr Lys His Lys Cys Asn Gln Thr Cys Leu Asp Arg Ile Ala
                195                 200                 205

Ala Gly Thr Phe Asp Ala Gly Glu Phe Ser Leu Pro Thr Phe Asp Ser
210                 215                 220

Leu Asn Ile Thr Ala Ala Ser Leu Asn Asp Asp Gly Leu Asp Asn His
225                 230                 235                 240

Thr

<210> SEQ ID NO 94
<211> LENGTH: 250
<212> TYPE: PRT
<213> ORGANISM: influenza B/Malaysia/2506/20/03
<220> FEATURE:
<223> OTHER INFORMATION: Globular Head Domain
<220> FEATURE:
<221> NAME/KEY: misc_feature
<222> LOCATION: (157)..(157)
<223> OTHER INFORMATION: Xaa = Ile or Thr

<400> SEQUENCE: 94

Asn Leu Lys Gly Thr Glu Thr Arg Gly Lys Leu Cys Pro Lys Cys Leu
 1               5                  10                  15

Asn Cys Thr Asp Leu Asp Val Ala Leu Gly Arg Pro Lys Cys Thr Gly
                20                  25                  30

Asn Ile Pro Ser Ala Arg Val Ser Ile Leu His Glu Val Arg Pro Val
                35                  40                  45

Thr Ser Gly Cys Phe Pro Ile Met His Asp Arg Thr Lys Ile Arg Gln
 50                  55                  60

Leu Pro Asn Leu Leu Arg Gly Tyr Glu His Ile Arg Leu Ser Thr His
 65                  70                  75                  80

Asn Val Ile Asn Ala Glu Asn Ala Pro Gly Gly Pro Tyr Lys Ile Gly
                 85                  90                  95

Thr Ser Gly Ser Cys Pro Asn Val Thr Asn Gly Asn Gly Phe Phe Ala
                100                 105                 110

Thr Met Ala Trp Ala Val Pro Lys Asn Asp Asn Asn Lys Thr Ala Thr
                115                 120                 125

Asn Ser Leu Thr Ile Glu Val Pro Tyr Ile Cys Thr Glu Gly Glu Asp
                130                 135                 140

Gln Ile Thr Val Trp Gly Phe His Ser Asp Asn Glu Xaa Gln Met Ala
```

```
                145                 150                 155                 160
Lys Leu Tyr Gly Asp Ser Lys Pro Gln Lys Phe Thr Ser Ser Ala Asn
                    165                 170                 175
Gly Val Thr Thr His Tyr Val Ser Gln Ile Gly Gly Phe Pro Asn Gln
                180                 185                 190
Thr Glu Asp Gly Gly Leu Pro Gln Ser Gly Arg Ile Val Val Asp Tyr
            195                 200                 205
Met Val Gln Lys Ser Gly Lys Thr Gly Thr Ile Thr Tyr Gln Arg Gly
        210                 215                 220
Ile Leu Leu Pro Gln Lys Val Trp Cys Ala Ser Gly Arg Ser Lys Val
225                 230                 235                 240
Ile Lys Gly Ser Leu Pro Leu Ile Gly Glu
                    245                 250

<210> SEQ ID NO 95
<211> LENGTH: 533
<212> TYPE: PRT
<213> ORGANISM: influenza B/Malaysia/2506/20/03
<220> FEATURE:
<223> OTHER INFORMATION: Ectodomain
<220> FEATURE:
<221> NAME/KEY: misc_feature
<222> LOCATION: (199)..(199)
<223> OTHER INFORMATION: Xaa = Ile or Thr

<400> SEQUENCE: 95

Asp Arg Ile Cys Thr Gly Ile Thr Ser Ser Asn Ser Pro His Val Val
1               5                   10                  15
Lys Thr Ala Thr Gln Gly Glu Val Asn Val Thr Gly Val Ile Pro Leu
                20                  25                  30
Thr Thr Thr Pro Thr Lys Ser His Phe Ala Asn Leu Lys Gly Thr Glu
            35                  40                  45
Thr Arg Gly Lys Leu Cys Pro Lys Cys Leu Asn Cys Thr Asp Leu Asp
        50                  55                  60
Val Ala Leu Gly Arg Pro Lys Cys Thr Gly Asn Ile Pro Ser Ala Arg
65                  70                  75                  80
Val Ser Ile Leu His Glu Val Arg Pro Val Thr Ser Gly Cys Phe Pro
                85                  90                  95
Ile Met His Asp Arg Thr Lys Ile Arg Gln Leu Pro Asn Leu Leu Arg
            100                 105                 110
Gly Tyr Glu His Ile Arg Leu Ser Thr His Asn Val Ile Asn Ala Glu
        115                 120                 125
Asn Ala Pro Gly Gly Pro Tyr Lys Ile Gly Thr Ser Gly Ser Cys Pro
130                 135                 140
Asn Val Thr Asn Gly Asn Gly Phe Phe Ala Thr Met Ala Trp Ala Val
145                 150                 155                 160
Pro Lys Asn Asp Asn Asn Lys Thr Ala Thr Asn Ser Leu Thr Ile Glu
                165                 170                 175
Val Pro Tyr Ile Cys Thr Glu Gly Glu Asp Gln Ile Thr Val Trp Gly
            180                 185                 190
Phe His Ser Asp Asn Glu Xaa Gln Met Ala Lys Leu Tyr Gly Asp Ser
        195                 200                 205
Lys Pro Gln Lys Phe Thr Ser Ser Ala Asn Gly Val Thr Thr His Tyr
    210                 215                 220
Val Ser Gln Ile Gly Gly Phe Pro Asn Gln Thr Glu Asp Gly Gly Leu
225                 230                 235                 240
```

```
Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
            275                 280                 285

Leu Ile Gly Glu Ala Asp Cys Leu His Glu Lys Tyr Gly Gly Leu Asn
        290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg Gly Phe Phe Gly Ala
            340                 345                 350

Ile Ala Gly Phe Leu Glu Gly Gly Trp Glu Gly Met Ile Ala Gly Trp
            355                 360                 365

His Gly Tyr Thr Ser His Gly Ala His Gly Val Ala Val Ala Ala Asp
        370                 375                 380

Leu Lys Ser Thr Gln Glu Ala Ile Asn Lys Ile Thr Lys Asn Leu Asn
385                 390                 395                 400

Ser Leu Ser Glu Leu Glu Val Lys Asn Leu Gln Arg Leu Ser Gly Ala
                405                 410                 415

Met Asp Glu Leu His Asn Glu Ile Leu Glu Leu Asp Glu Lys Val Asp
            420                 425                 430

Asp Leu Arg Ala Asp Thr Ile Ser Ser Gln Ile Glu Leu Ala Val Leu
            435                 440                 445

Leu Ser Asn Glu Gly Ile Ile Asn Ser Glu Asp Glu His Leu Leu Ala
450                 455                 460

Leu Glu Arg Lys Leu Lys Lys Met Leu Gly Pro Ser Ala Val Glu Ile
465                 470                 475                 480

Gly Asn Gly Cys Phe Glu Thr Lys His Lys Cys Asn Gln Thr Cys Leu
            485                 490                 495

Asp Arg Ile Ala Ala Gly Thr Phe Asp Ala Gly Glu Phe Ser Leu Pro
            500                 505                 510

Thr Phe Asp Ser Leu Asn Ile Thr Ala Ala Ser Leu Asn Asp Asp Gly
            515                 520                 525

Leu Asp Asn His Thr
            530
```

INFLUENZA VIRUS HEMAGGLUTININ PROTEINS AND USES THEREOF

This application is a divisional of U.S. patent application Ser. No. 16/305,845, filed Nov. 29, 2018, now U.S. Pat. No. 11,266,734, which is a U.S. National Stage Application under 35 U.S.C. § 371 of International Patent Application No. PCT/US2017/037384, filed Jun. 14, 2017, which claims the benefit of U.S. Provisional Patent Application No. 62/350,701, filed Jun. 15, 2016, and U.S. Provisional Patent Application No. 62/355,679, filed Jun. 28, 2016, the disclosure of each of which is incorporated by reference herein in its entirety.

This invention was made with government support under grant number HHSO100201500010C, awarded by Biomedical Advanced Research and Development Authority, and grant numbers 5T32AI007647, AI109946, 1P01AI097092, and HHSN272201400008C, awarded by the National Institutes of Health. The government has certain rights in the invention.

This application incorporates by reference in its entirety the Computer Readable Form (CRF) of a Sequence Listing in ASCII text format submitted via EFS-Web. The Sequence Listing text file submitted via EFS-Web is entitled "06923-377-999_SL.txt", was created on Jan. 14, 2022 and is 211,639 bytes in size.

1. INTRODUCTION

Provided herein are chimeric influenza virus hemagglutinin proteins.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza A viruses are mainly avians, but influenza A viruses (including those of avian origin) also can infect and cause illness in humans and other animal hosts (bats, canines, pigs, horses, sea mammals, and mustelids). For example, the H5N1 avian influenza A virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; March 2003). In the United States, influenza viruses infect an estimated 10-15% of the population (Glezen and Couch R B (1978) Interpandemic influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

An effective way to protect against influenza virus infection is through vaccination; however, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The possibility of a novel subtype of influenza virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine in advance of a pandemic. Thus, there is a need for vaccines that cross-protect subjects against different strains and/or subtypes of influenza virus.

3. SUMMARY

In one aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within an antigenic loop of the globular head domain of the influenza B virus HA, wherein the amino acid substitutions substitute 2, 3, 4, 5, 6, 7, 8, 9, 10, 11, 12 or more amino acid residues in the loop of the globular head of the influenza B virus HA with amino acid residues found in a corresponding region of the globular domain of an influenza A virus HA. In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within the 120 loop, 150 loop, 160 loop or 190 helix of the globular head domain of the influenza B virus HA, wherein the amino acid substitutions substitute 2, 3, 4, 5, 6, 7, 8, 9, 10, 11, 12 or more amino acid residues in the 120 loop, 150 loop, 160 loop or 190 helix of the globular head of the influenza B virus HA with amino acid residues found in a corresponding region of the globular domain of an influenza A virus HA. In one embodiment, provided herein are chimeric hemagglutinin (HA) polypeptides comprising an HA ectodomain of an influenza B virus comprising 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA. In specific embodiments, the following underlined and bold amino acid residues in the 120 loop of influenza B virus B/Yamagata/16/88 T<u>I</u>P and N<u>I</u>RLSTH-NVINAE<u>R</u>APGGPYRL (SEQ ID NO: 1) are substituted with the following underlined and bold amino acid residues F<u>I</u>P and K<u>I</u>QLSTK<u>N</u>VINAE<u>H</u>APGGPYRL (SEQ ID NO: 2) from influenza A virus A/Vietnam/1203/04 (HALo). In specific embodiments, the following amino acid residues in influenza B virus B/Yamagata/16/88 TIP and NIRLSTH-NVINAERAPGGPYRL (SEQ ID NO: 1) are substituted with amino acid residues FIP and KIQLSTKNVINAE-HAPGGPYRL (SEQ ID NO: 2). In specific embodiments, the following underlined and bold amino acid residues in the 120 loop of influenza B virus B/Yamagata/16/88 T<u>I</u>P and N<u>I</u>RLST<u>H</u>NVINAE<u>R</u>APGGPYRL (SEQ ID NO: 1) are substituted with the following underlined and bold amino acid residues H<u>I</u>P and R<u>I</u>RLST<u>Y</u>NVINAE<u>T</u>APGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRL-STYNVINAETAPGGPYRL (SEQ ID NO: 51). In specific embodiments, the following underlined and bold amino acid residues in the 120 loop of influenza B virus B/Yamagata/16/88 T<u>I</u>P and N<u>I</u>RLST<u>H</u>NVINAE<u>R</u>APGGPYRL (SEQ ID NO: 1) are substituted with the following underlined and bold amino acid residues L<u>I</u>P and K<u>I</u>ELST<u>S</u>NVINAE<u>V</u>APGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAER-APGGPYRL (SEQ ID NO: 1) are substituted with amino acid residues LIP and KIELSTSNVINAEVAPGGPYRL (SEQ ID NO: 55). In specific embodiments, the following underlined and bold amino acid residues in the 120 loop of influenza B virus B/Yamagata/16/88 T<u>I</u>P and N<u>I</u>RLSTH-NVINAE<u>R</u>APGGPYRL (SEQ ID NO: 1) are substituted with the following underlined and bold amino acid residues Y<u>I</u>P and R<u>I</u>KLSTF<u>N</u>VINAE<u>T</u>APGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKL-STFNVINAETAPGGPYRL (SEQ ID NO: 63). In specific embodiments, the following underlined and bold amino acid residues in the 120 loop of influenza B virus B/Yamagata/16/88 T<u>I</u>P and N<u>I</u>RLST<u>H</u>NVINAE<u>R</u>APGGPYRL (SEQ ID NO: 1) are substituted with the following underlined and bold amino acid residues N<u>I</u>P and R<u>I</u>ELSTHNVINAE-VAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAER-APGGPYRL (SEQ ID NO: 1) are substituted with amino acid residues NIP and RIELSTHNVINAEVAPGGPYRL (SEQ ID NO: 59). In another embodiment, provided herein are chimeric hemagglutinin (HA) polypeptides comprising an HA ectodomain of an influenza B virus comprising 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA. In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In another embodiment, provided herein are chimeric hemagglutinin (HA) polypeptides comprising an HA ectodomain of an influenza B virus comprising 2, 3, 4, 5 or more amino acid substitutions within 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA. In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In another embodiment, provided herein are chimeric hemagglutinin (HA) polypeptides comprising an HA ectodomain of an influenza B virus comprising 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA. In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In some embodiments, the chimeric HA polypeptide may also comprise the signal peptide, transmembrane domain, and cytoplasmic tail domain from the influenza B virus HA. In other embodiments, the chimeric HA polypeptide comprises the signal peptide from the influenza B virus HA but lacks the transmembrane and cytoplasmic tail domains. In some embodiments, the chimeric HA polypeptide may also comprise the signal peptide, transmembrane domain, and cytoplasmic tail domain from an influenza A virus HA. In other embodiments, the chimeric HA polypeptide comprises the signal peptide from an influenza A virus HA but lacks the transmembrane and cytoplasmic tail domains. In some embodiments, the chimeric HA comprises the signal peptide of the HA of the influenza virus backbone of the chimeric HA. For example, if the chimeric HA is engineered for an influenza A virus backbone (e.g., the influenza virus comprising or engineered to express the chimeric HA is an influenza A virus), then the chimeric HA comprises the signal peptide of the influenza A virus. In some embodiments, the chimeric HA comprises the signal peptide, transmembrane domain, and cytoplasmic domain of the HA of the influenza virus backbone of the chimeric HA. In some embodiments, the chimeric HA polypeptide may also comprise the signal peptide from the HA of the influenza virus that is engineered to express the chimeric HA. In some embodiments, the chimeric HA polypeptide may also comprise the signal peptide, transmembrane domain, and cytoplasmic tail domain from the HA of the influenza virus that is engineered to express the chimeric HA. Also provided herein are nucleic acids comprising nucleotide sequences encoding such a chimeric HA. In some embodiments, the nucleic acids comprise nucleotide sequences encoding such a chimeric HA and the 5' and 3' non-coding regions from the influenza B virus HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In specific embodiments, the chimeric HA polypeptide is soluble. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid).

In another aspect, provided herein are chimeric hemagglutinin (HA) polypeptides comprising an HA ectodomain of an influenza B virus comprising one, two, three or all of the following: (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A/virus HA; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In some embodiments, the chimeric HA polypeptide may also comprise the signal peptide, transmembrane domain, and cytoplasmic tail domain from the influenza B virus HA. In other embodiments, the chimeric HA polypeptide comprises the signal peptide from the influenza B virus HA but lacks the transmembrane and cytoplasmic tail domains. In some embodiments, the chimeric HA polypeptide may also comprise the signal peptide, transmembrane domain, and cytoplasmic tail domain from an influenza A virus HA. In other embodiments, the chimeric HA polypeptide comprises the signal peptide from an influenza A virus HA but lacks the transmembrane and cytoplasmic tail domains. In some embodiments, the chimeric HA comprises the signal peptide of the HA of the influenza virus backbone of the chimeric HA. For example, if the chimeric HA is engineered for an influenza A virus backbone (e.g., the influenza virus comprising or engineered to express the chimeric HA is an influenza A virus), then the chimeric HA comprises the signal peptide of the influenza A virus. In some embodiments, the chimeric HA comprises the signal peptide, transmembrane domain, and cytoplasmic domain of the HA of the influenza virus backbone of the chimeric HA. In some embodiments, the chimeric HA polypeptide may also comprise the signal peptide from the HA of the influenza virus that is engineered to express the chimeric HA. In some embodiments, the chimeric HA polypeptide may also comprise the signal peptide, transmembrane domain, and cytoplasmic tail domain from the HA of the influenza virus that is engineered to express the chimeric HA. Also provided herein are nucleic acids comprising nucleotide sequences encoding such a chimeric HA. In some embodiments, the nucleic acids comprise nucleotide sequences encoding such a chimeric HA and the 5' and 3' non-coding regions from the influenza B virus HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In specific embodiments, the chimeric HA polypeptide is soluble. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid).

In another aspect, provided herein are chimeric hemagglutinin (HA) polypeptides comprising (i) a hemagglutinin ectodomain from a first influenza B virus strain with 2, 3, 4, 5, 6, 7, 8, 9, 10, 11, 12 or more amino acid substitutions within the 120 loop, 150 loop, 160 loop or 190 helix of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8, 9, 10, 11, 12 or more amino acid residues in the 120 loop, 150 loop, 160 loop or 190 helix of the globular head of the first influenza B virus strain HA with amino acid residues found in a corresponding region of the globular domain of an influenza A virus HA. In one embodiment, provided herein are chimeric hemagglutinin (HA) polypeptides comprising (i) a hemagglutinin ectodomain from a first influenza B virus strain with 2, 3, 4, 5, 6, 7, 8, 9, 10, 11, 12, 13, 14, 15, 16, 17, 18, 19, 20 or more amino acid substitutions within the 120 loop of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the first influenza B virus strain HA with amino acid residues found in a corresponding region of the globular domain of an influenza A virus HA. In another embodiment, provided herein are chimeric hemagglutinin (HA) polypeptides comprising (i) a hemagglutinin ectodomain from a first influenza B virus strain with 2, 3, 4, 5, 6, 7, 8, 9 or more amino acid substitutions within the 150 loop of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8, 9 or more amino acid residues in the 150 loop of the globular head of the first influenza B virus strain HA with amino acid residues found in a corresponding region of the globular domain of an influenza A virus HA. In another embodiment, provided herein are chimeric hemagglutinin (HA) polypeptides comprising (i) a hemagglutinin ectodomain from a first influenza B virus strain with 2, 3, 4, 5 or more amino acid substitutions within the 160 loop of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5 or more amino acid residues in the 160 loop of the globular head of the first influenza B virus strain HA with amino acid residues found in a corresponding region of the globular domain of an influenza A virus HA. In another embodiment, provided herein are chimeric hemagglutinin (HA) polypeptides comprising (i) a hemagglutinin ectodomain from a first influenza B virus strain with 2, 3, 4, 5, 6, 7, 8 or more amino acid substitutions within the 190 helix of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8 or more amino acid residues in the 190 helix of the globular head of the first influenza B virus strain HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTH-NVINAERAPGGPYRL (SEQ ID NO: 1) are substituted with amino acid residues FIP and KIQLSTKNVINAE-HAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRL-STYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NAS-TGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTH-NVINAERAPGGPYRL (SEQ ID NO: 1) are substituted with amino acid residues LIP and KIELSTSNVINAE-VAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the first influenza B virus strain and the second influenza B virus strain are from the same lineage. In some embodiments, the first influenza B virus strain and the second influenza B virus strain are from the same lineage but are different strains. In a specific embodiment, the first influenza B virus strain is the same strain as the second influenza B virus strain. In another embodiment, the first influenza B virus strain is a different strain than the second influenza B virus strain. In some embodiments, the first influenza B virus strain and the second influenza B virus strain are from different lineages. In some embodiments, the first influenza B virus strain is from the Yamagata lineage. In other embodiments, the first influenza B virus is from the Victoria lineage. In some embodiments, the second influenza B virus strain is from the Yamagata lineage. In other embodiments, the second influenza B virus is from the Victoria lineage. In a specific embodiment, the second influenza B virus strain is the same strain as the influenza virus backbone of an influenza virus either containing, expressing, or both the chimeric HA. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99).

In another aspect, provided herein are chimeric hemagglutinin (HA) polypeptides comprising: (a) a hemagglutinin ectodomain from a first influenza B virus strain with one, two, three or all of the following (i) 2, 3, 4, 5, 6, 7, 8, 9, 10, 11, 12, 13, 14, 15, 16, 17, 18, 19, 20 or more amino acid substitutions within the 120 loop of the globular head domain of the first influenza B virus strain HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the first influenza B virus strain HA with amino acid residues found in a corresponding region of the globular domain of an influenza A virus HA; (ii) 2, 3, 4, 5, 6, 7, 8, 9 or more amino acid substitutions within the 150 loop of the globular head domain of the first influenza B virus strain HA, wherein the amino acid substitutions substitute 2, 3, 4, 5, 6, 7, 8, 9 or more amino acid residues in the 150 loop of the globular head of the first influenza B virus strain HA with amino acid residues found in a corresponding region of the globular domain of an influenza A virus HA; (iii) 2, 3, 4, 5 or more amino acid substitutions within the 160 loop of the globular head domain of the first influenza B virus strain HA, wherein the amino acid substitutions substitute 2, 3, 4, 5 or more amino acid residues in the 160 loop of the globular head of the first influenza B virus strain HA with amino acid residues found in a corresponding region of the globular domain of an influenza A virus HA; and (iv) 2, 3, 4, 5, 6, 7, 8 or more amino acid substitutions within the 190 helix of the globular head domain of the first influenza B virus strain HA, wherein the amino acid substitutions substitute 2, 3, 4, 5, 6, 7, 8 or more amino acid residues in the 190 helix of the globular head of the first influenza B virus strain HA with amino acid residues found in a corresponding region of the globular domain of an influenza A virus HA; and (b) a signal peptide, a transmembrane domain and a cytoplasmic tail domain from a second influenza B virus. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 13. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 T<u>I</u>P and <u>N</u>IRLST<u>H</u>NVINAE<u>R</u>APGGPYRL (SEQ ID NO: 1) are substituted with the following underlined and bold amino acid residues H<u>I</u>P and <u>R</u>IRLST<u>Y</u>NVINAE<u>T</u>APGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 <u>R</u>DNKTA (SEQ ID NO: 5) are substituted with the following bold and underlined amino acid residues <u>K</u>KKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 <u>R</u>DNKTA (SEQ ID NO: 5) are substituted with the following bold and underlined amino acid residues <u>K</u>KKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>ADAKMQT</u> (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>PDAKMQT</u> (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 15. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 T<u>I</u>P and <u>N</u>IRLST<u>H</u>NVINAE<u>R</u>APGGPYRL (SEQ ID NO: 1) are substituted with the following underlined and bold amino acid residues L<u>I</u>P and <u>K</u>IELST<u>S</u>NVINAE<u>V</u>APGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 <u>R</u>DNKTA (SEQ ID NO: 5) are substituted with the following bold and underlined amino acid residues <u>H</u>QSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>TTLKMHQ</u> (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>ATLKMHQ</u> (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 17. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 T<u>I</u>P and N<u>I</u>RLST<u>H</u>NVINAE<u>R</u>APGGPYRL (SEQ ID NO: 1) are substituted with the following underlined and bold amino acid residues Y<u>I</u>P and R<u>IK</u>LSTFNVINAE<u>T</u>APGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 <u>R</u>DNKT<u>A</u> (SEQ ID NO: 5) are substituted with amino acid residues <u>L</u>KSGQ<u>F</u> (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 <u>N</u>KNQMK<u>N</u> (SEQ ID NO: 7) are substituted with the following underlined and bold amino acid residues <u>P</u>TSDMQ<u>I</u> (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 T<u>I</u>P and N<u>I</u>RLSTHNVINAE<u>R</u>APGGPYRL (SEQ ID NO: 1) are substituted with the following underlined and bold amino acid residues N<u>I</u>P and R<u>I</u>ELST<u>H</u>NVINAE<u>V</u>APGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 <u>N</u>KNQMK<u>N</u> (SEQ ID NO: 7) are substituted with the following underlined and bold amino acid residues <u>V</u>STNMA<u>K</u> (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of one, two, three, or all of the following: the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the first influenza B virus strain and the second influenza B virus strain are from the same lineage. In some embodiments, the first influenza B virus strain and the second influenza B virus strain are from the same lineage but are different strains. In a specific embodiment, the first influenza B virus strain is the same strain as the second influenza B virus strain. In another embodiment, the first influenza B virus strain is a different strain than the second influenza B virus strain. In some embodiments, the first influenza B virus strain and the second influenza B virus strain are from different lineages. In some embodiments, the first influenza B virus strain is from the Yamagata lineage. In other embodiments, the first influenza B virus is from the Victoria lineage. In some embodiments, the second influenza B virus strain is from the Yamagata lineage. In other embodiments, the second influenza B virus is from the Victoria lineage. In a specific embodiment, the second influenza B virus strain is the same strain as the influenza virus backbone of an influenza virus either containing, expressing, or both the chimeric HA. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99).

In another aspect, provided herein are chimeric hemagglutinin (HA) polypeptides comprising (i) a hemagglutinin ectodomain from an influenza B virus with 2, 3, 4, 5, 6, 7, 8, 9, 10, 11, 12 or more amino acid substitutions within the 120 loop, 150 loop, 160 loop or 190 helix of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9, 10, 11, 12 or more amino acid residues in the 120 loop, 150 loop, 160 loop or 190 helix of the globular head of the influenza B virus HA with amino acid residues found in a corresponding region of the globular domain of an influenza A virus HA. In one embodiment, provided herein are chimeric hemagglutinin (HA) polypeptides comprising (i) a hemagglutinin ectodomain from an influenza B virus with 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA. In another embodiment, provided herein are chimeric hemagglutinin (HA) polypeptides comprising (i) a hemagglutinin ectodomain from an influenza B virus with 2, 3, 4, 5, 6, 7, 8, 9 or more amino acid substitutions within the 150 loop of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA. In another embodiment, provided herein are chimeric hemagglutinin (HA) polypeptides comprising (i) a hemagglutinin ectodomain from an influenza B virus with 2, 3, 4, 5 or more amino acid substitutions within the 160 loop of the globular head domain of the influenza B virus HA and (ii) a signal peptide, a transmembrane domain and a cytoplasmic tail domain from an influenza A virus, wherein the amino acid substitutions substitute 2, 3, 4, 5 or more amino acid residues in the 160 loop of the globular head of the influenza B virus HA with amino acid residues found in a corresponding region of the globular domain of an influenza A virus HA. In another embodiment, provided herein are chimeric hemagglutinin (HA) polypeptides comprising (i) a hemagglutinin ectodomain from an influenza B virus with 2, 3, 4, 5, 6, 7, 8 or more amino acid substitutions within the 190 helix of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the influenza B virus is from the Yamagata lineage. In other embodiments, the influenza B virus is from the Victoria lineage. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding a chimeric HA polypeptide and the 5' non-coding region and 3' non-coding region from an influenza A virus. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA.

In another aspect, provided herein are chimeric hemagglutinin (HA) polypeptides comprising: (a) a hemagglutinin ectodomain from an influenza B virus with one, two, three or all of the following (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA; and (b) a signal peptide, a transmembrane domain and a cytoplasmic tail domain from an influenza A virus. In specific embodiments, the following underlined and bold amino acid residues in the 120 loop of influenza B virus B/Yamagata/16/88 T<u>I</u>P and N<u>I</u>RLST<u>H</u>NVINAER-APGGPYRL (SEQ ID NO: 1) are substituted with the following underlined and bold amino acid residues F<u>I</u>P and K<u>I</u>QLSTKNVINAE<u>H</u>APGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVIN-AERAPGGPYRL (SEQ ID NO: 1) are substituted with amino acid residues FIP and KIQLSTKNVINAE-HAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 R<u>D</u>NKTA (SEQ ID NO: 5) are substituted with the following bold and underlined amino acid residues K<u>K</u>NSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 N<u>K</u>NQ<u>MK</u>N (SEQ ID NO: 7) are substituted with the following underlined and bold amino acid residues N<u>D</u>A<u>AM</u>QT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 T<u>I</u>P and N<u>I</u>RLSTH-NVINAE<u>R</u>APGGPYRL (SEQ ID NO: 1) are substituted with the following underlined and bold amino acid residues H<u>I</u>P and R<u>I</u>RLST<u>Y</u>NVINAE<u>T</u>APGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRL-STYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NAS-TGGQS (SEQ ID NO: 52). In specific embodiments, the following underlined and bold amino acid residues in the 160 loop of influenza B virus B/Yamagata/16/88 <u>R</u>DNKTA (SEQ ID NO: 5) are substituted with the following bold and underlined amino acid residues <u>K</u>KKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 <u>R</u>DNKTA (SEQ ID NO: 5) are substituted with the following bold and underlined amino acid residues <u>K</u>KKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>ADAKMQT</u> (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>PDAKMQT</u> (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 T<u>I</u>P and N<u>I</u>RLST<u>H</u>NVINAER-APGGPYRL (SEQ ID NO: 1) are substituted with the following underlined and bold amino acid residues L<u>I</u>P and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the influenza B virus is from the Yamagata lineage. In other embodiments, the influenza B virus is from the Victoria lineage. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding a chimeric HA polypeptide and the 5' non-coding region and 3' non-coding region from an influenza A virus. In some embodiments, the nucleic acids comprise nucleotide sequences encoding a chimeric HA polypeptide and the 5' non-coding region and 3' non-coding region from an influenza B virus. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In a specific embodiment, the nucleic acid comprises the nucleotide sequence set forth in FIG. 12A and FIG. 12B or the complement thereof. In a specific embodiment, the nucleic acid comprises the nucleotide sequence set forth in FIG. 14A and FIG. 14B or the complement thereof. In a specific embodiment, the nucleic acid comprises the nucleotide sequence set forth in FIG. 16A and FIG. 16B or the complement thereof. In a specific embodiment, the nucleic acid comprises the nucleotide sequence set forth in FIG. 18A and FIG. 18B or the complement thereof.

In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within an antigenic loop of the globular head domain of the influenza B virus HA (e.g., 120 loop, 150 loop, 160 loop and/or 190 helix), wherein the amino acid substitutions substitute 2, 3, 4, 5, 6, 7, 8, 9, 10, 11, 12 or more amino acid residues in the loop of the globular head of the influenza B virus HA with random amino acid residues that do not affect the conformation/structure of the HA. In addition to these amino acid residue substitutions, one or more substitutions outside of the antigenic loops may be introduced. The amino acid substitutions are selected such that the folding of the chimeric HA is not significantly impacted as determined by techniques known to one of skill in the art or described herein. In addition, the amino acid substitutions may be selected such that the coding sequence for N-linkd glycosylation sites (N-X-S/T) is not altered or not significantly altered. The effect of amino acid substitutions on the conformation/structure may be determined by assays known to one of skill in the art, e.g., structure programs, crystallography, or functional assays. See, e.g., Section 5.11, infra, and Section 6, infra. For example, the chimeric HA polypeptides may be evaluated for antigenic conservation using a panel of monoclonal antibodies that bind to conserved epitopes in the globular head domain of HA and the stem domain of HA. In a specific embodiment, the methods described in Section 6, infra, are used to evaluate antigenic conservation of the chimeric HA. In addition, the chimeric HA polypeptides described herein may be evaluated to determine whether the antigenic loops of the influenza B virus HA were mutated using techniques known to one of skill in the art or described herein (see, e.g., Section 6, infra, including the HI assay described therein). In particular, the chimeric HA polypeptides described herein may be evaluated to determine if the amino acid substitutions in the antigenic loop(s) of the influenza B virus HA result in loss of a variable region(s) of the influenza B virus HA using techniques known to one of skill in the art or described herein (see, e.g., Section 6, infra, including the HI assay described therein). In a specific embodiment, the chimeric HA polypeptides described herein may be evaluated to determine if the amino acid substitutions in the antigenic loop(s) of the influenza B virus HA reduce or eliminate the immundominant epitopes of the influenza B virus HA using techniques known to one of skill in the art or described herein (see, e.g., Section 6, infra, including the HI assay described therein). In a specific embodiment, a chimeric HA polypeptide described herein is assessed in an HI assay, such as described in Section 6, infra, to evaluate the replacement of the antigenic loop(s) in the influenza B virus HA.

In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within an antigenic loop of the influenza B virus HA, wherein the amino acid substitutions substitute 2, 3, 4, 5, 6, 7, 8, 9, 10, 11, 12 or more amino acid residues in the loop of the influenza B virus HA with amino acid residues found in a corresponding region of an influenza A virus HA. In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within the 120 loop, 150 loop, 160 loop or 190 helix of the influenza B virus HA, wherein the amino acid substitutions substitute 2, 3, 4, 5, 6, 7, 8, 9, 10, 11, 12 or more amino acid residues in the 120 loop, 150 loop, 160 loop or 190 helix of the influenza B virus HA with amino acid residues found in a corresponding region of an influenza A virus HA. In one embodiment, provided herein are chimeric hemagglutinin (HA) polypeptides comprising an HA ectodomain of an influenza B virus comprising 2, 3, 4, 5, 6, 7, 8, 9, 10, 11, 12, 13, 14, 15, 16, 17, 18, 19, 20 or more amino acid substitutions within the 120 loop of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the influenza B virus HA with amino acid residues found in a corresponding region of an influenza A virus HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAE-HAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTH-NVINAERAPGGPYRL (SEQ ID NO: 1) are substituted with amino acid residues HIP and RIRLSTYNVI-NAETAPGGPYRL (SEQ ID NO: 51). In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAE-VAPGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAER-APGGPYRL (SEQ ID NO: 1) are substituted with amino acid residues LIP and KIELSTSNVINAEVAPGGPYRL (SEQ ID NO: 55). In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKL-STFNVINAETAPGGPYRL (SEQ ID NO: 63). In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAE-VAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAER-APGGPYRL (SEQ ID NO: 1) are substituted with amino acid residues NIP and RIELSTHNVINAEVAPGGPYRL (SEQ ID NO: 59). In another embodiment, provided herein are chimeric hemagglutinin (HA) polypeptides comprising an HA ectodomain of an influenza B virus comprising 2, 3, 4, 5, 6, 7, 8, 9 or more amino acid substitutions within the 150 loop of the influenza B virus HA, wherein the amino acid substitutions substitute 2, 3, 4, 5, 6, 7, 8, 9 or more amino acid residues in the 150 loop of the influenza B virus HA with amino acid residues found in a corresponding region of an influenza A virus HA. In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In another embodiment, provided herein are chimeric hemagglutinin (HA) polypeptides comprising an HA ectodomain of an influenza B virus comprising 2, 3, 4, 5 or more amino acid substitutions within the 160 loop of the influenza B virus HA, wherein the amino acid substitutions substitute 2, 3, 4, 5 or more amino acid residues in the 160 loop of the influenza B virus HA with amino acid residues found in a corresponding region of an influenza A virus HA. In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In another embodiment, provided herein are chimeric hemagglutinin (HA) polypeptides comprising an HA ectodomain of an influenza B virus comprising 2, 3, 4, 5, 6, 7, 8 or more amino acid substitutions within the 190 helix of the influenza B virus HA, wherein the amino acid substitutions substitute 2, 3, 4, 5, 6, 7, 8 or more amino acid residues in the 190 helix of the influenza B virus HA with amino acid residues found in a corresponding region of an influenza A virus HA. In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In some embodiments, the chimeric HA polypeptide may also comprise the signal peptide, transmembrane domain, and cytoplasmic tail domain from the influenza B virus HA. In other embodiments, the chimeric HA polypeptide comprises the signal peptide from the influenza B virus HA but lacks the transmembrane and cytoplasmic tail domains. In some embodiments, the chimeric HA polypeptide may also comprise the signal peptide, transmembrane domain, and cytoplasmic tail domain from an influenza A virus HA. In other embodiments, the chimeric HA polypeptide comprises the signal peptide from an influenza A virus HA but lacks the transmembrane and cytoplasmic tail domains. In some embodiments, the chimeric HA comprises the signal peptide of the HA of the influenza virus backbone of the chimeric HA. For example, if the chimeric HA is engineered for an influenza A virus backbone (e.g., the influenza virus comprising or engineered to express the chimeric HA is an influenza A virus), then the chimeric HA comprises the signal peptide of the influenza A virus. In some embodiments, the chimeric HA comprises the signal peptide, transmembrane domain, and cytoplasmic domain of the HA of the influenza virus backbone of the chimeric HA. In some embodiments, the chimeric HA polypeptide may also comprise the signal peptide from the HA of the influenza virus that is engineered to express the chimeric HA. In some embodiments, the chimeric HA polypeptide may also comprise the signal peptide, transmembrane domain, and cytoplasmic tail domain from the HA of the influenza virus that is engineered to express the chimeric HA. Also provided herein are nucleic acids comprising nucleotide sequences encoding such a chimeric HA. In some embodiments, the nucleic acids comprise nucleotide sequences encoding such a chimeric HA and the 5' and 3' non-coding regions from the influenza B virus HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In specific embodiments, the chimeric HA polypeptide is soluble. In certain embodiments, the chimeric HA polypeptides comprise 1, 2, 3, 4, 5 or more amino acid substitutions in the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid).

In another aspect, provided herein are chimeric hemagglutinin (HA) polypeptides comprising an HA ectodomain of an influenza B virus comprising one, two, three or all of the following: (i) 2, 3, 4, 5, 6, 7, 8, 9, 10, 11, 12, 13, 14, 15, 16, 17, 18, 19, 20 or more amino acid substitutions within the 120 loop of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the influenza B virus HA with amino acid residues found in a corresponding region of an influenza A virus HA; (ii) 2, 3, 4, 5, 6, 7, 8, 9 or more amino acid substitutions within the 150 loop of the influenza B virus HA, wherein the amino acid substitutions substitute 2, 3, 4, 5, 6, 7, 8, 9 or more amino acid residues in the 150 loop of the influenza B virus HA with amino acid residues found in a corresponding region of an influenza A virus HA; (iii) 2, 3, 4, 5 or more amino acid substitutions within the 160 loop of the influenza B virus HA, wherein the amino acid substitutions substitute 2, 3, 4, 5 or more amino acid residues in the 160 loop of the influenza B virus HA with amino acid residues found in a corresponding region of an influenza A virus HA; and (iv) 2, 3, 4, 5, 6, 7, 8 or more amino acid substitutions within the 190 helix of the influenza B virus HA, wherein the amino acid substitutions substitute 2, 3, 4, 5, 6, 7, 8 or more amino acid residues in the 190 helix of the influenza B virus HA with amino acid residues found in a corresponding region of an influenza A virus HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAE-VAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKL-STFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTH-NVINAERAPGGPYRL (SEQ ID NO: 1) are substituted with amino acid residues NIP and RIELSTHNVINAE-VAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In some embodiments, the chimeric HA polypeptide may also comprise the signal peptide, transmembrane domain, and cytoplasmic tail domain from the influenza B virus HA. In other embodiments, the chimeric HA polypeptide comprises the signal peptide from the influenza B virus HA but lacks the transmembrane and cytoplasmic tail domains. In some embodiments, the chimeric HA polypeptide may also comprise the signal peptide, transmembrane domain, and cytoplasmic tail domain from an influenza A virus HA. In other embodiments, the chimeric HA polypeptide comprises the signal peptide from an influenza A virus HA but lacks the transmembrane and cytoplasmic tail domains. In some embodiments, the chimeric HA comprises the signal peptide of the HA of the influenza virus backbone of the chimeric HA. For example, if the chimeric HA is engineered for an influenza A virus backbone (e.g., the influenza virus comprising or engineered to express the chimeric HA is an influenza A virus), then the chimeric HA comprises the signal peptide of the influenza A virus. In some embodiments, the chimeric HA comprises the signal peptide, transmembrane domain, and cytoplasmic domain of the HA of the influenza virus backbone of the chimeric HA. In some embodiments, the chimeric HA polypeptide may also comprise the signal peptide from the HA of the influenza virus that is engineered to express the chimeric HA. In some embodiments, the chimeric HA polypeptide may also comprise the signal peptide, transmembrane domain, and cytoplasmic tail domain from the HA of the influenza virus that is engineered to express the chimeric HA. Also provided herein are nucleic acids comprising nucleotide sequences encoding such a chimeric HA. In some embodiments, the nucleic acids comprise nucleotide sequences encoding such a chimeric HA and the 5' and 3' non-coding regions from the influenza B virus HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In specific embodiments, the chimeric HA polypeptide is soluble. In certain embodiments, the chimeric HA polypeptides comprise 1, 2, 3, 4, 5 or more amino acid substitutions in the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid).

In another aspect, provided herein are chimeric hemagglutinin (HA) polypeptides comprising (i) a hemagglutinin ectodomain from an influenza B virus with 2, 3, 4, 5, 6, 7, 8, 9, 10, 11, 12 or more amino acid substitutions within the 120 loop, 150 loop, 160 loop or 190 helix of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9, 10, 11, 12 or more amino acid residues in the 120 loop, 150 loop, 160 loop or 190 helix of the influenza B virus HA with amino acid residues found in a corresponding region of an influenza A virus HA. In one embodiment, provided herein are chimeric hemagglutinin (HA) polypeptides comprising (i) a hemagglutinin ectodomain from an influenza B virus with 2, 3, 4, 5, 6, 7, 8, 9, 10, 11, 12, 13, 14, 15, 16, 17, 18, 19, 20 or more amino acid substitutions within the 120 loop of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the influenza B virus HA with amino acid residues found in a corresponding region of an influenza A virus HA. In another embodiment, provided herein are chimeric hemagglutinin (HA) polypeptides comprising (i) a hemagglutinin ectodomain from an influenza B virus with 2, 3, 4, 5, 6, 7, 8, 9 or more amino acid substitutions within the 150 loop of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9 or more amino acid residues in the 150 loop of the influenza B virus HA with amino acid residues found in a corresponding region of an influenza A virus HA. In another embodiment, provided herein are chimeric hemagglutinin (HA) polypeptides comprising (i) a hemagglutinin ectodomain from an influenza B virus with 2, 3, 4, 5 or more amino acid substitutions within the 160 loop of the influenza B virus HA and (ii) a signal peptide, a transmembrane domain and a cytoplasmic tail domain from an influenza A virus, wherein the amino acid substitutions substitute 2, 3, 4, 5 or more amino acid residues in the 160 loop of the influenza B virus HA with amino acid residues found in a corresponding region of an influenza A virus HA. In another embodiment, provided herein are chimeric hemagglutinin (HA) polypeptides comprising (i) a hemagglutinin ectodomain from an influenza B virus with 2, 3, 4, 5, 6, 7, 8 or more amino acid substitutions within the 190 helix of the influenza B virus HA and (ii) a signal peptide, a transmembrane domain and a cytoplasmic tail domain from an influenza A virus, wherein the amino acid substitutions substitute 2, 3, 4, 5, 6, 7, 8 or more amino acid residues in the 190 helix of the influenza B virus HA with amino acid residues found in a corresponding region of an influenza A virus HA. In specific embodiments, the following underlined and bold amino acid residues in the 120 loop of influenza B virus B/Yamagata/16/88 T<u>I</u>P and N<u>I</u>RLSTH-NVINAE<u>R</u>APGGPYRL (SEQ ID NO: 1) are substituted with the following underlined and bold amino acid residues F<u>I</u>P and K<u>I</u>QLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 T<u>I</u>P and N<u>I</u>RLSTH- NVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the influenza B virus is from the Yamagata lineage. In other embodiments, the influenza B virus is from the Victoria lineage. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding such a chimeric HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA.

In another aspect, provided herein are chimeric hemagglutinin (HA) polypeptides comprising (i) a hemagglutinin ectodomain from a first influenza B virus strain with 2, 3, 4, 5, 6, 7, 8, 9, 10, 11, 12 or more amino acid substitutions within the 120 loop, 150 loop, 160 loop or 190 helix of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8, 9, 10, 11, 12 or more amino acid residues in the 120 loop, 150 loop, 160 loop or 190 helix of the first influenza B virus strain HA with amino acid residues found in a corresponding region of an influenza A virus HA. In one embodiment, provided herein are chimeric hemagglutinin (HA) polypeptides comprising (i) a hemagglutinin ectodomain from a first influenza B virus strain with 2, 3, 4, 5, 6, 7, 8, 9, 10, 11, 12, 13, 14, 15, 16, 17, 18, 19, 20 or more amino acid substitutions within the 120 loop of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the first influenza B virus strain HA with amino acid residues found in a corresponding region of an influenza A virus HA. In another embodiment, provided herein are chimeric hemagglutinin (HA) polypeptides comprising (i) a hemagglutinin ectodomain from a first influenza B virus strain with 2, 3, 4, 5, 6, 7, 8, 9 or more amino acid substitutions within the 150 loop of the first influenza B virus strain HA and (ii) a signal peptide, a transmembrane domain and a cytoplasmic tail domain from a second influenza B virus, wherein the amino acid substitutions substitute 2, 3, 4, 5, 6, 7, 8, 9 or more amino acid residues in the 150 loop of the first influenza B virus strain HA with amino acid residues found in a corresponding region of an influenza A virus HA. In another embodiment, provided herein are chimeric hemagglutinin (HA) polypeptides comprising (i) a hemagglutinin ectodomain from a first influenza B virus strain with 2, 3, 4, 5 or more amino acid substitutions within the 160 loop of the first influenza B virus strain HA and (ii) a signal peptide, a transmembrane domain and a cytoplasmic tail domain from a second influenza B virus strain, wherein the amino acid substitutions substitute 2, 3, 4, 5 or more amino acid residues in the 160 loop of the first influenza B virus strain HA with amino acid residues found in a corresponding region of an influenza A virus HA. In another embodiment, provided herein are chimeric hemagglutinin (HA) polypeptides comprising (i) a hemagglutinin ectodomain from a first influenza B virus strain with 2, 3, 4, 5, 6, 7, 8 or more amino acid substitutions within the 190 helix of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8 or more amino acid residues in the 190 helix of the first influenza B virus strain HA with amino acid residues found in a corresponding region of an influenza A virus HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following amino acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 13. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 15. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 17. In specific embodiments, a chimeric HA polypeptide described herein comprises a one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTH-NVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the influenza B virus HA which are outside of one, two, three, or all of the following: the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the first influenza B virus strain and the second influenza B virus strain are from the same lineage. In some embodiments, the first influenza B virus strain and the second influenza B virus strain are from the same lineage but are different strains. In a specific embodiment, the first influenza B virus strain is the same strain as the second influenza B virus strain. In another embodiment, the first influenza B virus strain is a different strain than the second influenza B virus strain. In some embodiments, the first influenza B virus strain and the second influenza B virus strain are from different lineages. In some embodiments, the first influenza B virus strain is from the Yamagata lineage. In other embodiments, the first influenza B virus is from the Victoria lineage. In some embodiments, the second influenza B virus strain is from the Yamagata lineage. In other embodiments, the second influenza B virus is from the Victoria lineage. In a specific embodiment, the second influenza B virus strain is the same strain as the influenza virus backbone of an influenza virus either containing, expressing, or both the chimeric HA. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding such a chimeric HA and the 5' non-coding region and 3' non-coding region from an influenza B virus. In some embodiments, the nucleic acids comprise nucleotide sequences encoding such a chimeric HA and the 5' and 3' non-coding regions of the HA of the influenza virus backbone of an influenza virus either comprising, containing, or both the chimeric HA.

In another aspect, provided herein are chimeric hemagglutinin (HA) polypeptides comprising: (a) a hemagglutinin ectodomain from an influenza B virus with one, two, three or all of the following (i) 2, 3, 4, 5, 6, 7, 8, 9, 10, 11, 12, 13, 14, 15, 16, 17, 18, 19, 20 or more amino acid substitutions within the 120 loop of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the influenza B virus HA with amino acid residues found in a corresponding region of an influenza A virus HA; (ii) 2, 3, 4, 5, 6, 7, 8, 9 or more amino acid substitutions within the 150 loop of the influenza B virus HA, wherein the amino acid substitutions substitute 2, 3, 4, 5, 6, 7, 8, 9 or more amino acid residues in the 150 loop of the influenza B virus HA with amino acid residues found in a corresponding region of an influenza A virus HA; (iii) 2, 3, 4, 5 or more amino acid substitutions within the 160 loop of the influenza B virus HA, wherein the amino acid substitutions substitute 2, 3, 4, 5 or more amino acid residues in the 160 loop of the influenza B virus HA with amino acid residues found in a corresponding region of an influenza A virus HA; and (iv) 2, 3, 4, 5, 6, 7, 8 or more amino acid substitutions within the 190 helix of the influenza B virus HA, wherein the amino acid substitutions substitute 2, 3, 4, 5, 6, 7, 8 or more amino acid residues in the 190 helix of the influenza B virus HA with amino acid residues found in a corresponding region of an influenza A virus HA; and (b) a signal peptide, a transmembrane domain and a cytoplasmic tail domain from an influenza A virus. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 <u>RDNKTA</u> (SEQ ID NO: 5) are substituted with the following bold and underlined amino acid residues <u>KKKPDTY</u> (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>ADAKMQT</u> (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>PDAKMQT</u> (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 <u>TIP</u> and <u>NIRLSTHNVINAERAPGGPYRL</u> (SEQ ID NO: 1) are substituted with the following underlined and bold amino acid residues <u>LIP</u> and <u>KIELSTSNVINAEVAPGGPYRL</u> (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 <u>RDNKTA</u> (SEQ ID NO: 5) are substituted with the following bold and underlined amino acid residues <u>HQSGTY</u> (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>TTLKMHQ</u> (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 <u>NKNQMKN</u> (SEQ ID NO: 7) are substituted with the following underlined and bold amino acid residues <u>ATLKMHQ</u> (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 <u>TIP</u> and <u>NIRLSTHNVINAERAPGGPYRL</u> (SEQ ID NO: 1) are substituted with the following underlined and bold amino acid residues <u>YIP</u> and <u>RIKLSTFNVINAETAPGGPYRL</u> (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 <u>RDNKTA</u> (SEQ ID NO: 5) are substituted with amino acid residues <u>LKSGQF</u> (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the influenza B virus is from the Yamagata lineage. In other embodiments, the influenza B virus is from the Victoria lineage. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding such a chimeric HA and the 5' non-coding region and 3' non-coding region from an influenza A virus. In some embodiments, the nucleic acids comprise nucleotide sequences encoding a chimeric HA polypeptide and the 5' non-coding region and 3' non-coding region from an influenza B virus. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In a specific embodiment, the nucleic acid comprises the nucleotide sequence set forth in FIG. 12A and FIG. 12B or the complement thereof. In a specific embodiment, the nucleic acid comprises the nucleotide sequence set forth in FIG. 14A and FIG. 14B or the complement thereof. In a specific embodiment, the nucleic acid comprises the nucleotide sequence set forth in FIG. 16A and FIG. 16B or the complement thereof. In a specific embodiment, the nucleic acid comprises the nucleotide sequence set forth in FIG. 18A and FIG. 18B or the complement thereof.

In another aspect, provided herein are chimeric hemagglutinin (HA) polypeptides comprising: (a) a hemagglutinin ectodomain from a first influenza B virus strain with one, two, three or all of the following (i) 2, 3, 4, 5, 6, 7, 8, 9, 10, 11, 12, 13, 14, 15, 16, 17, 18, 19, 20 or more amino acid substitutions within the 120 loop of the first influenza B virus strain HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the first influenza B virus strain HA with amino acid residues found in a corresponding region of an influenza A virus HA; (ii) 2, 3, 4, 5, 6, 7, 8, 9 or more amino acid substitutions within the 150 loop of the first influenza B virus strain HA, wherein the amino acid substitutions substitute 2, 3, 4, 5, 6, 7, 8, 9 or more amino acid residues in the 150 loop of the first influenza B virus strain HA with amino acid residues found in a corresponding region of an influenza A virus HA; (iii) 2, 3, 4, 5 or more amino acid substitutions within the 160 loop of the first influenza B virus strain HA, wherein the amino acid substitutions substitute 2, 3, 4, 5 or more amino acid residues in the 160 loop of the first influenza B virus strain HA with amino acid residues found in a corresponding region of an influenza A virus HA; and (iv) 2, 3, 4, 5, 6, 7, 8 or more amino acid substitutions within the 190 helix of the first influenza B virus strain HA, wherein the amino acid substitutions substitute 2, 3, 4, 5, 6, 7, 8 or more amino acid residues in the 190 helix of the first influenza B virus strain HA with amino acid residues found in a corresponding region of an influenza A virus HA; and (b) a signal peptide, a transmembrane domain and a cytoplasmic tail domain from a second influenza B virus strain. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 13. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 15. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 17. In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises one, two, three, or all of the following: a 120 loop, a 150 loop, a 160 loop, and a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the influenza B virus HA which are outside of one, two, three, or all of the following: the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the first influenza B virus strain and the second influenza B virus strain are from the same lineage. In some embodiments, the first influenza B virus strain and the second influenza B virus strain are from the same lineage but are different strains. In a specific embodiment, the first influenza B virus strain is the same strain as the second influenza B virus strain. In another embodiment, the first influenza B virus strain is a different strain than the second influenza B virus strain. In some embodiments, the first influenza B virus strain and the second influenza B virus strain are from different lineages. In some embodiments, the first influenza B virus strain is from the Yamagata lineage. In other embodiments, the first influenza B virus is from the Victoria lineage. In some embodiments, the second influenza B virus strain is from the Yamagata lineage. In other embodiments, the second influenza B virus is from the Victoria lineage. In a specific embodiment, the second influenza B virus strain is the same strain as the influenza virus backbone of an influenza virus either comprising, containing, or both the chimeric HA. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding such a chimeric HA and the 5' and 3' non-coding regions of the HA of the influenza virus backbone of an influenza virus either comprising, containing, or both the chimeric HA. In a specific embodiment, the nucleic acid comprises the nucleotide sequence set forth in FIG. 29 or the complement thereof. In a specific embodiment, the nucleic acid comprises the nucleotide sequence set forth in FIG. 31 or the complement thereof. In a specific embodiment, the nucleic acid comprises the nucleotide sequence set forth in FIG. 33 or the complement thereof. In a specific embodiment, the nucleic acid comprises the nucleotide sequence set forth in FIG. 35 or the complement thereof.

In a specific embodiment, the influenza A virus HA utilized in the generation of a chimeric HA polypeptide described herein is the HA from an influenza virus of the H1, H2, H3, H4, H5, H6, H7, H8, H9, H10, H11, H12, H13, H14, H15, H16, H17, or H18 subtype. In a specific embodiment, the influenza A virus HA utilized in the generation of a chimeric HA polypeptide described herein is the HA from an influenza virus of the H2, H4, H5, H6, H7, H8, H9, H10, H11, H12, H13, H14, H15, H16, H17, or H18 subtype. In a specific embodiment, the influenza A virus HA utilized in the generation of a chimeric HA polypeptide described herein is the HA from an influenza virus of the H5, H8, H11, H12, or H13 subtype. In a specific embodiment, the influenza A virus HA utilized in the generation of a chimeric HA polypeptide described herein is the HA from an influenza virus of the H5 subtype. In a specific embodiment, the influenza A virus HA utilized in the generation of a chimeric HA polypeptide described herein is the HA from an influenza virus of the H8 subtype. In a specific embodiment, the influenza A virus HA utilized in the generation of a chimeric HA polypeptide described herein is the HA from an influenza virus of the H11 subtype. In a specific embodiment, the influenza A virus HA utilized in the generation of a chimeric HA polypeptide described herein is the HA from an influenza virus of the H12 subtype. In a specific embodiment, the influenza A virus HA utilized in the generation of a chimeric HA polypeptide described herein is the HA from an influenza virus of the H13 subtype. In a specific embodiment, the influenza A virus HA utilized in the generation of a chimeric HA polypeptide described herein is the HA from an avian influenza virus. In a specific embodiment, the influenza A virus HA utilized in the generation of a chimeric HA polypeptide described herein is the HA from influenza A/mallard/Sweden/24/2002 virus (GenBank Accession No. CY060249.1; GenBank GI No. 294441479; see, also, FIG. 21A and FIG. 21). In a specific embodiment, the influenza A virus HA utilized in the generation of a chimeric HA polypeptide described herein is the HA from influenza A/Vietnam/1203/04 virus (GenBank Accession No. EF541403.1; GenBank GI No. 145284465; see, also, FIG. 22A and FIG. 22B and Steel et al., 2009, Journal of Virology, 83(4):1742-1753 for the HA of influenza A/Vietnam/1203/04 (HALo) virus). In a specific embodiment, the influenza A virus HA utilized in the generation of a chimeric HA polypeptide described herein is the HA from influenza A/northern shoveler/Netherlands/18/99 virus (GenBank Accession No. CY060417.1; GenBank GI No. 294441876; see, also, FIG. 23A and FIG. 23B). In a specific embodiment, the influenza A virus HA utilized in the generation of a chimeric HA polypeptide described herein is the HA from influenza A_mallard_interior Alaska_7MP0167_2007 virus (GenBank Accession No. CY077198.1; GenBank GI No. 312652817; see, also, FIG. 24A and FIG. 24B). In a specific embodiment, the influenza A virus HA utilized in the generation of a chimeric HA polypeptide described herein is the HA from influenza A/black headed gull/Sweden/1/99 (GenBank Accession No. AY684887.1; see, also, FIG. 41A and FIG. 41). In a specific embodiment, the influenza A virus HA utilized in the generation of a chimeric HA polypeptide described herein is the HA from influenza A/Puerto Rico/8/34 virus (GenBank Accession No. AF389118.1; GenBank GI No. 21693168; see, also, FIG. 25A and FIG. 25B). In a specific embodiment, the influenza B virus HA utilized in the generation of a chimeric HA polypeptide described herein is the HA from influenza B/Yamagata/16/88 virus (see, FIG. 26A and FIG. 26B). In a specific embodiment, the influenza B virus HA utilized in the generation of a chimeric HA polypeptide described herein is the HA from a mouse-adapted influenza B/Malaysia/2506/04 virus (see, e.g., SEQ ID NO: 73 or 83). In a specific embodiment, the influenza B virus HA utilized in the generation of a chimeric HA polypeptide described herein is the HA from influenza B/Malaysia/2506/04 virus (see, e.g., GenBank Accession No. CY040449.1).

In a specific embodiment, a chimeric HA polypeptide is a chimeric HA polypeptide described in Section 6, infra.

In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within an antigenic loop of the influenza B virus HA (e.g., 120 loop, 150 loop, 160 loop and/or 190 helix), wherein the amino acid substitutions substitute 2, 3, 4, 5, 6, 7, 8, 9, 10, 11, 12 or more amino acid residues in the loop of the influenza B virus HA with random amino acid residues that do not affect the conformation/structure of the HA. In addition to these amino acid residue substitutions, one or more substitutions outside of the antigenic loops may be introduced. The amino acid substitutions are selected such that the folding of the chimeric HA is not significantly impacted as determined by techniques known to one of skill in the art or described herein. In addition, the amino acid substitutions may be selected such that the coding sequence for N-linkd glycosylation sites (N-X-S/T) is not altered or not significantly altered. The effect of amino acid substitutions on the conformation/structure may be determined by assays known to one of skill in the art, e.g., structure programs, crystallography, or functional assays. See, e.g., Section 5.11, infra, and Section 6, infra. For example, the chimeric HA polypeptides may be evaluated for antigenic conservation using a panel of monoclonal antibodies that bind to conserved epitopes in the globular head domain of HA and the stem domain of HA. In a specific embodiment, the methods described in Section 6, infra, are used to evaluate antigenic conservation of the chimeric HA. In addition, the chimeric HA polypeptides described herein may be evaluated to determine whether the antigenic loops of the influenza B virus HA were mutated using techniques known to one of skill in the art or described herein (see, e.g., Section 6, infra, including the HI assay described therein). In particular, the chimeric HA polypeptides described herein may be evaluated to determine if the amino acid substitutions in the antigenic loop(s) of the influenza B virus HA result in loss of a variable region(s) of the influenza B virus HA using techniques known to one of skill in the art or described herein (see, e.g., Section 6, infra, including the HI assay described therein). In a specific embodiment, the chimeric HA polypeptides described herein may be evaluated to determine if the amino acid substitutions in the antigenic loop(s) of the influenza B virus HA reduce or eliminate the immunodominant epitopes of the influenza B virus HA using techniques known to one of skill in the art or described herein (see, e.g., Section 6, infra, including the HI assay described therein). In a specific embodiment, a chimeric HA polypeptide described herein is assessed in an HI assay, such as described in Section 6, infra, to evaluate the replacement of the antigenic loop(s) in the influenza B virus HA.

In another aspect, provided herein are nucleic acid sequences comprising a nucleotide sequence encoding a chimeric HA polypeptide described herein. In a specific embodiment, provided herein is a nucleic acid sequence comprising a nucleotide sequence encoding a chimeric HA polypeptide described herein. In another specific embodiment, provided herein is an HA segment comprising the nucleic acid sequence encoding a chimeric HA polypeptide described herein. In a specific embodiment, the nucleic acid sequence comprises the nucleotide sequence set forth in FIG. 12, FIG. 14, FIG. 16, FIG. 18, FIG. 29, FIG. 31, FIG. 33, or FIG. 35. In certain embodiments, the HA segment or the nucleic acid sequence comprising the nucleotide sequence encoding a chimeric HA polypeptide described herein are transfected into cells (e.g., cell lines).

In another aspect, provided herein are host cells comprising or engineered to express a chimeric HA polypeptide described herein. In one embodiment, provided herein are host cells comprising a chimeric HA polypeptide described herein. In another embodiment, provided herein are host cells comprising an HA segment comprising the nucleic acid sequence encoding a chimeric HA polypeptide described herein. In another embodiment, provided herein are embryonated eggs (e.g., chicken embryonated eggs) comprising a chimeric HA polypeptide described herein. In another embodiment, provided herein are embryonated eggs (e.g., chicken embryonated eggs) comprising an HA segment comprising the nucleic acid sequence encoding a chimeric HA polypeptide described herein. In another embodiment, provided herein are embryonated eggs (e.g., chicken embryonated eggs) comprising an influenza virus, wherein said influenza virus comprises an HA segment comprising the nucleic acid sequence encoding a chimeric HA polypeptide described herein. In another embodiment, provided herein are embryonated eggs (e.g., chicken embryonated eggs) comprising an influenza virus, wherein the influenza virus comprises a chimeric HA polypeptide described herein.

In another aspect, provided herein are influenza viruses engineered to express a chimeric HA polypeptide described herein. In a specific embodiment, provided herein is an influenza A virus engineered to express a chimeric HA polypeptide described herein. In accordance with this embodiment, the signal peptide, transmembrane domain and cytoplasmic tail domain of the chimeric HA polypeptide are preferably derived from the same influenza A virus as the influenza A virus engineered to express the chimeric HA polypeptide. Thus, in accordance with this embodiment, a nucleic acid comprising nucleotide sequences encoding said chimeric HA polypeptide preferably comprises the 5' non-coding region, 3' non-coding region and nucleotide sequences encoding the signal peptide, transmembrane domain, and cytoplasmic domain derived from the same influenza A virus as the influenza A virus engineered to express the chimeric HA polypeptide. In specific embodiments, provided herein is an influenza A virus comprising 7 non-HA segments of an influenza A virus segments and an HA segment comprising the nucleic acid sequence encoding a chimeric HA polypeptide described herein. In accordance with these embodiments, the signal peptide, transmembrane domain and cytoplasmic tail domain of the chimeric HA polypeptide are preferably derived from the same influenza A virus as influenza A virus comprising the non-HA segments. In accordance with these embodiments, a nucleic acid comprising nucleotide sequences encoding the chimeric HA polypeptide preferably comprises the 5' non-coding region and the 3' non-coding region, and the nucleic sequences encoding the signal peptide, transmembrane domain, and cytoplasmic domain derived from the same influenza A virus as the influenza A virus comprising the non-HA segments. In another embodiment, provided herein is an influenza A virus engineered to express and contain a chimeric HA polypeptide described herein.

In a specific embodiment, provided herein is an influenza B virus engineered to express a chimeric HA polypeptide described herein. In specific embodiments, provided herein is an influenza B virus comprising 7 non-HA segments of an influenza B virus segments and an HA segment comprising the nucleic acid sequence encoding a chimeric HA polypeptide described herein. In certain embodiments, the 7 non-HA segments are from the same influenza B virus as the ectodomain of the chimeric HA polypeptide. In some embodiments, the 7 non-HA segments are from the same influenza B virus as the globular head domain of the chimeric HA polypeptide. In another embodiment, provided herein is an influenza B virus engineered to express and contain a chimeric HA polypeptide described herein.

In a specific embodiment, provided herein is an influenza B virus engineered to express a chimeric HA polypeptide described herein. In accordance with this embodiment, the signal peptide, transmembrane domain and cytoplasmic tail domain of the chimeric HA polypeptide are preferably derived from the same influenza B virus as the influenza B virus engineered to express the chimeric HA polypeptide. Thus, in accordance with this embodiment, a nucleic acid comprising nucleotide sequences encoding said chimeric HA polypeptide preferably comprises the 5' non-coding region, 3' non-coding region and nucleotide sequences encoding the signal peptide, transmembrane domain, and cytoplasmic domain derived from the same influenza B virus as the influenza B virus engineered to express the chimeric HA polypeptide. In specific embodiments, provided herein is an influenza B virus comprising 7 non-HA segments of an influenza B virus segment and an HA segment comprising the nucleic acid sequence encoding a chimeric HA polypeptide described herein. In accordance with these embodiments, the signal peptide, transmembrane domain and cytoplasmic tail domain of the chimeric HA polypeptide are preferably derived from the same influenza B virus as the influenza B virus comprising the non-HA segments. In accordance with these embodiments, a nucleic acid comprising nucleotide sequences encoding the chimeric HA polypeptide preferably comprises the 5' non-coding region and the 3' non-coding region, and the nucleic sequences encoding the signal peptide, transmembrane domain, and cytoplasmic domain derived from the same influenza B virus as the influenza B virus comprising the non-HA segments. In another embodiment, provided herein is an influenza B virus engineered to express and contain a chimeric HA polypeptide described herein.

In another aspect, provided herein are influenza viruses containing a chimeric HA polypeptide described herein. In a specific embodiment, provided herein is an influenza A virus containing a chimeric HA polypeptide described herein. In another embodiment, provided herein is an influenza B virus containing a chimeric HA polypeptide described herein. In certain embodiments, the influenza B virus containing the chimeric HA polypeptide is from the Yamagata lineage. In other embodiments, the influenza B virus containing the chimeric HA polypeptide is from the Victoria lineage. In specific embodiments, the influenza B virus containing the chimeric HA polypeptide is B/Malaysia/2506/04.

In a specific embodiment, provided herein is an influenza virus described in Section 6, infra.

In one embodiment, provided herein is a virus-like particle comprising a chimeric HA polypeptide described herein. In another embodiment, provided herein is a virosome comprising a chimeric HA polypeptide described herein.

In another aspect, provided herein are compositions (e.g., immunogenic compositions) comprising a chimeric HA polypeptide described herein, a nucleic acid sequence comprising a nucleotide sequence encoding a chimeric HA polypeptide described herein, an HA segment comprising the nucleic acid sequence encoding a chimeric HA polypeptide described herein, an influenza virus comprising/containing a chimeric HA polypeptide described herein, an influenza virus engineered to express a chimeric HA polypeptide described herein, a virus-like particle comprising a chimeric HA polypeptide described herein, or a virosome comprising a chimeric HA polypeptide described herein. In one embodiment, provided herein is an immunogenic composition comprising a chimeric HA polypeptide described herein. In another embodiment, provided herein is an immunogenic composition comprising a nucleic acid sequence comprising a nucleotide sequence encoding a chimeric HA polypeptide described herein or an HA segment comprising the nucleic acid sequence encoding a chimeric HA polypeptide described herein. In another embodiment, provided herein is an immunogenic composition comprising an influenza virus comprising a chimeric HA polypeptide described herein. In another embodiment, provided herein is an immunogenic composition comprising an influenza virus engineered to express a chimeric HA polypeptide described herein. In another embodiment, provided herein is an immunogenic composition comprising an influenza virus engineered to express and contain a chimeric HA polypeptide described herein. In certain embodiments, the influenza virus is a live attenuated influenza virus. In other embodiments, the influenza virus is an inactivated virus. In one embodiment, the composition is a subunit vaccine. In another embodiment, the composition is a split vaccine. In another embodiment, provided herein is an immunogenic composition comprising a virus-like particle described herein. In another embodiment, provided herein is an immunogenic composition comprising a virosome described herein. In some embodiments, the compositions further comprise one or more adjuvants (see, e.g., Section 5.7, infra, regarding adjuvants, such as ASO3 or MF59).

In another aspect, provided herein are methods for immunizing a subject against influenza virus, comprising administering to the subject a composition described herein. In a specific embodiment, provided herein is a method for immunizing a subject against influenza virus, comprising administering to the subject an effective amount of a composition described herein. In a specific embodiment, provided herein is a method for inducing an immune response (e.g., an antibody response) to an influenza B virus HA stem domain in a subject, comprising administering the subject a composition described herein. In another specific embodiment, provided herein is a method for inducing an immune response (e.g., an antibody response) to an influenza B virus HA globular head domain and stem domain in a subject, comprising administering to the subject a composition described herein. In another specific embodiment, provided herein is a method for inducing an immune response (e.g., an antibody response) to an influenza B virus HA stem domain and an influenza A virus globular head domain in a subject, comprising administering the subject a composition described herein. In another specific embodiment, provided herein is a method for inducing an immune response (e.g., an antibody response) to an influenza B virus HA globular head domain and stem domain, and an influenza A virus globular head domain in a subject, comprising administering to the subject a composition described herein. In particular embodiments, the subject is human.

In another embodiment, provided herein is a method of immunizing a subject against an influenza virus disease or infection comprising (i) a first administration of a first chimeric HA polypeptide, a first nucleic acid encoding such a polypeptide(s), a first vector either containing, expressing, or both such a polypeptide(s), or cells described herein to the subject; and (ii) a second administration of a second chimeric HA polypeptide, a second nucleic acid encoding such a polypeptide(s), a second vector either containing, expressing, or both such a polypeptide(s), or cells described herein to the subject, wherein the first and second chimeric HA polypeptides comprise an ectodomain with the same stem domains but have different 120 loops, 150 loops, 160 loops, and/or 190 helices. In specific embodiments, the first and second chimeric HA have either one, two, three, or four of the following: (i) different 120 loops, (ii) different 150 loops, (iii) different 160 loops, and (iv) different 190 helices. The first and second administrations may be separated by at least 1 day, 2 days, 3 days, 5 days, 10 days, 15 days, 30 days, 45 days, 2 months, 75 days, 3 months, or at least 6 months. In specific embodiments, the first and second administrations may be separated by 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In certain embodiments, booster inoculations may be administered to the subject at 6 to 12 month intervals following the second inoculation. In certain embodiments, the booster inoculation comprises a third chimeric HA polypeptide, a third nucleic acid encoding such a polypeptide(s), a third vector either containing, expressing, or both such a polypeptide(s), or cells described herein, wherein the first, second, and third chimeric HA polypeptides comprise an ectodomain with the same stem but have different 120 loops, 150 loops, 160 loops, and/or 190 helices. In specific embodiments, the first, second, and third chimeric HA have either one, two, three, or four of the following: (i) different 120 loops, (ii) different 150 loops, (iii) different 160 loops, and (iv) different 190 helices.

In another aspect, provided herein is a composition described herein for use in a method for immunizing a subject against influenza virus, wherein the method comprises administering to the subject the composition. In a specific embodiment, provided herein is a composition described herein for use in a method for immunizing a subject against influenza virus, wherein the method comprises administering to the subject an effective amount of the composition. In a specific embodiment, provided herein is a composition described herein for use in a method for inducing an immune response (e.g., an antibody response) to an influenza B virus HA stem domain in a subject, wherein the method comprises administering the subject the composition. In another specific embodiment, provided herein is a composition described herein for use in a method for inducing an immune response (e.g., an antibody response) to an influenza B virus HA globular head domain and stem domain in a subject, wherein the method comprises administering to the subject the composition. In another specific embodiment, provided herein is a composition described herein for use in a method for inducing an immune response (e.g., an antibody response) to an influenza B virus HA stem domain and an influenza A virus globular head domain in a subject, wherein the method comprises administering the subject the composition. In another specific embodiment, provided herein is a composition described herein for use in a method for inducing an immune response (e.g., an antibody response) to an influenza B virus HA globular head domain and stem domain, and an influenza A virus globular head domain in a subject, wherein the method comprises administering to the subject the composition. In particular embodiments, the subject is human.

In another embodiment, provided herein is a first immunogenic composition for use in a method of immunizing a subject against an influenza virus disease or infection, wherein the method comprises (i) a first administration of the first immunogenic composition to the subject, wherein the first immunogenic composition comprises a first chimeric HA polypeptide, a first nucleic acid encoding such a polypeptide(s), a first vector either containing, expressing, or both such a polypeptide(s), or cells described herein; and (ii) a second administration of a second immunogenic composition to the subject, wherein the second immunogenic composition comprises chimeric HA polypeptide, a second nucleic acid encoding such a polypeptide(s), a second vector either containing, expressing, or both such a polypeptide(s), or cells described herein, and wherein the first and second chimeric HA polypeptides comprise an ectodomain with the same stem domains but have different 120 loops, 150 loops, 160 loops, and/or 190 helices. In specific embodiments, the first and second chimeric HA have either one, two, three, or four of the following: (i) different 120 loops, (ii) different 150 loops, (iii) different 160 loops, and (iv) different 190 helices. The first and second administrations may be separated by at least 1 day, 2 days, 3 days, 5 days, 10 days, 15 days, 30 days, 45 days, 2 months, 75 days, 3 months, or at least 6 months. In specific embodiments, the first and second administrations may be separated by 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In certain embodiments, booster inoculations may be administered to the subject at 6 to 12 month intervals following the second inoculation. In certain embodiments, the booster inoculation comprises a third chimeric HA polypeptide, a third nucleic acid encoding such a polypeptide(s), a third vector either containing, expressing, or both such a polypeptide(s), or cells described herein, wherein the first, second, and third chimeric HA polypeptides comprise an ectodomain with the same stem but have different 120 loops, 150 loops, 160 loops, and/or 190 helices. In specific embodiments, the first, second, and third chimeric HA have either one, two, three, or four of the following: (i) different 120 loops, (ii) different 150 loops, (iii) different 160 loops, and (iv) different 190 helices.

Without being bound by any theory, the chimeric HA polypeptides described herein, when administered to a subject, focuses the immune response towards conserved epitopes in the globular head domain as well as the stem domain of an influenza B virus HA. Thus, in specific embodiments, provided herein is a method for inducing an immune response (e.g., an antibody response) to conserved epitopes in the globular head domain and stem domain of an influenza B virus HA in a subject, comprising administering to the subject a chimeric HA polypeptide described herein or a composition thereof.

In another aspect, provided herein are methods for preventing and/or treating an influenza virus infection or influenza virus disease, comprising administering to a subject in need thereof a composition described herein. In a specific embodiment, provided herein is a method for preventing an influenza virus disease, comprising administering to a subject in need thereof a composition described herein. In another specific embodiment, provided herein is a method for treating an influenza virus infection, comprising administering to a subject in need thereof a composition described herein. In another specific embodiment, provided herein is a method for treating an influenza virus disease, comprising administering to a subject in need thereof a composition described herein. In particular embodiments, the subject is human.

In another aspect, provided herein is a composition described herein for use in a method for preventing and/or treating an influenza virus infection or influenza virus disease, wherein the method comprises administering to a subject in need thereof the composition. In a specific embodiment, provided herein is a composition described herein for use in a method for preventing an influenza virus disease, wherein the method comprises administering to a subject in need thereof the composition. In another specific embodiment, provided herein is a composition described herein for use in a method for treating an influenza virus infection, wherein the method comprises administering to a subject in need thereof the composition. In another specific embodiment, provided herein is a composition described herein for use in a method for treating an influenza virus disease, wherein the method comprises administering to a subject in need thereof the composition. In particular embodiments, the subject is human.

The chimeric HA polypeptides, nucleic acids encoding such polypeptides, or vectors comprising such nucleic acids or polypeptides described herein may be used to elicit neutralizing antibodies against influenza, for example, against the stalk region of an influenza virus hemagglutinin polypeptide and/or subdominant epitopes in the globular head domain of an influenza virus hemagglutinin polypeptide. In a specific embodiment, the chimeric HA polypeptide, nucleic acids encoding such polypeptides, or vectors comprising such nucleic acids or polypeptides described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

3.1 Terminology

As used herein, the term "120 loop" refers to an antigenic region in an influenza B virus HA. In a specific embodiment, the term "120 loop" refers to amino acid residues 116 to 137 of the HA1 domain of influenza B virus B/Hong Kong/8/73 or amino acid residues in the HA1 domain of an influenza B virus other than B/Hong Kong/8/73 that correspond to amino acid residues 116 to 137 of the HA1 domain of influenza B virus B/Hong Kong/8/73 (wherein the amino acid residues 116-137 correspond to the numbered positions of the influenza B virus B/Hong Kong/8/73 HA not including the signal peptide, i.e., the numbering of the mature HA). In another specific embodiment, the term "120 loop" refers to amino acid residues 75 to 77, and 116 to 137 of the HA1 domain of influenza B virus B/Hong Kong/8/73 or amino acid residues in the HA1 domain of an influenza B virus other than B/Hong Kong/8/73 that correspond to amino acid residues 75 to 77, and 116 to 137 of the HA1 domain of influenza B virus B/Hong Kong/8/73 (wherein the amino acid residues 75 to 77 and 116-137 correspond to the numbered positions of the influenza B virus B/Hong Kong/8/73 HA not including the signal peptide, i.e., the numbering of the mature HA). In another specific embodiment, the term "120 loop" refers to amino acid residues 75, 77, and 116 to 137 of the HA1 domain of influenza B virus B/Hong Kong/8/73 or amino acid residues in the HA1 domain of an influenza B virus other than B/Hong Kong/8/73 that correspond to amino acid residues 75, 77, and 116 to 137 of the HA1 domain of influenza B virus B/Hong Kong/8/73 (wherein the amino acid residues 75, 77, and 116-137 correspond to the numbered positions of the influenza B virus B/Hong Kong/8/73 HA not including the signal peptide, i.e., the numbering of the mature HA). In another specific embodiment, the term "120 loop" refers to amino acid residues 75, 77, 116, 118, 122, 129, and 137 of the HA1 domain of influenza B virus B/Hong Kong/8/73 or amino acid residues in the HA1 domain of an influenza B virus other than B/Hong Kong/8/73 that correspond to amino acid residues 75, 77, 116, 118, 122, 129, and 137 of the HA1 domain of influenza B virus B/Hong Kong/8/73 (wherein the amino acid residues 75, 77, 116, 118, 122, 129, and 137 correspond to the numbered positions of the influenza B virus B/Hong Kong/8/73 HA not including the signal peptide, i.e., the numbering of the mature HA). In another specific embodiment, the term "120 loop" refers to the antigenic region defined by Wang et al., 2008, Journal of Virology 82: 3011-3020 as 120 loop or the equivalent thereof in other influenza B viruses.

As used herein, the term "150 loop" refers to an antigenic region in an influenza B virus HA. In a specific embodiment, the term "150 loop" refers to amino acid residues 141 to 150 of the HA1 domain of influenza B virus B/Hong Kong/8/73 or amino acid residues in the HA1 domain of an influenza B virus other than B/Hong Kong/8/73 that correspond to amino acid residues 141 to 150 of the HA1 domain of influenza B virus B/Hong Kong/8/73 (wherein the amino acid residues 141 to 150 correspond to the numbered positions of the influenza B virus B/Hong Kong/8/73 HA not including the signal peptide, i.e., the numbering of the mature HA). In another specific embodiment, the term "150 loop" refers to amino acid residues 141 and 144 to 150 of the HA1 domain of influenza B virus B/Hong Kong/8/73 or amino acid residues in the HA1 domain of an influenza B virus other than B/Hong Kong/8/73 that correspond to amino acid residues 141 and 144 to 150 of the HA1 domain of influenza B virus B/Hong Kong/8/73 (wherein the amino acid residues 141 and 144 to 150 correspond to the numbered positions of the influenza B virus B/Hong Kong/8/73 HA not including the signal peptide, i.e., the numbering of the mature HA). In another specific embodiment, the term "150 loop" refers to the antigenic region defined by Wang et al., 2008, Journal of Virology 82: 3011-3020 as 150 loop or the equivalent thereof in other influenza B viruses.

As used herein, the term "160 loop" refers to an antigenic region in an influenza B virus HA. In a specific embodiment, the term "160 loop" refers to amino acid residues 162 to 167 of the HA1 domain of influenza B virus B/Hong Kong/8/73 or amino acid residues in the HA1 domain of an influenza B virus other than B/Hong Kong/8/73 that correspond to amino acid residues 162 to 167 of the HA1 domain of influenza B virus B/Hong Kong/8/73 (wherein the amino acid residues 162 to 167 correspond to the numbered positions of the influenza B virus B/Hong Kong/8/73 HA not including the signal peptide, i.e., the numbering of the mature HA). In another specific embodiment, the term "160 loop" refers to the antigenic region defined by Wang et al., 2008, Journal of Virology 82: 3011-3020 as 160 loop or the equivalent thereof in other influenza B viruses.

As used herein, the term "190 helix" refers to an antigenic region in an influenza B virus HA. In a specific embodiment, the term "190 helix" refers to amino acid residues 194 to 202 of the HA1 domain of influenza B virus B/Hong Kong/8/73 or amino acid residues in the HA1 domain of an influenza B virus other than B/Hong Kong/8/73 that correspond to amino acid residues 194 to 202 of the HA1 domain of influenza B virus B/Hong Kong/8/73 (wherein the amino acid residues 194 to 202 correspond to the numbered positions of the influenza B virus B/Hong Kong/8/73 HA not including the signal peptide, i.e., the numbering of the mature HA). In a specific embodiment, the term "190 helix" refers to amino acid residues 194 to 200 of the HA1 domain of influenza B virus B/Hong Kong/8/73 or amino acid residues in the HA1 domain of an influenza B virus other than B/Hong Kong/8/73 that correspond to amino acid residues 194 to 200 of the HA1 domain of influenza B virus B/Hong Kong/8/73 (wherein the amino acid residues 194 to 200 correspond to the numbered positions of the influenza B virus B/Hong Kong/8/73 HA not including the signal peptide, i.e., the numbering of the mature HA). In a specific embodiment, the term "190 helix" refers to amino acid residues 194 to 200, 205 and 238 of the HA1 domain of influenza B virus B/Hong Kong/8/73 or amino acid residues in the HA1 domain of an influenza B virus other than B/Hong Kong/8/73 that correspond to amino acid residues 194 to 200, 205 and 238 of the HA1 domain of influenza B virus B/Hong Kong/8/73 (wherein the amino acid residues 194 to 200, 205 and 238 correspond to the numbered positions of the influenza B virus B/Hong Kong/8/73 HA not including the signal peptide, i.e., the numbering of the mature HA). In another specific embodiment, the term "190 helix" refers to amino acid residues 194 to 205 and 238 of the HA1 domain of influenza B virus B/Hong Kong/8/73 or amino acid residues in the HA1 domain of an influenza B virus other than B/Hong Kong/8/73 that correspond to amino acid residues 194 to 205 and 238 of the HA1 domain of influenza B virus B/Hong Kong/8/73 (wherein the amino acid residues 194 to 205 and 238 correspond to the numbered positions of the influenza B virus B/Hong Kong/8/73 HA not including the signal peptide, i.e., the numbering of the mature HA). In another specific embodiment, the term "190 helix" refers to the antigenic region defined by Wang et al., 2008, Journal of Virology 82: 3011-3020 as 190 helix or the equivalent thereof in other influenza B viruses.

The terms "about" or "approximate," when used in reference to an amino acid position refer to the particular amino acid position in a sequence or any amino acid that is within five, four, three, two, or one residues of that amino acid position, either in an N-terminal direction or a C-terminal direction. As used herein, the term "about" or "approximately" when used in conjunction with a number refers to any number within 1, 5 or 10% of the referenced number. In certain embodiments, the term "about" encompasses the exact number recited.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, may be determined using sequence alignment techniques well-known in the art, preferably computer algorithms designed for this purpose, using the default parameters of said computer algorithms or the software packages containing them. Non-limiting examples of computer algorithms and software packages incorporating such algorithms include the following. The BLAST family of programs exemplify a particular, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another particular example is the algorithm of Myers and Miller (1988 CABIOS 4:11-17) which is incorporated into the ALIGN program (version 2.0) and is available as part of the GCG sequence alignment software package. Also particular is the FASTA program (Pearson W. R. and Lipman D. J., *Proc. Nat. Acad. Sci. USA*, 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length; and BioEdit.

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As used herein, the terms "disease" and "disorder" are used interchangeably to refer to a condition in a subject. In some embodiments, the condition is a viral infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As described herein, the term "ectodomain" in reference to an influenza virus HA polypeptide would be understood by one of skill in the art. In specific embodiment, the ectodomain does not include the signal peptide, the transmembrane domain, and the cytoplasmic tail domain of an influenza virus HA. See, e.g., Table 1A, Table 1B and Table 1C, below, for an exemplary influenza B virus ectodomain sequence and location. In certain embodiments, the ectodomain of an influenza B virus HA polypeptide is a region of the influenza B virus HA polypeptide that aligns with the ectodomain of influenza B/Hong Kong/8/73 virus HA ectodomain set forth in Table 1A, below. In some embodiments, the ectodomain of an influenza B virus HA polypeptide is a region of the influenza B virus HA polypeptide that aligns with the ectodomain of influenza B/Malaysia/2506/04 virus HA ectodomain set forth in Table 1C, below.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (viii) prevent or reduce the spread of an influenza virus from one subject to another subject; (ix) reduce organ failure associated with an influenza virus infection; (x) reduce hospitalization of a subject; (xi) reduce hospitalization length; (xii) increase the survival of a subject with an influenza virus infection or disease associated therewith; (xiii) eliminate an influenza virus infection or disease associated therewith; (xiv) inhibit or reduce influenza virus replication; (xv) inhibit or reduce the entry of an influenza virus into a host cell(s); (xvi) inhibit or reduce replication of the influenza virus genome; (xvii) inhibit or reduce synthesis of influenza virus proteins; (xviii) inhibit or reduce assembly of influenza virus particles; (xix) inhibit or reduce release of influenza virus particles from a host cell(s); (xx) reduce influenza virus titer; and/or (xxi) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject with an influenza virus infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject with an influenza virus infection. In some embodiments, the effective amount results in a reduction in titer of influenza virus relative to an untreated subject with an influenza virus infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

"HA" and "hemagglutinin" refer to any hemagglutinin known to those of skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g. HA1 and HA2. Those of skill in the art will recognize that an immature HA0 might be cleaved to release a signal peptide (approximately 20 amino acids) yielding a mature hemagglutinin HA0. In another aspect, those of skill in the art will recognize that an immature HA0 might be cleaved to release a signal peptide (approximately 15 amino acids) yielding a mature hemagglutinin HA0. A hemagglutinin HA0 might be cleaved at another site to yield HA1 polypeptide (approximately 342 amino acids of influenza B/Hong Kong/8/73 virus, including the globular head domain and a portion of the stem domain) and HA2 polypeptide (approximately 169 amino acids of influenza B/Hong Kong/8/73 virus, including the remainder of the stem domain, a luminal domain, a transmembrane domain and a cytoplasmic domain). In another embodiment, a hemagglutinin HA0 might be cleaved at another site to yield HA1 polypeptide (approximately 344 amino acids of influenza B/Hong Kong/8/73 virus, including the globular head domain and a portion of the stem domain) and HA2 polypeptide (approximately 223 amino acids of influenza B/Hong Kong/8/73 virus, including the remainder of the stem domain, a luminal domain, a transmembrane domain and a cytoplasmic domain). Those of skill in the art will recognize that an influenza B virus has an elongated fusion domain (composed of the central coiled-coil structure from the HA2 domain), the extended regions from HA1 (amino acid residues 1-42), and HA1 (amino acid residues 288-342), a globular membrane-distal domain containing the receptor-binding subdomain, HA1 (amino acid residues 116-274), and a vestigial esterase subdomain, HA1 (amino acid residues 43-115) and HA1 (amino acid residues 275-287) (see Wang et al., 2008, Journal of Virology, 82(6):3011-3020). Those of skill in the art will recognize that the delineation of the domains of an influenza B virus HA may be determined from, e.g., crystal structure and/or by using structure prediction software (for example, the website for the Center for Biological Sequence Analysis, Technical University of Denmark DTU, or Pymol) in conjunction with protein alignments. Thus, in one aspect, one skilled in the art will recognize that the delineation of the domains of influenza B/Hong Kong/8/73 virus HA are as set forth in Table 1A, below. In another aspect, one skilled in the art will recognize the delineation of domains of the mouse adapted influenza B/Malaysia/2506/20/03 virus HA. See, e.g., Table 1 B, infra, for exemplary domains for the mouse adapted influenza B/Malaysia/2506/20/03 virus HA. In another aspect, one skilled in the art will recognize the delineation of domain of the influenza B/Malaysia/2506/04 virus HA. See, e.g., Table 1 C, infra, for exemplary domains of the influenza B/Malaysia/2506/04 virus HA.

TABLE 1A

Exemplary domains for influenza B/Hong Kong/8/73 virus HA.

| Domain for influenza B/Hong Kong/8/73 | nt length | aa residues (length) | aa residues (positions in influenza B/Hong Kong/8/73, inclusive of the signal peptide with exception of loops; immature HA) | aa residues (positions in influenza B/Hong Kong/8/73, not including the signal peptide; mature HA) | aa residues |
|---|---|---|---|---|---|
| Signal peptide yielding a mature HA HA0 | 45 | 15 | 1-15 | N/A | MKAIIVLLMVVTSNA (SEQ ID NO: 9) |
| HA1 polypeptide (does not include signal peptide) | 1032 | 344 | 16-359 | 1-344 | DRICTGITSSNSPHVVKTATQGEVNVT GVIPLTTTPTKSHFANLKGTQTRGKLC PNCLNCTDLDVALGRPKCMGTIPSAKA SILHEVKPVTSGCFPIMHDRTKIRQLP NLLRGYENIRLSARNVTNAETAPGGPY IVGTSGSCPNVTNGNGFFATMAWAVPK NKTATNPLTVEVPYICTKGEDQITVWG FHSDDETQMVKLYGDSKPQKFTSSANG VTTHYVSQIGGFPNQAEDEGLPQSGRI VVDYMVQKPGKTGTIAYQRGVLLPQKV WCASGRSKVIKGSLPLIGEADCLHEKY GGLNKSKPYYTGEHAKAIGNCPIWVKT PLKLANGTKYRPPAKLLKER (SEQ ID NO: 10) |
| HA2 polypeptide (not including stop codon) | 669 | 223 | 360-582 | 345-567 | GFFGAIAGFLEGGWEGMIAGWHGYTSH GAHGVAVAADLKSTQEAINKITKNLNS LSELEVKNLQRLSGAIVIDELHNEILE LDEKVDDLRADTISSQIELAVLLSNEG IINSEDEHLLALERKLKKMLGPSAVDI GNGCFETKHKCNQTCLDRIAAGTFNAG EFSLPTFDSLNITAASLNDDGLDNHTI LLYYSTAASSLAVTLMIAIFIVYMVSR DNVSCSICL (SEQ ID NO: 11) |
| Ectodomain (excludes signal peptide, transmembrane domain, cytoplasmic tail domain) | 1590 | 530 | 16-545 | 1-530 | DRICTGITSSNSPHVVKTATQGEVNVT GVIPLTTTPTKSHFANLKGTQTRGKLC PNCLNCTDLDVALGRPKCMGTIPSAKA SILHEVKPVTSGCFPIMHDRTKIRQLP NLLRGYENIRLSARNVTNAETAPGGPY IVGTSGSCPNVTNGNGFFATMAWAVPK NKTATNPLTVEVPYICTKGEDQITVWG FHSDDETQMVKLYGDSKPQKFTSSANG VTTHYVSQIGGFPNQAEDEGLPQSGRI VVDYMVQKPGKTGTIAYQRGVLLPQKV WCASGRSKVIKGSLPLIGEADCLHEKY GGLNKSKPYYTGEHAKAIGNCPIWVKT PLKLANGTKYRPPAKLLKERGFFGAIA GFLEGGWEGMIAGWHGYTSHGAHGVAV AADLKSTQEAINKITKNLNSLSELEVK NLQRLSGAMDELHNEILELDEKVDDLR ADTISSQIELAVLLSNEGIINSEDEHL LALERKLKKMLGPSAVDIGNGCFETKH KCNQTCLDRIAAGTFNAGEFSLPTFDS LNITAASLNDDGLDNHT(SEQ ID NO: 12) |
| Transmembrane domain | 81 | 27 | 546-572 | 531-557 | ILLYYSTAASSLAVTLMIAIFIVYMVS (SEQ ID NO: 13) |
| Cytoplasmic domain (not including stop codon) | 30 | 10 | 573-582 | 558-567 | RDNVSCSICL (SEQ ID NO: 14) |

TABLE 1A-continued

Exemplary domains for influenza B/Hong Kong/8/73 virus HA.

| Domain for influenza B/Hong Kong/8/73 | nt length | aa residues (length) | aa residues (positions in influenza B/Hong Kong/8/73, inclusive of the signal peptide with exception of loops; immature HA) | aa residues (positions in influenza B/Hong Kong/8/73, not including the signal peptide; mature HA) | aa residues |
|---|---|---|---|---|---|
| Stem domain (encompasses alanines at interface; does not include signal peptide or stop codon) Piece 1: | 126 | 42 | 16-57 | 1-42 | DRICTGITSSNSPHVVKTATQGEVNVT GVIPLTTTPTKSHFA (SEQ ID NO: 15) |
| Stem domain (encompasses alanines at interface; does not include signal peptide or stop codon) Piece 2: | 723 | 241 | 305-545 | 290-530 | ADCLHEKYGGLNKSKPYYTGEHAKAIG NCPIWVKTPLKLANGTKYRPPAKLLKE RGFFGAIAGFLEGGWEGMIAGWHGYTS HGAHGVAVAADLKSTQEAINKITKNLN SLSELEVKNLQRLSGAMDELHNEILEL DEKVDDLRADTISSQIELAVLLSNEGI INSEDEHLLALERKLKKMLGPSAVDIG NGCFETKHKCNQTCLDRIAAGTFNAGE FSLPTFDSLNITAASLNDDGLDNHT (SEQ ID NO: 16) |
| Globular head domain (not including alanines) | 741 | 247 | 58-304 | 43-289 | NLKGTQTRGKLCPNCLNCTDLDVALGR PKCMGTIPSAKASILHEVKPVTSGCFP IMHDRTKIRQLPNLLRGYENIRLSARN VTNAETAPGGPYIVGTSGSCPNVTNGN GFFATMAWAVPKNKTATNPLTVEVPYI CTKGEDQITVWGFHSDDETQMVKLYGD SKPQKFTSSANGVTTHYVSQIGGFPNQ AEDEGLPQSGRIVVDYMVQKPGKTGTI AYQRGVLLPQKVWCASGRSKVIKGSLP LIGE(SEQ ID NO: 17) |

Abbreviations:
nt = nucleotide;
aa = amino acid;
N/A = not applicable.

TABLE 1B

Exemplary domains for mouse adapted influenza B/Malaysia/2506/20/03 HA. The full length amino acid sequence for mouse adapted influenza B/Malaysia/2506/20/03 HA may be found in SEQ ID NO: 73.

| Domain | Amino acid sequence |
|---|---|
| Signal Peptide | MKAIIVLLMVVTSNA (SEQ ID NO: 74) |
| HAI Domain | DRICTGITSSNSPHVVKTATQGEVNVTGVIPLTTT PTKSHFANLKGIETRGKLCPKCLNCTDLDVALGRP KCTGNIPSARVSILHEVRPVTSGCFPIMHDRTKIR QLPNLLRGYEHIRLSTHNVINAENAPGGPYKIGTS GSCPNVINGNGFFATMAWAVPKNDNNKTATNSLTI EVPYICTEGEDQITVWGFHSDX$_1$EX$_2$QMAKLYGDS KPQKFTSSANGVTTHYVSQIGGFPNQTEDGGLPQS GRIVVDYMVQKSGKTGTITYQRGILLPQKVWCASG RSKVIKGSLPLIGEADCLHEKYGGLNKSKPYYTGE HAKAIGNCPIWVKTPLKLANGTKYRPPAKLLKER (SEQ ID NO: 75) X$_1$ = N or S; X$_2$ = N, I, T or S |

TABLE 1B-continued

Exemplary domains for mouse adapted influenza B/Malaysia/2506/20/03 HA. The full length amino acid sequence for mouse adapted influenza B/Malaysia/2506/20/03 HA may be found in SEQ ID NO: 73.

| Domain | Amino acid sequence |
|---|---|
| HA2 Domain | GFFGAIAGFLEGGWEGMIAGWHGYTSHGAHGVAVA ADLKSTQEAINKITKNLNSLSELEVKNLQRLSGAM DELHNEILELDEKVDDLRADTISSQIELAVLLSNE GIINSEDEHLLALERKLKKMLGPSAVEIGNGCFET KHKCNQTCLDRIAAGTFDAGEFSLPTFDSLNITAA SLNDDGLDNHTILLYYSTAASSLAVTLMIAIFVVY MVSRDNVSCSICL (SEQ ID NO: 76) |

TABLE 1B-continued

Exemplary domains for mouse adapted influenza B/Malaysia/2506/20/03 HA. The full length amino acid sequence for mouse adapted influenza B/Malaysia/2506/20/03 HA may be found in SEQ ID NO: 73.

| Domain | Amino acid sequence |
|---|---|
| N-Terminal Segment of Stalk (encompasses alanine at interface with globular head domain) | DRICTGITSSNSPHVVKTATQGEVNVTGVIPLTTT 50 PTKSHFA (SEQ ID NO: 78) |
| C-Terminal Segment of Stalk (encompasses alanine at interface with globular head domain) | ADCLHEKYGGLNKSKPYYTGEHAKAIGNCPIWVKT PLKLANGTKYRPPAKLLKERGFFGAIAGFLEGGWE GMIAGWHGYTSHGAHGVAVAADLKSTQEAINKITK NLNSLSELEVKNLQRLSGAMDELHNEILELDEKVD DLRADTISSQIELAVLLSNEGIINSEDEHLLALER KLKKMLGPSAVEIGNGCFETKHKCNQTCLDRIAAG TFDAGEFSLPTFDSLNITAASLNDDGLDNHT (SEQ ID NO: 79) |
| Globular Head Domain | NLKGTETRGKLCPKCLNCTDLDVALGRPKCTGNIP SARVSILHEVRPVTSGCFPIMHDRTKIRQLPNLLR GYEHIRLSTHNVINAENAPGGPYKIGTSGSCPNVT NGNGFFATMAWAVPKNDNNKTATNSLTIEVPYICT EGEDQITVWGFHSD$X_1$E$X_2$QMAKLYGDSKPQKFTS SANGVTTHYVSQIGGFPNQTEDGGLPQSGRIVVDY MVQKSGKTGTITYQRGILLPQKVWCASGRSKVIKG SLPLIGE (SEQ ID NO: 77) $X_1$ = N or S; $X_2$ = N, I, T or S |

TABLE 1C

Exemplary domains for influenza B/Malaysia/2506/20/03 HA. The full length amino acid sequence for influenza B/Malaysia/2506/20/03 HA may be found in SEQ ID NO: 88.

| Domain | Amino acid sequence |
|---|---|
| Signal Peptide | MKAIIVLLMVVTSNA(SEQ ID NO: 89) |
| HA1 Domain | DRICTGITSSNSPHVVKTATQGEVNVTGVIPLTTT PTKSHFANLKGTETRGKLCPKCLNCTDLDVALGRP KCTGNIPSARVSILHEVRPVTSGCFPIMHDRTKIR QLPNLLRGYEHIRLSTHNVINAENAPGGPYKIGTS GSCPNVTNGNGFFATMAWAVPKNDNNKTATNSLTI EVPYICTEGEDQITVWGFHSDNEXIQMAKLYGDSK PQKFTSSANGVTTHYVSQIGGFPNQTEDGGLPQSG RIVVDYMVQKSGKTGTITYQRGILLPQKVWCASGR SKVIKGSLPLIGEADCLHEKYGGLNKSKPYYTGEH AKAIGNCPIWVKTPLKLANGTKYRPPAKLLKER (SEQ ID NO: 90) $X_1$ = I or T |
| HA2 Domain | GFFGAIAGFLEGGWEGMIAGWHGYTSHGAHGVAVA ADLKSTQEAINKITKNLNSLSELEVKNLQRLSGAM DELHNEILELDEKVDDLRADTISSQIELAVLLSNE GIINSEDEHLLALERKLKKMLGPSAVEIGNGCFET KHKCNQTCLDRIAAGTFDAGEFSLPTFDSLNITAA SLNDDGLDNHTILLYYSTAASSLAVTLMIAIFVVY MVSRDNVSCSICL (SEQ ID NO: 91) |
| N-Terminal Segment of Stalk (encompasses alanine at interface with globular head domain) | DRICTGITSSNSPHVVKTATQGEVNVTGVIPLTTT PTKSHFA(SEQ ID NO: 92) |

TABLE 1C-continued

Exemplary domains for influenza B/Malaysia/2506/20/03 HA. The full length amino acid sequence for influenza B/Malaysia/2506/20/03 HA may be found in SEQ ID NO: 88.

| Domain | Amino acid sequence |
|---|---|
| C-Terminal Segment of Stalk (encompasses alanine at interface with globular head domain) | ADCLHEKYGGLNKSKPYYTGEHAKAIGNCPIWVKT PLKLANGTKYRPPAKLLKERGEFGAIAGFLEGGWE GMIAGWHGYTSHGAHGVAVAADLKSTQEAINKITK NLNSLSELEVKNLQRLSGAMDELHNEILELDEKVD DLRADTISSQIELAVLLSNEGIINSEDEHLLALER KLKKMLGPSAVEIGNGCFETKHKCNQTCLDRIAAG TFDAGEFSLPTFDSLNITAASLNDDGLDNHT (SEQ ID NO: 93) |
| Globular Head Domain | NLKGTETRGKLCPKCLNCTDLDVALGRPKCTGNIP SARVSILHEVRPVTSGCFPIMHDRTKIRQLPNLLR GYEHIRLSTHNVINAENAPGGPYKIGTSGSCPNVT NGNGFFATMAWAVPKNDNNKTATNSLTIEVPYICT EGEDQITVWGFHSDNE$_{X1}$QMAKLYGDSKPQKFTSS ANGVTTHYVSQIGGFPNQTEDGGLPQSGRIVVDYM VQKSGKTGTITYQRGILLPQKVWCASGRSKVIKGS LPLIGE (SEQ ID NO: 94) $X_1$ = I or T |
| Ectodomain | DRICTGITSSNSPHVVKTATQGEVNVTGVIPLTTT PTKSHFANLKGTETRGKLCPKCLNCTDLDVALGRP KCTGNIPSARVSILHEVRPVTSGCFPIMHDRTKIR QLPNLLRGYEHIRLSTHNVINAENAPGGPYKIGTS GSCPNVTNGNGFFATMAWAVPKNDNNKTATNSLTI EVPYICTEGEDQITVWGFHSDNE$_{X1}$QMAKLYGDSK PQKFTSSANGVTTHYVSQIGGFPNQTEDGGLPQSG RIVVDYMVQKSGKTGTITYQRGILLPQKVWCASGR SKVIKGSLPLIGEADCLHEKYGGLNKSKPYYTGEH AKAIGNCPIWVKTPLKLANGTKYRPPAKLLKERGE FGAIAGFLEGGWEGMIAGWHGYTSHGAHGVAVAAD LKSTQEAINKITKNLNSLSELEVKNLQRLSGAMDE LHNEILELDEKVDDLRADTISSQIELAVLLSNEGI INSEDEHLLALERKLKKMLGPSAVEIGNGCFETKH KCNQTCLDRIAAGTFDAGEFSLPTFDSLNITAASL NDDGLDNHT (SEQ ID NO: 95) $X_1$ = I or T |

In certain embodiments, a hemagglutinin protein comprises a signal peptide, a transmembrane domain and a cytoplasmic domain. In certain embodiments, a hemagglutinin protein comprises a signal peptide, an ectodomain, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

"HA2" refers to a polypeptide domain that corresponds to the HA2 domain of an influenza hemagglutinin polypeptide known to those of skill in the art. In certain embodiments, an HA2 consists of a stem domain, a luminal domain, a transmembrane domain and a cytoplasmic domain (see, e.g., Scheiffle et al., 2007, *EMBO J.* 16(18):5501-5508, the contents of which are incorporated by reference in their entirety). In certain embodiments, an HA2 consists of a stem domain, a luminal domain and a transmembrane domain. In certain embodiments, an HA2 consists of a stem domain and a luminal domain; in such embodiments, the HA2 might be soluble. In certain embodiments, an HA2 consists of a stem domain; in such embodiments, the HA2 might be soluble. In certain embodiments, an HA2 consists of amino acid residues 1-169 of the HA2 domain of an influenza B/Hong Kong/8/73 virus (see Wang et al., 2008, Journal of Virology 82: 3011-3020). In certain embodiments, an HA2 consists of amino acid residues 345-567 of a mature influenza B/Hong Kong/8/73 virus HA (i.e., the numbering is determined from an influenza B/Hong Kong/8/73 virus HA that does not include the signal peptide).

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a "heterologous polypeptide" may refer to a polypeptide derived from a different virus, e.g., a different influenza strain or subtype, or an unrelated virus or different species.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject. As another example, a first therapy (e.g., a first prophylactic or therapeutic agent) can be administered prior to (e.g., 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months before), concomitantly with, or subsequent to (e.g., about 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" refers to the pathological state resulting from the presence of an influenza (e.g., influenza A or B virus) virus in a cell or subject or the invasion of a cell or subject by an influenza virus. In specific embodiments, the term refers to a respiratory illness caused by an influenza virus.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide. An influenza virus hemagglutinin head domain polypeptide or influenza virus hemagglutinin head domain may comprise or consist of a known (e.g., wild-type) influenza virus hemagglutinin head domain or may comprise or consist of a derivative, e.g. an engineered derivative, of a known (e.g., wild-type) influenza virus hemagglutinin head domain. Those of skill in the art will recognize that an influenza B virus HA globular head domain typically comprises the amino acid residues corresponding to amino acid residues 43-289 of the HA1 domain of influenza B/Hong Kong/8/73 virus (wherein the numbering of the amino acid residues is with respect to the mature HA sequence, which does not comprise the 15 amino acid signal peptide). For example, one skilled in the art will recognize that the amino acid sequence for the HA globular head domain for influenza B/Hong Kong/8/73 virus typically consists of the amino acid sequence: NLKGTQTRGKLCPNCLNCTDLDVALGRPKCMGTIP-SAKASILTHEVKPVTSGCFPIMHDR TKIRQLPNLLR-GYENIRL SARNVT-NAETAPGGPYIVGTSGSCPNVTNGNGFFATMAWAV PKNKTATNPLTVEVPYICTKGEDQITVWGFHSDDE-TQMVKLYGDSKPQKFTSSANGVTT HYVSQI-GGFPNQAEDEGLPQSGRIVVDYMVQKPGKTG-TIAYQRGVLLPQKVWCASGRS KVIKGSLPLIGE (SEQ ID NO: 17). Those of skill in the art will recognize that the location of the influenza B virus HA globular head domain for a particular strain can be determined by alignment of the influenza B virus HA polypeptide for said strain to the sequence of an influenza A virus HA (FIG. 20). In specific embodiments, the influenza B virus globular head domain consists of the amino acid residues that align to amino acid residues 58-304 of the mature influenza B/Hong Kong/8/73 virus HA (i.e., wherein said numbering includes the signal peptide). See, e.g., Table 1A, above.

As used herein, the phrases "IFN deficient system" or "IFN-deficient substrate" refer to systems, e.g., cells, cell lines and animals, such as pigs, mice, chickens, turkeys, rabbits, rats, etc., which do not produce interferon (IFN) or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the numeric term "log" refers to $\log_{10}$.

As used herein, the phrase "multiplicity of infection" or "MOI" is the average number of infectious virus particles per infected cell. The MOI is determined by dividing the number of infectious virus particles added (ml added×PFU/ml) by the number of cells added (ml added×cells/ml).

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "prevent," "preventing" and "prevention" in the context of the administration of a therapy(ies) to a subject to prevent an influenza virus disease refer to one or more of the prophylactic/beneficial effects resulting from the administration of a therapy or a combination of therapies. In a specific embodiment, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition of the development or onset of an influenza virus disease or a symptom thereof; (ii) the inhibition of the recurrence of an influenza virus disease or a symptom associated therewith; and (iii) the reduction or inhibition in influenza virus infection and/or replication.

As used herein, the terms "purified" and "isolated" when used in the context of a polypeptide (including an antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide. In a specific embodiment, a chimeric HA polypeptide is chemically synthesized. In another specific embodiment, an influenza hemagglutinin stem domain polypeptide, an influenza hemagglutinin head domain polypeptide, non-chimeric HA polypeptide, and/or a chimeric influenza hemagglutinin polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the terms "stem domain polypeptide" and "influenza virus hemagglutinin stem domain polypeptide" and "stalk domain" refer to the stem domain of an influenza virus hemagglutinin polypeptide (which includes derivatives of an influenza HA polypeptide). A stem domain polypeptide might be a single polypeptide chain, two polypeptide chains or more polypeptide chains. Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). In a specific embodiment, the stem domain of an influenza B virus HA polypeptide is a trimer. See, e.g., Tables 1A and 1B, supra, for an example of the amino acid sequence and location of a stem domain of an influenza B virus.

As used herein, terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "seasonal influenza virus strain" refers to a strain of influenza virus to which a subject population is exposed to on a seasonal basis. In specific embodiments, the term seasonal influenza virus strain refers to a strain of influenza B virus. In specific embodiments, the term seasonal influenza virus strain refers to a strain of influenza virus that belongs to the Yamagata or the Victoria lineages, i.e., the two lineages that presently persist in the human subject population.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to (i) a nucleic acid encoding a chimeric HA polypeptide, (ii) a chimeric HA polypeptide), or (iii) a vector or composition comprising a nucleic acid encoding a chimeric HA polypeptide or comprising a chimeric HA polypeptide. In some embodiments, the term "therapy" refers to an antibody that specifically binds to a chimeric influenza virus hemagglutinin polypeptide.

As used herein, the terms "treat," "treatment," and "treating" refer in the context of administration of a therapy(ies) to a subject to treat an influenza virus disease or infection to obtain a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of an influenza virus infection or a disease or a symptom associated therewith; (ii) the reduction in the duration of an influenza virus infection or a disease or a symptom associated therewith; (iii) the regression of an influenza virus infection or a disease or a symptom associated therewith; (iv) the reduction of the titer of an influenza virus; (v) the reduction in organ failure associated with an influenza virus infection or a disease associated therewith; (vi) the reduction in hospitalization of a subject; (vii) the reduction in hospitalization length; (viii) the increase in the survival of a subject; (ix) the elimination of an influenza virus infection or a disease or symptom associated therewith; (x) the inhibition of the progression of an influenza virus infection or a disease or a symptom associated therewith; (xi) the prevention of the spread of an influenza virus from a cell, tissue, organ or subject to another cell, tissue, organ or subject; (xii) the inhibition or reduction in the entry of an influenza virus into a host cell(s); (xiii) the inhibition or reduction in the replication of an influenza virus genome; (xiv) the inhibition or reduction in the synthesis of influenza virus proteins; (xv) the inhibition or reduction in the release of influenza virus particles from a host cell(s); and/or (xvi) the enhancement or improvement the therapeutic effect of another therapy.

As used herein, in some embodiments, the phrase "wild-type" in the context of a viral polypeptide refers to a viral polypeptide that is found in nature and is associated with a naturally occurring virus.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIG. 1 depicts a strategy for generating influenza B virus chimeric HAs for use as universal influenza virus vaccine candidates and potential vaccination schematic.

Figures 3A, 3B, 3C:
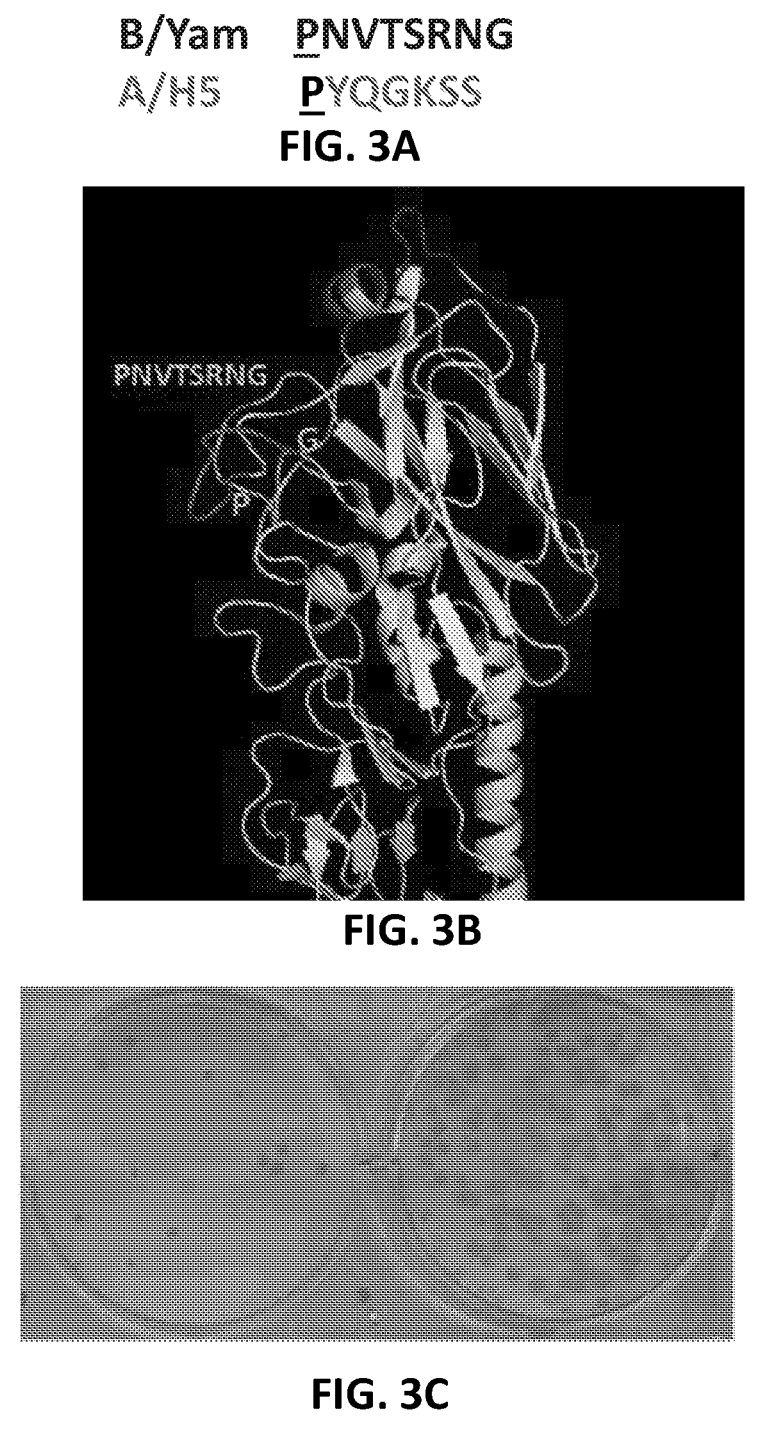

FIG. 3A depicts the amino acid sequence corresponding to the 150 loop of the influenza B/Yamagata/16/88 virus sequence (top, SEQ ID NO: 18) and the amino acid sequence of the modified 150 loop of the chimeric HA (bottom, SEQ ID NO: 19). FIG. 3B depicts the structure of the influenza B/Yamanashi/166/1998 virus globular head domain and points out the location of the 150 loop. FIG. 3C depicts an immunostain of a plaque assay used to visualize plaque morphology of the rescued virus expressing the chimeric HA.

FIG. 4 depicts growth curves of viruses expressing the indicated chimeric HA constructs at the indicated timepoints. The growth curves were performed in MDCK cells growth at 33 degrees Celsius.

FIG. 5 depicts immunofluorescent staining of 293T cells transfected with the indicated constructs and stained with anti-H5 serum.

Figures 6A, 6B, 6C:
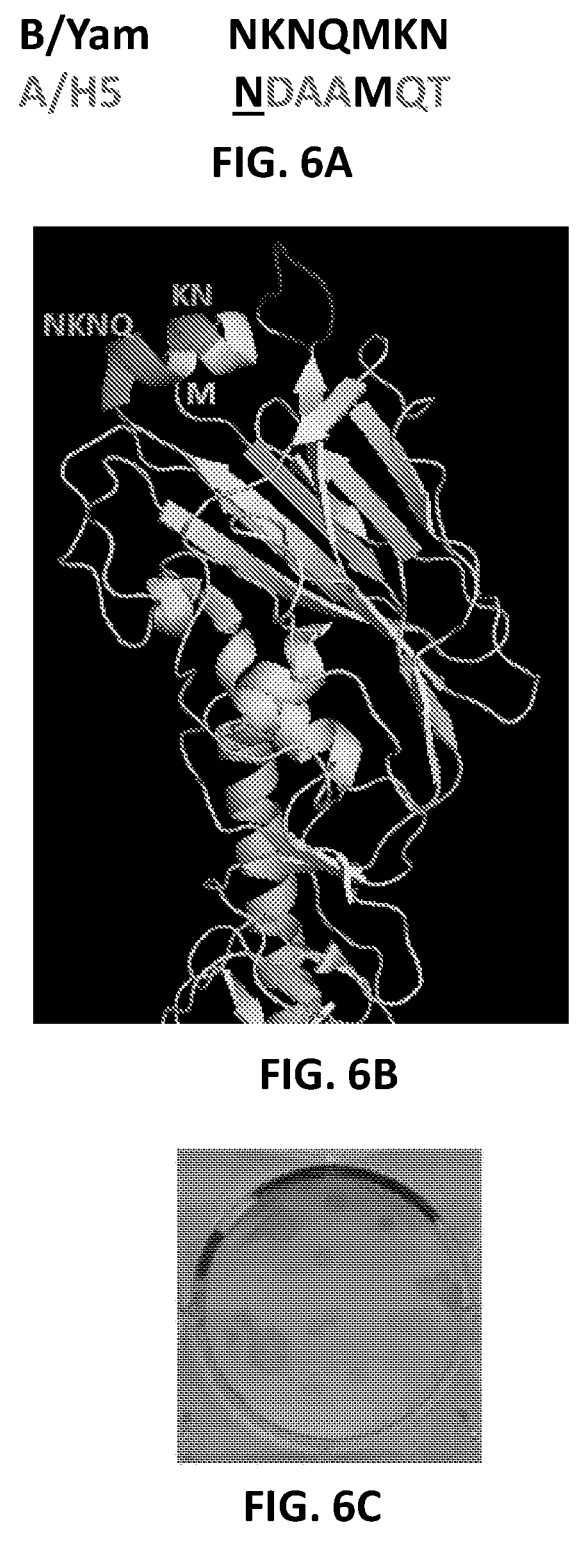

FIG. 6A depicts the amino acid sequence corresponding to the 190 helix of the influenza B/Yamagata/16/88 virus sequence (top, SEQ ID NO: 7) and the amino acid sequence of the modified 190 helix of the chimeric HA (bottom, SEQ ID NO: 8). FIG. 6B depicts the structure of the influenza B/Yamanashi/166/1998 virus globular head domain and points out the location of the 190 helix. FIG. 6C depicts an immunostain of a plaque assay used to visualize plaque morphology of the rescued virus expressing the chimeric HA.

Figures 7A, 7B, 7C:
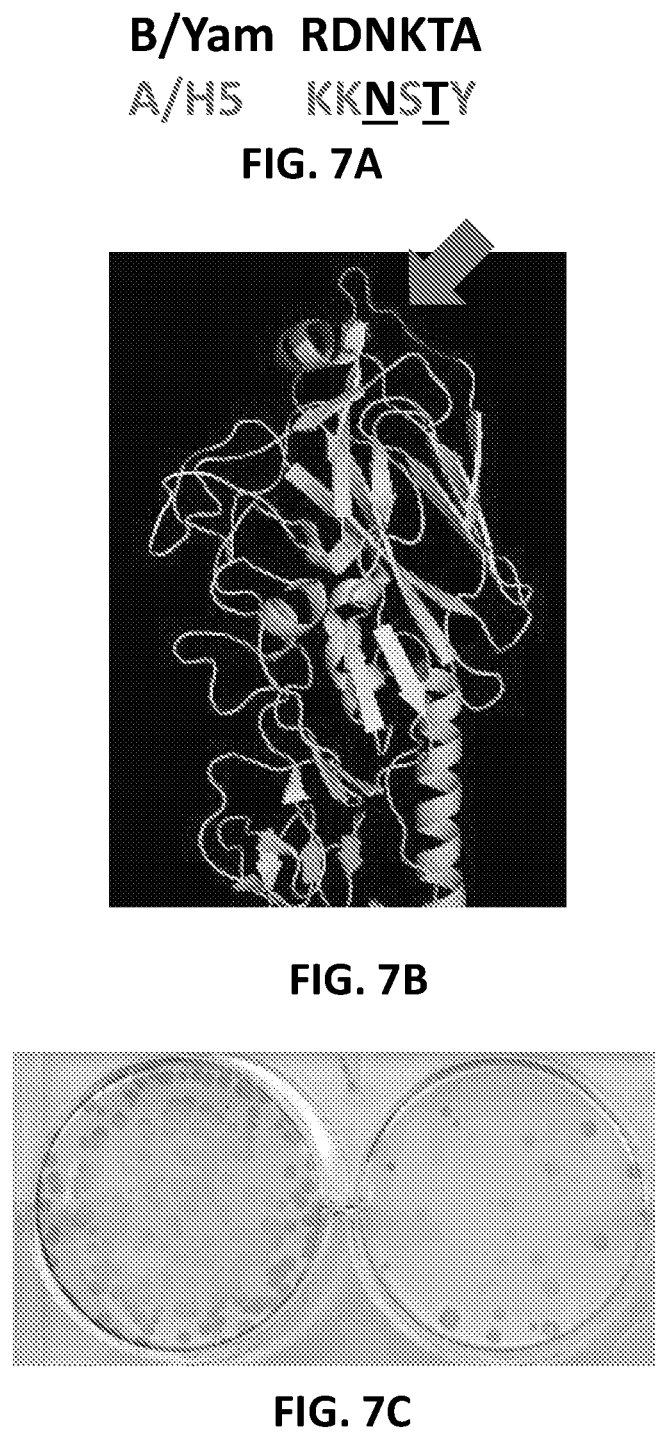

FIG. 7A depicts the amino acid sequence corresponding to the 160 loop of the influenza B/Yamagata/16/88 virus sequence (top, SEQ ID NO: 5) and the amino acid sequence of the modified 160 loop of the chimeric HA (bottom, SEQ ID NO: 6). FIG. 7B depicts the structure of the influenza B/Yamanashi/166/1998 virus globular head domain and points out the location of the 160 loop. FIG. 7C depicts an immunostain of a plaque assay used to visualize plaque morphology of the rescued virus expressing the chimeric HA.

FIG. 8A depicts the amino acid sequence corresponding to the 120 loop of the influenza B/Yamagata/16/88 virus sequence (top "B/Yam", SEQ ID NO: 1) and the amino acid sequence of the modified 120 loop of the chimeric HA (bottom "B/Yamagata ectodomain with A/H5", SEQ ID NO: 2). Also depicted is the mutation made at amino acid position T90 of influenza B/Yamagata/16/88 virus (wherein amino acid position T90 is with respect to the immature influenza B/Yamagata/16/88 virus HA, i.e., including the signal peptide). The amino acid numbering is with respect to the immature HA (i.e., inclusive of the signal peptide). FIG. 8B depicts the structure of the influenza B/Yamanashi/166/1998 virus globular head domain and points out the location of the 120 loop.

Figure 9:
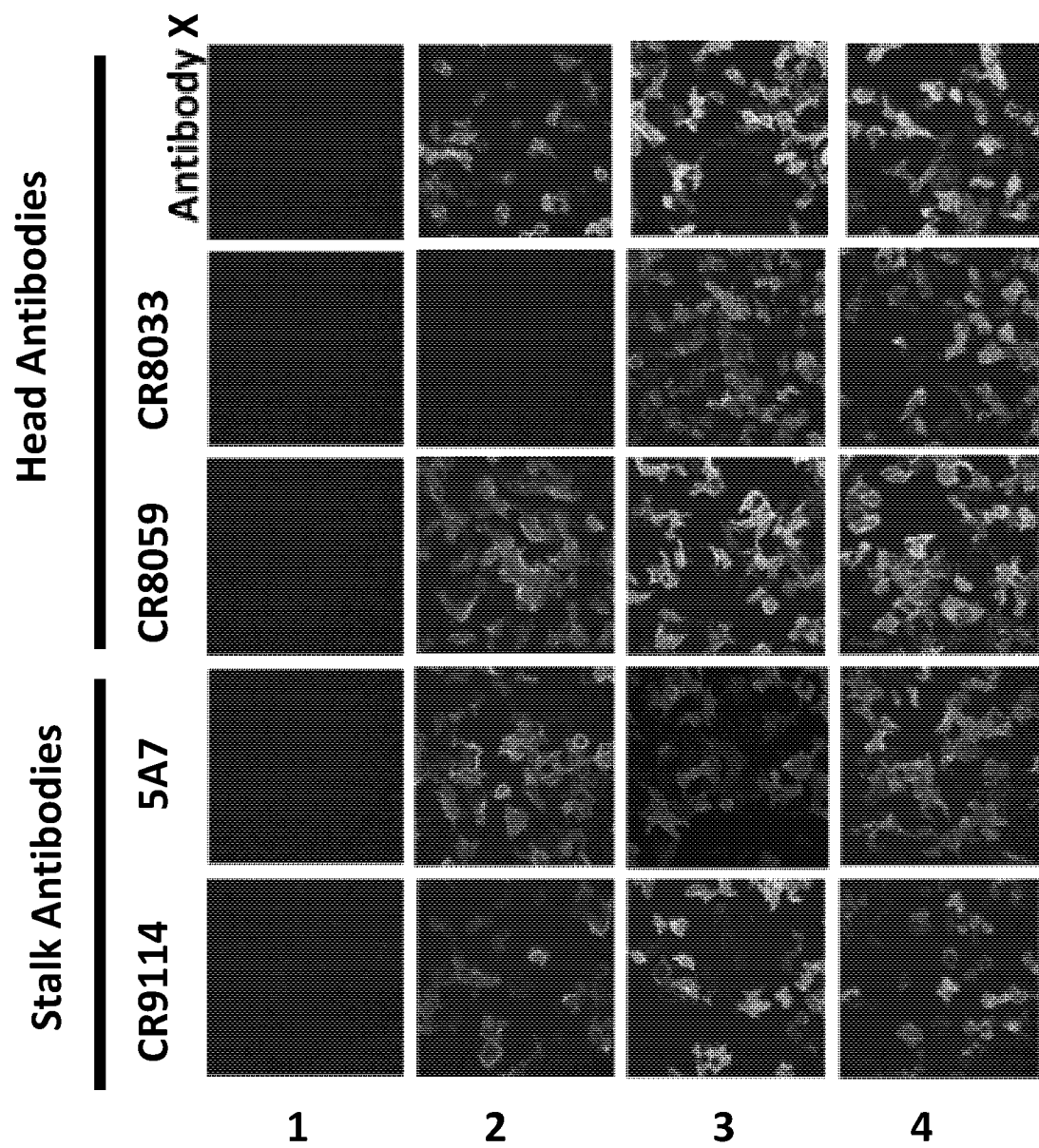

FIG. 9 depicts immunofluorescence of 293T with the indicated antibodies. Column 1 represents cells transfected with pDZ. Column 2 represents cells transfected with Yamagata ectodomain (influenza A/Puerto Rico/8/34 virus ("PR8") background) HA. Column 3 represents cells transfected with the chimeric HA comprising 150 loop, 160 loop, and 190 helix modified with influenza A virus H5 sequences. Column 4 represents cells transfected with the chimeric HA comprising 120 loop, 150 loop, 160 loop, and 190 helix modified with influenza A virus H5 sequences.

Figure 10A:
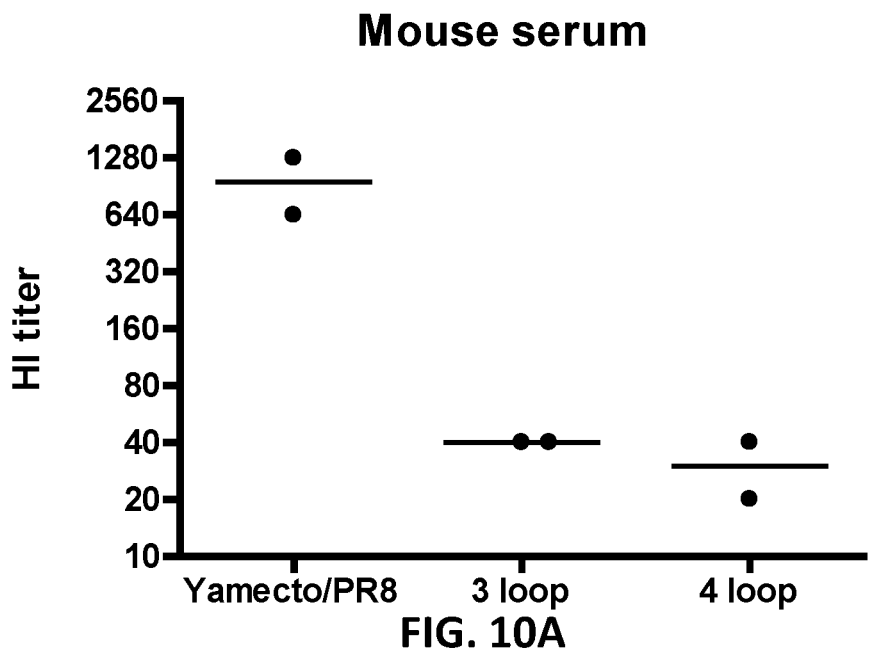
Figure 10B:
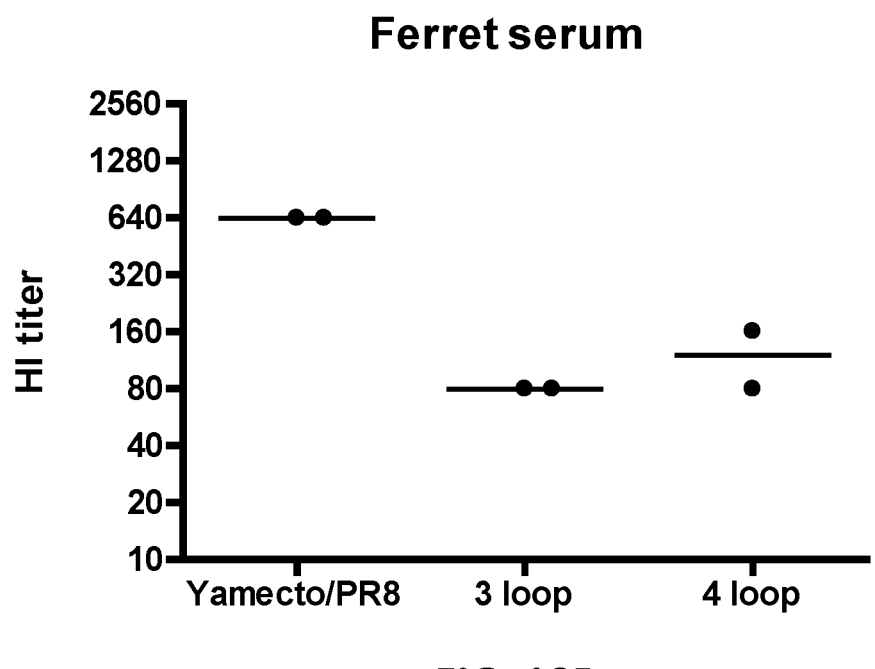

FIG. 10A depicts HI assay titers performed with mouse serum. FIG. 10B depicts HI assay titers performed with ferret serum. Yamecto/PR8 refers to a PR8 virus expressing an HA that has an influenza B/Yamagata/16/88 virus HA ectodomain. 3 loop refers to a PR8 virus expressing an HA that has an influenza B/Yamagata/16/88 virus HA ectodomain, in which three antigenic loops (150 loop, 160 loop, and 190 helix) of the ectodomain have been modified based on the amino acid sequence of influenza A/Vietnam/1203/04(HALo) virus HA. 4 loop refers to a PR8 virus expressing an HA that has an influenza B/Yamagata/16/88 virus HA ectodomain, in which four antigenic loops (120 loop, 150 loop, 160 loop, and 190 helix) of the ectodomain have been modified based on the amino acid sequence of influenza A/Vietnam/1203/04(HALo) virus HA.

Figure 11:
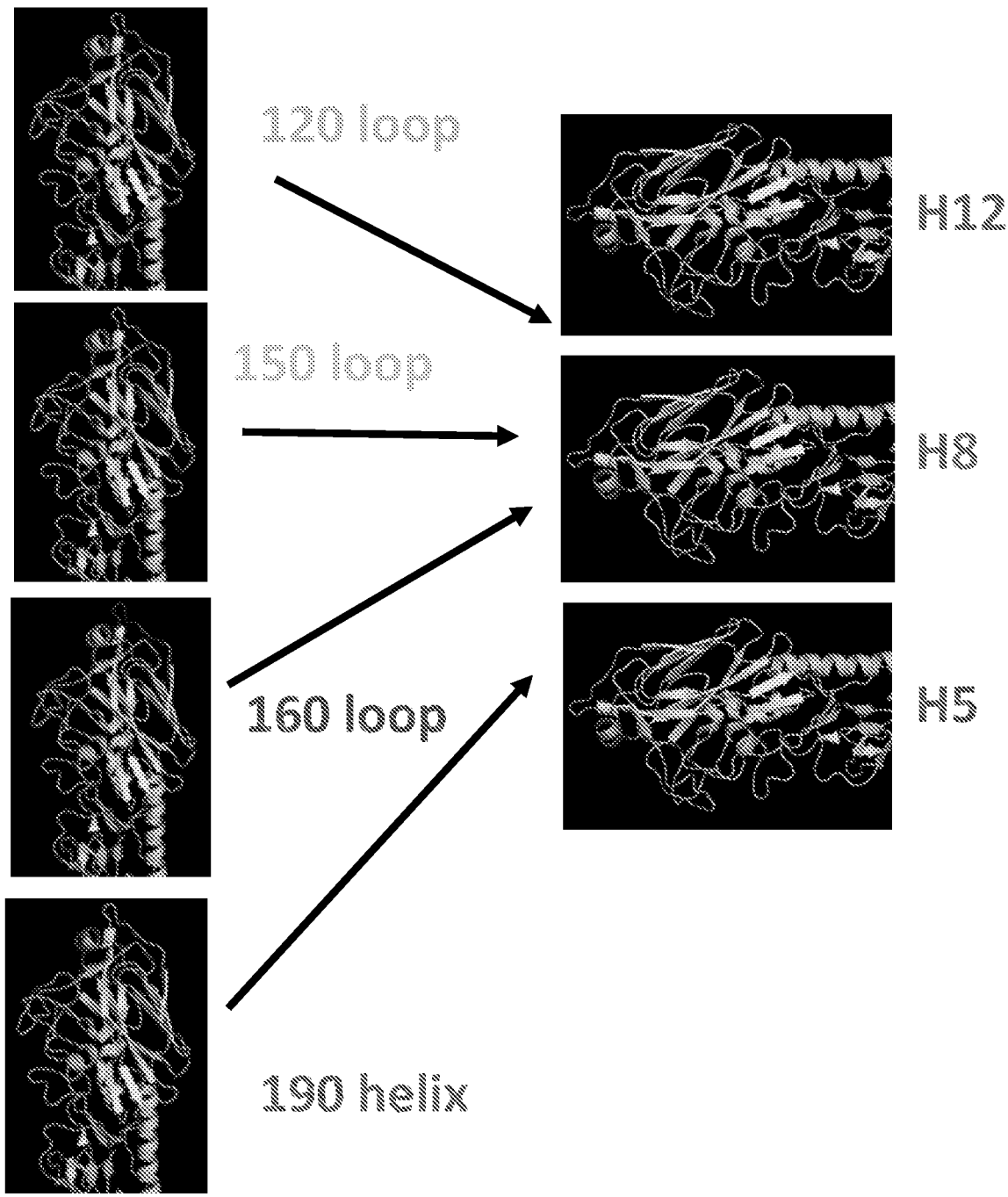

FIG. 11 demonstrates that chimeric HA may be generated in which each of the 120 loop, 150 loop, 160 loop, and 190 helix of an influenza B virus HA have been modified based on the amino acid sequence of an influenza A virus of the H5, H8, or H12 subtype.

FIG. 12A and FIG. 12B: Nucleic acid sequence encoding H5-4 loop chimeric HA (SEQ ID NO: 20). The background of the construct is Yamagata ectodomain in PR8 HA background in pDZ plasmid made by infusion cloning. Non-underlined nucleic acid sequences refer to the sequences encoding the ectodomain of Yamagata. Underlined nucleic acid sequences labeled "1" refer to the PR8 3' non-coding region sequence. Underlined nucleic acid sequences labeled "2" refer to the sequence encoding the PR8 signal peptide. Underlined nucleic acid sequences labeled "3" refer to the mutations introduced into the sequence encoding the 120 loop. Underlined nucleic acid sequences labeled "4" refer to the mutations introduced into the sequence encoding the 150 loop. Underlined nucleic acid sequences labeled "5" refer to mutations introduced into the sequence encoding the 160 loop. Underlined nucleic acid sequences labeled "6" refer to the mutations introduced into the sequence encoding the 190 helix. Underlined nucleic acid sequences labeled "7" refer to a H→Y mutation in the Yamagata ectodomain. Underlined nucleic acid sequences labeled "8" refer to the sequence encoding the PR8 transmembrane domain. Underlined nucleic acid sequences labeled "9" refer to the sequence encoding the PR8 cytoplasmic tail domain. Underlined nucleic acid sequences labeled "10" refer to the PR8 5' non-coding region.

FIG. 13: Amino acid sequence (SEQ ID NO: 21) of the nucleic acid of FIG. 12A and FIG. 12B. Underlined amino acid sequences labeled "1" refer to the PR8 signal peptide sequence. Underlined amino acid sequences labeled "2" refer to the mutations introduced into the 120 loop sequence. Underlined amino acid sequences labeled "3" refer to the mutations introduced into the 150 loop sequence. Underlined amino acid sequences labeled "4" refer to the mutations introduced into the 160 loop sequence. Underlined amino acid sequences labeled "5" refer to the mutations introduced into the 190 helix sequence. Underlined amino acid labeled "6" refers to a H→Y mutation in the Yamagata ectodomain, which matches influenza A virus HA at this position (determined by Flandorfer et al., Journal of Virology, 2003), which may lead to more efficient rescue. Underlined amino acid sequences labeled "7" refer to the PR8 transmembrane domain sequence. Underlined amino acid sequences labeled "8" refer to the PR8 cytoplasmic tail domain sequence.

FIG. 14A and FIG. 14B: Nucleic acid sequence encoding H8-4 loop chimeric HA (SEQ ID NO: 22). The background of the construct is Yamagata ectodomain in PR8 HA background in pDZ plasmid made by infusion cloning. Non-underlined nucleic acid sequences refer to the sequences encoding the ectodomain of Yamagata. Underlined nucleic acid sequences labeled "1" refer to the PR8 3' non-coding region sequence. Underlined nucleic acid sequences labeled "2" refer to the sequence encoding the PR8 signal peptide. Underlined nucleic acid sequences labeled "3" refer to the mutations introduced into the sequence encoding the 120 loop. Underlined nucleic acid sequences labeled "4" refer to an E→K mutation. Underlined nucleic acid sequences labeled "5" refer to the mutations introduced into the sequence encoding the 150 loop. Underlined nucleic acid sequences labeled "6" refer to mutations introduced into the sequence encoding the 160 loop. Underlined nucleic acid sequences labeled "7" refer to the mutations introduced into the sequence encoding the 190 helix. Underlined nucleic acid sequences labeled "8" refer to a H→Y mutation in the Yamagata ectodomain. Underlined nucleic acid sequences labeled "9" refer to the sequence encoding the PR8 transmembrane domain. Underlined nucleic acid sequences labeled "10" refer to the sequence encoding the PR8 cytoplasmic tail domain. Underlined nucleic acid sequences labeled "11" refer to the PR8 5' non-coding region.

FIG. 15: Amino acid sequence (SEQ ID NO: 23) of the nucleic acid of FIG. 14A and FIG. 14B. Underlined amino acid sequences labeled "1" refer to the PR8 signal peptide sequence. Underlined amino acid sequences labeled "2" refer to the mutations introduced into the 120 loop sequence. Underlined amino acid labeled "3" refers to an E→K mutation. Underlined amino acid sequences labeled "4" refer to the mutations introduced into the 150 loop sequence. Underlined amino acid sequences labeled "5" refer to the mutations introduced into the 160 loop sequence. Underlined amino acid sequences labeled "6" refer to the mutations introduced into the 190 helix sequence. Underlined amino acid labeled "7" refers to a H→Y mutation in the Yamagata ectodomain, which matches influenza A virus HA at this position (determined by Flandorfer et al., Journal of Virology, 2003), which may lead to more efficient rescue. Underlined amino acid sequences labeled "8" refer to the PR8 transmembrane domain sequence. Underlined amino acid sequences labeled "9" refer to the PR8 cytoplasmic tail domain sequence.

FIG. 16A and FIG. 16B: Nucleic acid sequence encoding H11-4 loop chimeric HA (SEQ ID NO: 24). The background of the construct is Yamagata ectodomain in PR8 HA background in pDZ plasmid made by infusion cloning. Non-underlined nucleic acid sequences refer to the sequences encoding the ectodomain of Yamagata. Underlined nucleic acid sequences labeled "1" refer to the PR8 3' non-coding region sequence. Underlined nucleic acid sequences labeled "2" refer to the sequence encoding the PR8 signal peptide. Underlined nucleic acid sequences labeled "3" refer to the mutations introduced into the sequence encoding the 120 loop. Underlined nucleic acid sequences labeled "4" refer to the E→K mutation. Underlined nucleic acid sequences labeled "5" refer to the mutations introduced into the sequence encoding the 150 loop. Underlined nucleic acid sequences labeled "6" refer to mutations introduced into the sequence encoding the 160 loop. Underlined nucleic acid sequences labeled "7" refer to the mutations introduced into the sequence encoding the 190 helix. Underlined nucleic acid sequences labeled "8" refer to a H→Y mutation in the Yamagata ectodomain. Underlined nucleic acid sequences labeled "9" refer to the sequence encoding the PR8 transmembrane domain. Underlined nucleic acid sequences labeled "10" refer to the sequence encoding the PR8 cytoplasmic tail domain. Underlined nucleic acid sequences labeled "11" refer to the PR8 5' non-coding region.

FIG. 17: Amino acid sequence (SEQ ID NO: 25) of the nucleic acid of FIG. 16A and FIG. 16B. Underlined amino acid sequences labeled "1" refer to the PR8 signal peptide sequence. Underlined amino acid sequences labeled "2" refer to the mutations introduced into the 120 loop sequence. Underlined amino acid labeled "3" refers to an E→K mutation. Underlined amino acid sequences labeled "4" refer to the mutations introduced into the 150 loop sequence. Underlined amino acid sequences labeled "5" refer to the mutations introduced into the 160 loop sequence. Underlined amino acid sequences labeled "6" refer to the mutations introduced into the 190 helix sequence. Underlined amino acid labeled "7" refers to a H→Y mutation in the Yamagata ectodomain, which matches influenza A virus HA at this position (determined by Flandorfer et al., Journal of Virology, 2003), which may lead to more efficient rescue. Underlined amino acid sequences labeled "8" refer to the PR8 transmembrane domain sequence. Underlined amino acid sequences labeled "9" refer to the PR8 cytoplasmic tail domain sequence.

FIG. 18A and FIG. 18B: Nucleic acid sequence encoding H12-4 loop chimeric HA (SEQ ID NO: 26). The background of the construct is Yamagata ectodomain in PR8 HA background in pDZ plasmid made by infusion cloning. Non-underlined nucleic acid sequences refer to the sequences encoding the ectodomain of Yamagata. Underlined nucleic acid sequences labeled "1" refer to the PR8 3' non-coding region sequence. Underlined nucleic acid sequences labeled "2" refer to the sequence encoding the PR8 signal peptide. Underlined nucleic acid sequences labeled "3" refer to the mutations introduced into the sequence encoding the 120 loop. Underlined nucleic acid sequences labeled "4" refer to an E→K mutation. Underlined nucleic acid sequences labeled "5" refer to the mutations introduced into the sequence encoding the 150 loop. Underlined nucleic acid sequences labeled "6" refer to mutations introduced into the sequence encoding the 160 loop. Underlined nucleic acid sequences labeled "7" refer to the mutations introduced into the sequence encoding the 190 helix. Underlined nucleic acid sequences labeled "8" refer to a H→Y mutation in the Yamagata ectodomain. Underlined nucleic acid sequences labeled "9" refer to the sequence encoding the PR8 transmembrane domain. Underlined nucleic acid sequences labeled "10" refer to the sequence encoding the PR8 cytoplasmic tail domain. Underlined nucleic acid sequences labeled "11" refer to the PR8 5' non-coding region.

FIG. 19: Amino acid sequence (SEQ ID NO: 27) of the nucleic acid of FIG. 18A and FIG. 18B. Underlined amino acid sequences labeled "1" refer to the PR8 signal peptide sequence. Underlined amino acid sequences labeled "2" refer to the mutations introduced into the 120 loop sequence. Underlined amino acid labeled "3" refers to an E→K mutation. Underlined amino acid sequences labeled "4" refer to the mutations introduced into the 150 loop sequence. Underlined amino acid sequences labeled "5" refer to the mutations introduced into the 160 loop sequence. Underlined amino acid sequences labeled "6" refer to the mutations introduced into the 190 helix sequence. Underlined amino acid labeled "7" refers to a H→Y mutation in the Yamagata ectodomain, which matches influenza A virus HA at this position (determined by Flandorfer et al., Journal of Virology, 2003), which may lead to more efficient rescue. Underlined amino acid sequences labeled "8" refer to the PR8 transmembrane domain sequence. Underlined amino acid sequences labeled "9" refer to the PR8 cytoplasmic tail domain sequence.

Figure 20:
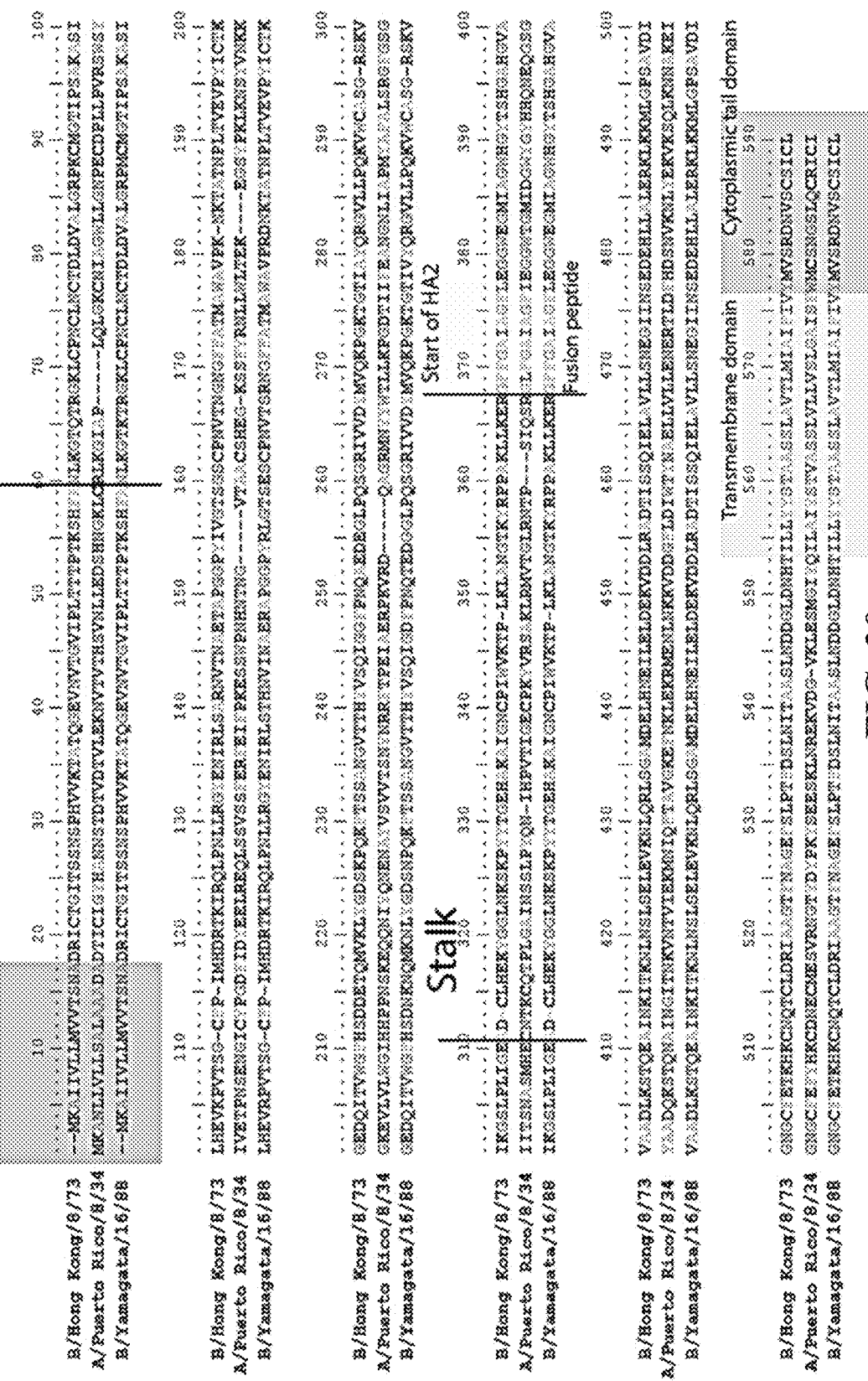

FIG. 20: Alignment of influenza B/Hong Kong/8/73 virus HA (SEQ ID NO: 28), influenza A/Puerto Rico/8/34 virus HA (SEQ ID NO: 29), and influenza B/Yamagata/16/88 virus HA (SEQ ID NO: 30). The locations of the signal peptide, stalk domain, head domain, start of the HA2 domain, fusion peptide, transmembrane domain, and cytoplasmic tail domain for the influenza B viruses are delineated based on the locations of the respective domains in the influenza A virus.

FIG. 21A: Nucleic acid sequence encoding influenza A/mallard/Sweden/24/2002 virus HA (SEQ ID NO 31). Underlined sequences are the 5' and 3' noncoding regions. FIG. 21B: Amino acid sequence (SEQ ID NO: 32) of the nucleic acid of FIG. 21A.

FIG. 22A: Nucleic acid sequence encoding influenza A/Vietnam/1203/04 (HALo) virus HA (SEQ ID NO: 33). FIG. 22B: Amino acid sequence (SEQ ID NO: 34) of the nucleic acid of FIG. 22A.

FIG. 23A: Nucleic acid sequence encoding influenza A/northern shoveler/Netherlands/18/99 virus HA (SEQ ID NO: 35). Underlined sequences are the 5' and 3' non-coding regions. FIG. 23B: Amino acid sequence (SEQ ID NO: 36) of the nucleic acid of FIG. 23A.

FIG. 24A: Nucleic acid sequence encoding A_mallard_interior Alaska_7MP0167_2007 virus HA (SEQ ID NO: 37). Underlined sequences are the 5' and 3' non-coding regions. FIG. 24B: Amino acid sequence (SEQ ID NO: 38) of the nucleic acid of FIG. 24A.

FIG. 25A: Nucleic acid sequence encoding influenza A/Puerto Rico/8/34 virus HA (SEQ ID NO: 39). Underlined sequences are the 5' and 3' non-coding regions. FIG. 25B: Amino acid sequence (SEQ ID NO: 40) of the nucleic acid of FIG. 25A.

FIG. 26A: Nucleic acid sequence encoding influenza B/Yamagata/16/88 virus HA (SEQ ID NO: 41). Underlined sequences are the 5' and 3' non-coding regions. FIG. 26B: Amino acid sequence (SEQ ID NO: 42) of the nucleic acid of FIG. 26A.

Figure 27:
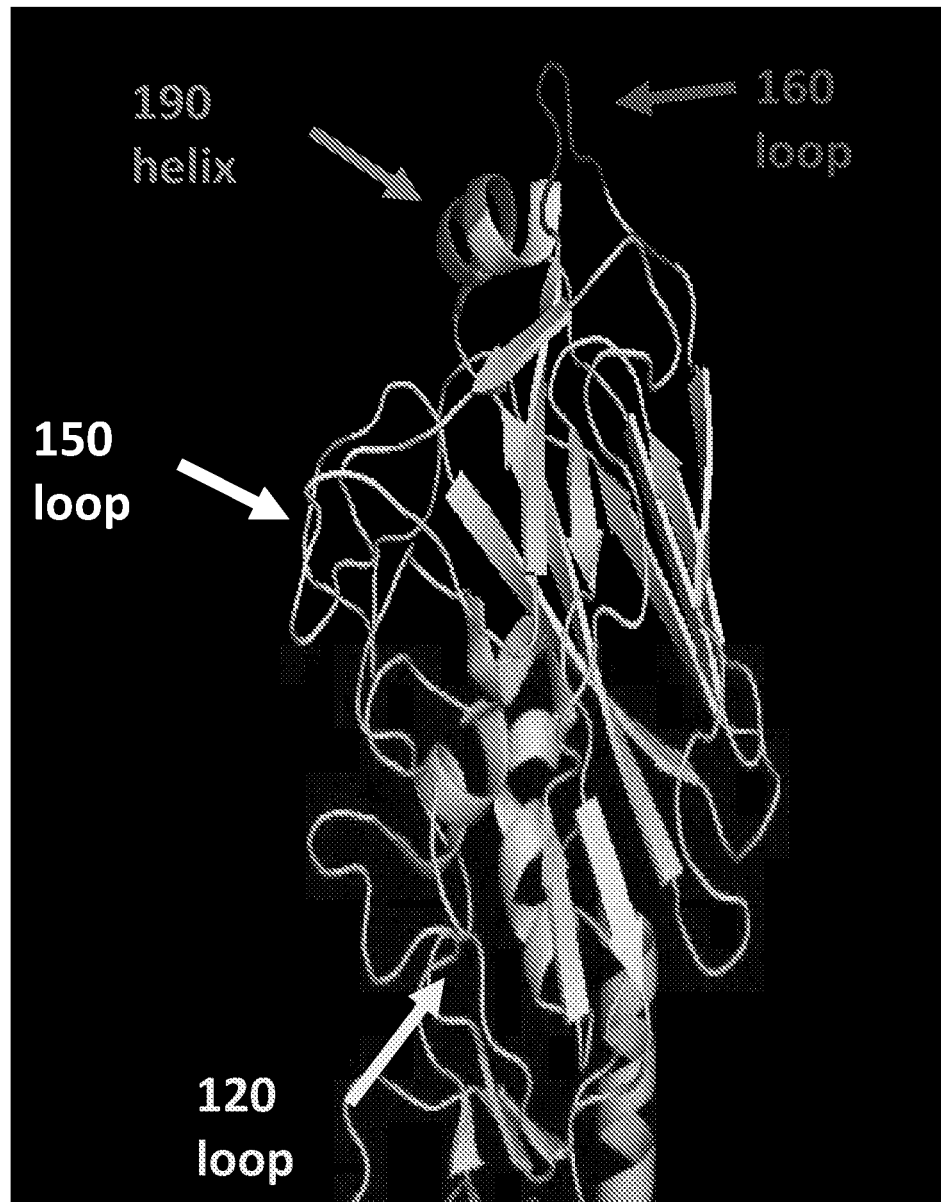

FIG. 27 depicts the four major antigenic sites of influenza B virus HA in the influenza virus B/Yamanashi/166/1988 (PDB: 4M40): 120 loop, 150 loop, 160 loop, and 190 helix.

Figure 28:
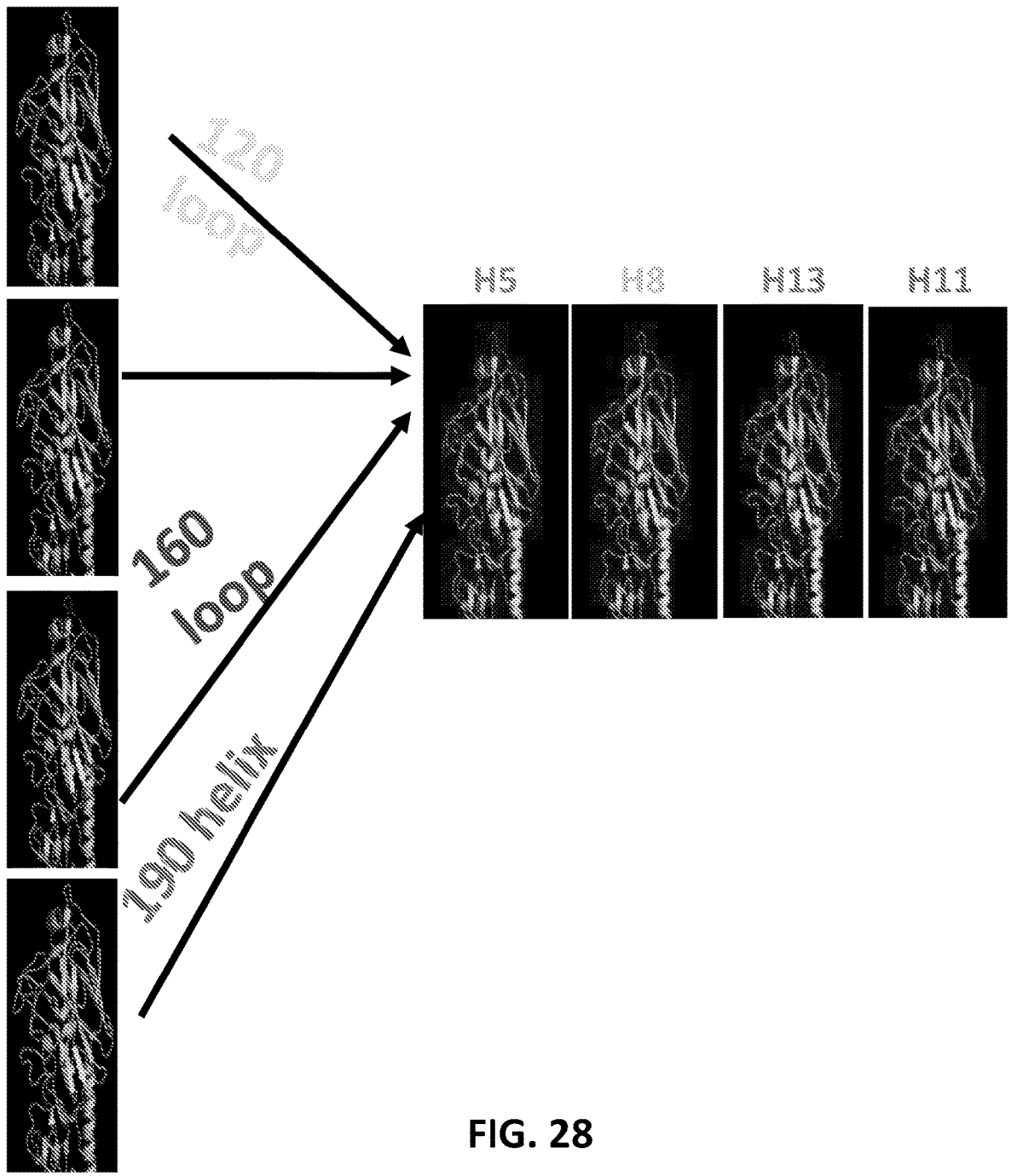

FIG. 28: Amino acid residues in four antigenic sites (120 loop, 150 loop, 160 loop, and 190 helix) of the influenza B/Yamagata/16/88 virus HA were replaced by corresponding amino acid sequences from influenza A virus HAs of the H5, H8, H11 or H13 subtypes. The resulting constructs are referred to herein as mH5/B, mH8/B, mH11/B, and mH13/B, respectively, chimeric HAs. Viruses encoding the chimeric HAs were rescued in an influenza B/Malaysia/2506/04 MA virus backbone.

FIG. 29: Nucleic acid sequence encoding mH5/B chimeric HA based on an influenza B/Yamagata/16/88 virus HA sequence, comprising nucleic acid sequences from the influenza A/Vietnam/1203/04(HALo) virus (H5) globular head domain (SEQ ID NO: 43). Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain. Uppercase bold sequences correspond to additional mutations introduced into the influenza B/Yamagata/16/88 virus HA ectodomain.

FIG. 30: Amino acid sequence (SEQ ID NO: 44) encoded by the nucleic acid of FIG. 29. Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain. Uppercase bold sequence corresponds to an additional mutation introduced into the influenza B/Yamagata/16/88 virus HA ectodomain.

FIG. 31: Nucleic acid sequence encoding mH8/B chimeric HA based on an influenza B/Yamagata/16/88 virus HA sequence, comprising nucleic acid sequences from the influenza A/Mallard/Sweden/24/2002 virus (H8) globular head domain (SEQ ID NO: 45). Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain. Uppercase bold sequences correspond to additional mutations introduced into the influenza B/Yamagata/16/88 virus HA ectodomain.

FIG. 32: Amino acid sequence (SEQ ID NO: 46) encoded by the nucleic acid of FIG. 31. Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain. Uppercase bold sequence corresponds to an additional mutation introduced into the influenza B/Yamagata/16/88 virus HA ectodomain.

FIG. 33: Nucleic acid sequence encoding mH11/B chimeric HA based on an influenza B/Yamagata/16/88 virus HA sequence, comprising nucleic acid sequences from the influenza A/northern shoveler/Netherlands/18/99 virus (H11) globular head domain (SEQ ID NO: 47). Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain. Uppercase bold sequence corresponds to an additional mutation introduced into the influenza B/Yamagata/16/88 virus HA ectodomain.

FIG. 34: Amino acid sequence (SEQ ID NO: 48) encoded by the nucleic acid of FIG. 33. Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain. Uppercase bold sequence corresponds to an additional mutation introduced into the influenza B/Yamagata/16/88 virus HA ectodomain.

FIG. 35: Nucleic acid sequence encoding mH13/B chimeric HA based on an influenza B/Yamagata/16/88 virus HA sequence, comprising nucleic acid sequences from the influenza A/black headed gull/Sweden/1/99 (H13) globular head domain (SEQ ID NO: 49). Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain.

FIG. 36: Amino acid sequence (SEQ ID NO: 50) encoded by the nucleic acid of FIG. 35. Bold, underlined, uppercase sequences correspond to mutations introduced into the 120 loop of the influenza B/Yamagata/16/88 virus HA ectodomain. Bold lowercase sequences correspond to mutations introduced into the 150 loop of the influenza B/Yamagata/16/88 virus HA ectodomain. Italicized, underlined lowercase sequences correspond to mutations introduced into the 160 loop of the influenza B/Yamagata/16/88 virus HA ectodomain. Underlined, bold, italicized, uppercase sequences correspond to mutations introduced into the 190 helix of the influenza B/Yamagata/16/88 virus HA ectodomain.

FIGS. 37A-37D: depicts growth curves for influenza viruses expressing mH5/B chimeric HA (FIG. 37A), mH8/B chimeric HA (FIG. 37B), mH11/B chimeric HA (FIG. 37C), or mH13/B chimeric HA (FIG. 37D) as compared to wild type influenza B/Malaysia/2506/04 MA virus. 10-day embryonated eggs were infected with 500 PFU/egg of the influenza virus expressing mH5/B chimeric HA (mH5/B Mal), mH8/B chimeric HA (mH8/B Mal), mH11/B chimeric HA (mH11/B Mal), or mH13/B chimeric HA (mH13/B Mal), or wild type influenza B/Malaysia/2506/04 MA virus (B/Ma104 MA) in triplicates and incubated at 33 degrees Celsius. Allantoic fluids were harvested at the indicated times and plaque assays were performed on Madin Darby Canine Kidney (MDCK) cells to determine virus titers. PFU refers to plaque forming unit. B/Ma104 MA refers to wild type influenza B/Malaysia/2506/04 MA virus. mH5/B Mal refers to influenza B/Malaysia/2506/04 MA virus encoding the mH5/B chimeric HA described in FIGS. 29 and 30. mH8/B Mal refers to influenza B/Malaysia/2506/04 MA virus encoding the mH8/B chimeric HA described in FIGS. 31 and 32. mH11/B Mal refers to influenza B/Malaysia/2506/04 MA virus encoding the mH11/B chimeric HA described in FIGS. 33 and 34. mH13/B Mal refers to influenza B/Malaysia/2506/04 MA virus encoding the mH13/B chimeric HA described in FIGS. 35 and 36.

FIGS. 38A-38D demonstrate that cross-protective subdominant conserved antigenic sites within influenza B virus HA were preserved in the chimeric HA. MDCK cells were infected with influenza viruses expressing mH5/B chimeric HA (FIG. 38A), mH8/B chimeric HA (FIG. 38B), mH11/B chimeric HA (FIG. 38C), or mH13/B chimeric HA (FIG. 38D) at an MOI of 5 without TPCK-trypsin and compared to uninfected cells or cells infected with B/Ma104 MA at an MOI of 5 without TPCK-trypsin. Cells were incubated at 33 degrees Celsius and 5% $CO_2$. 17 hours post infection, cells were fixed with methanol free 5% paraformaldehyde for immunofluorescence surface staining using the indicated anti-influenza B virus HA cross-protective human/mouse monoclonal antibodies and anti-influenza B virus HA polyclonal mouse serum. Secondary Alexa Fluor anti-human or anti-mouse antibody were used. Images were taken using Zeiss LSM 880 confocal microscope. PFU refers to plaque forming unit. B/Ma104 MA refers to wild type influenza B/Malaysia/2506/04 MA virus. mH5/B Mal refers to influenza B/Malaysia/2506/04 MA virus encoding the mH5/B chimeric HA described in FIGS. 29 and 30. mH8/B Mal refers to influenza B/Malaysia/2506/04 MA virus encoding the mH8/B chimeric HA described in FIGS. 31 and 32. mH11/B Mal refers to influenza B/Malaysia/2506/04 MA virus encoding the mH11/B chimeric HA described in FIGS. 33 and 34. mH13/B Mal refers to influenza B/Malaysia/

2506/04 MA virus encoding the mH13/B chimeric HA described in FIGS. 35 and 36. TPCK refers to L-1-Tosylamide-2-phenylethyl chloromethyl ketone.

FIGS. 39A-39D demonstrate that immunodominant epitopes on influenza B/Yamagata/88 HA head were ablated in the chimeric HAs. Mouse and ferret sera were raised against wild type influenza B virus strain B/Yamagata/16/88 to acquire hemagglutination inhibition (HI) reactivity. HI assays for the mouse and ferret sera were performed using turkey red blood cells (RBCs) with influenza viruses expressing mH5/B chimeric HA (FIG. 39A), mH8/B chimeric HA (FIG. 39B), mH11/B chimeric HA (FIG. 39C), or mH13/B chimeric HA (FIG. 39D) or wild type influenza B virus strain B/Yamagata/16/88 (FIGS. 39A-39D). B Yamagata 88 wild type refers to wild type influenza B/Yamagata/16/88 virus. mH5/B Mal refers to influenza B/Malaysia/2506/04 MA virus encoding the mH5/B chimeric HA described in FIGS. 29 and 30. mH8/B Mal refers to influenza B/Malaysia/2506/04 MA virus encoding the mH8/B chimeric HA described in FIGS. 31 and 32. mH11/B Mal refers to influenza B/Malaysia/2506/04 MA virus encoding the mH11/B chimeric HA described in FIGS. 33 and 34. mH13/B Mal refers to influenza B/Malaysia/2506/04 MA virus encoding the mH13/B chimeric HA described in FIGS. 35 and 36.

Figure 40B:
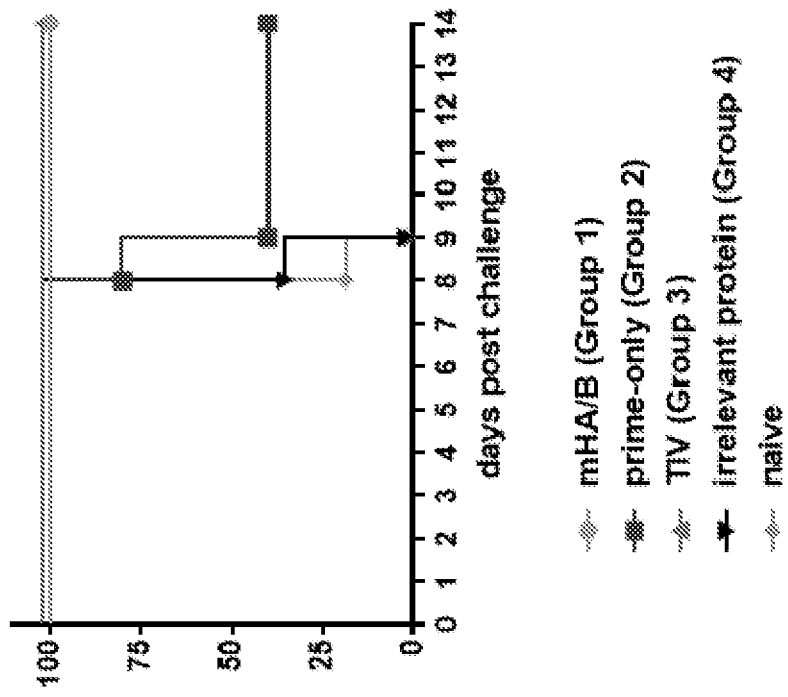
Figure 40A:
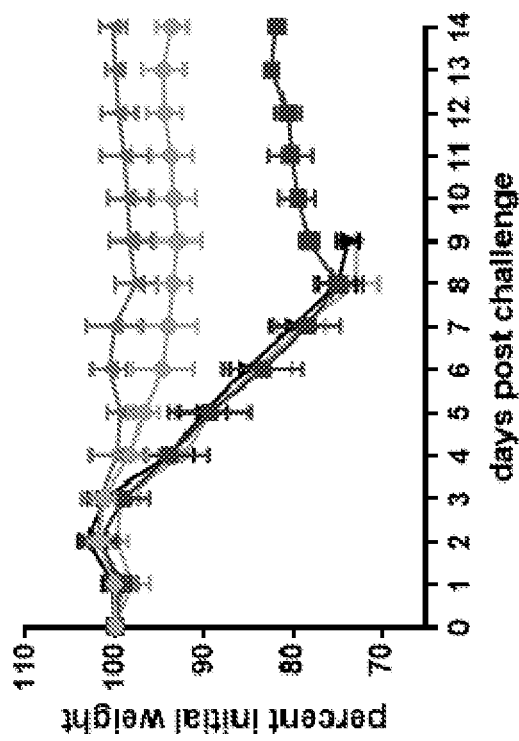

FIGS. 40A AND 40B depict weight loss (FIG. 40A) and survival (FIG. 40B) of chimeric HA-vaccinated mice after challenge with B/Malaysia/2506/04 (Victoria-like). Vaccination with the chimeric HA regiment resulted in complete protection from mortality with minimal weight loss. Circles: Group 1 (chimeric HA); squares: Group 2 (prime only); triangles pointing up: Group 3 (TIV); triangles pointing down: Group 4 (irrelevant protein); diamonds: naïve.

FIG. 41A: Nucleic acid sequence encoding influenza A/black headed gull/Sweden/1/99 virus HA (SEQ ID NO: 71). FIG. 41B: Amino acid sequence (SEQ ID NO: 72) of the nucleic acid of FIG. 41A.

5. DETAILED DESCRIPTION

5.1 Chimeric Influenza Virus Hemagglutinin Polypeptides

In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within an antigenic loop of the globular head domain of the influenza B virus HA, wherein the amino acid substitutions substitute 2, 3, 4, 5, 6, 7, 8, 9, 10, 11, 12 or more amino acid residues in the loop of the globular head of the influenza B virus HA with amino acid residues found in a corresponding region of the globular domain of an influenza A virus HA. In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within the 120 loop, 150 loop, 160 loop or 190 helix of the globular head domain of the influenza B virus HA, wherein the amino acid substitutions substitute 2, 3, 4, 5, 6, 7, 8, 9, 10, 11, 12 or more amino acid residues in the 120 loop, 150 loop, 160 loop or 190 helix of the globular head of the influenza B virus HA with amino acid residues found in a corresponding region of the globular domain of an influenza A virus HA. In one embodiment, provided herein are chimeric hemagglutinin (HA) polypeptides comprising an HA ectodomain of an influenza B virus comprising 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA. In another embodiment, provided herein are chimeric hemagglutinin (HA) polypeptides comprising an HA ectodomain of an influenza B virus comprising 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA. In another embodiment, provided herein are chimeric hemagglutinin (HA) polypeptides comprising an HA ectodomain of an influenza B virus comprising 2, 3, 4, 5 or more amino acid substitutions within 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA. In another embodiment, provided herein are chimeric hemagglutinin (HA) polypeptides comprising an HA ectodomain of an influenza B virus comprising 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/

99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTH-NVINAERAPGGPYRL (SEQ ID NO: 1) are substituted with amino acid residues NIP and RIELSTHNVINAE-VAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In some embodiments, the chimeric HA polypeptide may also comprise the signal peptide, transmembrane domain, and cytoplasmic tail domain from the influenza B virus HA. In other embodiments, the chimeric HA polypeptide comprises the signal peptide from the influenza B virus HA but lacks the transmembrane and cytoplasmic tail domains. In some embodiments, the chimeric HA polypeptide may also comprise the signal peptide, transmembrane domain, and cytoplasmic tail domain from an influenza A virus HA. In other embodiments, the chimeric HA polypeptide comprises the signal peptide from an influenza A virus HA but lacks the transmembrane and cytoplasmic tail domains. In some embodiments, the chimeric HA comprises the signal peptide of the HA of the influenza virus backbone of the chimeric HA. For example, if the chimeric HA is engineered for an influenza A virus backbone (e.g., the influenza virus comprising or engineered to express the chimeric HA is an influenza A virus), then the chimeric HA comprises the signal peptide of the influenza A virus. In some embodiments, the chimeric HA comprises the signal peptide, transmembrane domain, and cytoplasmic domain of the HA of the influenza virus backbone of the chimeric HA. In some embodiments, the chimeric HA polypeptide may also comprise the signal peptide from the HA of the influenza virus that is engineered to express the chimeric HA. In some embodiments, the chimeric HA polypeptide may also comprise the signal peptide, transmembrane domain, and cytoplasmic tail domain from the HA of the influenza virus that is engineered to express the chimeric HA. Also provided herein are nucleic acids comprising nucleotide sequences encoding such a chimeric HA. In some embodiments, the nucleic acids comprise nucleotide sequences encoding such a chimeric HA and the 5' and 3' non-coding regions from the influenza B virus HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In specific embodiments, the chimeric HA polypeptide is soluble. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid).

In another aspect, provided herein are chimeric hemagglutinin (HA) polypeptides comprising an HA ectodomain of an influenza B virus comprising one, two, three or all of the following: (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVIN-AERAPGGPYRL (SEQ ID NO: 1) are substituted with amino acid residues FIP and KIQLSTKNVINAE-HAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1)

are substituted with amino acid residues YIP and RIKL-STFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTH-NVINAERAPGGPYRL (SEQ ID NO: 1) are substituted with amino acid residues NIP and RIELSTHNVINAE-VAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In some embodiments, the chimeric HA polypeptide may also comprise the signal peptide, transmembrane domain, and cytoplasmic tail domain from the influenza B virus HA. In other embodiments, the chimeric HA polypeptide comprises the signal peptide from the influenza B virus HA but lacks the transmembrane and cytoplasmic tail domains. In some embodiments, the chimeric HA polypeptide may also comprise the signal peptide, transmembrane domain, and cytoplasmic tail domain from an influenza A virus HA. In other embodiments, the chimeric HA polypeptide comprises the signal peptide from an influenza A virus HA but lacks the transmembrane and cytoplasmic tail domains. In some embodiments, the chimeric HA comprises the signal peptide of the HA of the influenza virus backbone of the chimeric HA. For example, if the chimeric HA is engineered for an influenza A virus backbone (e.g., the influenza virus comprising or engineered to express the chimeric HA is an influenza A virus), then the chimeric HA comprises the signal peptide of the influenza A virus. In some embodiments, the chimeric HA comprises the signal peptide, transmembrane domain, and cytoplasmic domain of the HA of the influenza virus backbone of the chimeric HA. In some embodiments, the chimeric HA polypeptide may also comprise the signal peptide from the HA of the influenza virus that is engineered to express the chimeric HA. In some embodiments, the chimeric HA polypeptide may also comprise the signal peptide, transmembrane domain, and cytoplasmic tail domain from the HA of the influenza virus that is engineered to express the chimeric HA. Also provided herein are nucleic acids comprising nucleotide sequences encoding such a chimeric HA. In some embodiments, the nucleic acids comprise nucleotide sequences encoding such a chimeric HA and the 5' and 3' non-coding regions from the influenza B virus HA. In some embodiments, the nucleic acids comprise nucleotide sequences encoding such a chimeric HA and the 5' and 3' non-coding regions from an influenza A virus HA. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In specific embodiments, the chimeric HA polypeptide is soluble. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid).

In another aspect, provided herein are chimeric hemagglutinin (HA) polypeptides comprising (i) a hemagglutinin ectodomain from an influenza B virus with 2, 3, 4, 5, 6, 7, 8, 9, 10, 11, 12 or more amino acid substitutions within the 120 loop, 150 loop, 160 loop or 190 helix of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9, 10, 11, 12 or more amino acid residues in the 120 loop, 150 loop, 160 loop or 190 helix of the globular head of the influenza B virus HA with amino acid residues found in a corresponding region of the globular domain of an influenza A virus HA. In one embodiment, provided herein are chimeric hemagglutinin (HA) polypeptides comprising (i) a hemagglutinin ectodomain from an influenza B virus with 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA. In another embodiment, provided herein are chimeric hemagglutinin (HA) polypeptides comprising (i) a hemagglutinin ectodomain from an influenza B virus with 2, 3, 4, 5, 6, 7, 8, 9 or more amino acid substitutions within the 150 loop of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA. In another embodiment, provided herein are chimeric hemagglutinin (HA) polypeptides comprising (i) a hemagglutinin ectodomain from an influenza B virus with 2, 3, 4, 5 or more amino acid substitutions within the 160 loop of the globular head domain of the influenza B virus HA and (ii) a signal peptide, a transmembrane domain and a cytoplasmic tail domain from an influenza A virus, wherein the amino acid substitutions substitute 2, 3, 4, 5 or more amino acid residues in the 160 loop of the globular head of the influenza B virus HA with amino acid residues found in a corresponding region of the globular domain of an influenza A virus HA. In another embodiment, provided herein are chimeric hemagglutinin (HA) polypeptides comprising (i) a hemagglutinin ectodomain from an influenza B virus with 2, 3, 4, 5, 6, 7, 8 or more amino acid substitutions within the 190 helix of the globular head domain of the influenza B virus HA and (ii) a signal peptide, a transmembrane domain and a cytoplasmic tail domain from an influenza A virus, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRL-STYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the influenza B virus is from the Yamagata lineage. In other embodiments, the influenza B virus is from the Victoria lineage. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding such a chimeric HA and the 5' non-coding region and 3' non-coding region from an influenza A virus.

In another aspect, provided herein are chimeric hemagglutinin (HA) polypeptides comprising: (a) a hemagglutinin ectodomain from an influenza B virus with one, two, three or all of the following (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA; and (b) a signal peptide, a transmembrane domain and a cytoplasmic tail domain from an influenza A virus. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVIN-AERAPGGPYRL (SEQ ID NO: 1) are substituted with amino acid residues FIP and KIQLSTKNVINAE-HAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRL-STYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NAS-TGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAER-APGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTH-NVINAERAPGGPYRL (SEQ ID NO: 1) are substituted with amino acid residues LIP and KIELSTSNVINAE- VAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88

NKNQMKN (SEQ ID NO: 7) are substituted with amino acid residues VSTNMAK (SEQ ID NO: 62). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the influenza B virus is from the Yamagata lineage. In other embodiments, the influenza B virus is from the Victoria lineage. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding a chimeric HA polypeptide and the 5' non-coding region and 3' non-coding region from an influenza A virus. In some embodiments, the nucleic acids comprise nucleotide sequences encoding a chimeric HA polypeptide and the 5' non-coding region and 3' non-coding region from an influenza B virus. In some embodiments, the nucleic acids comprise nucleotide sequences encoding such a chimeric HA and the 5' and 3' non-coding regions of the HA of the influenza virus backbone of the chimeric HA. For example, if the chimeric HA is engineered for an influenza A virus backbone (e.g., the influenza virus comprising or engineered to express the chimeric HA is an influenza A virus), then the nucleic acids comprise nucleotide sequences encoding such a chimeric HA and the 5' and 3' non-coding regions of the influenza A virus. In some embodiments, the nucleic acids comprise nucleotide sequences encoding such a chimeric HA and the 5' and 3' non-coding regions from the influenza virus HA of the influenza virus that is engineered to express the chimeric HA. In a specific embodiment, the nucleic acid comprises the nucleotide sequence set forth in FIG. 12A and FIG. 12B or the complement thereof. In a specific embodiment, the nucleic acid comprises the nucleotide sequence set forth in FIG. 14A and FIG. 14B or the complement thereof. In a specific embodiment, the nucleic acid comprises the nucleotide sequence set forth in FIG. 16A and FIG. 16B or the complement thereof. In a specific embodiment, the nucleic acid comprises the nucleotide sequence set forth in FIG. 18A and FIG. 18B or the complement thereof.

In another aspect, provided herein are chimeric hemagglutinin (HA) polypeptides comprising (i) a hemagglutinin ectodomain from a first influenza B virus strain with 2, 3, 4, 5, 6, 7, 8, 9, 10, 11, 12 or more amino acid substitutions within the 120 loop, 150 loop, 160 loop or 190 helix of the globular head domain of the influenza B virus HA and (ii) a signal peptide, a transmembrane domain and a cytoplasmic tail domain from a second influenza B virus strain, wherein the amino acid substitutions substitute 2, 3, 4, 5, 6, 7, 8, 9, 10, 11, 12 or more amino acid residues in the 120 loop, 150 loop, 160 loop or 190 helix of the globular head of the first influenza B virus strain HA with amino acid residues found in a corresponding region of the globular domain of an influenza A virus HA. In one embodiment, provided herein are chimeric hemagglutinin (HA) polypeptides comprising (i) a hemagglutinin ectodomain from an first influenza B virus strain with 2, 3, 4, 5, 6, 7, 8, 9, 10, 11, 12, 13, 14, 15, 16, 17, 18, 19, 20 or more amino acid substitutions within the 120 loop of the globular head domain of the first influenza B virus strain and (ii) a signal peptide, a transmembrane domain and a cytoplasmic tail domain from a second influenza B virus strain, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the first influenza B virus strain HA with amino acid residues found in a corresponding region of the globular domain of an influenza A virus HA. In another embodiment, provided herein are chimeric hemagglutinin (HA) polypeptides comprising (i) a hemagglutinin ectodomain from an first influenza B virus strain with 2, 3, 4, 5, 6, 7, 8, 9 or more amino acid substitutions within the 150 loop of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5, 6, 7, 8, 9 or more amino acid residues in the 150 loop of the globular head of the in first influenza B virus strain HA with amino acid residues found in a corresponding region of the globular domain of a second influenza B virus strain HA. In another embodiment, provided herein are chimeric hemagglutinin (HA) polypeptides comprising (i) a hemagglutinin ectodomain from a first influenza B virus strain with 2, 3, 4, 5 or more amino acid substitutions within the 160 loop of the globular head domain of the first influenza B virus strain HA and (ii) a signal peptide, a transmembrane domain and a cytoplasmic tail domain from a second influenza B virus strain, wherein the amino acid substitutions substitute 2, 3, 4, 5 or more amino acid residues in the 160 loop of the globular head of the first influenza B virus strain HA with amino acid residues found in a corresponding region of the globular domain of an influenza A virus HA. In another embodiment, provided herein are chimeric hemagglutinin (HA) polypeptides comprising (i) a hemagglutinin ectodomain from a first influenza B virus strain with 2, 3, 4, 5, 6, 7, 8 or more amino acid substitutions within the 190 helix of the globular head domain of the influenza B virus HA and (ii) a signal peptide, a transmembrane domain and a cytoplasmic tail domain from a second influenza B virus strain, wherein the amino acid substitutions substitute 2, 3, 4, 5, 6, 7, 8 or more amino acid residues in the 190 helix of the globular head of the first influenza B virus strain HA with amino acid residues found in a corresponding region of the globular domain of an influenza A virus HA. In specific embodiments, the following underlined and bold amino acid residues in the 120 loop of influenza B virus B/Yamagata/16/88 TIP and NIRLSTH-NVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTH- NVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 13. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NAS-TGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 15. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 17. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 34. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues YIP and RIKLSTFNVINAETAPGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises a 120 loop, a 150 loop, a 160 loop, and/or a 190 helix with the amino acid sequences of the 120 loop, 150 loop, 160 loop, and/or 190 helix, respectively, set forth in FIG. 19. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues NIP and RIELSTHNVINAEVAPGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and/or 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of one, two, three, or all of the following: the 120 loop, 150 loop, 160 loop and/or 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the first influenza B virus strain and the second influenza B virus strain are from the same lineage. In some embodiments, the first influenza B virus strain and the second influenza B virus strain are from the same lineage but are different strains. In a specific embodiment, the first influenza B virus strain is the same strain as the second influenza B virus strain. In another embodiment, the first influenza B virus strain is a different strain than the second influenza B virus strain. In some embodiments, the first influenza B virus strain and the second influenza B virus strain are from different lineages. In some embodiments, the first influenza B virus strain is from the Yamagata lineage. In other embodiments, the first influenza B virus is from the Victoria lineage. In some embodiments, the second influenza B virus strain is from the Yamagata lineage. In other embodiments, the second influenza B virus is from the Victoria lineage. In a specific embodiment, the second influenza B virus strain is the same strain as the influenza virus backbone of an influenza virus either comprising, containing, or both the chimeric HA. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding a chimeric HA polypeptide and the 5' non-coding region and 3' non-coding region from the second influenza B virus. In some embodiments, the nucleic acids comprise nucleotide sequences encoding such a chimeric HA and the 5' and 3' non-coding regions of the HA of the influenza virus backbone of an influenza virus either comprising, containing, or both the chimeric HA.

In another aspect, provided herein are chimeric hemagglutinin (HA) polypeptides comprising: (a) a hemagglutinin ectodomain from a first influenza B virus strain with one, two, three or all of the following (i) 2, 3, 4, 5, 6, 7, 8, 9, 10, 11, 12, 13, 14, 15, 16, 17, 18, 19, 20 or more amino acid substitutions within the 120 loop of the globular head domain of the first influenza B virus strain HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the first influenza B virus strain HA with amino acid residues found in a corresponding region of the globular domain of an influenza A virus HA; (ii) 2, 3, 4, 5, 6, 7, 8, 9 or more amino acid substitutions within the 150 loop of the globular head domain of the first influenza B virus strain HA, wherein the amino acid substitutions substitute 2, 3, 4, 5, 6, 7, 8, 9 or more amino acid residues in the 150 loop of the globular head of the first influenza B virus strain HA with amino acid residues found in a corresponding region of the globular domain of an influenza A virus HA; (iii) 2, 3, 4, 5 or more amino acid substitutions within the 160 loop of the globular head domain of the first influenza B virus strain HA, wherein the amino acid substitutions substitute 2, 3, 4, 5 or more amino acid residues in the 160 loop of the globular head of the first influenza B virus strain HA with amino acid residues found in a corresponding region of the globular domain of an influenza A virus HA; and (iv) 2, 3, 4, 5, 6, 7, 8 or more amino acid substitutions within the 190 helix of the globular head domain of the first influenza B virus strain HA, wherein the amino acid substitutions substitute 2, 3, 4, 5, 6, 7, 8 or more amino acid residues in the 190 helix of the globular head of the first influenza B virus strain HA with amino acid residues found in a corresponding region of the globular domain of an influenza A virus HA; and (b) a signal peptide, a transmembrane domain and a cytoplasmic tail domain from a second influenza B virus strain. In a specific embodiment, the first influenza B virus strain is the same strain as the second influenza B virus strain. In another embodiment, the first influenza B virus strain is a different strain than the second influenza B virus strain. In a specific embodiment, the second influenza B virus strain is the same strain as the influenza virus backbone of an influenza virus either comprising, containing, or both the chimeric HA. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues FIP and KIQLSTKNVINAEHAPGGPYRL (SEQ ID NO: 2) from influenza A virus A/Vietnam/1203/04 (HALo). In specific embodiments, the following amino acid residues in influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4) from influenza A virus A/Vietnam/1203/04 (HALo). In specific embodiments, the following amino acid residues in the 150 loop of influenza B virus B/Yamagata/16/88 NVTSRNG (SEQ ID NO: 3) are substituted with amino acid residues YQGKSS (SEQ ID NO:4). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19) from influenza A virus A/Vietnam/1203/04 (HALo). In specific embodiments, the following amino acid residues in the 150 loop of influenza B virus B/Yamagata/16/88 PNVTSRNG (SEQ ID NO: 18) are substituted with amino acid residues PYQGKSS (SEQ ID NO:19). In specific embodiments, the following underlined and bold amino acid residues in the 160 loop of influenza B virus B/Yamagata/16/88 RDNKTA (SEQ ID NO: 5) are substituted with the following bold and underlined amino acid residues KKNSTY (SEQ ID NO: 6) from influenza A virus A/Vietnam/1203/04 (HALo). In specific embodiments, the following amino acid residues in the 160 loop of influenza B virus B/Yamagata/16/88 RDNKTA (SEQ ID NO: 5) are substituted with amino acid residues KKNSTY (SEQ ID NO: 6). In specific embodiments, the following underlined and bold amino acid residues in the 190 helix of influenza B virus B/Yamagata/16/88 NKNQMKN (SEQ ID NO: 7) are substituted with the following underlined and bold amino acid residues NDAAMQT (SEQ ID NO: 8) from influenza A virus A/Vietnam/1203/04 (HALo). In specific embodiments, the following amino acid residues in the 190 helix of influenza B virus B/Yamagata/16/88 NKNQMKN (SEQ ID NO: 7) are substituted with amino acid residues NDAAMQT (SEQ ID NO: 8). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 13. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 30. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues HIP and RIRLSTYNVINAETAPGGPYRL (SEQ ID NO: 51) from influenza A virus A/Mallard/Sweden/24/2002 virus. In specific embodiments, the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51). In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52) from influenza A virus A/Mallard/Sweden/24/2002 virus. In specific embodiments, the following amino acid residues in the 150 loop of influenza B virus B/Yamagata/16/88 PNVTSRNG (SEQ ID NO: 18) are substituted with amino acid residues NASTGGQS (SEQ ID NO: 52). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKADTY (SEQ ID NO: 53) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKADTY (SEQ ID NO: 53). In specific embodiments, the following underlined and bold amino acid residues in the 160 loop of influenza B virus B/Yamagata/16/88 RDNKTA (SEQ ID NO: 5) are substituted with the following bold and underlined amino acid residues KKKPDTY (SEQ ID NO: 68) from influenza A virus A/Mallard/Sweden/24/2002 virus. In specific embodiments, the following amino acid residues in the 160 loop of influenza B virus B/Yamagata/16/88 RDNKTA (SEQ ID NO: 5) are substituted with amino acid residues KKKPDTY (SEQ ID NO: 68). In specific embodiments, the following underlined and bold amino acid residues in the 190 helix of influenza B virus B/Yamagata/16/88 NKNQMKN (SEQ ID NO: 7) are substituted with the following underlined and bold amino acid residues ADAKMQT (SEQ ID NO: 54) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues ADAKMQT (SEQ ID NO: 54). In specific embodiments, the following underlined and bold amino acid residues in the 190 helix of influenza B virus B/Yamagata/16/88 NKNQMKN (SEQ ID NO: 7) are substituted with the following underlined and bold amino acid residues PDAKMQT (SEQ ID NO: 69) from influenza A virus A/Mallard/Sweden/24/2002 virus. In specific embodiments, the following amino acid residues in the 190 helix of influenza B virus B/Yamagata/16/88 NKNQMKN (SEQ ID NO: 7) are substituted with amino acid residues PDAKMQT (SEQ ID NO: 69). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 15. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 32. In specific embodiments, the following underlined and bold amino acid residues in the 120 loop of influenza B virus B/Yamagata/16/88 TIP and NIRLSTHNVINAERAPGGPYRL (SEQ ID NO: 1) are substituted with the following underlined and bold amino acid residues LIP and KIELSTSNVINAEVAPGGPYRL (SEQ ID NO: 55) from influenza A virus A/northern shoveler/Netherlands/18/99. In specific embodiments, the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55). In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues PFGSSNS (SEQ ID NO:56). In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67) from influenza A virus A/northern shoveler/Netherlands/18/99. In specific embodiments, the following amino acid residues in the 150 loop of influenza B virus B/Yamagata/16/88 PNVTSRNG (SEQ ID NO: 18) are substituted with amino acid residues KFGSSNS (SEQ ID NO:67). In specific embodiments, the following underlined and bold amino acid residues in the 160 loop of influenza B virus B/Yamagata/16/88 RDNKTA (SEQ ID NO: 5) are substituted with the following bold and underlined amino acid residues HQSGTY (SEQ ID NO: 57) from influenza A virus A/northern shoveler/Netherlands/18/99. In specific embodiments, the following amino acid residues in the 160 loop of influenza B virus B/Yamagata/16/88 RDNKTA (SEQ ID NO: 5) are substituted with amino acid residues HQSGTY (SEQ ID NO: 57). In specific embodiments, the following underlined and bold amino acid residues in the 190 helix of influenza B virus B/Yamagata/16/88 NKNQMKN (SEQ ID NO: 7) are substituted with the following underlined and bold amino acid residues TTLKMHQ (SEQ ID NO: 58) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues TTLKMHQ (SEQ ID NO: 58). In specific embodiments, the following underlined and bold amino acid residues in the 190 helix of influenza B virus B/Yamagata/16/88 NKNQMKN (SEQ ID NO: 7) are substituted with the following underlined and bold amino acid residues ATLKMHQ (SEQ ID NO: 70) from influenza A virus A/northern shoveler/Netherlands/18/99. In specific embodiments, the following amino acid residues in the 190 helix of influenza B virus B/Yamagata/16/88 NKNQMKN (SEQ ID NO: 7) are substituted with amino acid residues ATLKMHQ (SEQ ID NO: 70). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 17. In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 34. In specific embodiments, the following underlined and bold amino acid residues in the 120 loop of influenza B virus B/Yamagata/16/88 T̲IP and NIRLSTHNVINAER̲APGGPYRL (SEQ ID NO: 1) are substituted with the following underlined and bold amino acid residues Y̲IP and RIK̲LSTF̲NVINAET̲APGGPYRL (SEQ ID NO: 63) from influenza A virus A/mallard/interior Alaska/7MP0167/2007. In specific embodiments, the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63). In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64) from influenza A virus A/mallard/interior Alaska/7MP0167/2007. In specific embodiments, the following amino acid residues in the 150 loop of influenza B virus B/Yamagata/16/88 PNVTSRNG (SEQ ID NO: 18) are substituted with amino acid residues NNTSNQGS (SEQ ID NO:64). In specific embodiments, the following underlined and bold amino acid residues in the 160 loop of influenza B virus B/Yamagata/16/88 RDNKTA (SEQ ID NO: 5) are substituted with amino acid residues LKSGQF (SEQ ID NO: 65) from influenza A virus A/mallard/interior Alaska/7MP0167/2007. In specific embodiments, the following amino acid residues in the 160 loop of influenza B virus B/Yamagata/16/88 RDNKTA (SEQ ID NO: 5) are substituted with amino acid residues LKSGQF (SEQ ID NO: 65). In specific embodiments, the following underlined and bold amino acid residues in the 190 helix of influenza B virus B/Yamagata/16/88 NKNQMKN (SEQ ID NO: 7) are substituted with the following underlined and bold amino acid residues PTSDMQI (SEQ ID NO: 66) from influenza A virus A/mallard/interior Alaska/7MP0167/2007. In specific embodiments, the following amino acid residues in the 190 helix of influenza B virus B/Yamagata/16/88 NKNQMKN (SEQ ID NO: 7) are substituted with amino acid residues PTSDMQI (SEQ ID NO: 66). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 19. In specific embodiments, the following underlined and bold amino acid residues in the 120 loop of influenza B virus B/Yamagata/16/88 T̲IP and NIRLSTH̲NVINAER̲APGGPYRL (SEQ ID NO: 1) are substituted with the following underlined and bold amino acid residues N̲IP and RIELSTH̲NVINAEV̲APGGPYRL (SEQ ID NO: 59) from influenza A virus A/black headed gull/Sweden/1/99. In specific embodiments, the following amino acid residues in influenza B virus B/Yamagata/16/88 TIP and NIRLSTHNVINAERAPGGPYRL (SEQ ID NO: 1) are substituted with amino acid residues NIP and RIELSTHNVINAEVAPGGPYRL (SEQ ID NO: 59). In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60) from influenza A virus A/black headed gull/Sweden/1/99. In specific embodiments, the following amino acid residues in the 150 loop of influenza B virus B/Yamagata/16/88 PNVTSRNG (SEQ ID NO: 18) are substituted with amino acid residues PDKGASS (SEQ ID NO:60). In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61) from influenza A virus A/black headed gull/Sweden/1/99. In specific embodiments, the following amino acid residues in the 160 loop of influenza B virus B/Yamagata/16/88 RDNKTA (SEQ ID NO: 5) are substituted with amino acid residues KRGNQY (SEQ ID NO: 61). In specific embodiments, the following underlined and bold amino acid residues in the 190 helix of influenza B virus B/Yamagata/16/88 NKNQMKN (SEQ ID NO: 7) are substituted with the following underlined and bold amino acid residues VSTNMAK (SEQ ID NO: 62) from influenza A virus A/black headed gull/Sweden/1/99. In specific embodiments, the following amino acid residues in the 190 helix of influenza B virus B/Yamagata/16/88 NKNQMKN (SEQ ID NO: 7) are substituted with amino acid residues VSTNMAK (SEQ ID NO: 62). In specific embodiments, a chimeric HA polypeptide described herein comprises one, two, three, or all of the following: a 120 loop, a 150 loop, a 160 loop, and/or a 190 helix with the amino acid sequences of the 120 loop, 150 loop, 160 loop, and 190 helix, respectively, set forth in FIG. 36. In certain embodiments, the chimeric HA polypeptides comprise 1, 2, 3, 4, 5 or more amino acid substitutions in the globular head domain of the influenza B virus HA which are outside of one, two, three, or all of the following: the 120 loop, 150 loop, 160 loop and 190 helix. For example, the last amino acid of the ectodomain of an influenza B virus HA may be substituted with another amino acid and amino acid 147 of influenza B virus HA (including the signal peptide) may be substituted with another amino acid. As another example, amino acid position 156 (glutamic acid) of the immature influenza B/Yamagata/16/88 virus HA may be substituted with another amino acid (for example, lysine). As another example, amino acid position 250 (glycine) of the immature influenza B/Yamagata/16/88 virus HA may be substituted with another amino acid (for example, glutamic acid). In some embodiments, the first influenza B virus strain and the second influenza B virus strain are from the same lineage. In some embodiments, the first influenza B virus strain and the second influenza B virus strain are from the same lineage but are different strains. In a specific embodiment, the first influenza B virus strain is the same strain as the second influenza B virus strain. In another embodiment, the first influenza B virus strain is a different strain than the second influenza B virus strain. In some embodiments, the first influenza B virus strain and the second influenza B virus strain are from different lineages. In some embodiments, the first influenza B virus strain is from the Yamagata lineage. In other embodiments, the first influenza B virus is from the Victoria lineage. In some embodiments, the second influenza B virus strain is from the Yamagata lineage. In other embodiments, the second influenza B virus is from the Victoria lineage. In a specific embodiment, the second influenza B virus strain is the same strain as the influenza virus backbone of an influenza virus either comprising, containing, or both the chimeric HA. In specific embodiments, the influenza A virus from which the amino acid residues are derived for the amino acid substitutions in one, two, three or more of the loops is an H5 (e.g., A/Vietnam/1203/04(HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). Also provided herein are nucleic acids comprising nucleotide sequences encoding said chimeric HA polypeptides. In some embodiments, the nucleic acids comprise nucleotide sequences encoding a chimeric HA polypeptide and the 5' non-coding region and 3' non-coding region from the second influenza B virus strain. In some embodiments, the nucleic acids comprise nucleotide sequences encoding such a chimeric HA and the 5' and 3' non-coding regions of the HA of the influenza virus backbone of an influenza virus either comprising, containing, or both the chimeric HA. In a specific embodiment, the nucleic acid comprises the nucleotide sequence set forth in FIG. 29 or the complement thereof. In a specific embodiment, the nucleic acid comprises the nucleotide sequence set forth in FIG. 31 or the complement thereof. In a specific embodiment, the nucleic acid comprises the nucleotide sequence set forth in FIG. 33 or the complement thereof. In a specific embodiment, the nucleic acid comprises the nucleotide sequence set forth in FIG. 35 or the complement thereof.

In another aspect, provided herein are chimeric hemagglutinin (HA) polypeptides comprising an HA ectodomain of an influenza B virus comprising 2, 3, 4, 5, 6, 7, 8, 9, 10, 11, 12 or more amino acid substitutions within an antigenic loop of the globular head domain of the influenza B virus HA (e.g., 120 loop, 150 loop, 160 loop and/or 190 helix), wherein the amino acid substitutions substitute 2, 3, 4, 5, 6, 7, 8, 9, 10, 11, 12 or more amino acid residues in the loop of the globular head of the influenza B virus HA with random amino acid residues that do not affect the conformation/structure of the HA.

The amino acid residues in the globular head domain of an influenza A virus HA in a region corresponding to an antigenic loop (e.g., 120 loop, 150 loop, 160 loop and/or 190 helix) in the globular head domain of an influenza B virus HA may be identified using techniques known to one skilled in the art. In specific embodiments, the amino acid residues in the globular head domain of an influenza A virus HA in a region corresponding to an antigenic loop (e.g., 120 loop, 150 loop, 160 loop and/or 190 helix) in the globular head domain of an influenza B virus HA are identified by comparing the amino acid sequences and/or structural information (e.g., crystal structures) of influenza A viruses and influenza B viruses. In particular embodiments, alignments of the amino acid sequences of HA of influenza A viruses and influenza B viruses as well as assessing the viruses for structural similarity enables the skilled person in the art to select the amino acid residues in the influenza B virus HA antigenic loop to substitute with amino acid residues from a corresponding region in the globular head domain of an influenza A virus HA. For example, one might want to refrain from substituting amino acid residues, such as cysteine, proline or both, in the influenza B virus HA antigenic loop that may impact the folding of the chimeric HA with amino acid residues from a corresponding region in the globular head domain of an influenza A virus HA. In addition, one might want to refrain from substituting amino acid residues in the influenza B virus HA antigenic loop that impact the coding for N-linked glycosylation sites (N-X-S/T). In selecting the amino acid residues to substitute, care should be taken to maintain the conformation/structure of the HA. In some embodiments, amino acid residues that are highly conserved in an antigenic loop of the globular head domain of influenza B virus HAs, one might want to refrain from substituting with amino acid residues from a corresponding region in the globular head domain of an influenza A virus HA. For example, those amino acid residues identified by Wang et al., 2008, Journal of Virology 82: 3011-3020 as being variant among influenza B viruses may be selected as amino acid residues within an antigenic loop of the globular head domain of an influenza B virus to substitute with other amino acid residues (e.g., other amino acid residues from a corresponding region of the globular head domain of an influenza A virus HA), while those amino acid residues within the antigenic loop of the globular head domain of an influenza B virus HA may not be substituted. In a specific embodiment, when amino acid residues that are highly conserved in an antigenic loop of the globular head domain of influenza B virus HAs and amino acid residues in a corresponding region of the globular head domain of influenza A virus HAs, one might want to refrain from substituting with amino acid residues in the antigenic loop of the globular head domain of an influenza B virus HA with amino acid residues from a corresponding region in the globular head domain of an influenza A virus HA. For example, one of skill in the art may not want to substitute the methionine in the 190 helix of an influenza B virus with another amino acid residue. See, e.g., Section 6, infra. In certain embodiments, with respect to amino acid residues such as proline found in an antigenic loop of the globular head domain of an influenza B virus HA, one might want to refrain from substituting with amino acid residues from a corresponding region in the globular head domain of an influenza A virus HA. In some embodiments, with respect to amino acid residues such as cysteine, proline or both found in an antigenic loop of the globular head domain of an influenza B virus HA, one might want to refrain from substituting with amino acid residues from a corresponding region in the globular head domain of an influenza A virus HA. In certain embodiments, one might want to refrain from substituting amino acid residues such as proline found in an antigenic loop of the globular head domain of an influenza B virus HA with amino acid residues from a corresponding region in the globular head domain of an influenza A virus HA. In specific embodiments, the amino acid residues substituted in an antigenic loop of the globular head domain of an influenza B virus are not consecutive amino acid residues. For example, amino acid residues that are found conformationally close to one another may be substituted for other amino acid residues. In other embodiments, the amino acid residues substituted in an antigenic loop of the globular head domain of an influenza B virus are consecutive amino acid residues. In certain embodiments, an amino acid residue found in the antigenic loop of an influenza B virus is substituted with a conservative amino acid residue (i.e., a conservative substitution). The effect of amino acid substitutions on the conformation/structure may be determined by assays known to one of skill in the art, e.g., structure programs, crystallography, or functional assays. See, e.g., Section 5.11, infra, and Section 6, infra. In a particular embodiment, the chimeric HA polypeptides may be evaluated for antigenic conservation using a panel of monoclonal antibodies that bind to conserved epitopes in the globular head domain of HA and the stem domain of HA. In a specific embodiment, the methods described in Section 6, infra, are used to evaluate antigenic conservation of the chimeric HA. In addition, the chimeric HA polypeptides described herein may be evaluated to determine whether the antigenic loops of the influenza B virus HA were mutated using techniques known to one of skill in the art or described herein (see, e.g., Section 6, infra, including the HI assay described therein). In particular, the chimeric HA polypeptides described herein may be evaluated to determine if the amino acid substitutions in the antigenic loop(s) of the influenza B virus HA result in loss of a variable region(s) of the influenza B virus HA using techniques known to one of skill in the art or described herein (see, e.g., Section 6, infra, including the HI assay described therein). In a specific embodiment, the chimeric HA polypeptides described herein may be evaluated to determine if the amino acid substitutions in the antigenic loop(s) of the influenza B virus HA reduce or eliminate the immundominant epitopes of the influenza B virus HA using techniques known to one of skill in the art or described herein (see, e.g., Section 6, infra, including the HI assay described therein). In a specific embodiment, a chimeric HA polypeptide described herein is assessed in an HI assay, such as described in Section 6, infra, to evaluate the replacement of the antigenic loop(s) in the influenza B virus HA.

In some embodiments, 1, 2, 3, 4, 5, 6, 7, 8, 9, 10, 11, 12, 13, 14, 15, 16, 17, 18, 19, 20 or more amino acid residues in 120 loop of an influenza B virus HA are substituted with 1, 2, 3, 4, 5, 6, 7, 8, 9, 10, 11, 12, 13, 14, 15, 16, 17, 18, 19, 20 or more amino acid residues in site E of the globular head domain of an influenza A virus H3 HA. In some embodiments, 1, 2, 3, 4, 5, 6, 7, 8, 9, 10, 11, 12, 13, 14, 15, 16, 17, 18, 19, 20 or more amino acid residues in 120 loop of an influenza B virus HA are substituted with 1, 2, 3, 4, 5, 6, 7, 8, 9, 10, 11, 12, 13, 14, 15, 16, 17, 18, 19, 20 or more amino acid residues in site Sa of the globular head domain of an influenza A virus H1 HA. In certain embodiments, 1, 2, 3, 4, 5, 6, 7, 8, 9, 10, 11, 12, 13, 14, 15, 16, 17, 18, 19, 20 or more amino acid residues in 120 loop of an influenza B virus HA are substituted with 1, 2, 3, 4, 5, 6, 7, 8, 9, 10, 11, 12, 13, 14, 15, 16, 17, 18, 19, 20 or more amino acid residues in site Cb of the globular head domain of an influenza A virus H1 HA. In some embodiments, 1, 2, 3, 4, 5, 6, 7, 8, 9, 10, 11, 12, 13, 14, 15, 16, 17, 18, 19, 20 or more amino acid residues in 120 loop of an influenza B virus HA are substituted with 1, 2, 3, 4, 5, 6, 7, 8, 9, 10, 11, 12, 13, 14, 15, 16, 17, 18, 19, 20 or more amino acid residues in sites Sa and/or Cb of the globular head domain of an influenza A virus HI HA.

In certain embodiments, 1, 2, 3, 4, 5, 6, 7, 8, 9 or more amino acid residues in 150 loop of an influenza B virus HA are substituted with 1, 2, 3, 4, 5, 6, 7, 8, 9 or more amino acid residues in site A of the globular head domain of an influenza A virus H3 HA. In some embodiments, 1, 2, 3, 4, 5, 6, 7, 8, 9 or more amino acid residues in 150 loop of an influenza B virus HA are substituted with 1, 2, 3, 4, 5, 6, 7, 8, 9 or more amino acid residues in site Ca of the globular head domain of an influenza A virus H1 HA.

In certain embodiments, 1, 2, 3, 4, 5 or more amino acid residues in 160 loop of an influenza B virus HA are substituted with 1, 2, 3, 4, 5 or more amino acid residues in site B of the globular head domain of an influenza A virus H3 HA. In some embodiments, 1, 2, 3, 4, 5 or more amino acid residues in 160 loop of an influenza B virus HA are substituted with 1, 2, 3, 4, 5 or more amino acid residues in site Sa of the globular head domain of an influenza A virus H1 HA.

In certain embodiments, 1, 2, 3, 4, 5, 6, 7, 8 or more amino acid residues in 190 helix of an influenza B virus HA are substituted with 1, 2, 3, 4, 5, 6, 7, 8 or more amino acid residues in site B of the globular head domain of an influenza A virus H3 HA. In some embodiments, 1, 2, 3, 4, 5, 6, 7, 8 or more amino acid residues in 190 helix of an influenza B virus HA are substituted with 1, 2, 3, 4, 5, 6, 7, 8 or more amino acid residues in site Sb of the globular head domain of an influenza A virus H1 HA.

In a specific embodiment, the influenza A virus HA utilized in the generation of a chimeric HA polypeptide described herein is the HA from an influenza virus of the H1, H2, H3, H4, H5, H6, H7, H8, H9, H10, H11, H12, H13, H14, H15, H16, H17, or H18 subtype. In a specific embodiment, the influenza A virus HA utilized in the generation of a chimeric HA polypeptide described herein is the HA from an influenza virus of the H2, H3, H4, H5, H6, H7, H8, H9, H10, H11, H12, H13, H14, H15, H16, H17, or H18 subtype. In a specific embodiment, the influenza A virus HA utilized in the generation of a chimeric HA polypeptide described herein is the HA from an influenza virus of the H5, H8, H11, H12, or H13 subtype. In a specific embodiment, the influenza A virus HA utilized in the generation of a chimeric HA polypeptide described herein is the HA from an influenza virus of the H5 subtype. In a specific embodiment, the influenza A virus HA utilized in the generation of a chimeric HA polypeptide described herein is the HA from an influenza virus of the H8 subtype. In a specific embodiment, the influenza A virus HA utilized in the generation of a chimeric HA polypeptide described herein is the HA from an influenza virus of the H11 subtype. In a specific embodiment, the influenza A virus HA utilized in the generation of a chimeric HA polypeptide described herein is the HA from an influenza virus of the H12 subtype. In a specific embodiment, the influenza A virus HA utilized in the generation of a chimeric HA polypeptide described herein is the HA from an influenza virus of the H13 subtype. In a specific embodiment, the influenza A virus HA utilized in the generation of a chimeric HA polypeptide described herein is the HA from an avian influenza virus. In a specific embodiment, the influenza A virus HA utilized in the generation of a chimeric HA polypeptide described herein is the HA from influenza A/mallard/Sweden/24/2002 virus (GenBank Accession No. CY060249.1; GenBank GI No. 294441479; see, also, FIG. 21A and FIG. 21). In a specific embodiment, the influenza A virus HA utilized in the generation of a chimeric HA polypeptide described herein is the HA from influenza A/Vietnam/1203/04 virus (GenBank Accession No. EF541403.1; GenBank GI No. 145284465; see, also, FIG. 22A and FIG. 22B and Steel et al., 2009, Journal of Virology, 83(4):1742-1753 for the HA of influenza A/Vietnam/1203/04 (HALo) virus). In a specific embodiment, the influenza A virus HA utilized in the generation of a chimeric HA polypeptide described herein is the HA from influenza A/northern shoveler/Netherlands/18/99 virus (GenBank Accession No. CY060417.1; GenBank GI No. 294441876; see, also, FIG. 23A and FIG. 23B). In a specific embodiment, the influenza A virus HA utilized in the generation of a chimeric HA polypeptide described herein is the HA from influenza A_mallard_interior Alaska_7MP0167_2007 virus (GenBank Accession No. CY077198.1; GenBank GI No. 312652817; see, also, FIG. 24A and FIG. 24B). In a specific embodiment, the influenza A virus HA utilized in the generation of a chimeric HA polypeptide described herein is the HA from influenza A/Puerto Rico/8/34 virus (GenBank Accession No. AF389118.1; GenBank GI No. 21693168; see, also, FIG. 25A and FIG. 25B). In a specific embodiment, the influenza A virus HA utilized in the generation of a chimeric HA polypeptide described herein is the HA from influenza A/black headed gull/Sweden/1/99 (GenBank Accession No. AY684887.1; see, also, FIGS. 41A and 41). In a specific embodiment, the influenza B virus HA utilized in the generation of a chimeric HA polypeptide described herein is an HA from an influenza B virus of the Yamagata lineage. In a specific embodiment, the influenza B virus HA utilized in the generation of a chimeric HA polypeptide described herein is an HA from an influenza B virus of the Victoria lineage. In a specific embodiment, the influenza B virus HA utilized in the generation of a chimeric HA polypeptide described herein is the HA from influenza B/Yamagata/16/88 virus (see, FIG. 26A and FIG. 26B). In a specific embodiment, the influenza B virus HA utilized in the generation of a chimeric HA polypeptide described herein is the HA from an influenza B/Malaysia/2506/04 mouse adapted (MA) virus (see, e.g., SEQ ID NO:73 and 83). In a specific embodiment, the influenza B virus HA utilized in the generation of a chimeric HA polypeptide described herein is the HA from influenza B/Malaysia/2506/04 virus (see, e.g., GenBank Accession No. CY040449.1).

In a specific embodiment, a chimeric HA polypeptide is a chimeric HA polypeptide described in Section 6, infra. In a specific embodiment, a chimeric HA polypeptide comprises the amino acid sequence of the chimeric HA polypeptide in FIG. 13, 15, 17, 19, 30, 32, 34, or 36. In another specific embodiment, a chimeric HA polypeptide comprises the amino acid sequence of the chimeric HA polypeptide in FIG. 13, 15, 17, 19, 30, 32, 24 or 36 without the signal peptide. In another specific embodiment, a chimeric HA polypeptide comprises the amino acid sequences of the ectodomain of the chimeric HA polypeptide in FIG. 13, 15, 17, 19, 30, 32, 34 or 36.

In a specific embodiment, the influenza B virus HA sequence utilized to generate a chimeric HA polypeptide described herein is the HA sequence from an influenza B virus described in Section 5.4, infra. In a specific embodiment, the influenza B virus HA sequence utilized to generate a chimeric HA polypeptide described herein is the HA sequence from an influenza B virus described in Section 6, infra. In a specific embodiment, the influenza A virus HA sequence utilized to generate a chimeric HA polypeptide described herein is the HA sequence from an influenza A virus described in Section 5.4, infra. In a specific embodiment, the influenza A virus HA sequence utilized to generate a chimeric HA polypeptide described herein is the HA sequence from an influenza A virus described in Section 6, infra. For example, the influenza A virus HA may be from a group 1 or a group 2 virus. In specific embodiments, the influenza A virus HA is from an H1, H2, H3, H4, H5, H6, H7, H8, H9, H10, H11, H12, H13, H14, H15, H16, or H17 influenza A virus.

In certain embodiments, the chimeric influenza virus hemagglutinin polypeptides provided herein are capable of forming a three dimensional structure that is similar to the three dimensional structure of a native influenza hemagglutinin. Structural similarity might be evaluated based on any technique deemed suitable by those of skill in the art. For instance, reaction, e.g. under non-denaturing conditions, of a chimeric influenza virus hemagglutinin polypeptide with a neutralizing antibody or antiserum that recognizes a native influenza hemagglutinin might indicate structural similarity. Useful neutralizing antibodies or antisera are described in, e.g. Sui, et al., 2009, Nat. Struct. Mol. Biol. 16(3):265-273, Ekiert et al., Feb. 26, 2009, Science [DOI: 10.1126/science.1171491], and Kashyap et al., 2008, Proc. Natl. Acad. Sci. USA 105(16):5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, a chimeric influenza hemagglutinin (HA) polypeptide described herein retains one, two, or more, or all of the functions of a wild-type influenza HA. Nonlimiting examples of functions of a wild-type influenza HA include fusogenic activity, receptor binding activity, budding, and particle formation. In a specific embodiment, a chimeric influenza hemagglutinin (HA) polypeptide described herein has fusogenic activity. Assays known to one skilled in the art can be utilized the assess the fusogenic activity of a chimeric influenza hemagglutinin (HA) polypeptide described herein, such as, for example, immunofluorescence assays and pseudotyped virus-like-particle assays.

5.2 Nucleic Acids Encoding Chimeric Hemagglutinin (HA) Polypeptide

Provided herein are nucleic acids comprising nucleotide sequences that encode the chimeric influenza virus hemagglutinin polypeptides described herein. Due to the degeneracy of the genetic code, any nucleic acid that encodes a chimeric hemagglutinin (HA) polypeptide described herein is encompassed herein. In certain embodiments, nucleic acids corresponding to naturally occurring influenza virus nucleic acids encoding an HA1 domain (e.g., an HA1 stem segment (such as, an HA1 N-terminal stem segment and an HA1 C-terminal stem segment)), HA2 domain, HA luminal domain, HA transmembrane domain, and/or HA cytoplasmic domain are used to produce a chimeric influenza virus hemagglutinin polypeptide. In certain embodiments, the nucleic acid comprises one, two, or three of the following: nucleotide sequences encoding an influenza virus HA signal peptide, nucleotide sequences encoding an influenza virus HA transmembrane domain, and nucleotide sequences encoding an influenza virus HA cytoplasmic domain. In specific embodiments, the nucleic acid comprises nucleotide sequences encoding said chimeric HA polypeptide and preferably comprises the 5' non-coding region and 3' non-coding region from the HA of the same influenza virus as the influenza virus engineered to express the chimeric HA polypeptide. In specific embodiments, the nucleic acid comprises nucleotide sequences encoding said chimeric HA polypeptide, the 5' 5' non-coding region and 3' non-coding region from the HA of the same influenza virus as the influenza virus engineered to express the chimeric HA polypeptide, and nucleotide sequences encoding the influenza virus HA signal peptide from the HA of the same influenza virus as the influenza virus engineered to express the chimeric HA polypeptide. In specific embodiments, the nucleic acid comprises nucleotide sequences encoding said chimeric HA polypeptide, the 5' 5' non-coding region and 3' non-coding region from the HA of the same influenza virus as the influenza virus engineered to express the chimeric HA polypeptide, and nucleotide sequences encoding one, two, or three of the following: the influenza virus HA signal peptide, the influenza virus HA transmembrane domain, and the influenza virus HA cytoplasmic domain from the HA of the same influenza virus as the influenza virus engineered to express the chimeric HA polypeptide.

Also provided herein are nucleic acids capable of hybridizing to a nucleic acid encoding a chimeric influenza virus hemagglutinin polypeptide. In certain embodiments, provided herein are nucleic acids capable of hybridizing to a fragment of a nucleic acid encoding a chimeric influenza virus hemagglutinin polypeptide. In other embodiments, provided herein are nucleic acids capable of hybridizing to the full length of a nucleic acid encoding a chimeric influenza virus hemagglutinin polypeptide. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents. In specific embodiments, the nucleic acid is capable of hybridizing under high stringency conditions to the full length of the nucleotide sequence set forth in SEQ ID NO: 20. In specific embodiments, the nucleic acid is capable of hybridizing under high stringency conditions to the full length of the coding sequence of the nucleotide sequence set forth in SEQ ID NO: 20. In specific embodiments, the nucleic acid is capable of hybridizing under high stringency conditions to the full length of the nucleotide sequence set forth in SEQ ID NO: 22. In specific embodiments, the nucleic acid is capable of hybridizing under high stringency conditions to the full length of the coding sequence of the nucleotide sequence set forth in SEQ ID NO: 22. In specific embodiments, the nucleic acid is capable of hybridizing under high stringency conditions to the full length of the nucleotide sequence set forth in SEQ ID NO: 24. In specific embodiments, the nucleic acid is capable of hybridizing under high stringency conditions to the full length of the coding sequence of the nucleotide sequence set forth in SEQ ID NO: 24. In specific embodiments, the nucleic acid is capable of hybridizing under high stringency conditions to the full length of the nucleotide sequence set forth in SEQ ID NO: 26. In specific embodiments, the nucleic acid is capable of hybridizing under high stringency conditions to the full length of the coding sequence of the nucleotide sequence set forth in SEQ ID NO: 26. In specific embodiments, the nucleic acid is capable of hybridizing under high stringency conditions to the full length of the nucleotide sequence set forth in SEQ ID NO: 43. In specific embodiments, the nucleic acid is capable of hybridizing under high stringency conditions to the full length of the coding sequence of the nucleotide sequence set forth in SEQ ID NO: 43. In specific embodiments, the nucleic acid is capable of hybridizing under high stringency conditions to the full length of the nucleotide sequence set forth in SEQ ID NO: 45. In specific embodiments, the nucleic acid is capable of hybridizing under high stringency conditions to the full length of the coding sequence of the nucleotide sequence set forth in SEQ ID NO: 45. In specific embodiments, the nucleic acid is capable of hybridizing under high stringency conditions to the full length of the nucleotide sequence set forth in SEQ ID NO: 47. In specific embodiments, the nucleic acid is capable of hybridizing under high stringency conditions to the full length of the coding sequence of the nucleotide sequence set forth in SEQ ID NO: 47. In specific embodiments, the nucleic acid is capable of hybridizing under high stringency conditions to the full length of the nucleotide sequence set forth in SEQ ID NO: 49. In specific embodiments, the nucleic acid is capable of hybridizing under high stringency conditions to the full length of the coding sequence of the nucleotide sequence set forth in SEQ ID NO: 49. In a specific embodiment, a chimeric HA is encoded by the nucleic acid sequence set forth in FIG. 12A and FIG. 12B, or the complement thereof. In a specific embodiment, a chimeric HA is encoded by a nucleic acid sequence comprising the nucleotide sequence encoding the ectodomain set forth in FIG. 12A and FIG. 12B (i.e., excluding the 5' and 3' noncoding regions and nucleic acid sequences encoding the signal peptide, transmembrane domain, and cytoplasmic domain set forth in FIG. 12A and FIG. 12B), or the complement thereof. In a specific embodiment, a chimeric HA is encoded by the nucleic acid sequence set forth in FIG. 14A and FIG. 14B, or the complement thereof. In a specific embodiment, a chimeric HA is encoded by a nucleic acid sequence comprising the nucleotide sequence encoding the ectodomain set forth in FIG. 14A and FIG. 14B (i.e., excluding the 5' and 3' noncoding regions and nucleic acid sequences encoding the signal peptide, transmembrane domain, and cytoplasmic domain set forth in FIG. 14A and FIG. 14B), or the complement thereof. In a specific embodiment, a chimeric HA is encoded by the nucleic acid sequence set forth in FIG. 16A and FIG. 16B, or the complement thereof. In a specific embodiment, a chimeric HA is encoded by a nucleic acid sequence comprising a nucleotide sequence encoding the ectodomain set forth in FIG. 16A and FIG. 16B (i.e., excluding the 5' and 3' noncoding regions and nucleic acid sequences encoding the signal peptide, transmembrane domain, and cytoplasmic domain set forth in FIG. 16A and FIG. 16B), or the complement thereof. In a specific embodiment, a chimeric HA is encoded by the nucleic acid sequence set forth in FIG. 18A and FIG. 18B, or the complement thereof. In a specific embodiment, a chimeric HA is encoded by a nucleic acid sequence comprising the nucleotide sequence encoding the ectodomain set forth in FIG. 18A and FIG. 18B (i.e., excluding the 5' and 3' noncoding regions and nucleic acid sequences encoding the signal peptide, transmembrane domain, and cytoplasmic domain set forth in FIG. 18A and FIG. 18B), or the complement thereof. In a specific embodiment, a chimeric HA is encoded by the nucleic acid sequence set forth in FIG. 29, or the complement thereof. In a specific embodiment, a chimeric HA is encoded by a nucleic acid sequence comprising the nucleotide sequence encoding the ectodomain set forth in FIG. 29 (i.e., excluding the 5' and 3' noncoding regions and nucleic acid sequences encoding the signal peptide, transmembrane domain, and cytoplasmic domain set forth in FIG. 29), or the complement thereof. In a specific embodiment, a chimeric HA is encoded by the nucleic acid sequence set forth in FIG. 31, or the complement thereof. In a specific embodiment, a chimeric HA is encoded by a nucleic acid sequence comprising the nucleotide sequence encoding the ectodomain set forth in FIG. 31 (i.e., excluding the 5' and 3' noncoding regions and nucleic acid sequences encoding the signal peptide, transmembrane domain, and cytoplasmic domain set forth in FIG. 31), or the complement thereof. In a specific embodiment, a chimeric HA is encoded by the nucleic acid sequence set forth in FIG. 33, or the complement thereof. In a specific embodiment, a chimeric HA is encoded by a nucleic acid sequence comprising the nucleotide sequence encoding the ectodomain set forth in FIG. 33 (i.e., excluding the 5' and 3' noncoding regions and nucleic acid sequences encoding the signal peptide, transmembrane domain, and cytoplasmic domain set forth in FIG. 33), or the complement thereof. In a specific embodiment, a chimeric HA is encoded by the nucleic acid sequence set forth in FIG. 35, or the complement thereof. In a specific embodiment, a chimeric HA is encoded by a nucleic acid sequence comprising the nucleotide sequence encoding the ectodomain set forth in FIG. 35 (i.e., excluding the 5' and 3' noncoding regions and nucleic acid sequences encoding the signal peptide, transmembrane domain, and cytoplasmic domain set forth in FIG. 35), or the complement thereof.

In a specific embodiment, a chimeric HA polypeptide is encoded by a nucleic acid sequence comprising the nucleotide sequence encoding the ectodomain set forth in FIG. 12 or a complement thereof, and one, two or all of the following: (1) the nucleotide sequence encoding the signal peptide set forth in FIG. 12, or a complement thereof; (2) the nucleotide sequence encoding the transmembrane domain set forth in FIG. 12, or a complement thereof, and (3) the nucleotide sequence encoding the cytoplasmic domain set forth in FIG. 12, or a complement thereof. In a specific embodiment, a chimeric HA polypeptide is encoded by a nucleic acid sequence comprising the nucleotide sequence encoding the ectodomain set forth in FIG. 14 or a complement thereof, and one, two or all of the following: (1) the nucleotide sequence encoding the signal peptide set forth in FIG. 14, or a complement thereof; (2) the nucleotide sequence encoding the transmembrane domain set forth in FIG. 14, or a complement thereof, and (3) the nucleotide sequence encoding the cytoplasmic domain set forth in FIG. 14, or a complement thereof. In a specific embodiment, a chimeric HA polypeptide is encoded by a nucleic acid sequence comprising the nucleotide sequence encoding the ectodomain set forth in FIG. 16 or a complement thereof, and one, two or all of the following: (1) the nucleotide sequence encoding the signal peptide set forth in FIG. 16, or a complement thereof; (2) the nucleotide sequence encoding the transmembrane domain set forth in FIG. 16, or a complement thereof, and (3) the nucleotide sequence encoding the cytoplasmic domain set forth in FIG. 16, or a complement thereof. In a specific embodiment, a chimeric HA polypeptide is encoded by a nucleic acid sequence comprising the nucleotide sequence encoding the ectodomain set forth in FIG. 18 or a complement thereof, and one, two or all of the following: (1) the nucleotide sequence encoding the signal peptide set forth in FIG. 18, or a complement thereof; (2) the nucleotide sequence encoding the transmembrane domain set forth in FIG. 18, or a complement thereof, and (3) the nucleotide sequence encoding the cytoplasmic domain set forth in FIG. 18, or a complement thereof. In a specific embodiment, a chimeric HA polypeptide is encoded by a nucleic acid sequence comprising the nucleotide sequence encoding the ectodomain set forth in FIG. 29 or a complement thereof, and one, two or all of the following: (1) the nucleotide sequence encoding the signal peptide set forth in FIG. 29, or a complement thereof; (2) the nucleotide sequence encoding the transmembrane domain set forth in FIG. 29, or a complement thereof, and (3) the nucleotide sequence encoding the cytoplasmic domain set forth in FIG. 29, or a complement thereof. In a specific embodiment, a chimeric HA polypeptide is encoded by a nucleic acid sequence comprising the nucleotide sequence encoding the ectodomain set forth in FIG. 31 or a complement thereof, and one, two or all of the following: (1) the nucleotide sequence encoding the signal peptide set forth in FIG. 31, or a complement thereof; (2) the nucleotide sequence encoding the transmembrane domain set forth in FIG. 31, or a complement thereof, and (3) the nucleotide sequence encoding the cytoplasmic domain set forth in FIG. 31, or a complement thereof. In a specific embodiment, a chimeric HA polypeptide is encoded by a nucleic acid sequence comprising the nucleotide sequence encoding the ectodomain set forth in FIG. 33 or a complement thereof, and one, two or all of the following: (1) the nucleotide sequence encoding the signal peptide set forth in FIG. 33, or a complement thereof; (2) the nucleotide sequence encoding the transmembrane domain set forth in FIG. 33, or a complement thereof, and (3) the nucleotide sequence encoding the cytoplasmic domain set forth in FIG. 33, or a complement thereof. In a specific embodiment, a chimeric HA polypeptide is encoded by a nucleic acid sequence comprising the nucleotide sequence encoding the ectodomain set forth in FIG. 35 or a complement thereof, and one, two or all of the following: (1) the nucleotide sequence encoding the signal peptide set forth in FIG. 35, or a complement thereof; (2) the nucleotide sequence encoding the transmembrane domain set forth in FIG. 35, or a complement thereof, and (3) the nucleotide sequence encoding the cytoplasmic domain set forth in FIG. 35, or a complement thereof.

In a specific embodiment, a nucleic acid sequence encoding a chimeric HA polypeptide comprises the nucleotide sequence set forth in FIG. 12, 14, 16, 18, 29, 31, 33, or 35, or a complement thereof. In another specific embodiment, a nucleic acid sequence encoding a chimeric HA polypeptide comprises the nucleotide sequence set forth in FIG. 12, 14, 16, 18, 29, 31, 33, or 35, or a complement thereof, without the signal peptide. In another specific embodiment, a nucleic acid sequence encoding a chimeric HA polypeptide comprises the nucleotide sequence set forth in FIG. 12, 14, 16, 18, 29, 31, 33, or 35, or a complement thereof, without the 5' non-coding region, 3' non-coding region or both. In another specific embodiment, a nucleic acid sequence encoding a chimeric HA polypeptide comprises the nucleotide sequence set forth in FIG. 12, 14, 16, 18, 29, 31, 33, or 35, or a complement thereof, without the signal peptide and without the 5' non-coding region, 3' non-coding region or both.

In some embodiments, a nucleic acid encoding a chimeric influenza virus hemagglutinin polypeptide is isolated. In certain embodiments, an "isolated" nucleic acid refers to a nucleic acid molecule which is separated from other nucleic acid molecules which are present in the natural source of the nucleic acid. In other words, the isolated nucleic acid can comprise heterologous nucleic acids that are not associated with it in nature. In other embodiments, an "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In addition, provided herein are nucleic acids encoding the individual components of a chimeric influenza virus hemagglutinin polypeptide. In specific embodiments, nucleic acids encoding the globular head domain and/or the stem domain of the chimeric influenza virus hemagglutinin polypeptide are provided. Nucleic acids encoding components of a chimeric influenza virus hemagglutinin polypeptide may be assembled using standard molecular biology techniques known to one of skill in the art. In specific embodiments, the individual components of a chimeric influenza virus hemagglutinin polypeptide can be expressed by the same or different vector.

5.3 Expression of Chimeric Hemagglutinin (HA) Polypeptide

Provided herein are vectors, including expression vectors, containing a nucleic acid encoding a chimeric influenza virus hemagglutinin polypeptide described herein. In a specific embodiment, the vector is an expression vector that is capable of directing the expression of a nucleic acid encoding a chimeric influenza virus hemagglutinin polypeptide. Non-limiting examples of expression vectors include, but are not limited to, plasmids and viral vectors, such as replication defective retroviruses, adenoviruses, adeno-associated viruses and baculoviruses. Expression vectors also may include, without limitation, transgenic animals and non-mammalian cells/organisms, e.g., mammalian cells/organisms that have been engineered to perform mammalian N-linked glycosylation.

In some embodiments, provided herein are expression vectors encoding components of a chimeric hemagglutinin (HA) polypeptide (e.g., the stem domain and the head domain, or portions of either domain). Such vectors may be used to express the components in one or more host cells and the components may be isolated and conjugated together with a linker using techniques known to one of skill in the art.

An expression vector comprises a nucleic acid encoding a chimeric hemagglutinin (HA) polypeptide described herein and in a form suitable for expression of the nucleic acid in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome. In specific embodiments, the host cell is a cell line.

Expression vectors can be designed for expression of a chimeric hemagglutinin (HA) polypeptide described herein using prokaryotic (e.g., E. coli) or eukaryotic cells (e.g., insect cells (using baculovirus expression vectors, see, e.g., Treanor et al., 2007, JAMA, 297(14):1577-1582 incorporated by reference herein in its entirety), yeast cells, plant cells, algae, avian, or mammalian cells). Examples of yeast host cells include, but are not limited to S. pombe and S. cerevisiae and examples, infra. An example of avian includes, but is not limited to EB66 cells. Examples of mammalian host cells include, but are not limited to, Crucell Per.C6 cells, Vero cells, CHO cells, VERO cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g. Chinese hamster ovary or baby hamster kidney cells) is used for expression of a chimeric hemagglutinin (HA) polypeptide. In another embodiment, a plant cell culture system is used for expression of a chimeric hemagglutinin (HA) polypeptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems. In specific embodiments, plant cell culture systems are not used for expression of a chimeric hemagglutinin (HA) polypeptide. The host cells comprising the nucleic acids that encode the chimeric hemagglutinin (HA) polypeptides described herein can be isolated, i.e., the cells are outside of the body of a subject. In certain embodiments, the cells are engineered to express nucleic acids that encode the chimeric influenza virus hemagglutinin polypeptides described herein. In specific embodiments, the host cells are cells from a cell line.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding a chimeric hemagglutinin (HA) polypeptide. In other embodiments, a host cell is stably transfected with an expression vector containing a nucleic acid encoding a chimeric hemagglutinin (HA) polypeptide.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

As an alternative to recombinant expression of a chimeric hemagglutinin (HA) polypeptide using a host cell, an expression vector containing a nucleic acid encoding a chimeric hemagglutinin (HA) polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a chimeric hemagglutinin (HA) polypeptide.

Once a chimeric hemagglutinin (HA) polypeptide has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins.

Accordingly, provided herein are methods for producing a chimeric hemagglutinin (HA) polypeptide. In one embodiment, the method comprises culturing a host cell containing a nucleic acid encoding the polypeptide in a suitable medium such that the polypeptide is produced. In some embodiments, the method further comprises isolating the polypeptide from the medium or the host cell.

Also provided herein are methods for producing a virus comprising a chimeric HA described herein, comprising propagating the virus in any substrate that allows the virus to grow to titers that permit their use in accordance with the methods described herein. In one embodiment, the substrate allows the viruses to grow to titers comparable to those determined for the corresponding wild-type viruses. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In certain embodiments, the virus is propagated in MDCK cells, Vero cells, 293T cells, or other cell lines known in the art. In certain embodiments, the virus is propagated in cells derived from embryonated eggs.

5.4 Influenza Virus Vectors

In one aspect, provided herein are influenza viruses containing a chimeric influenza virus hemagglutinin polypeptide described herein. In a specific embodiment, the chimeric hemagglutinin (HA) polypeptide is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to a chimeric hemagglutinin (HA) polypeptide. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a chimeric hemagglutinin (HA) polypeptide may be produced by supplying in trans the chimeric hemagglutinin (HA) polypeptide during production of virions using techniques known to one skilled in the art, such as reverse genetics and helper-free plasmid rescue. Alternatively, the replication of a parental influenza virus comprising a genome engineered to express a chimeric hemagglutinin (HA) polypeptide in cells susceptible to infection with the virus wherein hemagglutinin function is provided in trans will produce progeny influenza viruses containing the chimeric hemagglutinin (HA) polypeptide.

In another aspect, provided herein are influenza viruses comprising a genome engineered to express a chimeric hemagglutinin (HA) polypeptide. In a specific embodiment, the genome of a parental influenza virus is engineered to encode a chimeric hemagglutinin (HA) polypeptide, which is expressed by progeny influenza virus. In another specific embodiment, the genome of a parental influenza virus is engineered to encode a chimeric hemagglutinin (HA) polypeptide, which is expressed and incorporated into the virions of progeny influenza virus. Thus, the progeny influenza virus resulting from the replication of the parental influenza virus contain a chimeric hemagglutinin (HA) polypeptide. The virions of the parental influenza virus may have incorporated into them a chimeric hemagglutinin (HA) polypeptide that contains a stem and/or head domain from the same or a different lineage or strain of influenza B virus. Alternatively, the virions of the parental influenza virus may have incorporated into them a moiety that is capable of functionally replacing one or more of the activities of influenza virus hemagglutinin polypeptide (e.g., the receptor binding and/or fusogenic activities of influenza virus hemagglutinin). In specific embodiments, the parental influenza virus is an influenza A virus. In specific embodiments, the parental influenza virus is an influenza B virus.

In some embodiments, the virions of the parental influenza virus have incorporated into them a heterologous polypeptide. In certain embodiments, the genome of a parental influenza virus is engineered to encode a heterologous polypeptide and a chimeric hemagglutinin (HA) polypeptide, which are expressed by progeny influenza virus. In specific embodiments, the chimeric hemagglutinin (HA) polypeptide, the heterologous polypeptide or both are incorporated into virions of the progeny influenza virus.

Since the genome of influenza A and B viruses consist of eight (8) single-stranded, negative sense segments (influenza C viruses consist of seven (7) single-stranded, negative sense segments), the genome of a parental influenza virus may be engineered to express a chimeric hemagglutinin (HA) polypeptide (and any other polypeptide, such as a heterologous polypeptide) using a recombinant segment and techniques known to one skilled in the art, such a reverse genetics and helper-free plasmid rescue. In one embodiment, the recombinant segment comprises a nucleic acid encoding the chimeric hemagglutinin (HA) polypeptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, International Publication No. WO 2011/014645, all of which are incorporated by reference herein in their entireties). In a specific embodiment, the recombinant segment uses the 3' and 5' noncoding and/or nontranslated sequences of segments of influenza viruses that are from a different or the same lineage or strain as the parental influenza virus. In some embodiments, the recombinant segment comprises the 3' noncoding region of an influenza virus hemagglutinin polypeptide, the untranslated regions of an influenza virus hemagglutinin polypeptide, and the 5' non-coding region of an influenza virus hemagglutinin polypeptide. In specific embodiments, the recombinant segment comprises the 3' and 5' noncoding and/or nontranslated sequences of the HA segment of an influenza virus that is the same lineage or strain as the influenza virus lineage or strain as the HA1 stem segment, the globular head domain, and/or the HA2 of a chimeric hemagglutinin (HA) polypeptide. In specific embodiments, the recombinant segment comprises packaging signals, such as the 5' and 3' non-coding regions and signal peptide of the HA segment of an influenza virus, from the same type, lineage, or strain as the influenza virus backbone. For example, if the chimeric HA is engineered to be expressed from an influenza A virus, then the nucleotide sequence encoding chimeric HA comprises the 5' and 3' non-coding regions and the nucleotide sequence encoding the signal peptide of the HA segment of the influenza A virus. In another example, if the chimeric HA is engineered to be expressed from an influenza B virus, then the nucleotide sequence encoding chimeric HA comprises the 5' and 3' non-coding regions and the nucleotide sequence encoding the signal peptide of the HA segment of the influenza B virus. In certain embodiments, the recombinant segment encoding the chimeric hemagglutinin (HA) polypeptide may replace the HA segment of a parental influenza virus.

In some embodiments, a chimeric hemagglutinin gene segment encodes a chimeric hemagglutinin (HA) polypeptide. In specific embodiments, the chimeric hemagglutinin (HA) gene segment and at least one other influenza virus gene segment comprise packaging signals that enable the chimeric hemagglutinin (HA) gene segment and the at least one other gene segment to segregate together during replication of a recombinant influenza virus (see, Gao & Palese 2009, PNAS 106:15891-15896; and International Application Publication No. WO11/014645).

In some embodiments, the genome of a parental influenza virus may be engineered to express a chimeric hemagglutinin (HA) polypeptide using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. Nos. 6,887,699, 6,001,634, 5,854,037 and 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238). Thus, in certain embodiments, a parental influenza virus is engineered to contain a bicistronic RNA segment that expresses the chimeric hemagglutinin (HA) polypeptide and another polypeptide, such as a gene expressed by the parental influenza virus. In some embodiments, the parental influenza virus gene is the HA gene.

Techniques known to one skilled in the art may be used to produce an influenza virus containing a chimeric hemagglutinin (HA) polypeptide and an influenza virus comprising a genome engineered to express a chimeric hemagglutinin (HA) polypeptide. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing a chimeric hemagglutinin (HA) polypeptide and an influenza virus comprising a genome engineered to express a chimeric hemagglutinin (HA) polypeptide. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

The influenza viruses described herein may be propagated in any substrate that allows the virus to grow to titers that permit their use in accordance with the methods described herein. Thus, in certain embodiments, provided herein is a method for producing a virus described herein comprising propagating the virus in a substrate. In one embodiment, the substrate allows the viruses to grow to titers comparable to those determined for the corresponding wild-type viruses. In certain embodiments, the substrate is one which is biologically relevant to the influenza virus or to the virus from which the HA function is derived. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In certain embodiments, the virus is propagated in a cell line susceptible to influenza virus infection. In certain embodiments, the virus is propagated in MDCK cells, Vero cells, 293T cells, or other cell lines known in the art. In certain embodiments, the virus is propagated in cells derived from embryonated eggs.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype or strain. In other embodiments, the influenza viruses, or influenza virus polypeptides, genes or genome segments for use as described herein are obtained or derived from two or more influenza A virus subtypes or strains. In a specific embodiment, the influenza A virus is an influenza virus of the H1, H2, H3, H4, H5, H6, H7, H8, H9, H10, H11, H12, H13, H14, H15, H16, H17, or H18 subtype. In a specific embodiment, the influenza A virus is an influenza virus of the H2, H4, H5, H6, H7, H8, H9, H10, H11, H12, H13, H14, H15, H16, H17, or H18 subtype. In a specific embodiment, the influenza A virus is an influenza virus of the H5, H8, H11, H12, or H13 subtype. In a specific embodiment, the influenza A virus is an influenza virus of the H5 subtype. In a specific embodiment, the influenza A virus is an influenza virus of the H8 subtype. In a specific embodiment, the influenza A virus is an influenza virus of the H11 subtype. In a specific embodiment, the influenza A virus is an influenza virus of the H12 subtype. In a specific embodiment, the influenza A virus is an influenza virus of the H13 subtype. In a specific embodiment, the influenza A virus is an avian influenza virus.

In some embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from a single influenza B virus lineage or strain. In other embodiments, the influenza viruses, or influenza virus polypeptides, genes or genome segments for use as described herein are obtained or derived from two or more influenza B virus lineages or strains. In other embodiments, the influenza viruses, or influenza virus polypeptides, genes or genome segments for use as described herein are obtained or derived from a combination of influenza A and influenza B virus subtypes, lineages, or strains.

In some embodiments, the influenza viruses, or influenza virus polypeptides, genes or genome segments for use as described herein are obtained or derived from an influenza C virus. In certain embodiments, the influenza viruses, or influenza virus polypeptides, genes or genome segments for use as described herein are obtained or derived from a single influenza C virus subtype or strain. In other embodiments, the influenza viruses, or influenza virus polypeptides, genes or genome segments for use as described herein are obtained or derived from two or more influenza C virus subtypes or strains. In other embodiments, the influenza viruses, or influenza virus polypeptides, genes or genome segments for use as described herein are obtained or derived from a combination of influenza C virus and influenza A virus and/or influenza B virus subtypes or strains.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/Victoria/361/2011 (H3N2); A/California/4/2009 (H1N1); A/California/7/2009 (H1N1); A/Perth/16/2009 (H3N2); A/Brisbane/59/2007 (H1N1); A/Brisbane/10/2007 ((H3N2); A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselunne/2617/03 hp (H1N1); A/sw/Loningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S/IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1 N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1); A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Non-limiting examples of influenza B viruses include strain Aichi/5/88, strain B/Brisbane/60/2008; Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, strain B/Wisconsin/1/2010; and strain Rochester/02/2001. In a specific embodiment, the influenza B virus is B/Malaysia/2506/04.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, the influenza viruses provided herein have an attenuated phenotype. In specific embodiments, the attenuated influenza virus is based on influenza A virus. In other embodiments, the attenuated influenza virus is based on influenza B virus. In yet other embodiments, the attenuated influenza virus is based on influenza C virus. In other embodiments, the attenuated influenza virus may comprise genes or genome segments from one or more strains or subtypes of influenza A, influenza B, and/or influenza C virus. In some embodiments, the attenuated backbone virus comprises genes from an influenza A virus and an influenza B virus. In specific embodiments, the attenuated influenza virus comprises, encodes, or both, a chimeric HA and has a backbone of an influenza A virus. In specific embodiments, the attenuated influenza virus comprises, encodes, or both, a chimeric HA and has a backbone of an influenza B virus.

In specific embodiments, attenuation of influenza virus is desired such that the virus remains, at least partially, infectious and can replicate in vivo, but only generate low titers resulting in subclinical levels of infection that are nonpathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function (e.g., truncated NS1 protein (see, e.g., Hai et al., 2008, Journal of Virology 82(21):10580-10590, which is incorporated by reference herein in its entirety) or NS1 deletion (see, e.g., Wressnigg et al., 2009, Vaccine 27:2851-2857, which is incorporated by reference herein in its entirety)), or selecting for conditional virus mutants (e.g., cold-adapted viruses, see, e.g., Alexandrova et al., 1990, Vaccine, 8:61-64, which is incorporated by reference herein in its entirety). Alternatively, naturally occurring attenuated influenza viruses may be used as influenza virus backbones for the influenza virus vectors.

In certain embodiments, an influenza virus comprising a chimeric HA described herein has one, two, or more of the functions of an influenza virus comprising a wild-type influenza virus HA. Nonlimiting examples of functions of a wild-type influenza virus HA include fusogenic activity, receptor binding activity, budding, and particle formation. In a specific embodiment, an influenza virus comprising a chimeric influenza HA polypeptide described herein has fusogenic activity. Assays known to one skilled in the art can be utilized to assess the fusogenic activity of an influenza virus comprising a chimeric influenza HA polypeptide described herein, such as, for example, immunofluorescence assays and pseudotyped virus-like-particle assays. In a specific embodiment, an influenza virus comprising a chimeric influenza HA polypeptide described herein has replication activity. Assays known to one skilled in the art can be utilized the assess the replication activity of an influenza virus comprising a chimeric influenza HA polypeptide described herein, such as, for example, plaque assay and western blot analyses.

5.5 Virus-Like Particles and Virosomes

The chimeric influenza virus hemagglutinin polypeptides described herein can be incorporated into virus-like particle (VLP) vectors, e.g., purified/isolated VLPs. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLPs comprise a chimeric hemagglutinin (HA) polypeptide and a viral structural protein, such as HIV gag. In a specific embodiment, the VLPs comprise a chimeric hemagglutinin (HA) polypeptide and an HIV gag polypeptide. In another specific embodiment, the VLPs comprise a chimeric hemagglutinin (HA) polypeptide and influenza virus neuraminidase polypeptide. In another specific embodiment, the VLPs comprise a chimeric hemagglutinin (HA) polypeptide, influenza virus neuraminidase polypeptide, and influenza virus M1 polypeptide.

Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992) 89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein. In a specific embodiment, the VLPs comprising chimeric hemagglutinin (HA) polypeptide described herein are generated using baculovirus, as described in the Examples section below. In other embodiments, the VLPs comprising chimeric hemagglutinin (HA) polypeptides described herein are generated using 293T cells.

In specific embodiments, VLPs, e.g., VLPs comprising a chimeric hemagglutinin (HA) polypeptide are expressed in cells (such as, e.g., mammalian cells (e.g., 293T cells) and insect cells (e.g., High Five cells and Sf9 cells). In certain embodiments, the VLPs are expressed in cells that express surface glycoproteins that comprise sialic acid. In certain embodiments, VLPs, e.g., VLPs comprising a chimeric hemagglutinin (HA) polypeptide, are expressed in cells that do not express surface glycoproteins that comprise sialic acid.

In a specific embodiment, a chimeric hemagglutinin (HA) polypeptide may be incorporated into a virosome. A virosome containing a chimeric hemagglutinin (HA) polypeptide may be produced using techniques known to those skilled in the art. For example, a virosome may be produced by disrupting a purified virus, extracting the genome, and reassembling particles with the viral proteins (e.g., a chimeric hemagglutinin (HA) polypeptide) and lipids to form lipid particles containing viral proteins.

Also provided herein are methods for producing and characterizing recombinantly produced VLPs comprising a chimeric HA described herein. Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992) 89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein. In a specific embodiment, the VLPs comprising chimeric HA polypeptides described herein are generated using baculovirus. In other embodiments, the VLPs comprising chimeric HA polypeptides described herein are generated using 293T cells.

In specific embodiments, VLPs, e.g., VLPs comprising a chimeric HA polypeptide, are expressed in cells (e.g., 293T cells). In certain embodiments, the VLPs are expressed in cells that express surface glycoproteins that comprise sialic acid. In accordance with such embodiments, the cells are cultured in the presence of neuraminidase (e.g., viral of bacterial neuraminidase). In certain embodiments, VLPs, e.g., VLPs comprising a chimeric HA polypeptide, are expressed in cells that do not express surface glycoproteins that comprise sialic acid.

In a specific embodiment, a chimeric HA polypeptide may be incorporated into a virosome. A virosome containing a chimeric HA polypeptide may be produced using techniques known to those skilled in the art. For example, a virosome may be produced by disrupting a purified virus, extracting the genome, and reassembling particles with the viral proteins (e.g., a chimeric HA polypeptide) and lipids to form lipid particles containing viral proteins.

5.6 Generation of Antibodies Against Chimeric Hemagglutinin (HA) Polypeptides The chimeric hemagglutinin (HA) polypeptides, nucleic acids encoding such polypeptides, or vectors comprising such nucleic acids or polypeptides described herein may be used to elicit antibodies (e.g., neutralizing antibodies) against influenza, for example, against the stalk region of an influenza virus hemagglutinin polypeptide (e.g., subdominant epitopes of the stalk region of the influenza virus hemagglutinin polypeptide). In specific embodiments, the chimeric HA polypeptides, nucleic acids encoding such polypeptides, or vectors comprising such nucleic acids or polypeptides described herein may be used to elicit antibodies against conserved epitopes in the globular head domain of the chimeric HA. In specific embodiments, the chimeric HA polypeptides, nucleic acids encoding such polypeptides, or vectors comprising such nucleic acids or polypeptides described herein may be used to elicit antibodies against conserved epitopes in the stalk domain of the chimeric HA. In specific embodiments, the chimeric HA polypeptides, nucleic acids encoding such polypeptides, or vectors comprising such nucleic acids or polypeptides described herein may be used to elicit antibodies against conserved epitopes in the globular head domain and the stalk domain of the chimeric HA. In a specific embodiment, the chimeric hemagglutinin (HA) polypeptide, nucleic acids encoding such polypeptides, or vectors comprising such nucleic acids or polypeptides described herein, or immunogenic compositions described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

In certain embodiments, the non-human subjects administered a chimeric HA polypeptide(s), nucleic acid(s) encoding such polypeptide(s), or vector(s) comprising such nucleic acid(s) or polypeptide(s) described herein, or an immunogenic composition(s) described herein herein are transgenic animals (e.g., transgenic mice) that are capable of producing human antibodies. Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. Companies such as Abgenix, Inc. (Freemont, Calif.), Genpharm (San Jose, Calif.), Regeneron (Tarryton, N.J.), and Medarex, Inc. (Princeton, N.J.) can be engaged to provide human antibodies directed against a selected antigen.

Alternatively, the chimeric hemagglutinin (HA) polypeptide described herein may be used to screen for antibodies from antibody libraries. For example, an isolated chimeric hemagglutinin (HA) polypeptide may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to the isolated chimeric hemagglutinin (HA) polypeptides. Any screening assay, such as a panning assay, ELISA, surface plasmon resonance, or other antibody screening assay known in the art may be used to screen for antibodies that bind to the chimeric hemagglutinin (HA) polypeptide. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies identified in the methods described herein may be tested for neutralizing activity and lack of autoreactivity using the biological assays known in the art or described herein. In one embodiment, an antibody isolated from a non-human animal or an antibody library neutralizes a hemagglutinin polypeptide from more than one influenza strain of a particular lineage or lineages. In some embodiments, an antibody elicited or identified using a chimeric hemagglutinin (HA) polypeptide, a nucleic acid encoding such a polypeptide(s), or a vector encoding such a nucleic acid or polypeptide neutralizes an influenza B virus of the Victoria lineage and/or an influenza B virus of the Yamagata lineage. In one embodiment, the neutralizing antibody neutralizes one or more influenza A viruses and one or more influenza B viruses.

Antibodies identified or elicited using a chimeric hemagglutinin (HA) polypeptide, a nucleic acid encoding such a polypeptide(s), or a vector comprising such a nucleic acid or polypeptide include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a chimeric hemagglutinin (HA) polypeptide, nucleic acids encoding such a polypeptide(s) or a vector comprising such a nucleic acid or polypeptide may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize hemagglutinin polypeptides and the specificity of the antibodies for the polypeptides may be tested prior to using the antibodies in passive immunotherapy.

Antibodies elicited or identified using a chimeric hemagglutinin (HA) polypeptide, a nucleic acid encoding such a polypeptide(s), or a vector comprising such a nucleic acid or polypeptide may be used to monitor the efficacy of a therapy and/or disease progression. Without being bound by any particular theory, the level of antibodies elicited or identified using a chimeric hemagglutinin (HA) polypeptide may be indicative of the degree of protection against influenza virus disease: for example, a low level of influenza-specific antibodies may indicate that revaccination, or booster vaccination(s), are required. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few. Further, without being bound by any particular theory, elicited or identified can be utilized in an assay to determine the anti-influenza properties of the antibody(ies), which may be indicative of the level of protected provided by vaccination with the chimeric hemagglutinin (HA) polypeptide, the nucleic acid encoding such a polypeptide(s), or the vector comprising such a nucleic acid or polypeptide. Any assay known in the art for evaluating anti-influenza properties may be used for this purpose including, but not limited to, hemagglutinin inhibition assays, influenza virus growth curves, and plaque reduction assays, to name but a few.

Antibodies elicited or identified using a chimeric hemagglutinin (HA) polypeptide, a nucleic acid encoding such a polypeptide(s), or a vector comprising such a nucleic acid or polypeptide may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann. Immunol. (Paris) 125c:373; Jerne et al., 1982, EMBO J. 1:234, incorporated herein by reference in its entirety).

5.7 Compositions

The nucleic acids, vectors, polypeptides, antibodies, or cells described herein (sometimes referred to herein as "active compounds") may be incorporated into compositions. In specific embodiments, an active compound described herein is a chimeric hemagglutinin (HA) polypeptide described herein, a nucleic acid encoding such a polypeptide(s), a vector (e.g., a viral vector) either containing, expressing, or both such a polypeptide(s), or cells described herein. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing or treating an influenza virus disease.

In one embodiment, a pharmaceutical composition comprises a chimeric hemagglutinin (HA) polypeptide, in an admixture with a pharmaceutically acceptable carrier. In another embodiment, a pharmaceutical composition (e.g., an immunogenic composition) comprises a nucleic acid encoding a chimeric hemagglutinin (HA) polypeptide described herein, in an admixture with a pharmaceutically acceptable carrier. In another embodiment, a pharmaceutical composition (e.g., an immunogenic composition) comprises an expression vector comprising a nucleic acid encoding a chimeric hemagglutinin (HA) polypeptide, in an admixture with a pharmaceutically acceptable carrier. In another embodiment, a pharmaceutical composition (e.g., an immunogenic composition) comprises an influenza virus or non-influenza virus containing a chimeric hemagglutinin (HA) polypeptide, in an admixture with a pharmaceutically acceptable carrier. In another embodiment, a pharmaceutical composition (e.g., an immunogenic composition) comprises an influenza virus or non-influenza virus having a genome engineered to express a chimeric hemagglutinin (HA) polypeptide, in admixture with a pharmaceutically acceptable carrier. In another embodiment, a pharmaceutical composition (e.g., an immunogenic composition) comprises a virus-like particle or virosome containing a chimeric hemagglutinin (HA) polypeptide, in an admixture with a pharmaceutically acceptable carrier. In certain embodiments, the composition further comprises one or more adjuvants (see, e.g., Section 5.7.5, infra, such as AS03 or MF59).

In some embodiments, a pharmaceutical composition may comprise one or more other therapies in addition to a therapy that utilizes a chimeric hemagglutinin (HA) polypeptide described herein.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. In some embodiments, the active compounds are prepared with carriers that increase the protection of the compound against rapid elimination from the body, such as a controlled release formulation, including implants and microencapsulated delivery systems. Methods for preparation of such formulations will be apparent to those skilled in the art. Liposomes or micelles can also be used as pharmaceutically acceptable carriers. These can be prepared according to methods known to those skilled in the art, for example, as described in U.S. Pat. No. 4,522,811. In certain embodiments, the pharmaceutical compositions comprise one or more adjuvants (see, e.g., Section 5.7, infra, for adjuvants, such as AS03 or MF49).

In specific embodiments, immunogenic compositions described herein are monovalent formulations. In other embodiments, immunogenic compositions described herein are multivalent formulations. In one example, a multivalent formulation comprises more than one vector expressing a chimeric hemagglutinin (HA) polypeptide. In another example, a multivalent formulation comprises more than one virus containing a chimeric hemagglutinin (HA) polypeptide. In certain embodiments, a multivalent formulation may comprise one or more different chimeric hemagglutinin (HA) polypeptides expressed using a single vector. In certain embodiments, immunogenic compositions described herein are trivalent vaccines which comprise one chimeric hemagglutinin (HA) polypeptide. In some embodiments, immunogenic compositions described herein are trivalent vaccines which comprise three different influenza viruses, each influenza virus comprising a different chimeric HA. In some embodiments, immunogenic compositions described herein are quadravalent vaccines which comprise at least two different chimeric hemagglutinin (HA) polypeptides described herein. In some embodiments, immunogenic compositions described herein are quadravalent vaccines which comprise four different influenza viruses, each influenza virus comprising a different chimeric HA. In certain embodiments, a composition described herein comprises one or more of the chimeric hemagglutinin (HA) polypeptides described in International Publication Nos. WO 2014/099931 and WO 2013/043729 and one or more of the chimeric HA polypeptides described herein. In certain embodiments, a compositions described herein may comprise a chimeric HA described herein and a recombinant HA, wherein the recombinant HA comprises the globular head domain of an HA of one subtype of an influenza A virus and the stem domain of an HA of a different subtype of an influenza A virus. For example, the recombinant HA may comprise the globular head domain of an HA of an influenza A virus of the H5 subtype and the stem domain of an HA of an influenza A virus of the H1 or H3 subtype. In another example, the recombinant HA may comprise the globular head domain of an HA of an influenza A virus of the H7 subtype and the stem domain of an influenza A virus of the H1 or H3 subtype.

In certain embodiments, the pharmaceutical compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative. In a specific embodiment, thimerosal is used during the manufacture of a pharmaceutical composition described herein and the thimerosal is removed via purification steps following production of the pharmaceutical composition, i.e., the pharmaceutical composition contains trace amounts of thimerosal (<0.3 μg of mercury per dose after purification; such pharmaceutical compositions are considered thimerosal-free products).

In certain embodiments, the pharmaceutical compositions described herein additionally comprise egg protein (e.g., ovalbumin or other egg proteins). The amount of egg protein in the pharmaceutical compositions described herein may range from about 0.0005 to about 1.2. μg of egg protein to 1 ml of pharmaceutical composition. In other embodiments, the pharmaceutical compositions described herein do not comprise egg protein.

In certain embodiments, the pharmaceutical compositions described herein additionally comprise one or more antimicrobial agents (e.g., antibiotics) including, but not limited to gentamicin, neomycin, polymyxin (e.g., polymyxin B), and kanamycin, streptomycin. In other embodiments, the pharmaceutical compositions described herein do not comprise any antibiotics.

In certain embodiments, the pharmaceutical compositions described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions described herein additionally comprise gelatin. In other embodiments, the pharmaceutical compositions described herein do not comprise gelatin.

In certain embodiments, the pharmaceutical compositions described herein additionally comprise one or more buffers, e.g., phosphate buffer and sucrose phosphate glutamate buffer. In other embodiments, the pharmaceutical compositions described herein do not comprise buffers.

In certain embodiments, the pharmaceutical compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the pharmaceutical compositions described herein do not comprise salts.

In specific embodiments, the pharmaceutical compositions described herein are low-additive influenza virus vaccines, i.e., the pharmaceutical compositions do not comprise one or more additives commonly found in influenza virus vaccines. Low-additive influenza vaccines have been described (see, e.g., International Application No. PCT/IB2008/002238 published as International Publication No. WO 09/001217, which is herein incorporated by reference in its entirety).

The pharmaceutical compositions described herein can be included in a container, pack, or dispenser together with instructions for administration.

The pharmaceutical compositions described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110776, which is herein incorporated by reference in its entirety, for methods of storing compositions comprising influenza vaccines without refrigeration).

In certain embodiments, when the active compound in a pharmaceutical composition described herein is a cell engineered to express a chimeric hemagglutinin (HA) polypeptide, the cell is not a mammalian cell (e.g., the cell is a CB-1 cell).

5.7.1 Subunit Vaccines

In a specific embodiment, provided herein are subunit vaccines comprising a chimeric hemagglutinin (HA) polypeptide described herein. In some embodiments, a subunit vaccine comprises a chimeric hemagglutinin (HA) polypeptide, and one or more surface glycoproteins (e.g., influenza virus neuraminidase), other targeting moieties, or adjuvants. In a specific embodiment, the adjuvant is a type of, or a specific, adjuvant described in Section 5.7.5, infra. In specific embodiments, a subunit vaccine comprises a single chimeric hemagglutinin (HA) polypeptide. In other embodiments, a subunit vaccine comprises two, three, four or more chimeric hemagglutinin (HA) polypeptides. In specific embodiments, the chimeric hemagglutinin (HA) polypeptide(s) used in a subunit vaccine are not membrane-bound, i.e., are soluble. In specific embodiments, the polypeptide components of the subunit vaccine are generated in a baculovirus expression system. In a particular embodiment, a subunit vaccine comprises a purified chimeric HA polypeptide described herein which is produced in a continuous insect cell line, such as one derived from the fall armyworm *Spodoptera frugiperda* using a baculovirus vector (e.g., *Autographa californica* nuclear polyhedrosis virus). The chimeric HA polypeptide may be extracted from the cells and further purified by column chromatography. In some embodiments, a subunit vaccine comprises more than one chimeric HA polypeptide described herein.

In a specific embodiment, the subunit vaccine is prepared using influenza virus that was propagated in embryonated chicken eggs (i.e., the components of the subunit vaccine (e.g., a chimeric HA polypeptide) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a chimeric polypeptide) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) (i.e., the components of the subunit vaccine (e.g., a chimeric HA polypeptide) are isolated from virus that was propagated in mammalian cells). In another specific embodiment, the chimeric HA polypeptide(s) in a subunit vaccine are prepared using an expression vector, e.g., a viral vector, plant vector, baculovirus vector, or a bacterial vector (i.e., the chimeric HA polypeptide(s) in the subunit vaccine are obtained/isolated from an expression vector).

5.7.2 Live Virus Vaccines

In one embodiment, provided herein are immunogenic compositions (e.g., vaccines) comprising live influenza virus containing a chimeric hemagglutinin (HA) polypeptide. In another embodiment, provided herein are immunogenic compositions (e.g., vaccines) comprising live influenza virus that is engineered to encode a chimeric hemagglutinin (HA) polypeptide, which is expressed by progeny virus produced in the subjects administered the compositions. In specific embodiments, the chimeric hemagglutinin (HA) polypeptide is membrane-bound. In other specific embodiments, the chimeric hemagglutinin (HA) polypeptide is not membrane-bound, i.e., it is soluble. In some embodiments, the live influenza virus is attenuated. In some embodiments, an immunogenic composition comprises two, three, four or more live influenza viruses containing or engineered to express two, three, four or more different chimeric hemagglutinin (HA) polypeptides.

An immunogenic composition comprising a live influenza virus for administration to a subject may be preferred because multiplication of the virus in the subject may lead to a prolonged stimulus of similar kind and magnitude to that occurring in natural infections, and therefore, confer substantial, long lasting immunity.

In a specific embodiment, the live virus that contains a chimeric HA polypeptide is propagated in embryonated chicken eggs before its use in an immunogenic composition described herein. In another specific embodiment, the live virus that contains a chimeric HA polypeptide is not propagated in embryonated chicken eggs before its use in an immunogenic composition described herein. In another specific embodiment, the live virus that contains a chimeric HA polypeptide is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

5.7.3 Inactivated Virus Vaccines

In one embodiment, provided herein are immunogenic compositions (e.g., vaccines) comprising an inactivated influenza virus containing a chimeric hemagglutinin (HA) polypeptide. In specific embodiments, the chimeric hemagglutinin (HA) polypeptide is membrane-bound. In some embodiments, an immunogenic composition comprises two, three, four or more inactivated influenza viruses containing two, three, four or more different chimeric hemagglutinin (HA) polypeptides. In certain embodiments, the inactivated influenza virus immunogenic compositions comprise one or more adjuvants. In a specific embodiment, the adjuvant is a type of, or a specific, adjuvant described in Section 5.7.5, infra.

Techniques known to one of skill in the art may be used to inactivate viruses containing a chimeric hemagglutinin (HA) polypeptide. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

5.7.4 Split Virus Vaccines

In one embodiment, an immunogenic composition comprising a chimeric hemagglutinin (HA) polypeptide is a split virus vaccine. In some embodiments, split virus vaccine contains two, three, four or more different chimeric hemagglutinin (HA) polypeptides. In certain embodiments, the chimeric hemagglutinin (HA) polypeptide is/was membrane-bound. In certain embodiments, the split virus vaccines comprise one or more adjuvants.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100—A registered trademark of Union Carbide, Co.) producing a "split virus." The split virus is then further purified by chemical means and suspended in sodium phosphate-buffered isotonic sodium chloride solution.

5.7.5 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a chimeric hemagglutinin (HA) polypeptide, but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to the chimeric hemagglutinin (HA) polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In specific embodiments, the adjuvant is AS03 (GlaxoSmithKline). In specific embodiments, the adjuvant is MF59 (Novartis). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine. It should be understood that different formulations of chimeric HA polypeptides may comprise different adjuvants or may comprise the same adjuvant.

5.8 Prophylactic and Therapeutic Uses

In one aspect, provided herein are methods for inducing an immune response in a subject utilizing an active compound (e.g., a chimeric hemagglutinin (HA) polypeptide described herein, a nucleic acid encoding such a polypeptide(s), a vector (e.g., a viral vector) either containing, expressing, or both, such a polypeptide(s), cells described herein) or a composition described herein. In a specific embodiment, a method for inducing an immune response to an influenza virus hemagglutinin polypeptide in a subject comprises administering to a subject in need thereof an effective amount of a chimeric hemagglutinin (HA) polypeptide described herein or an immunogenic composition thereof. In another embodiment, a method for inducing an immune response to an influenza virus hemagglutinin polypeptide in a subject comprises administering to a subject in need thereof an effective amount of a nucleic acid encoding a chimeric hemagglutinin (HA) polypeptide described herein or an immunogenic composition thereof. In another embodiment, a method for inducing an immune response to an influenza virus hemagglutinin polypeptide in a subject comprises administering to a subject in need thereof an effective amount of a viral vector either containing, expressing, or both a chimeric hemagglutinin (HA) polypeptide described herein or an immunogenic composition thereof. In certain embodiments, a chimeric hemagglutinin (HA) polypeptide described herein used in the method is a purified chimeric hemagglutinin (HA) polypeptide described herein derived from a mammalian cell, a plant cell, or an insect cell.

In a specific embodiment, a method for inducing an immune response to an influenza virus hemagglutinin polypeptide in a subject comprises administering to a subject in need thereof a subunit vaccine described herein. In another embodiment, a method for inducing an immune response to an influenza virus hemagglutinin polypeptide in a subject comprises administering to a subject in need thereof a live influenza virus vaccine described herein. In particular embodiments, the live influenza virus vaccine comprises an attenuated influenza virus. In another embodiment, a method for inducing an immune response to an influenza virus hemagglutinin polypeptide in a subject comprises administering to a subject in need thereof an inactivated influenza virus vaccine described herein. In another embodiment, a method for inducing an immune response to an influenza virus hemagglutinin polypeptide in a subject comprises administering to a subject in need thereof a split virus vaccine described herein. In another embodiment, a method for inducing an immune response to an influenza virus hemagglutinin polypeptide in a subject comprises administering to a subject in need thereof a virus-like particle vaccine described herein. In another embodiment, a method for inducing an immune response to an influenza hemagglutinin polypeptide comprises administering to a subject in need thereof a virosome described herein. In certain embodiments, a chimeric hemagglutinin (HA) polypeptide described herein used in the method is a purified chimeric hemagglutinin (HA) polypeptide described herein derived from a mammalian cell, a plant cell, or an insect cell.

In a specific embodiment, a method for inducing an immune response to an influenza virus hemagglutinin polypeptide in a subject comprises: (a) administering to a subject in need thereof a first immunogenic composition comprising a chimeric HA described herein; and (b) a certain period of time after the administration of the first immunogenic composition, administering to the subject a second immunogenic composition comprising a second chimeric HA described herein. In specific embodiments, the first and second chimeric HA polypeptides comprise an ectodomain with the same stem domains but have one, two, three or all of the following: different 120 loops, different 150 loops, different 160 loops, and different 190 helices. In specific embodiments, the method further comprises administering to the subject a third immunogenic composition comprising a third chimeric HA described herein. In specific embodiments, the first, second, and third chimeric HA polypeptides comprise an ectodomain with the same stem domains but have one, two, three or all of the following: different 120 loops, different 150 loops, different 160 loops, and different 190 helices. In specific embodiments, the second immunogenic composition is administered about 6 weeks, about 12 weeks, about 4 months, about 6 months, or about 9 months after the administration of the first immunogenic composition. In another specific embodiment, the second immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the first immunogenic composition. In specific embodiments, the third immunogenic composition is administered about 6 weeks, about 12 weeks, about 4 months, about 6 months, or about 9 months after the administration of the second immunogenic composition. In another specific embodiment, the third immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the second immunogenic composition.

In another embodiment, provided herein is a method of immunizing a subject against an influenza virus disease or infection (e.g., an influenza B virus disease or infection) comprising (i) a first administration of a first chimeric HA polypeptide to the subject, a first nucleic acid encoding such a polypeptide(s), a first vector either containing, expressing, or both such a polypeptide(s), or cells described herein; and (ii) a second administration of a second chimeric HA polypeptide, a second nucleic acid encoding such a polypeptide(s), a second vector either containing, expressing, or both such a polypeptide(s), or cells described herein to the subject, wherein the first and second chimeric HA polypeptides comprise an ectodomain with the same stem domains but have one, two, three or all of the following: (i) different 120 loops, (ii) different 150 loops, (iii) different 160 loops, and (iv) different 190 helices. The first and second administrations may be separated by at least 1 day, 2 days, 3 days, 5 days, 10 days, 15 days, 30 days, 45 days, 2 months, 75 days, 3 months, or at least 6 months. In certain embodiments, the first and second administrations may be separated by 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In certain embodiments, booster inoculations may be administered to the subject at 6 to 12 month intervals following the second inoculation. In certain embodiments, the booster inoculation may be administered to the subject at 1 week to 9 month, 3 week to 8 month, 6 week to 12 week, 4 week to 6 month, 5 week to 5 month, 6 week to 4 month, 7 week to 4 month, 8 week to 4 month, 8 week to 3 month, 3 month to 6 month, 3 month to 9 month, or 6 month to 9 month intervals following the second inoculation. In certain embodiments, the booster inoculation comprises a third chimeric HA polypeptide, a third nucleic acid encoding such a polypeptide(s), a third vector either containing, expressing, or both such a polypeptide(s), or cells described herein, wherein the first, second, and third chimeric HA polypeptides comprise an ectodomain with the same stem domains but have either one, two, three, or all of the following: (i) different 120 loops, (ii) different 150 loops, (iii) different 160 loops, and (iv) different 190 helices.

In another embodiment, provided herein is a method of immunizing a subject against an influenza virus disease or infection (e.g., an influenza B virus infection or disease) comprising (i) a first administration of a first immunogenic composition to the subject, wherein the first immunogenic composition comprises a live attenuated influenza virus either containing, expressing, or both, a first chimeric HA polypeptide described herein; and (ii) a second administration of a second immunogenic composition to the subject, wherein the second immunogenic composition is an inactivated influenza virus vaccine comprising a second chimeric HA polypeptide described herein and an adjuvant (see, e.g., Section 5.75 for adjuvants), wherein the first and second chimeric HA polypeptides comprise an ectodomain with the same stem domains but have one, two, three or all of the following: (i) different 120 loops, (ii) different 150 loops, (iii) different 160 loops, and (iv) different 190 helices. The first and second administrations may be separated by at least 1 day, 2 days, 3 days, 5 days, 10 days, 15 days, 30 days, 45 days, 2 months, 75 days, 3 months, or at least 6 months. In certain embodiments, the first and second administrations may be separated by 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In certain embodiments, booster inoculations may be administered to the subject at 6 to 12 month intervals following the second inoculation. In certain embodiments, the booster inoculation may be administered to the subject at 1 week to 9 month, 3 week to 8 month, 6 week to 12 week, 4 week to 6 month, 5 week to 5 month, 6 week to 4 month, 7 week to 4 month, 8 week to 4 month, 8 week to 3 month, 3 month to 6 month, 3 month to 9 month, or 6 month to 9 month intervals following the second inoculation. In certain embodiments, the booster inoculation comprises a third chimeric HA polypeptide, a third nucleic acid encoding such a polypeptide(s), a third vector either containing, expressing, or both such a polypeptide(s), or cells described herein, wherein the first, second, and third chimeric HA polypeptides comprise an ectodomain with the same stem domains but have either one, two, three, or all of the following: (i) different 120 loops, (ii) different 150 loops, (iii) different 160 loops, and (iv) different 190 helices.

In another embodiment, provided herein is a method of immunizing a subject against an influenza virus disease or infection (e.g., an influenza B virus disease or infection)

comprising (i) a first administration of a first immunogenic composition to the subject, wherein the first immunogenic composition comprises a live attenuated influenza virus either containing, expressing, or both, a first chimeric HA polypeptide described herein; and (ii) a second administration of a second immunogenic composition to the subject, wherein the second immunogenic composition is a subunit influenza virus vaccine comprising a second chimeric HA polypeptide described herein and an adjuvant (see, e.g., Section 5.75 for adjuvants, such as AS03 or MF59), wherein the first and second chimeric HA polypeptides comprise an ectodomain with the same stem domains but have one, two, three or all of the following: (i) different 120 loops, (ii) different 150 loops, (iii) different 160 loops, and (iv) different 190 helices. The first and second administrations may be separated by at least 1 day, 2 days, 3 days, 5 days, 10 days, 15 days, 30 days, 45 days, 2 months, 75 days, 3 months, or at least 6 months. In certain embodiments, the first and second administrations may be separated by 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In certain embodiments, booster inoculations may be administered to the subject at 6 to 12 month intervals following the second inoculation. In certain embodiments, the booster inoculation may be administered to the subject at 1 week to 9 month, 3 week to 8 month, 6 week to 12 week, 4 week to 6 month, 5 week to 5 month, 6 week to 4 month, 7 week to 4 month, 8 week to 4 month, 8 week to 3 month, 3 month to 6 month, 3 month to 9 month, or 6 month to 9 month intervals following the second inoculation. In certain embodiments, the booster inoculation comprises a third chimeric HA polypeptide, a third nucleic acid encoding such a polypeptide(s), a third vector either containing, expressing, or both such a polypeptide(s), or cells described herein, wherein the first, second, and third chimeric HA polypeptides comprise an ectodomain with the same stem domains but have either one, two, three, or all of the following: (i) different 120 loops, (ii) different 150 loops, (iii) different 160 loops, and (iv) different 190 helices.

In another embodiment, provided herein is a method of immunizing a subject against an influenza virus disease or infection (e.g., influenza B virus disease or infection) comprising (i) a first administration of a first immunogenic composition to the subject, wherein the first immunogenic composition comprises a live attenuated influenza virus either containing, expressing, or both, a first chimeric HA polypeptide described herein; and (ii) a second administration of a second immunogenic composition to the subject, wherein the second immunogenic composition is a split influenza virus vaccine comprising a second chimeric HA polypeptide described herein and an adjuvant (see, e.g., Section 5.75 for adjuvants, such as ASO3 or MF59), wherein the first and second chimeric HA polypeptides comprise an ectodomain with the same stem domains but have one, two, three or all of the following: (i) different 120 loops, (ii) different 150 loops, (iii) different 160 loops, and (iv) different 190 helices. The first and second administrations may be separated by at least 1 day, 2 days, 3 days, 5 days, 10 days, 15 days, 30 days, 45 days, 2 months, 75 days, 3 months, or at least 6 months. In certain embodiments, the first and second administrations may be separated by 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In certain embodiments, booster inoculations may be administered to the subject at 6 to 12 month intervals following the second inoculation. In certain embodiments, the booster inoculation may be administered to the subject at 1 week to 9 month, 3 week to 8 month, 6 week to 12 week, 4 week to 6 month, 5 week to 5 month, 6 week to 4 month, 7 week to 4 month, 8 week to 4 month, 8 week to 3 month, 3 month to 6 month, 3 month to 9 month, or 6 month to 9 month intervals following the second inoculation. In certain embodiments, the booster inoculation comprises a third chimeric HA polypeptide, a third nucleic acid encoding such a polypeptide(s), a third vector either containing, expressing, or both such a polypeptide(s), or cells described herein, wherein the first, second, and third chimeric HA polypeptides comprise an ectodomain with the same stem domains but have either one, two, three, or all of the following: (i) different 120 loops, (ii) different 150 loops, (iii) different 160 loops, and (iv) different 190 helices.

In a specific embodiment, provided herein is a method for immunizing a subject against an influenza virus disease or infection (e.g., influenza B virus disease or infection), the method comprising: (a) a first administration of a nucleic acid encoding a first chimeric HA polypeptide, wherein the first chimeric HA polypeptide comprises a first ectodomain of a first influenza B virus comprising: (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a first subtype; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the first subtype; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the first subtype; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the first subtype; and (b) a second administration of a second chimeric HA polypeptide to the subject a first period of time after the first administration, wherein the second chimeric HA polypeptide comprises a second ectodomain of a second influenza B virus comprising: (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a second subtype; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the second subtype; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the second subtype; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the second subtype; and (c) a booster inoculation comprising a third chimeric HA polypeptide to the subject a second period of time after the second administration, wherein the third chimeric HA polypeptide comprises a third ectodomain of a third influenza B virus comprising (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a third subtype; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the third subtype; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the third subtype; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the third subtype. In a specific embodiment, the first, second, and third ectodomains comprise the same stem domain. In a particulat embodiment, the stem domain is the stem domain of influenza B/Yamagata/16/88. In specific embodiment, the first, second, and third subtypes are different from each other. In a specific embodiment, the first subtype is the H13 subtype, the second subtype is the H5 subtype, and the third subtype is the H8 subtype. In some embodiments, the first, second, and third subtypes are different and the subtypes are selected from H5, H8, H11, H12, and H13. In a specific embodiment, the first chimeric HA polypeptide comprises the 120 loop, the 150 loop, the 160 loop, and the 190 helix of the chimeric HA of FIG. 36. In a specific embodiment, the second chimeric HA polypeptide comprises the 120 loop, the 150 loop, the 160 loop, and the 190 helix of the chimeric HA of FIG. 30. In a specific embodiment, the third chimeric HA polypeptide comprises the 120 loop, the 150 loop, the 160 loop, and the 190 helix of the chimeric HA of FIG. 32. In specific embodiments, the first period of time after the first administration is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In specific embodiments, the second period of time after the second administration is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months.

In a specific embodiment, a method for immunizing a subject against an influenza virus disease or infection (e.g., influenza B virus disease or infection), the method comprising: (a) a first administration of a first immunogenic composition comprising a first chimeric HA polypeptide, wherein the first chimeric HA polypeptide comprises a first ectodomain of a a first influenza B virus comprising: (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of the H13 subtype; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the first subtype; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the first subtype; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the first subtype; and (b) a second administration of a second immunogenic composition comprising a second chimeric HA polypeptide to the subject a first period of time after the first administration, wherein the second chimeric HA polypeptide comprises a second ectodomain of a second influenza B virus comprising: (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a second subtype; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the second subtype; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the second subtype; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the second subtype; and (c) an third immunogenic composition comprising a third chimeric HA polypeptide to the subject a second period of time after the second administration, wherein the third chimeric HA polypeptide comprises a third ectodomain of a third influenza B virus comprising (i) 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a third subtype; (ii) 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the third subtype; (iii) 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the third subtype; and (iv) 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the third subtype. In a specific embodiment, the first, second, and third ectodomains comprise the same stem domain. In a particulate embodiment, the stem domain is the stem domain of influenza B/Yamagata/16/88. In specific embodiment, the first, second, and third subtypes are different from each other. In a specific embodiment, the first subtype is the H13 subtype, the second subtype is the H5 subtype, and the third subtype is the H8 subtype. In some embodiments, the first, second, and third subtypes are different and the subtypes are selected from H5, H8, H11, H12, and H13. In a specific embodiment, the first chimeric HA polypeptide comprises the 120 loop, the 150 loop, the 160 loop, and the 190 helix of the chimeric HA of FIG. 36. In a specific embodiment, the second chimeric HA polypeptide comprises the 120 loop, the 150 loop, the 160 loop, and the 190 helix of the chimeric HA of FIG. 30. In a specific embodiment, the third chimeric HA polypeptide comprises the 120 loop, the 150 loop, the 160 loop, and the 190 helix of the chimeric HA of FIG. 32. In specific embodiments, either first, second or third chimeric HA polypeptides, or two or three of the first, second and third chimeric HA polypeptides may be administered to the subject as protein, in an influenza virus or other vector, or as a nucleic acid sequence. In specific embodiments, the first period of time after the first administration is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months. In specific embodiments, the second period of time after the second administration is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months.

In some embodiments, the immune response induced by an active compound or a composition described herein is effective to prevent and/or treat an influenza virus infection caused by one or both lineages of influenza B virus. In certain embodiments, the immune response induced by an active compound or a composition described herein is effective to prevent and/or treat an influenza virus infection caused by one or more strains within the same lineage of influenza B virus. In a specific embodiment, the immune response induced by an active compound or a composition described herein induces antibodies to the stem domain of an influenza B virus HA. In a specific embodiment, the immune response induced by an active compound or a composition described herein induces antibodies to subdominant epitopes in the globular head domain and the stem domain of an influenza B virus HA.

In some embodiments, the immune response induced by an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or a composition described herein is effective to reduce symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or a composition described herein is effective to reduce the hospitalization of a subject suffering from an influenza virus disease/infection. In some embodiments, the immune response induced by an active compound or a composition described herein is effective to reduce the duration of hospitalization of a subject suffering from an influenza virus disease/infection.

In another aspect, provided herein are methods for preventing and/or treating an influenza virus infection in a subject utilizing an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or a composition described herein. In one embodiment, a method for preventing or treating an influenza virus infection in a subject comprises administering to a subject in need thereof a chimeric hemagglutinin (HA) polypeptide, a nucleic acid encoding such a polypeptide(s), a vector either containing, expressing, or both such a polypeptide(s), or a composition of any one of the foregoing. In a specific embodiment, a method for preventing or treating an influenza virus infection in a subject comprises administering to a subject in need thereof a subunit vaccine, a live influenza virus vaccine, an inactivated influenza virus vaccine, a split virus vaccine, a virus-like particle vaccine, or virosome.

In another aspect, provided herein are methods for preventing and/or treating an influenza virus disease in a subject utilizing a chimeric hemagglutinin (HA) polypeptide described herein, a nucleic acid encoding such a polypeptide(s), a vector either containing, expressing, or both such a polypeptide(s), or cells described herein. In a specific embodiment, a method for preventing or treating an influenza virus disease in a subject comprises administering to a subject in need thereof an effective amount of a chimeric hemagglutinin (HA) polypeptide or an immunogenic composition thereof. In another embodiment, a method for preventing or treating an influenza virus disease in a subject comprises administering to a subject in need thereof an effective amount of a nucleic acid encoding a chimeric hemagglutinin (HA) polypeptide or an immunogenic composition thereof. In another embodiment, a method for preventing or treating an influenza virus disease in a subject comprises administering to a subject in need thereof an effective amount of a viral vector either containing, expressing, or both a chimeric hemagglutinin (HA) polypeptide or an immunogenic composition thereof.

In a specific embodiment, a method for preventing or treating an influenza virus disease in a subject comprises administering to a subject in need thereof a subunit vaccine described herein. In another embodiment, a method for preventing or treating an influenza virus disease in a subject comprises administering to a subject in need thereof a live influenza virus vaccine described herein. In particular embodiments, the live influenza virus vaccine comprises an attenuated virus. In another embodiment, a method for preventing or treating an influenza virus disease in a subject comprises administering to a subject in need thereof an inactivated influenza virus vaccine described herein. In another embodiment, a method for preventing or treating an influenza virus disease in a subject comprises administering to a subject in need thereof a split virus vaccine described herein. In another embodiment, a method for preventing or treating an influenza virus disease comprises administering to a subject in need thereof a virus-like particle vaccine described herein. In another embodiment, a method for preventing or treating an influenza virus disease in a subject, comprising administering to a subject in need thereof a virosome described herein.

In another aspect, provided herein are methods of preventing and/or treating an influenza virus disease in a subject by administering antibodies (e.g., neutralizing antibodies) described herein. In a specific embodiment, a method for preventing or treating an influenza virus disease in a subject comprises administering to a subject in need thereof an effective amount of an antibody described herein, or a pharmaceutical composition thereof. In particular embodiments, the antibody is a monoclonal antibody. In particular embodiments, the antibody is a human antibody. In particular embodiments, the antibody is a humanized antibody.

In certain embodiments, the methods for preventing or treating an influenza virus disease or infection in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

5.8.1 Combination Therapies

In various embodiments, a chimeric hemagglutinin (HA) polypeptide described herein, a nucleic acid encoding such a polypeptide(s), a vector (e.g., a viral vector) either containing, expressing, or both such a polypeptide(s), cells described herein, or a neutralizing antibody may be administered to a subject in combination with one or more other therapies (e.g., an antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the treatment or prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

5.8.2 Patient Populations

In certain embodiments, an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In one embodiment, an active compound or composition described herein is administered to a subject that does not have a disease caused by the specific influenza virus, or has not been and is not infected with the specific influenza virus to which the chimeric hemagglutinin (HA) polypeptide. An active compound or composition described herein may also be administered to a subject that is and/or has been infected with the influenza virus or another lineage, type, subtype or strain of the influenza virus to which the chimeric hemagglutinin (HA) polypeptide induces an immune response.

In certain embodiments, an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization). In some embodiments, an active compound or composition described herein is administered to a patient that is infected with or has been diagnosed with a different lineage or strain of influenza B virus than that of the influenza B virus from which the chimeric hemagglutinin (HA) polypeptide of the active compound or composition was derived.

In some embodiments, a subject to be administered an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In specific embodiments, a subject administered an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein is a human infant. As used herein, the term "human infant" refers to a newborn to 1 year old human. In specific embodiments, a subject administered an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein is a human child. As used herein, the term "human child" refers to a human that is 1 year to 18 years old. In specific embodiments, a subject administered an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein is a a human adult. As used herein, the term "human adult" refers to a human that is 18 years or older. In specific embodiments, a subject administered an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition described herein is an elderly human. As used herein, the term "elderly human" refers to a human 65 years or older.

In certain embodiments, an immunogenic formulation comprising a live influenza virus vector is not given concurrently with other live-virus vaccines.

5.9 Modes of Administration 5.9.1 Routes of Delivery

An active compound (e.g., a chimeric hemagglutinin (HA) polypeptide described herein (e.g., a nucleic acid encoding such a polypeptide(s), a vector (e.g., a viral vector) either containing, expressing, or both such a polypeptide(s), cells described herein) or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In cases where the antigen is a viral vector or a virus-like particle vector, for example, it may be preferable to introduce an immunogenic composition via the natural route of infection of the backbone virus from which the vector was derived. Alternatively, it may be preferable to introduce a chimeric hemagglutinin (HA) polypeptide via the natural route of infection of the influenza virus from which polypeptide is derived. The ability of an antigen, particularly a viral vector, to induce a vigorous secretory and cellular immune response can be used advantageously. For example, infection of the respiratory tract by a viral vector may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In a specific embodiment, a subunit vaccine is administered intramuscularly. In another embodiment, a live influenza virus vaccine is administered intranasally. In another embodiment, an inactivated influenza virus vaccine, or a split influenza virus vaccine is administered intramuscularly. In another embodiment, a virus-like particle or composition thereof is administered intramuscularly.

5.9.2 Dosage and Frequency of Administration

The amount of an active compound (e.g., a chimeric hemagglutinin (HA) polypeptide described herein, a nucleic acid encoding such a polypeptide(s), a vector (e.g., a viral vector) either containing, expressing, or both such a polypeptide(s), cells described herein) or composition which will be effective in the treatment and/or prevention of an influenza virus infection or an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, the dose of a viral vector (e.g., an influenza virus) described herein may be $10^4$ plaque forming units (PFU) to $10^8$ PFU. In certain embodiments, the dose of a chimeric hemagglutinin (HA) polypeptide described herein (e.g., as provided in split virus vaccines and subunit vaccines) may range from about 1 µg to 150 µg. In certain embodiments, the dose for VLPs may range from about 1 µg to about 150 µg of a chimeric HA polypeptide. In some embodiments, an inactivated vaccine is formulated such that it may contain about 1 µg to about 150 µg of a chimeric hemagglutinin (HA) polypeptide described herein.

In certain embodiments, an in vitro assay is employed to help identify optimal dosage ranges. Effective doses may be extrapolated from dose response curves derived from in vitro or animal model test systems.

5.10 Assessment of Antibodies in a Subject

In another aspect, chimeric HA described herein, or virus containing, or expressing, or both a chimeric HA described herein, can be used to assess the antibody response of a subject (e.g., a naive subject or an immunized/vaccinated subject) or a population of subjects to an influenza virus hemagglutinin polypeptide (e.g., a chimeric HA). In specific embodiments, a chimeric HA or a virus containing, expressing, or both a chimeric HA can be used to assess the presence of stem-specific antibodies in the subject or population of subjects.

In a specific embodiment, the antibody response of a subject or a population of subjects that has been an immunized/vaccinated with a chimeric HA described herein, or a virus containing, or expressing, or both a chimeric HA described herein, is assessed to identify the types of stalk-specific antibodies in the subject or population of subjects. Such an assessment may allow for the identification surrogate markers/endpoints important in determining the clinical response to administration of chimeric HA described herein, or a virus containing, expressing, or both a chimeric HA described herein. In such an approach, a biological sample, e.g., blood, from the subject or population of subjects may be isolated and tested directly for the presence of antibodies, or may be processed (e.g., to obtain sera) and subsequently tested for the presence of antibodies.

In another specific embodiment, the antibody profile of a naive subject (i.e., a subject that has not been immunized/vaccinated with a chimeric HA described herein, or a virus containing or expressing or both a chimeric HA) or a population of naive subjects is assessed to determine whether said subject or population of subjects possesses globular head-specific and/or stem specific antibodies against various influenza virus strains or subtypes. Such an assessment may allow for the generation of a chimeric HA, or viruses containing, expressing, or both chimeric HA, that are suitable for administration to said subject or population of subjects, e.g., chimeric HAs, comprising a head domain to which said subject or population of subjects is naive (does not have antibodies against). Such an assessment may determine an immunization strategy for the patient.

In another specific embodiment, provided herein is a method of assessing/detecting the presence of antibodies in a subject that are specific for a stem domain of a particular influenza virus strain or lineage comprising contacting in vitro a biological sample (e.g., blood, sera) from said subject with a chimeric HA described herein, wherein said chimeric HA comprises a stem domain from the strain or lineage of interest. In another specific embodiment, provided herein is a method of assessing/detecting the presence of antibodies in a subject that are specific for a stem domain of a particular influenza virus strain or lineage comprising contacting in vitro a biological sample (e.g., blood, sera) from said subject with a virus expressing/containing a chimeric HA described herein, wherein said chimeric HA comprises a stem domain from the strain or lineage of interest.

5.11 Biological Assays

Also provided herein are biological assays that may be used to characterize chimeric HA, nucleic acid encoding such chimeric HA, and viruses containing, expressing, or both such chimeric HA. See, also, Section 6, infra.

5.11.1 Assays for Testing Activity of Chimeric Influenza Virus Hemagglutinin Polypeptides Assays for testing the expression of a chimeric hemagglutinin (HA) polypeptide in a vector disclosed herein may be conducted using any assay known in the art. For example, an assay for incorporation into a viral vector comprises growing the virus as described in this section or Sections 5.4 or 5.5, purifying the viral particles by centrifugation through a sucrose cushion, and subsequent analysis for chimeric hemagglutinin (HA) polypeptide expression by an immunoassay, such as Western blotting, using methods well known in the art. Methods for determining whether a hemagglutinin polypeptide is chimeric are known to those of skill in the art (see, e.g., the Examples 3 and 4 of International Publication No. WO 2013/043729, which is incorporated herein by reference in its entirety).

In one embodiment, a chimeric hemagglutinin (HA) polypeptide disclosed herein is assayed for proper folding and functionality by testing its ability to bind specifically to a neutralizing antibody directed to an influenza virus hemagglutinin polypeptide, such as the stalk region of the chimeric hemagglutinin (HA) polypeptide, respectively, using any assay for antibody-antigen interaction known in the art. Neutralizing antibodies for use in such assays include, for example, the neutralizing antibodies described in Ekiert et al., 2009, Science Express, 26 Feb. 2009; Kashyap et al., 2008, *Proc Natl Acad Sci USA* 105: 5986-5991; Sui et al. 2009, *Nature Structural and Molecular Biology*, 16:265-273; Wang et al., 2010, *PLOS Pathogens* 6(2):1-9; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. These antibodies include CR6261, CR6325, CR6329, CR6307, CR6323, 2A, D7, D8, F10, G17, H40, A66, D80, E88, E90, H98, C179 (FERM BP-4517), AI3C (FERM BP-4516), among others.

In another embodiment, a chimeric hemagglutinin (HA) polypeptide disclosed herein is assayed for proper folding by determination of the structure or conformation of the chimeric hemagglutinin (HA) polypeptide using any method known in the art such as, e.g., NMR, X-ray crystallographic methods, or secondary structure prediction methods, e.g., circular dichroism.

In another embodiment, a chimeric HA disclosed herein is assayed for retention of one, two, or more, or all of the functions of a wild-type influenza HA. Nonlimiting examples of functions of a wild-type influenza HA include fusogenic activity, receptor binding activity, budding, and particle formation. In a specific embodiment, a chimeric HA disclosed herein is assayed for fusogenic activity. Assays known to one skilled in the art can be utilized the assess the fusogenic activity of a chimeric influenza hemagglutinin (HA) polypeptide described herein, such as, for example, immunofluorescence assays and pseudotyped virus-like-particle assays. In certain embodiments, the activity of a chimeric HA polypeptide described herein is assessed in one or more of the following assays: hemagglutination assay(s), fusion assay(s) or budding assay(s).

5.11.2 Assays for Testing Activity of Antibodies Generated Using Chimeric Influenza Virus Hemagglutinin Polypeptides Antibodies described herein may be characterized in a variety of ways known to one of skill in the art (e.g. ELISA, Surface Plasmon resonance display (BIAcore), Western blot, immunofluorescence, immunostaining and/or microneutralization assays). Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to a chimeric hemagglutinin (HA) polypeptide or a domain thereof and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to a chimeric hemagglutinin (HA) polypeptide or a domain thereof and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody for a chimeric hemagglutinin (HA) polypeptide and the binding off-rates can be determined from the data by Scatchard plot analysis. Competition with a second antibody can also be determined using radioimmunoassays. In this case, a chimeric hemagglutinin (HA) polypeptide is incubated with the test antibody conjugated to a labeled compound (e.g., $^{3}H$ or $^{125}I$) in the presence of increasing amounts of an unlabeled second antibody.

In a specific embodiment, the binding affinity of an antibody to a chimeric HA polypeptide or a domain thereof is determined using an assay described in Nachbagauer et al., mBio. 2016 January-February; 7(1): e01996-15.

In certain embodiments, antibody binding affinity and rate constants are measured using the KinExA 3000 System (Sapidyne Instruments, Boise, Id.). In some embodiments, surface plasmon resonance (e.g., BIAcore kinetic) analysis is used to determine the binding on and off rates of the antibodies to an influenza virus hemagglutinin polypeptide. In specific embodiments, an assay described in Tan et al., PLoS Pathog. 2016 April; 12(4): e1005578 is used to determine the binding on and off rates of antibodies to a chimeric HA polypeptide.

The neutralizing activity of an antibody can be determined utilizing any assay known to one skilled in the art. Antibodies described herein can be assayed for their ability to inhibit the binding of an influenza virus, or any other composition comprising a chimeric hemagglutinin (HA) polypeptide to its host cell receptor (i.e., sialic acid) using techniques known to those of skill in the art. In a specific embodiment, an assay described in one of the following articles is used to determine the neutralizinag activity of an antibody Tan et al., PLoS Pathog. 2016 April; 12(4): e1005578; Pica et al., Proc Natl Acad Sci USA. 2012 February 14; 109(7): 2573-2578; and Nachbagauer et al., mBio. 2016 January-February; 7(1): e01996-15.

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody). In a specific embodiment, a reporter assay described in Heaton et al., J Virol. 2013 August; 87(15):8272-81 is used.

5.11.3 Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, MDCK cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of antibodies (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

5.11.4 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Active compounds or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an active compound can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An active compound that exhibits large therapeutic indices is preferred. While an active compound that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an active compound for use in humans. The dosage of such agents lies preferably within a range of circulating concentrations that include the $ED_{50}$ with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of the active compounds and compositions described herein, for example, by measuring viral infection or a condition or symptoms associated therewith.

The cytotoxicity assays described herein and known to those skilled in the art are particularly useful for live attenuated influenza viruses.

5.11.5 In Vivo Antiviral Activity

Active compounds and compositions thereof are preferably assayed in vivo for the desired therapeutic or prophylactic activity prior to use in humans. For example, in vivo assays can be used to determine whether it is preferable to administer an active compound or composition thereof and/or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. To assess the use of an active compound or composition thereof to treat an influenza virus infection or disease associated therewith, the compound or composition may be administered after infecting the animal with influenza virus. In a specific embodiment, an active compound or composition thereof is administered to the animal more than one time.

Active compounds and compositions thereof can be tested for antiviral activity in animal model systems including, but are not limited to, rats, mice, chicken, cows, monkeys, pigs, ferrets, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this section.

In general, animals are infected with influenza virus and concurrently or subsequently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+(epithelial layer columnar and even in outline with only slightly increased proliferation; cilia still visible on many cells); 2+(prominent changes in the epithelial layer ranging from attenuation to marked proliferation; cells disorganized and layer outline irregular at the luminal border); 3+(epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+(focal squamous metaplasia of the epithelial layer); 2+(diffuse squamous metaplasia of much of the epithelial layer, cilia may be evident focally); 2.5+(diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+(few infected cells); 1+(few infected cells, as widely separated individual cells); 1.5+(few infected cells, as widely separated singles and in small clusters); 2+(moderate numbers of infected cells, usually affecting clusters of adjacent cells in portions of the epithelial layer lining bronchioles, or in small sublobular foci in alveoli); 3+(numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.11.5.1.1 Assays in Humans

In one embodiment, an active compound or composition thereof that modulates replication of an influenza virus are assessed in infected human subjects. In accordance with this embodiment, an active compound or composition thereof is administered to the human subject, and the effect of the active compound or composition on viral replication is determined by, e.g., analyzing the level of the virus or viral nucleic acids in a biological sample (e.g., serum or plasma). An active compound or composition thereof that alters virus replication can be identified by comparing the level of virus replication in a subject or group of subjects treated with a control to that in a subject or group of subjects treated with an active compound or composition thereof. Alternatively, alterations in viral replication can be identified by comparing the level of the virus replication in a subject or group of subjects before and after the administration of an active compound or composition thereof. Techniques known to those of skill in the art can be used to obtain the biological sample and analyze the mRNA or protein expression.

In another embodiment, the effect of an active compound or composition thereof on the severity of one or more symptoms associated with an influenza virus infection/disease are assessed in an infected subject. In accordance with this embodiment, an active compound or composition thereof or a control is administered to a human subject suffering from influenza virus infection and the effect of the active compound or composition on one or more symptoms of the virus infection is determined. An active compound or composition thereof that reduces one or more symptoms can be identified by comparing the subjects treated with a control to the subjects treated with the active compound or composition. In a specific embodiment, administration of an active compound (e.g., a chimeric hemagglutinin (HA) polypeptide described herein an) or composition thereof results in a decrease in hospitalization of a human or population of humans caused by influenza virus disease or infection. In another specific embodiment, administration of an active compound (e.g., a chimeric hemagglutinin (HA) polypeptide described herein) or composition thereof results in a reduced need for respiratory/breathing assistance in a human or population of humans with an influenza virus disease or infection. In another specific embodiment, administration of an active compound (e.g., a chimeric hemagglutinin (HA) polypeptide described herein) or composition thereof results in a reduced length of illness of a human or population of humans with an influenza virus disease or infection. In another specific embodiment, administration of an active compound (e.g., a chimeric hemagglutinin (HA) polypeptide described herein) or composition thereof results in improvement (e.g., an increase) in lung volume as assessed by, e.g., whole body or lung plethysmography. In another embodiment, an active compound or composition thereof is administered to a healthy human subject and monitored for efficacy as a vaccine (e.g., the subject is monitored for the onset of symptoms of influenza virus infection; the ability of influenza virus to infect the subject; and/or a reduction in/absence of one or more symptoms associated with influenza virus infection). Techniques known to physicians familiar with infectious diseases can be used to determine whether an active compound or composition thereof reduces one or more symptoms associated with the influenza virus disease.

5.12 Kits

Provided herein is a pharmaceutical pack or kit comprising one or more containers filled with one or more of the ingredients of the pharmaceutical/immunogenic compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein. In one embodiment, a kit comprises an active compound described herein, preferably one or more chimeric hemagglutinin (HA) polypeptides, in one or more containers. In certain embodiments, a kit comprises a vaccine described herein, e.g., a split virus vaccine, a subunit vaccine, an inactivated influenza virus vaccine, or a live influenza virus vaccine, wherein said vaccine comprises one or more chimeric hemagglutinin (HA) polypeptides described herein.

6. EXAMPLES

6.1 Example 1: Design and Incorporation of Chimeric Hemagglutinins as a Universal Vaccination Strategy Against Influenza B Viruses While much of the focus for universal vaccination strategies has been targeted against influenza A virus strains, influenza B viruses remain an important component of the annual vaccine. One strategy to universally target influenza B virus strains is to replace dominant antigenic sites on the head of the hemagglutinin (HA) with sequences from exotic influenza A virus strains. Through replacement of these antigenic loops, chimeric HAs have been generated that are easily incorporated into functional viruses through reverse genetics. Initial in vitro characterization of the chimeric HA and viruses expressing these HA, including growth analysis and surface expression were performed. Additionally, through replacement of antigenic sites, a decrease in HI endpoint titer in viruses with chimeric HA compared to wild type HA was apparent, emphasizing that antigenic sites have functionally been changed. These chimeric viruses will be further assessed for their ability to provide protection in animals during challenge in future studies.

6.1.1 Materials and Methods

Structural Overlays: Structural overlays were performed using Pymol software.

Sequence Alignments: Sequence alignments of HAs to determine corresponding loop/helix sequences were performed using BioEdit software.

Plaque Assay: Step 1: 2× media was prepared for agarose overlay (50 mL total volume: 25 mL 2×MEM, 8 ML WFI water, 660 µL sodium bicarbonate, 500 µL dextrin) and stored in water bath at 37° C. Step 2: Viral dilutions (dilutions used depend on sample and expected titer) were performed as follows: (a) PBS/1% BSA+1% penicillin/streptomycin was combined with $Ca^{2+}/Mg^{2+}$, and 450 µL was added to each tube for dilutions; (b) 50 µL of virus was added to the first tube, the tube was mixed, and then 50 µL from the tube was added to the next tube, etc. Step 3: Pre-plated cells were washed in 6-well plates with 1 mL PBS. Step 4: 300 µL virus dilution (from step 2) was added to each well; most dilute to least dilute to avoid concentration variance. Step 5: Adsorption: cells were incubated at 33° C. or 37° C. (depending on the virus) for 1 hour; and were rocked every 10-15 minutes. Step 6: When adsorption was almost finished, 2% agarose was heated in microwave and 15 mL was added to media from step 1. Step 7: TPCK (N-tosyl-L-phenylalanyl chloromethyl ketone) treated trypsin (1 mg/mL) at 1/1000 dilution was added to media from step 1 (resulting concentrating is 1 ug/mL). Step 8: agarose/media/trypsin mixture was poured evenly on 6 well plates (2 mL/well) and allowed to harden without disturbing overlay. Plates were stored at 33° C. for 72 hours or 37° C. for 48 hours depending on the virus.

Immunostaining: Plaque assays were fixed using 4% formaldehyde in PBS. Cells were blocked with PBS/nonfat dried milk solution and antibodies were also prepared in this mixture. Polyclonal mouse serum raised against A/Puerto Rico/8/34 (PR8) virus or PR8 virus containing a luciferase gene was used as a primary antibody and was incubated for at least 2 hours. Wells were washed with PBS prior to application of the secondary antibody. Secondary anti-mouse HRP antibody was added in the PBS/nonfat dried milk blocking solution and was incubated for at least 1 hour. Staining was performed using TrueBlue stain that was removed with a water wash.

Growth curves in MDCK cells: Cells were plated to form a confluent monolayer in 6 well tissue culture treated plates. Viruses to be characterized were diluted in PBS/BSA. Prior to addition of virus sample to each well of cells, the growth media was removed and cells were washed one time with PBS. 300 microliters of each virus sample was added per well, with each virus with its respective time point having a separate well. Plates with inoculum added were incubated for 1 hour at 33 degrees Celsius. At each designated time point (8, 24, 48, 72 hours) supernatant was removed from the well and stored. Plaque assays were performed with a range of dilutions for each sample in order to titrate the amount of virus present in the sample obtained from the time course. Data was plotted using GraphPad Prism software.

Surface staining: 293T cells were plated the day prior to transfection. Cells were transfected with 500 ng of empty vector plasmid (pDZ), or the desired HA construct using Lipofectamine 2000. 1-2 days later, cells were fixed and stained using the appropriate antibody (polyclonal serum or monoclonal antibody) for that assay. Anti-mouse Alexa488 antibody was used as a secondary antibody for visualization. Stained cells were visualized on a fluorescent microscope.

HI assay: Prior to performing HI assay, any serum that was to be used as antibody was pretreated with Receptor-Destroying Enzyme (BioWhittaker, Walkersville, MID), 100 units/mL, prepared according to manufacturer's instructions. This resulted in serum being at a 1:10 dilution starting concentration (at the highest) for the HI assay. The HA assay was performed on test virus and positive control virus and the dilution that yielded 8 HAU (4 positive wells) was determined. This standardized virus was used for the assay. To find the dilution that would yield 4 wells, the last positive well was divided by 8. This provided the dilution factor, i.e., if the last dilution to have positive agglutination was 128 HAU, then to obtain 8 HAU the following calculation was performed: 128/8=16. To make 8 HAU, a 1:16 dilution was performed. In order to make sure the titer of the new dilution was 8 HAU, back titration was performed.

The following lanes of controls were included on the plate: (A) lane with PBS+virus (no antibody); (B) lane with 50 μL PBS (no antibody) and no virus. To plate, 50 μL antibody was added to column 1 and 25 μL PBS was added to other wells. 25 μL from the first column to the second column (2 fold dilutions of antibody) was transferred until the last columns with PBS alone and no antibody. Each well had 25 μL of the dilution. 25 μL of the appropriate virus was added to all other wells (either test virus, or positive control virus). PBS was added for "no virus" control. Virus and antibody were pre-incubated at room temperature for 30 minutes. 50 uL of 0.5% RBCs (chicken or turkey) in PBS was added as usual for hemagglutination assay. The plates were kept at 4° C. for 30 minutes. Pictures of the results were captured with a scanner.

Generation of chimeric HAs: Design of the HA constructs was based on determining corresponding residues for each loop or helix that was described by Wang et al., 2008, Journal of Virology, 82(6):3011-3020. Corresponding residues were determined by protein structural alignments as well as sequence alignments. The non-coding regions, signal peptide, transmembrane domain, and cytoplasmic tail domain were derived from influenza A/Puerto Rico/8/34 virus. In some instances, the non-coding regions, signal peptide, transmembrane domain, and cytoplasmic tail domain will be derived from other influenza A virus HA sequences or from influenza B HA sequences from viruses of Victoria, Yamagata, or potentially more historic lineages.

For generation of chimeric HA constructs, HAs were synthesized. Alternatively, the HA segment was generated by performing PCR on previously constructed plasmids and by using these PCR products (with at least 15 nucleotides overlap between each product) during the In-Fusion® (Clontech) cloning reaction. To insert the HA segment into its vector, plasmid pDZ was linearized with SAPI restriction enzyme. Each HA fragment contained 15 nucleotide overlap with the pDZ linearized vector. This overlap region was included during design for synthesis of the HA, or was artificially added on by adding this sequence to the primers amplifying from the non-coding regions of the HA during PCR.

In-Fusion® cloning reactions were performed with the generated HA products and linearized pDZ by using the reaction buffer as described by the manufacturer Clontech. Amounts of PCR fragments of HA, synthesized HA, or linearized pDZ vector were adjusted to have equal molar ratios (calculated based on fragment length). The In-Fusion® reaction incubated in a PCR machine at 50 degrees Celsius for 15 minutes then was removed. The resulting cloning product was transformed into Stellar cells and was plated in LB plates containing ampicillin. Resulting colonies were screened for presence of the correct HA insertion sequence and could be grown up and purified as mini-, midi-, or maxi-preps of the DNA. This resulted in the final plasmid product. The concentration of the final product was determined by methods such as using a Nanodrop.

6.1.2 Results

Figure 1:
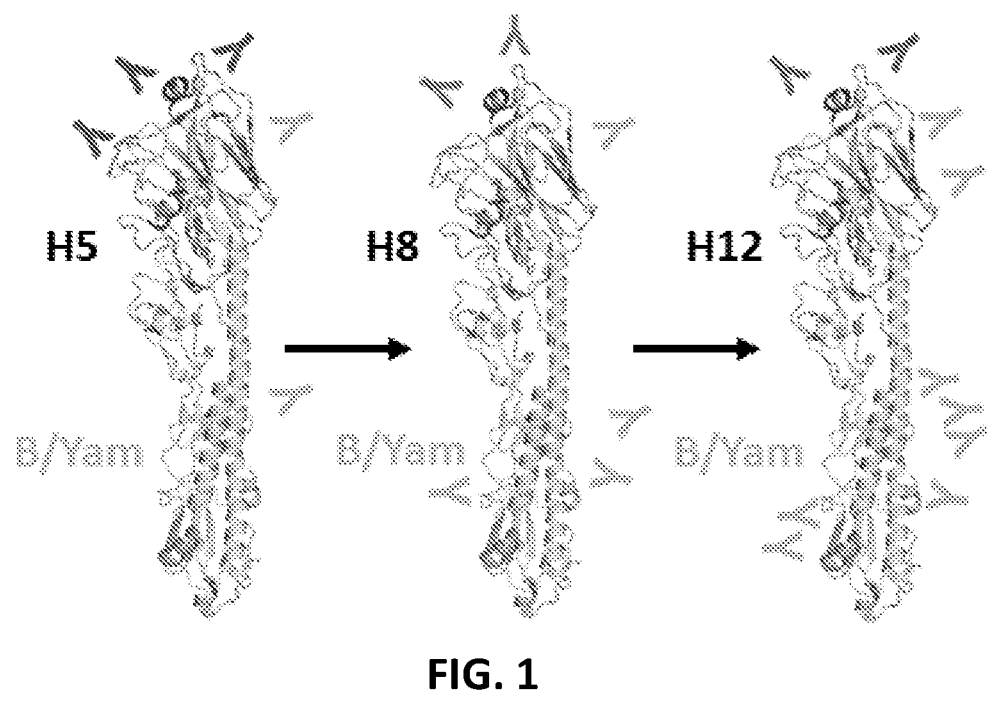
Figure 2:
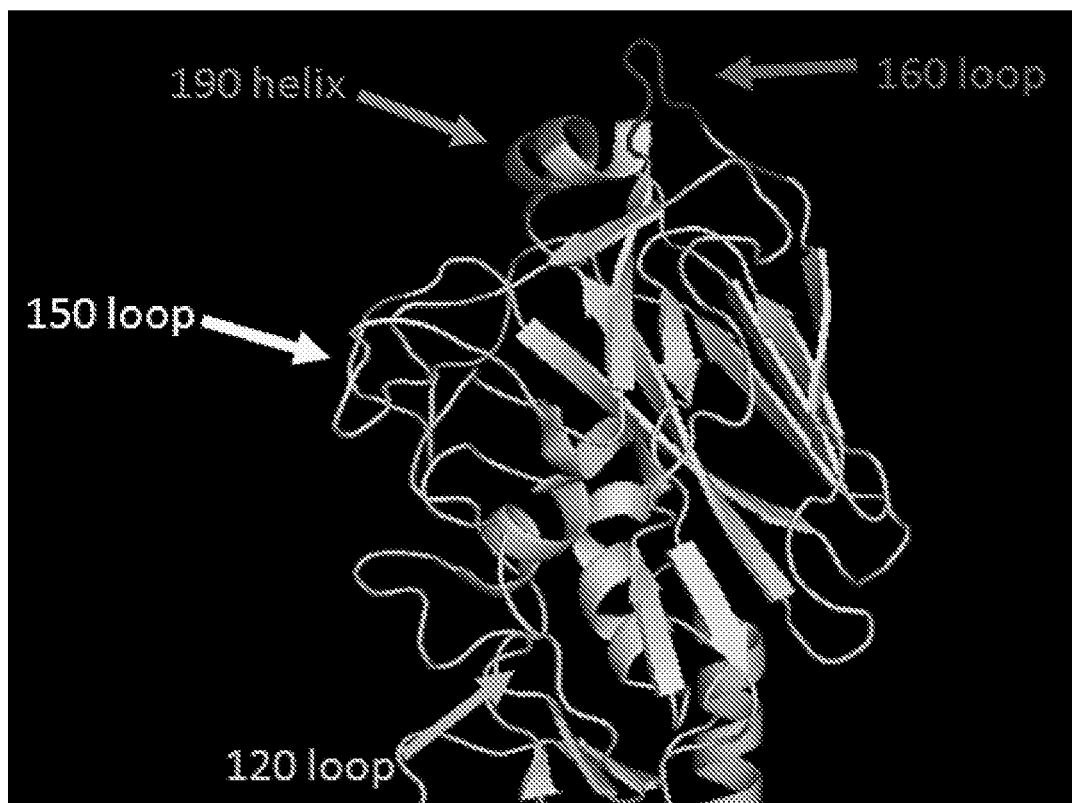
FIG. 2 depicts the 120 loop, 150 loop, 160 loop, and 190 helix in the influenza B/Yamanashi/166/1998 virus globular head as was defined by Wang et al., 2008, Journal of Virology 82: 3011-3020.

To generate influenza B virus chimeric HAs that could serve as universal vaccine candidates, key antigenic sites in the influenza B virus globular head domain of an influenza B/Yamagata/16/88 virus were modified based on antigenic sites from the globular head domain of influenza A viruses of the H5, H8, or H12 subtypes (influenza A/Vietnam/1203/04 virus (HALo), influenza A/mallard/Sweden/24/2002 virus, and influenza A_mallard_interior Alaska_7MP0167_2007 virus, respectively) (referred to as "chimeric HAs") (FIG. 1). Constructs were also generated in which key antigenic sites in the influenza B virus globular head domain of an influenza B/Yamagata/16/88 virus were modified based on antigenic sites from the globular head domain of influenza A virus of the H11 subtype (influenza A/northern shoveler/Netherlands/18/99 virus). In particular, the antigenic sites of the influenza B virus globular head domain that were modified based on antigenic sites from the globular head domain of influenza A viruses were the 120 loop, the 150 loop, the 160 loop, and/or the 190 helix (see Wang et al., 2008, Journal of Virology, 82(6):3011-3020 for a description of the 120 loop, 150 loop, 160 loop, and 190 helix) (FIG. 2). Viruses expressing these chimeric HAs were rescued.

Amino acid residues relating to the 150 loop of the influenza B/Yamagata/16/88 virus HA globular head were modified based on amino acids from the influenza A/Vietnam/1203/04(HALo) virus globular head domain (FIG. 3A, FIG. 3B). In particular, the amino acid sequence PNVTSRNG (SEQ ID NO:18) of the influenza B/Yamagata/16/88 virus HA 150 loop was replaced with the amino acid sequence PYQGKSS (SEQ ID NO: 19) from influenza A/Vietnam/1203/04(HALo) virus globular head domain (FIG. 3A). Influenza A/Puerto Rico/8/34 virus ("PR8") was used as the backbone (i.e., the PB2, PB1, PA, NP, NA, M, and NS are from PR8) to rescue virus expressing this chimeric HA construct. In addition, the non-coding regions, signal peptide, transmembrane domain, and cytoplasmic tail of the chimeric HA construct were from PR8. This virus was successfully rescued, having a stock titer of $5.0 \times 10^8$ plaque forming units (PFU)/mL (FIG. 3C). Furthermore, this virus was not attenuated when grown in MDCK cells grown at 33 degrees Celsius, as compared to a control PR8 virus expressing an HA comprising the PR8 the non-coding regions, signal peptide, transmembrane domain, and cytoplasmic tail and the ectodomain of the influenza B/Yamagata/16/88 virus hemagglutinin (FIG. 4). This virus with 150 loop amino acid residues from the HA polypeptide of B/Yamagata/16/88 replaced with amino acid residues from the A/Vietnam/1203/04 (HALo) HA polypeptide had similar growth kinetics and grew to a similar peak titer in MDCK cells compared to its viral counterpart in which the 150 loop residues remained from B/Yamagata/16/88. This demonstrated that by replacing the 150 loop antigenic site that growth was not impaired for this virus. This chimeric HA polypeptide retained its ability to be recognized by anti-influenza A virus H5 serum, as determined by immunofluorescent staining of 293T cells transfected with plasmid expressing this chimeric HA polypeptide with anti-influenza A virus H5 serum (FIG. 5). FIG. 5 assessed whether the H5 150 loop epitope that was transplanted into a B/Yamagata/16/88 HA ectodomain remained conformationally intact. An intact conformation was investigated using mouse polyclonal serum with anti-H5 activity. As expected, cells transfected with empty vector (pDZ) were not stained by the anti-H5 serum. Also as expected, anti-H5 serum did not bind the second negative control in which the transfected HA had a B/Yamagata/16/88 ectodomain and A/Puerto Rico/8/34 packaging signals (non-coding region (nucleotides), signal peptide, transmembrane domain, and cytoplasmic tail domain). This was expected since no H5 regions were present in the ectodomain. Staining was seen with the anti-H5 serum against the positive control cH5/3 HA. This construct expresses an HA protein that has an H5 head domain and a Perth (H3) stalk domain. Only the HA head would be stained in this case (not the stalk). Finally, the construct with an H5 150 loop, B/Yamagata/16/88 ectodomain, and A/Puerto Rico/8/34 packaging signals (non-coding region (nucleotides), signal peptide, transmembrane domain, and cytoplasmic tail domain) was able to be stained with anti-H5 serum. The staining that was observed occurred to a lesser degree than that observed with cH5/3 HA. Without being bound by any particular theory, the decreased staining may be because the anti-H5 serum would only recognize the transplanted 150 loop in comparison to the entire HA head. Similar chimeric HAs were also constructed by replacing the 150 loop of influenza B/Yamagata/16/88 virus HA with amino acids from influenza A/mallard Sweden/24/2002 virus (H8), or influenza A/northern shoveler/Netherlands/18/99 virus (H11) and viruses were rescued in a similar manner. A similar chimeric HA was also constructed by replacing the 150 loop of influenza B/Yamagata/16/88 virus HA with amino acids from influenza A_mallard_interior Alaska_7MP0167_2007 virus (H12).

An additional chimeric HA construct was generated by modifying the NKNQMKN (SEQ ID NO: 7) sequence of the 190 helix of the influenza B/Yamagata/16/88 virus HA globular head with amino acid residues from the influenza A/Vietnam/1203/04(HALo) virus globular head domain. In particular, it was sought to replace the amino acid sequence NKNQMKN (SEQ ID NO: 7) sequence of the 190 helix of the influenza B/Yamagata/16/88 virus HA with the amino acid sequence NDAAEQT from the influenza A/Vietnam/1203/04(HALo) virus globular head domain. However, virus expressing this construct could not be rescued thus far. Thus, the M amino acid residue of the amino acid sequence NKNQMKN (SEQ ID NO: 7) from the 190 helix of the influenza B/Yamagata/16/88 virus HA globular head domain, which is a conserved residue, was retained. Accordingly, the NKNQMKN (SEQ ID NO: 7) sequence of the 190 helix of the influenza B/Yamagata/16/88 virus HA globular head domain with the amino acid sequence NDAAMQT (SEQ ID NO: 8) (FIG. 6A and FIG. 6B). As above, PR8 was used as the backbone (i.e., the PB2, PB1, PA, NP, NA, M, and NS are from PR8) to rescue virus expressing this chimeric HA construct. In addition, the non-coding regions, signal peptide, transmembrane domain, and cytoplasmic tail of this chimeric HA construct were from PR8. This virus was successfully rescued, having a stock titer of $5.3 \times 10^8$ plaque forming units (PFU)/mL (FIG. 6C).

An additional chimeric HA construct was generated by modification of the RDNKTA (SEQ ID NO: 5) sequence of the 160 loop of the influenza B/Yamagata/16/88 virus with amino acid residues from the influenza A/Vietnam/1203/04 (HALo) virus globular head domain. In particular, the amino acid sequence RDNKTA (SEQ ID NO: 5) sequence of the 160 loop of the influenza B/Yamagata/16/88 virus were replaced with the amino acid sequence KKNSTY (SEQ ID NO: 6) (the N and T amino acids, which are not present in the influenza A/Vietnam/1203/04(HALo) virus globular head domain, had to be retained from the influenza B/Yamagata/16/88 virus HA globular head domain in order to rescue the virus) (FIG. 7A and FIG. 7B). As above, PR8 was used as the backbone (i.e., the PB2, PB1, PA, NP, NA, M, and NS are from PR8) to rescue virus expressing this chimeric HA construct. In addition, the non-coding regions, signal peptide, transmembrane domain, and cytoplasmic tail of this chimeric HA construct were from PR8. This virus was successfully rescued, having a stock titer of $7.3 \times 10^8$ plaque forming units (PFU)/mL (FIG. 7C).

An additional chimeric HA construct was generated by modifying amino acid residues of the 120 loop of the influenza B/Yamagata/16/88 virus globular head domain with amino acid residues from the influenza A/Vietnam/1203/04(HALo) virus globular head domain. The amino acid sequence of the 120 loop is NIRLSTHNVINAER-APGGPYRL (SEQ ID NO: 1) and the amino acid sequence at positions 90-92 (corresponding to the numbering of the immature HA, i.e., including the signal sequence) of the globular head is TIP (FIG. 8A). Amino acid substitutions were made based on the amino acid sequence of the globular head domain of the influenza A/Vietnam/1203/04(HALo) virus. The resulting chimeric HA polypeptide comprised the sequences: FIP and KIQLSTKNVINAEHAPGGPYRL (SEQ ID NO: 2), in place of the TIP and NIRLSTHNVIN-AERAPGGPYRL (SEQ ID NO: 1) sequences, respectively (FIG. 8A and FIG. 8B) and TIP at positions 90-92.

The ability of these chimeric HAs to bind cross-protective antibodies that bind the influenza virus stalk and/or head domains was evaluated. To this end, antibodies CR9114, 5A7, CR8059, CR8033, and Antibody X were utilized. A summary of these antibodies is provided in Table 2, below.

TABLE 2

Cross-protective antibodies utilized

| Antibody | Head or stalk reactive? | Lineage specificity? |
|---|---|---|
| CR9114 | Stalk | Binds influenza A virus and influenza B virus (both lineages). Neutralizes influenza A but not B by micro-neutralization. Is protective against influenza A and B in vivo |
| 5A7 | Stalk. Near C-terminal of HA1 (near head/stalk interface) | Broadly neutralizes viruses (in vitro) from Victoria and Yamagata lineages |
| CR8059 (CR8071 is stable variant) | Head | Binds and neutralizes Yamagata and Victoria lineages (microneutralization); no HI reactivity against either) |
| CR8033 | Head | Binds and neutralizes Yamagata and Victoria lineages (microneutralization); HI activity against Yamagata lineage only. |
| Antibody X | Head | Binds and neutralizes Yamagata and Victoria lineages (plaque reduction, microneutralization); no HI activity. |

The tested chimeric HA polypeptides retained their abilities to be recognized by the tested anti-stalk and anti-head antibodies (FIG. 9). Surface staining was performed on transfected 293T cells with monoclonal antibodies known to bind influenza B HA head or stalk domains (FIG. 9).

Finally, the HI activity of the chimeric HAs were tested to determine whether the antigenic loops of the influenza B virus were successfully replaced. Specifically, HI assays were performed with mouse (FIG. 10A) or ferret (FIG. 10B) serum. The chimeric HA polypeptides displayed drastically reduced strain specific HI activity.

In FIG. 10A, a hemagglutination inhibition (HI) assay was performed with mouse serum and viruses with either an influenza B/Yamagata/16/88 HA ectodomain and A/Puerto Rico/8/34 HA packaging signals (non-coding region (nucleotides), signal peptide, transmembrane domain, and cytoplasmic tail domain) or viruses within that context and either 3 loops (150 loop, 160 loop, 190 helix) or 4 loops (120 loop, 150 loop, 160 loop, 190 helix) were replaced with A/Vietnam/1203/04 H5 HA amino acid sequences. Viruses with 3 of 4 loops had a lower HI titer compared to those with a complete influenza B virus HA ectodomain. This was an indirect method for evaluating that antigenic sites within the influenza B virus HA had either been replaced, or in the least ablated, by swapping in exotic influenza A virus HA sequences (such as those from H5).

Table 3 provides a summary of the chimeric HA constructs cloned, expressed, and rescued in the influenza A virus backbone thus far. Such chimeric HA constructs may also be rescued in an influenza B virus backbone. All chimeric HA constructs were generated using the HA sequence from influenza B/Yamagata/16/88 virus, and the HA sequence from one or more of the following: influenza A/Vietnam/1203/04(HALo) (H5) virus, influenza A/mallard/Sweden/24/2002 virus (H8), influenza A/northern shoveler/Netherlands/18/99 virus (H11), and/or influenza A_mallard_interior Alaska_7MP0167_2007 virus (H12). 3 loop design refers to a chimeric HA construct in which the 150 loop, 160 loop, and the 190 helix have been modified with the corresponding loops from the indicated influenza virus HA subtype (H5, H8, H11, or H12). 4 loop design refers to a chimeric HA construct in which the 120 loop, 150 loop, 160 loop, and the 190 helix have been modified with the corresponding regions from the indicated influenza virus HA subtype (H5, H8, H11, or H12).

TABLE 3

The influenza B virus HA sequence is from influenza B/Yamagata/16/88 virus.
The influenza A virus H5 HA sequence is from influenza A/Vietnam/1203/04(HALo) virus. The influenza A virus H8 HA sequence is from influenza A/mallard/Sweden/24/2002 virus. The influenza A virus H11 HA sequence is from influenza A/northern shoveler/Netherlands/18/99 virus. The influenza A virus H12 HA sequence is from influenza A_mallard_interior Alaska_7MP0167_2007 virus.

|  | Cloned | Expressed | Rescued in A backbone |
|---|---|---|---|
| H5 - 3 loop design (150, 160, 190) | Yes | Yes | Yes |
| H5 - 4 loop design (120, 150, 160, 190) | Yes (see, FIGS. 12A, 12B, and 13) | Yes | Yes |
| H8 - 3 loop design (150, 160, 190) | Yes | Not tested | Not tested |
| H8 - 4 loop design (120, 150, 160, 190) | Yes (see, FIGS. 14A, 14B, and 15) | Not tested | Not tested |
| H11 - 3 loop design (150, 160, 190) | Yes | Yes | Yes |
| H11 -4 loop design (120, 150, 160, 190) | Yes (see, FIGS. 16A, 16B, and 17) | Not tested | Not tested |
| H12-3 loop design (150, 160, 190) | Yes | Not tested | Not tested |
| H12 - 4 loop design (120, 150, 160, 190) | Yes (see, FIGS. 18A, 18B, and 19) | Not tested | Not tested |

In FIG. 10B, a hemagglutination inhibition (HI) assay was performed with ferret serum and viruses with either an influenza B/Yamagata/16/88 HA ectodomain and A/Puerto Rico/8/34 HA packaging signals (non-coding region (nucleotides), signal peptide, transmembrane domain, and cytoplasmic tail domain) or viruses within that context and either 3 loops (150 loop, 160 loop, 190 helix) or 4 loops (120 loop, 150 loop, 160 loop, 190 helix) were replaced with A/Vietnam/1203/04 H5 HA amino acid sequences. Viruses with 3 of 4 loops had a lower HI titer compared to those with a complete influenza B virus HA ectodomain. This was an indirect method for evaluating that antigenic sites within the influenza B virus HA had either been replaced, or in the least ablated, by swapping in exotic influenza A virus HA sequences (such as those from H5).

Chimeric HAs may also be generated by modifying each of the 120 loop, the 150 loop, the 160 loop, and the 190 helix of an influenza B virus HA with amino acid residues from influenza A viruses (e.g., of the H5, H8, H11, or H12 subtypes) (see, e.g., FIG. 11). Alternatively, the 120 loop, the 150 loop, the 160 loop, and/or the 190 helix may be modified with randomized amino acid residues or amino acid residues from an influenza A virus, e.g., an influenza A virus of an H11 subtype.

In conclusion, chimeric HA constructs can be incorporated into rescued influenza A viruses that grow efficiently in eggs. The chimeric HA constructs retain conserved epitopes in both the stalk and the head domain. Finally, the chimeric HA constructs display drastically decreased strain specific HI activity as compared to control HA constructs.

6.2 Example 2: Design and Characterization of Chimeric Ha

This example provides and analyzes chimeric HA constructs which were prepared according to similar methods as described in Example 1 (Section 6.1, supra).

Through replacement of dominant antigenic sites on the head of the influenza B virus hemagglutinin (HA) with sequences from exotic influenza A virus strains (FIGS. 27 and 28), chimeric HAs have been generated that are easily incorporated into functional viruses through reverse genetics. Initial in vitro characterization of the chimeric HA and viruses expressing these HA, including growth analysis (FIG. 37) and surface expression (FIG. 38) were performed. Additionally, through replacement of antigenic sites, a decrease in HI endpoint titer in viruses with chimeric HA compared to wild type HA was apparent (FIG. 39), emphasizing that antigenic sites have functionally been changed.

6.2.1 Materials and Methods

Structural Overlays: Structural overlays were performed using Pymol software.

Sequence Alignments: Sequence alignments of HAs to determine corresponding loop/helix sequences were performed using BioEdit software.

Plaque Assay: Step 1: 2× media was prepared for agarose overlay (50 mL total volume: 25 mL 2×MEM, 9 ML WFI water, 660 µL 7.5% sodium bicarbonate, 500 µL 1% dextran) and stored in water bath at 37° C. Step 2: Viral dilutions (dilutions used depend on sample and expected titer) were performed as follows: (a) PBS/0.3% BSA+1% penicillin/streptomycin was combined with $Ca^{2+}/Mg^{2+}$, and 450 µL was added to each tube for dilutions; (b) 50 µL of virus was added to the first tube, the tube was mixed, and then 50 µL from the tube was added to the next tube, etc. Step 3: Pre-plated cells were washed in 6-well plates with 1 mL PBS. Step 4: 300 µL virus dilution (from step 2) was added to each well; most dilute to least dilute to avoid concentration variance. Step 5: Adsorption: cells were incubated at 33° C. or 37° C. (depending on the virus) for 1 hour; and were rocked every 10-15 minutes. Step 6: When adsorption was almost finished, 2% agarose was heated in microwave and 15 mL was added to media from step 1. Step 7: TPCK (N-tosyl-L-phenylalanyl chloromethyl ketone) treated trypsin (1 mg/mL) at 1/1000 dilution was added to media from step 1 (resulting concentrating is 1 ug/mL). Step 8: agarose/media/trypsin mixture was poured evenly on 6 well plates (2 mL/well) and allowed to harden without disturbing overlay. Plates were stored at 33° C. for 72 hours or 37° C. for 48 hours depending on the virus.

Surface staining: MDCK cells were plated the day prior to infection. Cells were infected with indicated viruses at a multiplicity of infection (MOI) of 5 without TPCK-trypsin and incubated at 33 degrees Celsius. 17 hours post-infection, cells were fixed with methanol-free 4% PFA for immunofluorescence surface staining using the indicated anti-influenza B HA cross-protective human/mouse monoclonal antibodies and anti-influenza B virus HA polyclonal mouse serum. Secondary Alexa-Fluor 488 anti-human or anti-mouse antibody was used. Images were taken using Zeiss LSM 880 confocal microscope.

Growth curves in eggs: 10-day old embryonated chicken eggs were infected with 500 plaque forming units/egg of wild type influenza B/Malaysia/2506/04 MA virus or influenza B/Malaysia/2506/04 MA virus expressing chimeric HA. Growth curves were performed in triplicate. Allantoic fluids were harvested at 8 hours, 24 hours, 48 hours, and 72 hours post infection. Plaque assays were performed on MDCK cells as described above to determine virus titers.

HI assay: Mouse and ferret sera were raised against wild type influenza B virus strain B/Yamagata/16/88 to acquire hemagglutination inhibition (HI) reactivity. Prior to performing HI assay, any serum that was to be used as antibody for the HI assay was pretreated with Receptor-Destroying Enzyme (BioWhittaker, Walkersville, Md.), 100 units/mL, prepared according to manufacturer's instructions. This resulted in serum being at a 1:10 dilution starting concentration (at the highest) for the HI assay. The HA assay was performed on test virus and positive control virus and the dilution that yielded 8 HAU (4 positive wells) was determined. This standardized virus was used for the assay. To find the dilution that would yield 4 wells, the last positive well was divided by 8. This provided the dilution factor, i.e., if the last dilution to have positive agglutination was 128 HAU, then to obtain 8 HAU the following calculation was performed: 128/8=16. To make 8 HAU, a 1:16 dilution was performed. In order to make sure the titer of the new dilution was 8 HAU, back titration was performed.

The following lanes of controls were included on the plate: (A) lane with PBS+virus (no antibody); (B) lane with 50 µL PBS (no antibody) and no virus. To plate, 50 µL antibody was added to column 1 and 25 µL PBS was added to other wells. 25 µL from the first column to the second column (2 fold dilutions of antibody) was transferred until the last columns with PBS alone and no antibody. Each well had 25 µL of the dilution. 25 µL of the appropriate virus was added to all other wells (either test virus, or positive control virus). PBS was added for "no virus" control. Virus and antibody were pre-incubated at room temperature for 30 minutes. 50 uL of 0.5% RBCs (turkey) in PBS was added as usual for hemagglutination assay. The plates were kept at 4° C. for 30 minutes. Pictures of the results were captured with a scanner.

Generation of chimeric HAs: Design of the HA constructs was based on determining corresponding residues for each loop or helix that was described by Wang et al., 2008, Journal of Virology, 82(6):3011-3020. Corresponding residues were determined by protein structural alignments as well as sequence alignments.

For generation of chimeric HA constructs, HAs were synthesized. Alternatively, the HA segment was generated by performing PCR on previously constructed plasmids and by using these PCR products (with at least 15 nucleotides overlap between each product) during the In-Fusion® (Clontech) cloning reaction. To insert the HA segment into its vector, plasmid pDZ was linearized with SAPI restriction enzyme. Each HA fragment contained 15 nucleotide overlap with the pDZ linearized vector. This overlap region was included during design for synthesis of the HA, or was artificially added on by adding this sequence to the primers amplifying from the non-coding regions of the HA during PCR.

In-Fusion® cloning reactions were performed with the generated HA products and linearized pDZ by using the reaction buffer as described by the manufacturer Clontech. Amounts of PCR fragments of HA, synthesized HA, or linearized pDZ vector were adjusted to have equal molar ratios (calculated based on fragment length). The In-Fusion® reaction incubated in a PCR machine at 50 degrees Celsius for 15 minutes then was removed. The resulting cloning product was transformed into Stellar cells and was plated in LB plates containing ampicillin. Resulting colonies were screened for presence of the correct HA insertion sequence and could be grown up and purified as mini-, midi-, or maxi-preps of the DNA. This resulted in the final plasmid product. The concentration of the final product was determined by methods such as using a Nanodrop.

6.2.2 Results

To generate influenza B virus chimeric HAs that could serve as universal vaccine candidates, key antigenic sites (the 120 loop, the 150 loop, the 160 loop, and/or the 190 helix (see Wang et al., 2008, Journal of Virology, 82(6): 3011-3020 for a description of the 120 loop, 150 loop, 160 loop, and 190 helix)) in the influenza B virus globular head domain of influenza B/Yamagata/16/88 virus HA were modified based on antigenic sites from the globular head domain of influenza A viruses of the H5, H8, H11, or H13 subtypes (influenza A/Vietnam/1203/04 virus (HALo) (H5), influenza A/Mallard/Sweden/24/2002 virus (H8), influenza A/northern shoveler/Netherlands/18/99 virus (H11)), or A/black headed gull/Sweden/1/99 (H13), respectively) (referred to as mH5/B, mH8/B, mH11/B, and mH13/B, respectively, chimeric HAs) (FIG. 27 and FIG. 28).

Figure 37A:
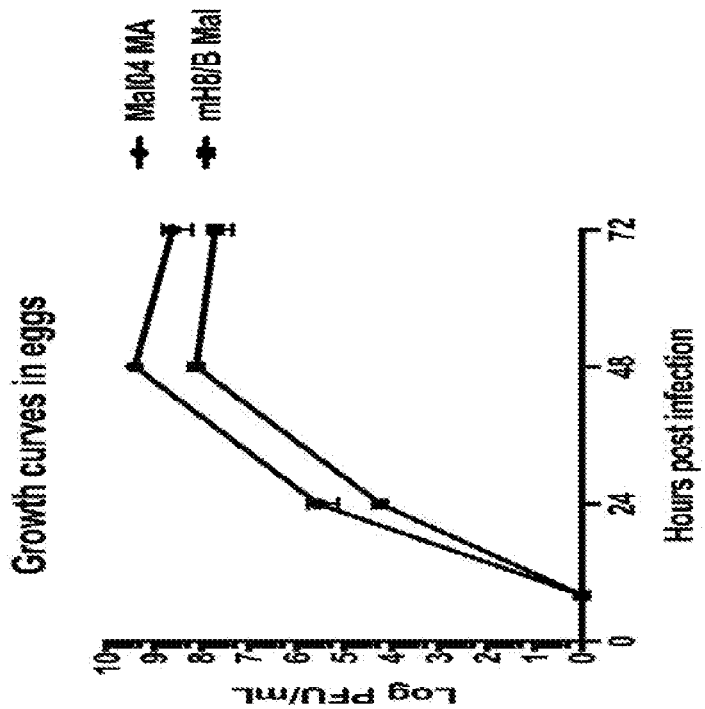

To generate the mH5/B chimeric HA for rescue in an influenza B/Malaysia/2506/04 MA virus backbone, amino acid residues relating to the 120 loop, 150 loop, 160 loop, and 190 helix of the influenza B/Yamagata/16/88 virus HA globular head were modified based on amino acids from the influenza A/Vietnam/1203/04 (HALo) (H5) virus globular head domain (FIGS. 29 and 30). In particular, the amino acid sequences from of the influenza B/Yamagata/16/88 virus HA 120 loop (TIP and NIRLSTHNVINAERAPGGPYRL (SEQ ID NO: 1)), 150 loop (PNVTSRNG (SEQ ID NO: 18)), 160 loop (RDNKTA (SEQ ID NO: 5)), and 190 helix (NKNQMKN (SEQ ID NO: 7)) were replaced with amino acid sequences FIP, KIQLSTKNVINAEHAPGGPYRL (SEQ ID NO: 2), PYQGKSS (SEQ ID NO: 19), KKNSTY (SEQ ID NO: 6), and NDAAMQT (SEQ ID NO: 8), respectively, based on amino acid sequences of the influenza A/Vietnam/1203/04(HALo) (H5) virus globular head domain. Influenza B/Malaysia/2506/04 MA virus was used as the backbone (i.e., the PB2, PB1, PA, NP, NA, M, and NS are from influenza B/Malaysia/2506/04 MA virus) to rescue virus expressing this chimeric HA construct. Additionally, the glutamic acid (E) amino acid at position 156 of the immature influenza B/Yamagata/16/88 virus HA was substituted with a lysine (K) (i.e., an E156K mutation) in the chimeric HA. This virus was successfully rescued, having a stock titer of $6.95 \times 10^8$ PFU/mL. This virus was slightly attenuated when grown in 10-day old embryonated eggs (500 PFU/egg inoculant) at 33 degrees Celsius, as compared to a control influenza B/Malaysia/2506/04 MA virus (FIG. 37A). The peak titer p value was 0.0005.

Figure 37B:
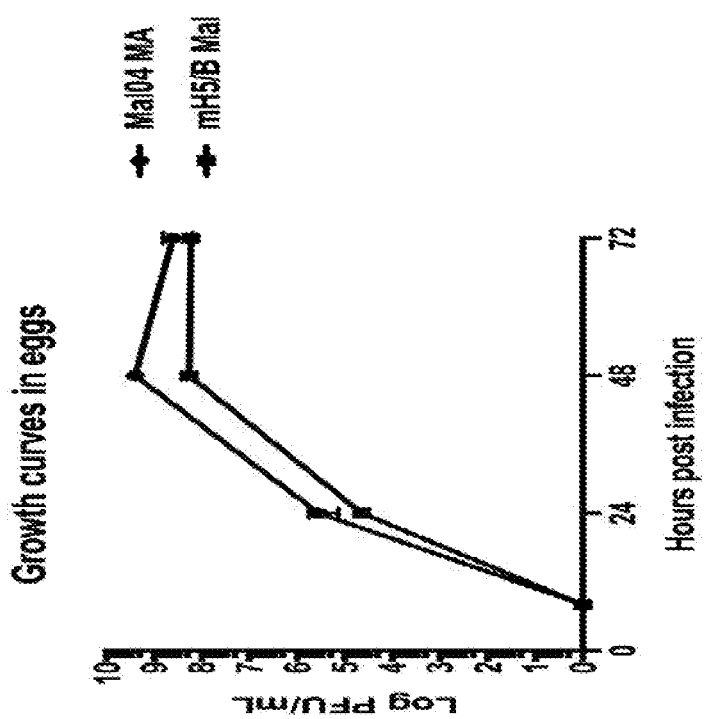

To generate the mH8/B chimeric HA for rescue in an influenza B/Malaysia/2506/04 MA virus backbone, amino acid residues relating to the 120 loop, 150 loop, 160 loop, and 190 helix of the influenza B/Yamagata/16/88 virus HA globular head were modified based on amino acids from the influenza A/Mallard/Sweden/24/2002 virus (H8) globular head domain (FIGS. 31 and 32). In particular, the amino acid sequences of the influenza B/Yamagata/16/88 virus HA 120 loop (TIP and NIRLSTHNVINAERAPGGPYRL (SEQ ID NO: 1)), 150 loop (PNVTSRNG (SEQ ID NO: 18)), 160 loop (RDNKTA (SEQ ID NO: 5)), and 190 helix (NKNQMKN (SEQ ID NO: 7)) were replaced with amino acid sequences HIP, RIRLSTYNVINAETAPGGPYRL (SEQ ID NO: 51), NASTGGQS (SEQ ID NO: 52), KKKADTY (SEQ ID NO: 53), and ADAKMQT (SEQ ID NO: 54), respectively, based on amino acid sequences of the influenza A/Mallard/Sweden/24/2002 virus (H8) globular head domain. Influenza B/Malaysia/2506/04 MA virus was used as the backbone (i.e., the PB2, PB1, PA, NP, NA, M, and NS are from influenza B/Malaysia/2506/04 MA virus) to rescue virus expressing this chimeric HA construct. Additionally, the glutamic acid (E) amino acid at position 156 of the immature influenza B/Yamagata/16/88 virus HA was substituted with a lysine (K) (i.e., an E156K mutation) in the chimeric HA. This virus was successfully rescued, having a stock titer of $1.16 \times 10^9$ PFU/mL. This virus was slightly attenuated when grown in 10-day old embryonated eggs (500 PFU/egg inoculant) at 33 degrees Celsius, as compared to a control influenza B/Malaysia/2506/04 MA virus expressing an HA comprising the influenza B/Malaysia/2506/04 MA virus (FIG. 37B). The peak titer p value was 0.0004.

Figure 37C:
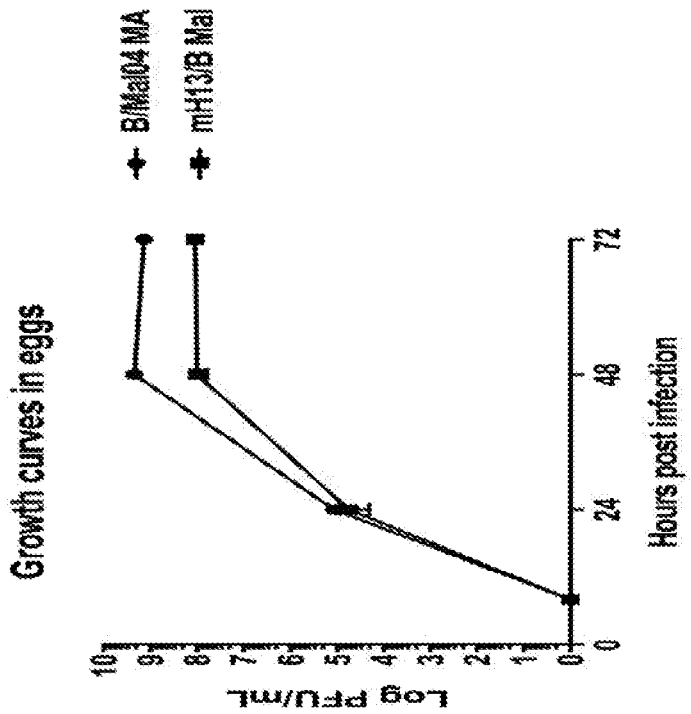

To generate the mH11/B chimeric HA for rescue in an influenza B/Malaysia/2506/04 MA virus backbone, amino acid residues relating to the 120 loop, 150 loop, 160 loop, and 190 helix of the influenza B/Yamagata/16/88 virus HA globular head were modified based on amino acids from the influenza A/northern shoveler/Netherlands/18/99 virus (H11) globular head domain (FIGS. 33 and 34). In particular, the amino acid sequences of the influenza B/Yamagata/16/88 virus HA 120 loop (TIP and NIRLSTHNVINAER-APGGPYRL (SEQ ID NO: 1)), 150 loop (PNVTSRNG (SEQ ID NO: 18)), 160 loop (RDNKTA (SEQ ID NO: 5)), and 190 helix (NKNQMKN (SEQ ID NO: 7)) were replaced with amino acid sequences LIP, KIELSTSNVINAE-VAPGGPYRL (SEQ ID NO: 55), PFGSSNS (SEQ ID NO: 56), HQSGTY (SEQ ID NO: 57), and TTLKMHQ (SEQ ID NO: 58), respectively, based on amino acid sequences of the influenza A/northern shoveler/Netherlands/18/99 virus (H11) globular head domain. Influenza B/Malaysia/2506/04 MA virus was used as the backbone (i.e., the PB2, PB1, PA, NP, NA, M, and NS are from influenza B/Malaysia/2506/04 MA virus; see SEQ ID NOs: 80, 81, 82, 84, 85, 86, and 87 for the nucleotide sequences) to rescue virus expressing this chimeric HA construct. Additionally, the glycine (G) amino acid at position 250 of the immature influenza B/Yamagata/16/88 virus HA was substituted with a glutamic acid (E) (i.e., a G250E mutation) in the chimeric HA. This virus was successfully rescued, having a stock titer of $1.42 \times 10^8$ PFU/mL. This virus was slightly attenuated when grown in 10-day old embryonated eggs (500 PFU/egg inoculant) at 33 degrees Celsius, as compared to a control influenza B/Malaysia/2506/04 MA virus (FIG. 37C). The peak titer p value was 0.2310.

Figure 37D:
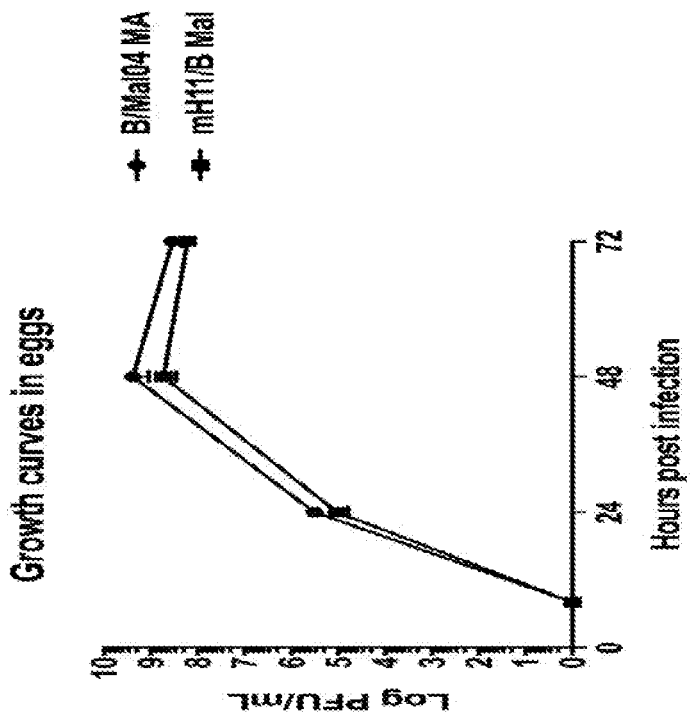
Figure 38A:
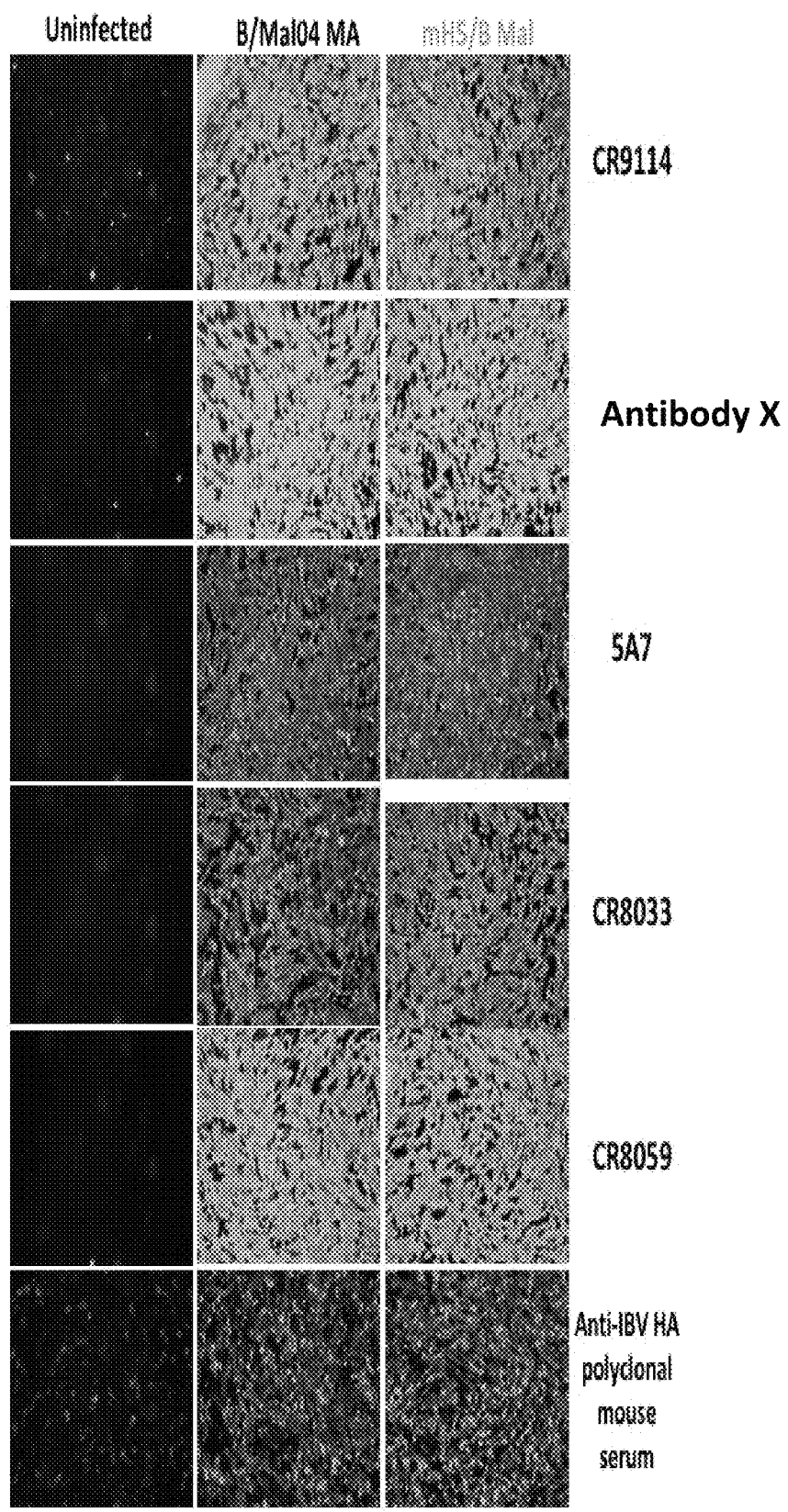
Figure 38B:
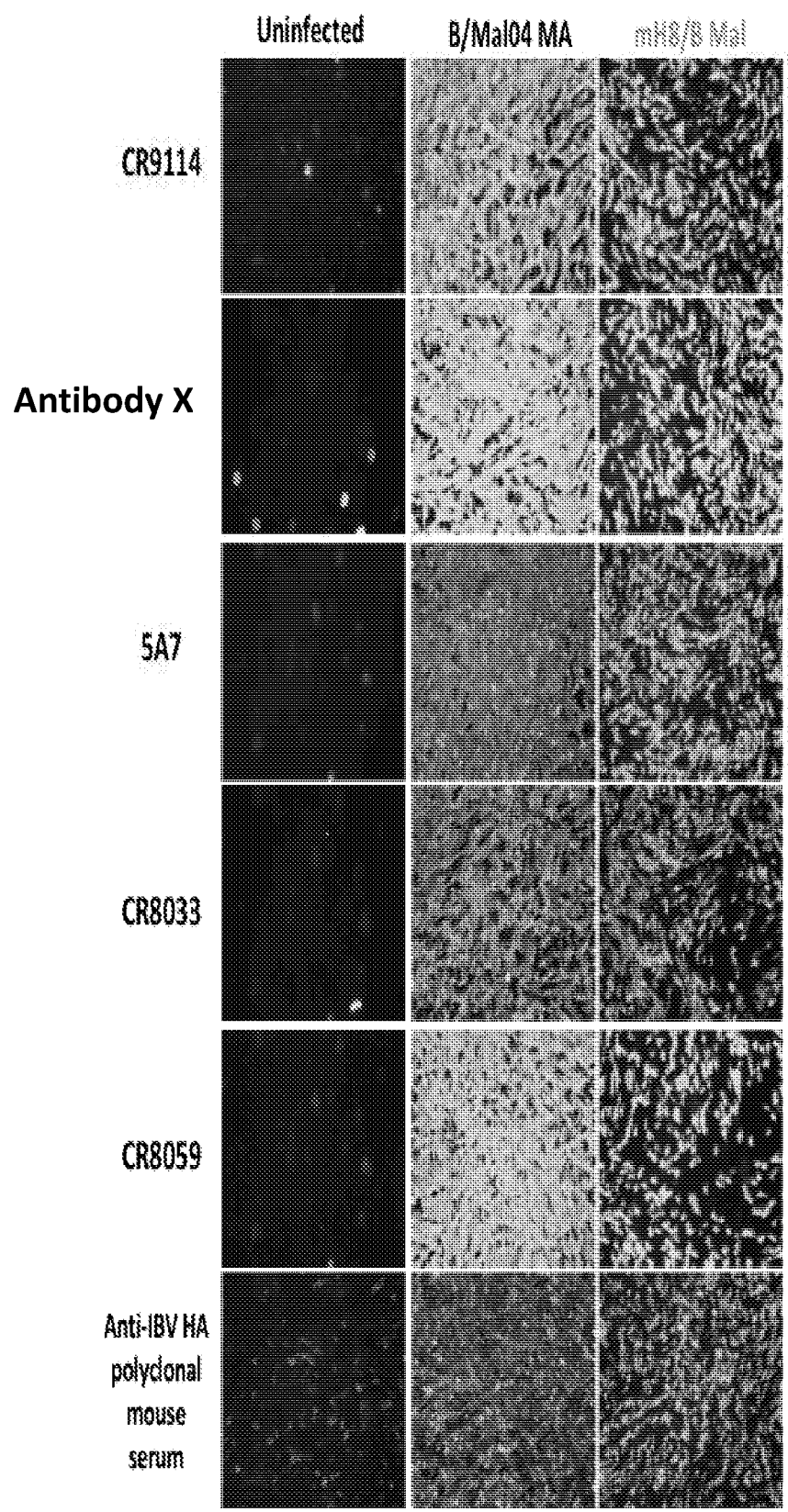
Figure 38C:
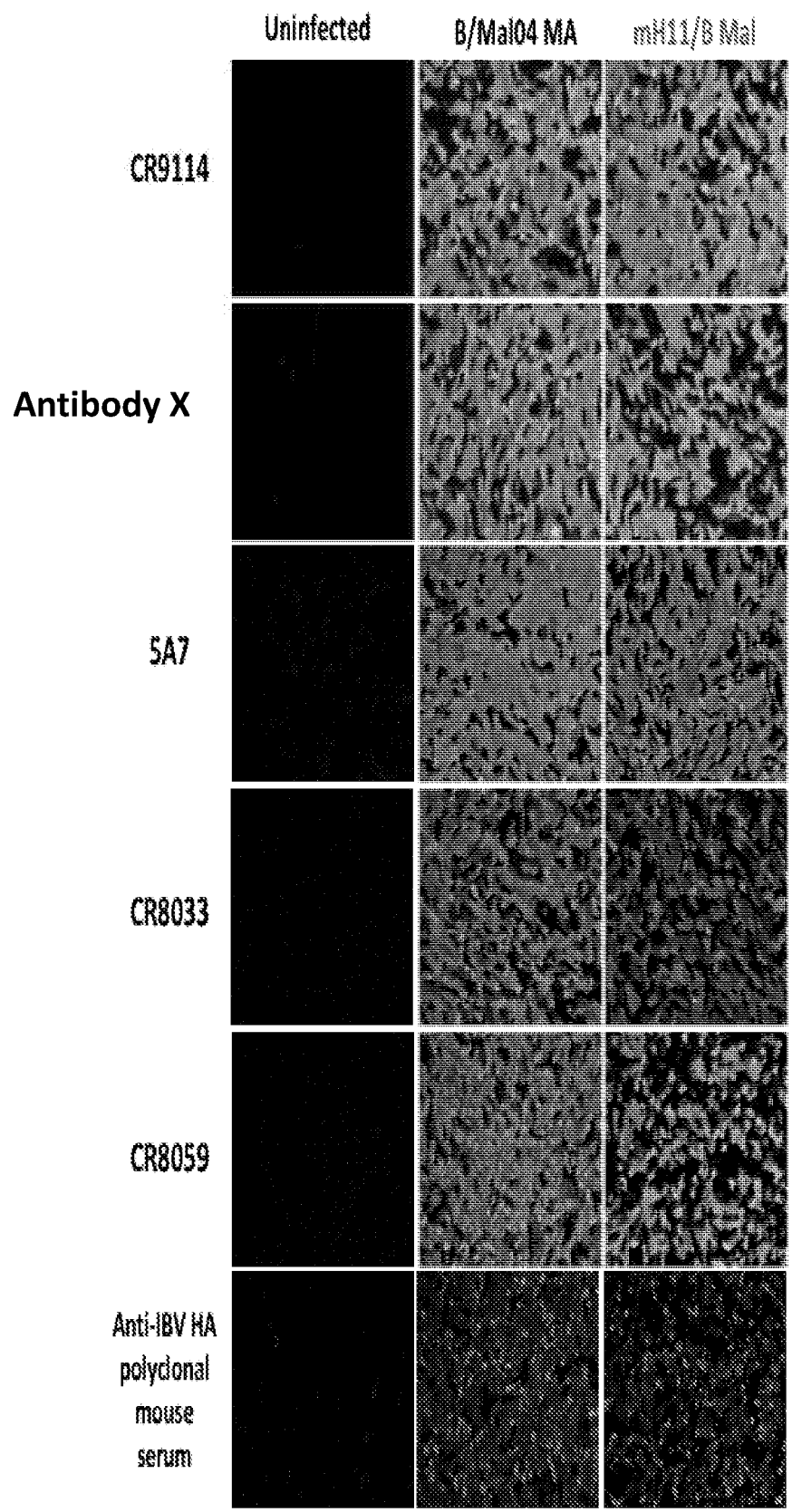
Figure 38D:
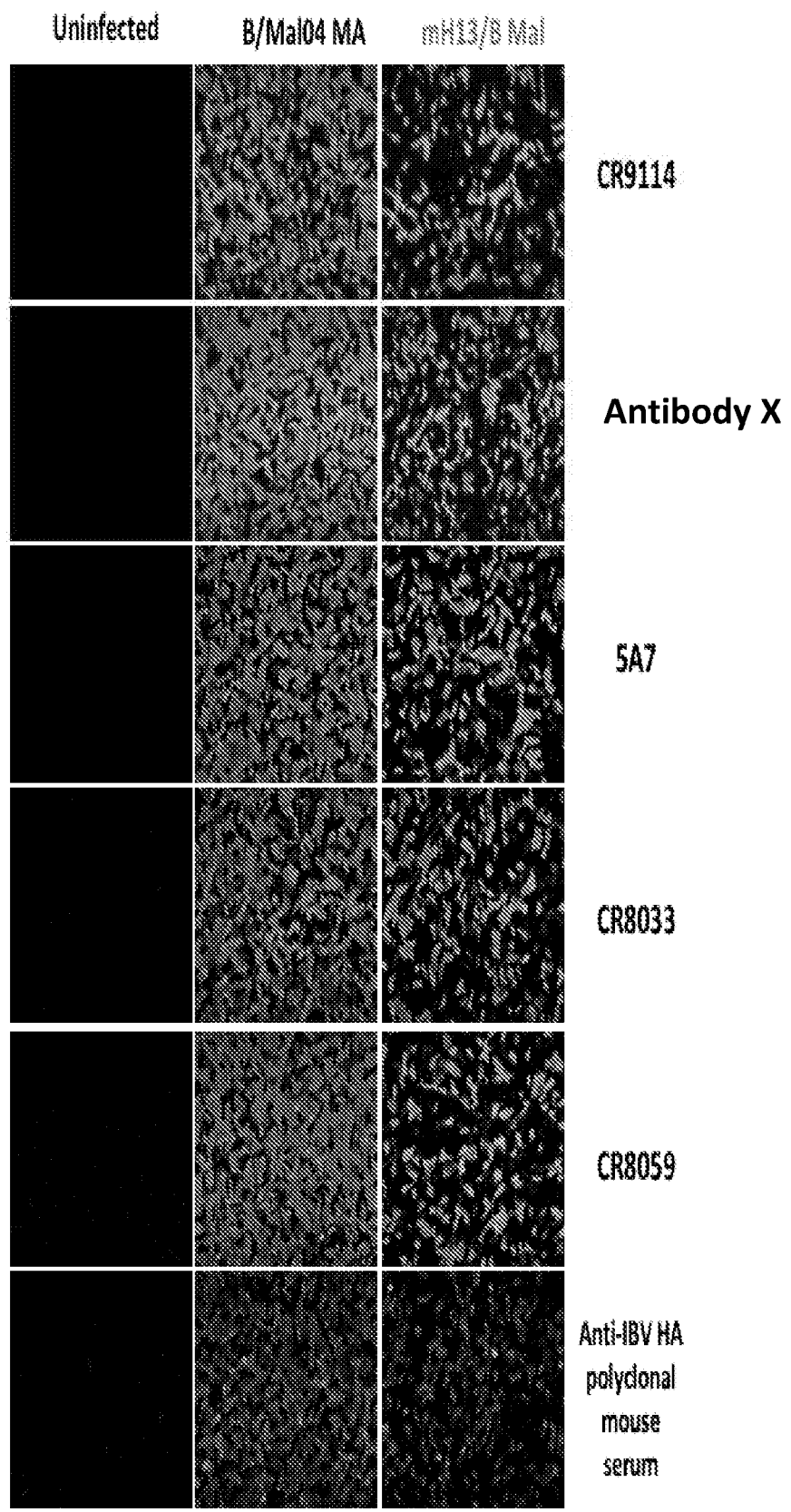
Figures 39A, 39B:
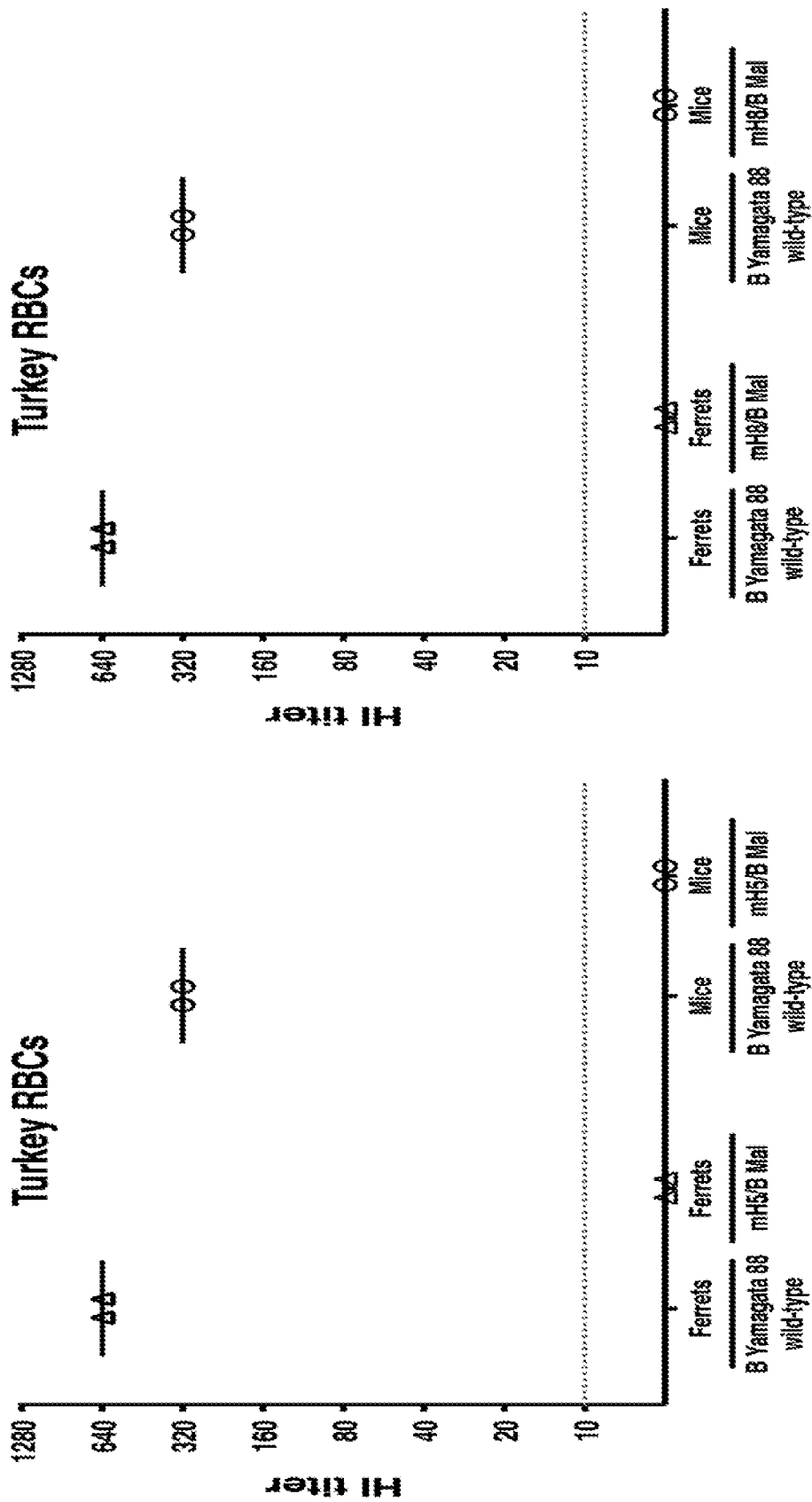
Figure 39D:
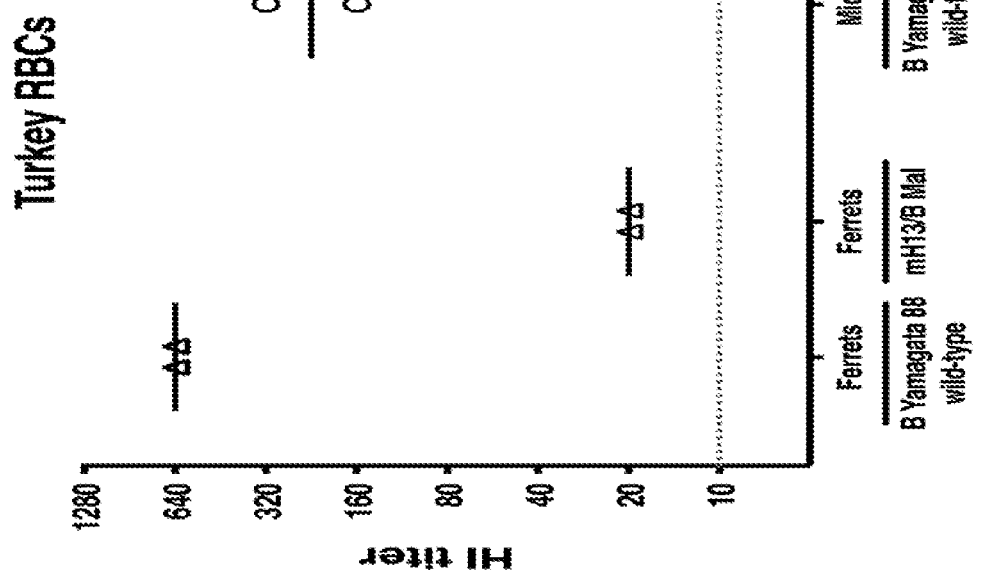
Figure 39C:
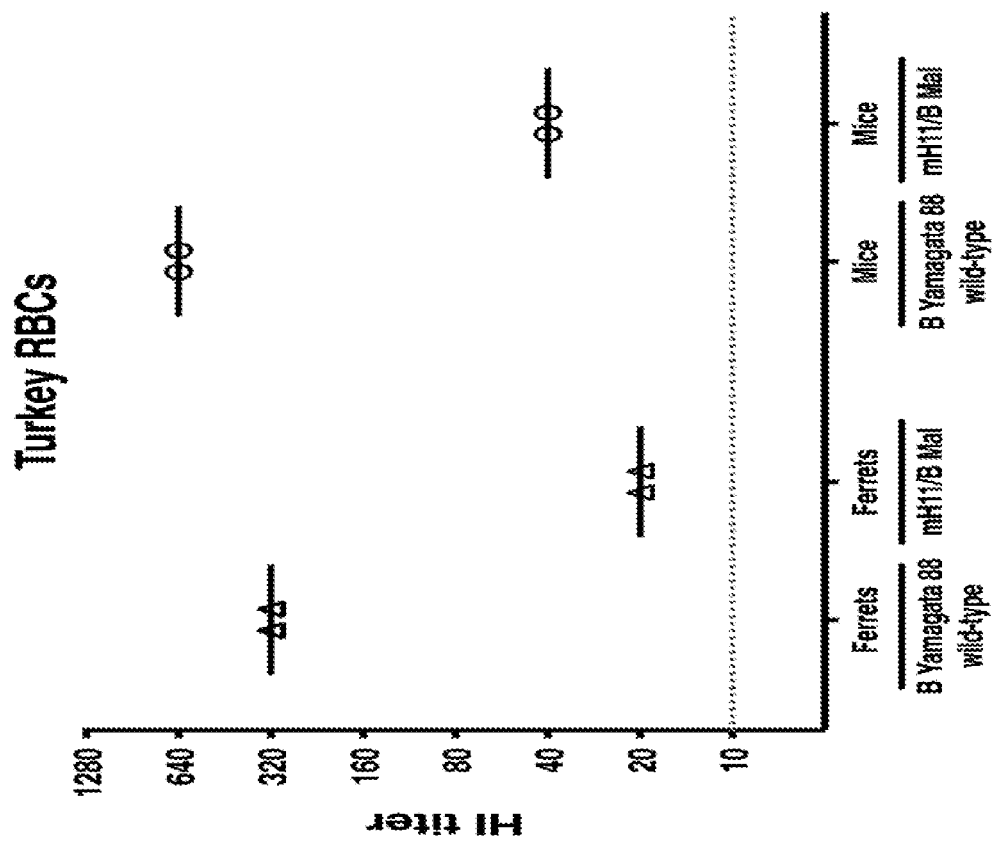

To generate the mH13/B chimeric HA for rescue in an influenza B/Malaysia/2506/04 MA virus backbone, amino acid residues relating to the 120 loop, 150 loop, 160 loop, and 190 helix of the influenza B/Yamagata/16/88 virus HA globular head were modified based on amino acids from the influenza A/black headed gull/Sweden/1/99 virus globular head domain (FIGS. 35 and 36). In particular, the amino acid sequences of the influenza B/Yamagata/16/88 virus HA 120 loop (TIP and NIRLSTHNVINAERAPGGPYRL (SEQ ID NO: 1)), 150 loop (PNVTSRNG (SEQ ID NO: 18)), 160 loop (RDNKTA (SEQ ID NO: 5)), and 190 helix (NKNQMKN (SEQ ID NO: 7)) were replaced with amino acid sequences NIP, RIELSTHNVINAEVAPGGPYRL (SEQ ID NO: 59), PDKGASS (SEQ ID NO: 60), KRGNQY (SEQ ID NO: 61), and VSTNMAK (SEQ ID NO: 62), respectively, based on amino acid sequences of the influenza A/black headed gull/Sweden/1/99 virus globular head domain. Influenza B/Malaysia/2506/04 MA virus was used as the backbone (i.e., the PB2, PB1, PA, NP, NA, M, and NS are from influenza B/Malaysia/2506/04 MA virus) to rescue virus expressing this chimeric HA construct. Additionally, the glutamic acid (E) amino acid at position 156 of the immature influenza B/Yamagata/16/88 virus HA was substituted with a lysine (K) (i.e., an E156K mutation) in the chimeric HA. This virus was successfully rescued, having a stock titer of $2.19 \times 10^8$ PFU/mL. This virus was slightly attenuated when grown in 10-day old embryonated eggs (500 PFU/egg inoculant) at 33 degrees Celsius, as compared to a control influenza B/Malaysia/2506/04 MA virus (FIG. 37D). The peak titer p value was 0.0072.

The ability of these chimeric HAs to bind cross-protective antibodies that bind the influenza virus stalk and/or head domains was evaluated. To this end, antibodies CR9114, 5A7, CR8059, CR8033, and Antibody X (sometimes referred to as IIC7) were utilized. A summary of these antibodies is provided in Table 2, above. The tested chimeric HA polypeptides retained their abilities to be recognized by the tested anti-stalk and anti-head antibodies (FIGS. 38A-38D). Surface staining was performed on MDCK cells infected with the indicated viruses at a multiplicity of infection of 5 without TPCK-trypsin at 17 hours post-infection with monoclonal antibodies known to bind influenza B HA head or stalk domains (FIGS. 38A-38D).

The HI activity of the chimeric HAs was tested to determine whether the antigenic loops of the influenza B virus were successfully replaced. Specifically, HI assays were performed with mouse or ferret serum raised against wild type influenza B/Yamagata/16/88 virus (FIGS. 39A-39D). The chimeric HA polypeptides displayed drastically reduced strain specific HI activity (FIGS. 39A-39D). This was an indirect method for evaluating that antigenic sites within the influenza B virus HA had either been replaced, or in the least ablated, by swapping in exotic influenza A virus HA sequences (such as those from H5, H8, H11, or H13).

In conclusion, chimeric HA constructs can be incorporated into rescued influenza B viruses that grow to robust titers in eggs, despite being attenuated compared to the wild type virus. The chimeric HAs appeared to lose their B HA immunodominant head epitopes, while sub-dominant conserved, cross-protective epitopes on B HA were preserved.

6.3 Example 3: Vaccination Regimens Comprising Chimeric HA

Generation of Chimeric HA Constructs: mH5/B, mH8/B, and mH13/B chimeric HA constructs were generated as described in Section 6.2, supra. pDZ plasmid (see Martinez-Sobrido L, Garcia-Sastre A. Generation of Recombinant Influenza Virus from Plasmid DNA. Journal of Visualized Experiments: JoVE. 2010; (42):2057. doi:10.3791/2057, which is incorporated by reference herein in its entirety) encoding the mH13/B chimeric HA was giga-prepped (service provided by Genewiz) to prepare the DNA used for the prime (see Table 4, infra). mH5/B and mH8/B chimeric HA recombinant proteins were synthesized using baculovirus expression system as previously described in Margine I, Palese P, Krammer F. Expression of Functional Recombinant Hemagglutinin and Neuraminidase Proteins from the Novel H7N9 Influenza Virus Using the Baculovirus Expression System. Journal of Visualized Experiments: JoVE. 2013; (81):51112. doi:10.3791/51112, which is incorporated by reference herein in its entirety.

Mouse Models and In Vivo Analyses: Five 6 to 8 weeks old female BALB/c mice/group (ten groups in total) were used in this example (see Table 4, infra). Mice are vaccinated as indicated in Table 4, below. Specifically, mice are primed with either: (i) 80 μg of pDZ plasmid encoding mH13/B administered by electroporation (Groups 1, 2, 5-7, and 10); (ii) 1 μg of Fluzone (2006-2007 season, comprising an influenza B virus of the Victoria lineage; Sanofi Pasteur) administered intramuscularly (Group 3); (iii) 1 μg of Flulaval (2008-2009 season, comprising an influenza B virus of the Yamagata lineage; GlaxoSmithKline) administered intramuscularly (Group 8); or (iv) mock primed (Groups 4 and 9). Three weeks post-prime, mice in Groups 1, 2, 4-7, 9, and 10 are boosted with: (i) intramuscular administration of 5 μg of mH5/B protein adjuvanted with 5 μg of polyL:C and intranasal administration of 5 μg of mH5/B protein adjuvanted with 5 μg of polyL:C (Groups 1, 5, 6, and 10); or (ii) intramuscular administration of 5 μg of bovine serum albumin (BSA) adjuvanted with 5 μg of polyL:C and intranasal administration of 5 μg of BSA adjuvanted with 5 μg of polyL:C (Groups 2, 4, 7, and 9). Mice in Groups 3 and 8 do not receive a boost three-weeks post-prime. Six weeks post-prime, mice are boosted with: (i) intramuscular administration of 5 μg of mH8/B protein adjuvanted with 5 μg of polyL:C and intranasal administration of 5 μg of mH8/B protein adjuvanted with 5 μg of polyL:C (Groups 1, 5, 6, and 10); (ii) intramuscular administration of 5 μg of BSA adjuvanted with 5 μg of polyL:C and intranasal administration of 5 μg of BSA adjuvanted with 5 μg of polyL:C (Groups 2, 4, 7, and 9); (iii) 1 μg of Fluzone administered intramuscularly (Group 3); or (iv) 1 μg of Flulaval administered intramuscularly (Group 8). Four weeks later (i.e., 10 weeks after the prime), mice in Groups 1-4 were challenged with influenza B/Malaysia/2506/04 virus (Victoria lineage) at 5 mouse lethal dose 50 ("LD50"), intranasally, and mice in Groups 1-4 were monitored for weight loss (FIG. 40A) and survival (FIG. 40B) compared to naive mice. Mice in Group 1 were completely protected from mortality with minimal weight loss.

Additionally, 10 weeks after the prime, mice in Groups 6-9 are challenged with influenza B/Florida/4/06 virus (Yamagata lineage) at 5 mouse LD50, intranasally, and mice in Groups 5 and 10 are terminally bled (for, e.g., passive transfer studies). The challenged mice are monitored for weight loss and survival.

TABLE 4

Chimeric HA vaccination in mice. TIV = trivalent influenza vaccine;
BSA = bovine serum albumin; IM = intramuscular; IN = intranasally;
VIC indicates that the virus is from the influenza B virus Victoria lineage;
YAM indicates that the virus is from the influenza B virus Yamagata lineage.
mH5/B refers to mH5/B chimeric HA described in FIGS. 29 and 30. mH8/B refers
to the mH8/B chimeric HA described in FIGS. 31 and 32. mH13/B refers to
the mH13/B chimeric HA described in FIGS. 35 and 36.

| Group | Prime | Boost 1 (3 weeks later) | Boost 2 (3 weeks later) | Challenge (4 weeks later) |
|---|---|---|---|---|
| 1 | mH13/B DNA 80 μg | mH5/B protein 10 μg (5 μg IM, 5 μg IN) 10 μg polyI:C | mH8/B protein 10 μg (5 μg IM, 5 μg IN) 10 μg polyI:C | B/Malaysia/2506/04 (Vic) |
| 2 | mH13/B DNA 80 μg | BSA 10 μg (5 μg IM, 5 μg IN) 10 μg polyI:C | BSA 10 μg (5 μg IM, 5 μg IN) 10 μg polyI:C | B/Malaysia/2506/04 (Vic) |
| 3 | Fluzone 1 μg (IM) (TIV) | None | Fluzone 1 μg (IM) (TIV) | B/Malaysia/2506/04 (Vic) |
| 4 | Mock | BSA 10 μg (5 μg IM, 5 μg IN) 10 μg polyI:C | BSA 10 μg (5 μg IM, 5 μg IN) 10 μg polyI:C | B/Malaysia/2506/04 (Vic) |

TABLE 4-continued

Chimeric HA vaccination in mice. TIV = trivalent influenza vaccine;
BSA = bovine serum albumin; IM = intramuscular; IN = intranasally;
VIC indicates that the virus is from the influenza B virus Victoria lineage;
YAM indicates that the virus is from the influenza B virus Yamagata lineage.
mH5/B refers to mH5/B chimeric HA described in FIGS. 29 and 30. mH8/B refers
to the mH8/B chimeric HA described in FIGS. 31 and 32. mH13/B refers to
the mH13/B chimeric HA described in FIGS. 35 and 36.

| Group | Prime | Boost 1 (3 weeks later) | Boost 2 (3 weeks later) | Challenge (4 weeks later) |
|---|---|---|---|---|
| 5 | mH13/B DNA 80 μg | mH5/B protein 10 μg (5 μg IM, 5 μg IN) 10 μg polyI:C | mH8/B protein 10 μg (5 μg IM, 5 μg IN) 10 μg polyI:C | Terminal Bleed |
| 6 | mH13/B DNA 80 μg | mH5/B protein 10 μg (5 μg IM, 5 μg IN) 10 μg polyI:C | mH8/B protein 10 μg (5 μg IM, 5 μg IN) 10 μg polyI:C | B/Florida/4/06 (Yam) |
| 7 | mH13/B DNA 80 μg | BSA 10 μg (5 μg IM, 5 μg IN) 10 μg polyI:C | BSA 10 μg (5 μg IM, 5 μg IN) 10 μg polyI:C | B/Florida/4/06 (Yam) |
| 8 | Flulaval 1 μg (IM) (TIV) | None | Flulaval 1 μg (IM) (TIV) | B/Florida/4/06 (Yam) |
| 9 | Mock | BSA 10 μg (5 μg IM, 5 μg IN) 10 μg polyI:C | BSA 10 μg (5 μg IM, 5 μg IN) 10 μg polyI:C | B/Florida/4/06 (Yam) |
| 10 | mH13/B DNA 80 μg | mH5/B protein 10 μg (5 μg IM, 5 μg IN) 10 μg polyI:C | mH8/B protein 10 μg (5 μg IM, 5 μg IN) 10 μg polyI:C | Terminal Bleed |

7. EMBODIMENTS

Provided herein are the following exemplary embodiments:

1. A chimeric hemagglutinin (HA) polypeptide comprising a hemagglutinin ectodomain from an influenza B virus comprising one, two, three or all of the following:
   a. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA;
   b. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA;
   c. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and
   d. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA.

2. A chimeric hemagglutinin (HA) polypeptide comprising a hemagglutinin ectodomain from an influenza B virus comprising one, two, three or all of the following:
   a. 2, 3, 4, 5, 6, 7, 8, 9, 10, 11, 12, 13, 14, 15, 16, 17, 18, 19, 20 or more amino acid substitutions within the 120 loop of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the influenza B virus HA with amino acid residues found in a corresponding region of an influenza A virus HA;
   b. 2, 3, 4, 5, 6, 7, 8, 9 or more amino acid substitutions within the 150 loop of the influenza B virus HA, wherein the amino acid substitutions substitute 2, 3, 4, 5, 6, 7, 8, 9 or more amino acid residues in the 150 loop of the influenza B virus HA with amino acid residues found in a corresponding region of an influenza A virus HA;
   c. 2, 3, 4, 5 or more amino acid substitutions within the 160 loop of the influenza B virus HA, wherein the amino acid substitutions substitute 2, 3, 4, 5 or more amino acid residues in the 160 loop of the influenza B virus HA with amino acid residues found in a corresponding region of an influenza A virus HA; and
   d. 2, 3, 4, 5, 6, 7, 8 or more amino acid substitutions within the 190 helix of the influenza B virus HA, wherein the amino acid substitutions substitute 2, 3, 4, 5, 6, 7, 8 or more amino acid residues in the 190 helix of the influenza B virus HA with amino acid residues found in a corresponding region of an influenza A virus HA.

3. The chimeric HA polypeptide of embodiment 1 or 2 which further comprises the signal peptide of the influenza B virus HA.

4. The chimeric HA polypeptide of embodiment 1, 2, or 3 which further comprises the transmembrane domain and cytoplasmic tail domain of the influenza B virus HA.

5. The chimeric HA polypeptide of any one of embodiments 1 to 4, wherein the influenza B virus is of the Yamagata lineage or of the Victoria lineage.

6. The chimeric HA polypeptide of any one of embodiments 1 to 4, wherein the influenza B virus is influenza B/Yamagata/16/88.

7. The chimeric HA polypeptide of any one of embodiments 1 to 6, wherein the influenza A virus is an influenza A virus of an H4, H5, H6, H7, H8, H9, H10, H11, H12, H13, H14, H15, H16, H17, or H18.

8. The chimeric HA polypeptide of any one of embodiments 1 to 6, wherein the influenza A virus is an H5 HA subtype.

9. The chimeric HA polypeptide of embodiment 7, wherein
   a. the following amino acid residues in the 120 loop of influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2);
   b. the following amino acid residues in the 150 loop of influenza B virus B/Yamagata/16/88 PNVTSRNG (SEQ ID NO: 18) are substituted with amino acid residues PYQGKSS (SEQ ID NO:19);
   c. the following acid residues in the 160 loop of influenza B virus B/Yamagata/16/88 RDNKTA (SEQ ID NO: 5) are substituted with amino acid residues KKNSTY (SEQ ID NO: 6); and/or
   d. the following amino acid residues in the 190 helix of influenza B virus B/Yamagata/16/88 NKNQMKN (SEQ ID NO: 7) are substituted with amino acid residues NDAAMQT (SEQ ID NO: 8).

10. The chimeric HA polypeptide of embodiment 8 or 9, wherein the chimeric HA comprises one, two, or more amino acid substitutions outside of one, two, three, or all of the following: the 120 loop, the 150 loop, the 160 loop, and the 190 helix.

11. The chimeric HA polypeptide of any one of embodiments 8 to 10, wherein the H5 subtype is influenza A/Vietnam/1203/04 (HALo) virus.

12. The chimeric HA polypeptide of any one of embodiments 1 to 6, wherein the influenza A virus is an H8 HA subtype.

13. The chimeric HA polypeptide of embodiment 12, wherein
   a. the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51);
   b. the following amino acid residues in the 150 loop of influenza B virus B/Yamagata/16/88 PNVTSRNG (SEQ ID NO: 18) are substituted with amino acid residues NASTGGQS (SEQ ID NO: 52);
   c. the following amino acid residues in the 160 loop of influenza B virus B/Yamagata/16/88 RDNKTA (SEQ ID NO: 5) are substituted with amino acid residues KKKADTY (SEQ ID NO: 53); and/or
   d. the following amino acid residues in the 190 helix of influenza B virus B/Yamagata/16/88 NKNQMKN (SEQ ID NO: 7) are substituted with amino acid residues ADAKMQT (SEQ ID NO: 54).

14. The chimeric HA polypeptide of embodiment 12, wherein
   a. the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51);
   b. the following amino acid residues in the 150 loop of influenza B virus B/Yamagata/16/88 PNVTSRNG (SEQ ID NO: 18) are substituted with amino acid residues NASTGGQS (SEQ ID NO: 52);
   c. the following amino acid residues in the 160 loop of influenza B virus B/Yamagata/16/88 RDNKTA (SEQ ID NO: 5) are substituted with amino acid residues KKKADTY (SEQ ID NO: 53) or KKKPDTY (SEQ ID NO: 68); and/or
   d. the following amino acid residues in the 190 helix of influenza B virus B/Yamagata/16/88 NKNQMKN (SEQ ID NO: 7) are substituted with amino acid residues ADAKMQT (SEQ ID NO: 54) or PDAKMQT (SEQ ID NO: 69).

15. The chimeric HA polypeptide of embodiment 12 or 13, wherein the chimeric HA comprises one, two, or more amino acid substitutions outside of one, two, three, or all of the following: the 120 loop, the 150 loop, the 160 loop, and the 190 helix.

16. The chimeric HA polypeptide of embodiment 12, 13 or 15, wherein the H8 subtype is influenza A/Mallard/Sweden/24/2002 virus.

17. The chimeric HA polypeptide of any one of embodiments 1 to 6, wherein the influenza A virus is an H11 HA subtype.

18. The chimeric HA polypeptide of embodiment 17, wherein
   a. the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55);
   b. following amino acid residues in the 150 loop of influenza B virus B/Yamagata/16/88 PNVTSRNG (SEQ ID NO: 18) are substituted with amino acid residues PFGSSNS (SEQ ID NO:56);
   c. the following amino acid residues in the 160 loop of influenza B virus B/Yamagata/16/88 RDNKTA (SEQ ID NO: 5) are substituted with amino acid residues HQSGTY (SEQ ID NO: 57); and/or
   d. the following amino acid residues in the 190 helix of influenza B virus B/Yamagata/16/88 NKNQMKN (SEQ ID NO: 7) are substituted with amino acid residues TTLKMHQ (SEQ ID NO: 58) or ATLKMHQ (SEQ ID NO: 70).

19. The chimeric HA polypeptide of embodiment 17, wherein
   a. the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55);
   b. following amino acid residues in the 150 loop of influenza B virus B/Yamagata/16/88 PNVTSRNG (SEQ ID NO: 18) are substituted with amino acid residues PFGSSNS (SEQ ID NO:56) or KFGSSNS (SEQ ID NO:67);
   c. the following amino acid residues in the 160 loop of influenza B virus B/Yamagata/16/88 RDNKTA (SEQ ID NO: 5) are substituted with amino acid residues HQSGTY (SEQ ID NO: 57); and/or
   d. the following amino acid residues in the 190 helix of influenza B virus B/Yamagata/16/88 NKNQMKN (SEQ ID NO: 7) are substituted with amino acid residues TTLKMHQ (SEQ ID NO: 58) or ATLKMHQ (SEQ ID NO: 70).

20. The chimeric HA polypeptide of embodiment 17 or 18, wherein the chimeric HA comprises one, two, or more amino acid substitutions outside of one, two, three, or all of the following: the 120 loop, the 150 loop, the 160 loop, and the 190 helix.

21. The chimeric HA polypeptide of embodiment 17, 18 or 20, wherein the H11 subtype is influenza A/northern shoveler/Netherlands/18/99. 22. The chimeric HA polypeptide of any one of embodiments 1 to 6, wherein the influenza A virus is an H12 HA subtype.

23. The chimeric HA polypeptide of embodiment 22, wherein
  a. the following amino acid residues in influenza B virus B/Yamagata/16/88 TIP and NIRLSTHNVINAER-APGGPYRL (SEQ ID NO: 1) are substituted with amino acid residues YIP and RIKLSTFNVI-NAETAPGGPYRL (SEQ ID NO: 63);
  b. the following amino acid residues in the 150 loop of influenza B virus B/Yamagata/16/88 PNVTSRNG (SEQ ID NO: 18) are substituted with amino acid residues NNTSNQGS (SEQ ID NO:64);
  c. the following amino acid residues in the 160 loop of influenza B virus B/Yamagata/16/88 RDNKTA (SEQ ID NO: 5) are substituted with amino acid residues LKSGQF (SEQ ID NO: 65); and/or
  d. the following amino acid residues in the 190 helix of influenza B virus B/Yamagata/16/88 NKNQMKN (SEQ ID NO: 7) are substituted with amino acid residues PTSDMQI (SEQ ID NO: 66).

24. The chimeric HA polypeptide of embodiment 22 or 23, wherein the chimeric HA comprises one, two, or more amino acid substitutions outside of one, two, three, or all of the following: the 120 loop, the 150 loop, the 160 loop, and the 190 helix.

25. The chimeric HA polypeptide of any one of embodiments 22 to 24, wherein the H12 subtype is influenza A/mallard/interior Alaska/7MP0167/2007.

26. The chimeric HA polypeptide of any one of embodiments 1 to 6, wherein the influenza A virus is an H13 HA subtype.

27. The chimeric HA polypeptide of embodiment 26, wherein
  a. the following amino acid residues in influenza B virus B/Yamagata/16/88 TIP and NIRLSTHNVINAER-APGGPYRL (SEQ ID NO: 1) are substituted with amino acid residues NIP and RIELSTHNVINAE-VAPGGPYRL (SEQ ID NO: 59);
  b. the following amino acid residues in the 150 loop of influenza B virus B/Yamagata/16/88 PNVTSRNG (SEQ ID NO: 18) are substituted with amino acid residues PDKGASS (SEQ ID NO:60);
  c. the following amino acid residues in the 160 loop of influenza B virus B/Yamagata/16/88 RDNKTA (SEQ ID NO: 5) are substituted with amino acid residues KRGNQY (SEQ ID NO: 61); and/or
  d. the following amino acid residues in the 190 helix of influenza B virus B/Yamagata/16/88 NKNQMKN (SEQ ID NO: 7) are substituted with amino acid residues VSTNMAK (SEQ ID NO: 62).

28. The chimeric HA polypeptide of embodiment 26 or 27, wherein the chimeric HA comprises one, two, or more amino acid substitutions outside of one, two, three, or all of the following: the 120 loop, the 150 loop, the 160 loop, and the 190 helix.

29. The chimeric HA polypeptide of any one of embodiments 26 to 28, wherein the H13 subtype is influenza A/black headed gull/Sweden/1/99.

30. A chimeric hemagglutinin (HA) polypeptide comprising:
  a. a hemagglutinin ectodomain from an influenza B virus with one, two, three or all of the following
    i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA;
    ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA;
    iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and
    iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA; and
  b. a signal peptide, a transmembrane domain and a cytoplasmic tail domain from an influenza A virus.

31. A chimeric hemagglutinin (HA) polypeptide comprising:
  a. a hemagglutinin ectodomain from an influenza B virus with one, two, three or all of the following
    i. 2, 3, 4, 5, 6, 7, 8, 9, 10, 11, 12, 13, 14, 15, 16, 17, 18, 19, 20 or more amino acid substitutions within the 120 loop of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the influenza B virus HA with amino acid residues found in a corresponding region of an influenza A virus HA;
    ii. 2, 3, 4, 5, 6, 7, 8, 9 or more amino acid substitutions within the 150 loop of the influenza B virus HA, wherein the amino acid substitutions substitute 2, 3, 4, 5, 6, 7, 8, 9 or more amino acid residues in the 150 loop of the influenza B virus HA with amino acid residues found in a corresponding region of an influenza A virus HA;
    iii. 2, 3, 4, 5 or more amino acid substitutions within the 160 loop of the influenza B virus HA, wherein the amino acid substitutions substitute 2, 3, 4, 5 or more amino acid residues in the 160 loop of the influenza B virus HA with amino acid residues found in a corresponding region of an influenza A virus HA; and iv. 2, 3, 4, 5, 6, 7, 8 or more amino acid substitutions within the 190 helix of the influenza B virus HA, wherein the amino acid substitutions substitute 2, 3, 4, 5, 6, 7, 8 or more amino acid residues in the 190 helix of the influenza B virus HA with amino acid residues found in a corresponding region of an influenza A virus HA; and b. a signal peptide, a transmembrane domain and a cytoplasmic tail domain from an influenza A virus.

32. The chimeric HA polypeptide of embodiment 30 or 31, wherein the influenza B virus is of the Yamagata lineage or of the Victoria lineage.

33. The chimeric HA polypeptide of embodiment 32, wherein the influenza B virus is influenza B/Yamagata/16/88.

34. The chimeric HA polypeptide of any one of embodiments 30 to 33, wherein the influenza A virus is an influenza A virus of an H4, H5, H6, H7, H8, H9, H10, H11, H12, H13, H14, H15, H16, H17, or H18.

35. The chimeric HA polypeptide of any one of embodiments 30 to 33, wherein the influenza A virus HA is an H5 HA subtype.

36. The chimeric HA polypeptide of embodiment 35, wherein
a. the following amino acid residues in the 120 loop of influenza B virus B/Yamagata/16/88 TIP and NIRLSTHNVINAERAPGGPYRL (SEQ ID NO: 1) are substituted with amino acid residues FIP and KIQLSTKNVINAEHAPGGPYRL (SEQ ID NO: 2);
b. the following amino acid residues in the 150 loop of influenza B virus B/Yamagata/16/88 PNVTSRNG (SEQ ID NO: 18) are substituted with amino acid residues PYQGKSS (SEQ ID NO:19);
c. the following acid residues in the 160 loop of influenza B virus B/Yamagata/16/88 RDNKTA (SEQ ID NO: 5) are substituted with amino acid residues KKNSTY (SEQ ID NO: 6); and/or
d. the following amino acid residues in the 190 helix of influenza B virus B/Yamagata/16/88 NKNQMKN (SEQ ID NO: 7) are substituted with amino acid residues NDAAMQT (SEQ ID NO: 8).

37. The chimeric HA polypeptide of embodiment 35 or 36, wherein the chimeric HA comprises one, two, or more amino acid substitutions outside of one, two, three, or all of the following: the 120 loop, the 150 loop, the 160 loop, and the 190 helix.

38. The chimeric HA polypeptide of any one of embodiments 35 to 37, wherein the H5 subtype is influenza A/Vietnam/1203/04 (HALo) virus.

39. The chimeric HA polypeptide of any one of embodiments 30 to 33, wherein the influenza A virus HA is an H8 HA subtype.

40. The chimeric HA polypeptide of embodiment 39, wherein
a. the following amino acid residues in influenza B virus B/Yamagata/16/88 TIP and NIRLSTHNVINAERAPGGPYRL (SEQ ID NO: 1) are substituted with amino acid residues HIP and RIRLSTYNVINAETAPGGPYRL (SEQ ID NO: 51);
b. the following amino acid residues in the 150 loop of influenza B virus B/Yamagata/16/88 PNVTSRNG (SEQ ID NO: 18) are substituted with amino acid residues NASTGGQS (SEQ ID NO: 52);
c. the following amino acid residues in the 160 loop of influenza B virus B/Yamagata/16/88 RDNKTA (SEQ ID NO: 5) are substituted with amino acid residues KKKADTY (SEQ ID NO: 53); and/or
d. the following amino acid residues in the 190 helix of influenza B virus B/Yamagata/16/88 NKNQMKN (SEQ ID NO: 7) are substituted with amino acid residues ADAKMQT (SEQ ID NO: 54).

41. The chimeric HA polypeptide of embodiment 39 or 40, wherein the chimeric HA comprises one, two, or more amino acid substitutions outside of one, two, three, or all of the following: the 120 loop, the 150 loop, the 160 loop, and the 190 helix.

42. The chimeric HA polypeptide of any one of embodiments 39 to 41, wherein the H8 subtype is influenza A/Mallard/Sweden/24/2002 virus.

43. The chimeric HA polypeptide of any one of embodiments 30 to 33, wherein the influenza A virus HA is an H11 HA subtype.

44. The chimeric HA polypeptide of embodiment 43, wherein
a. the following amino acid residues in influenza B virus B/Yamagata/16/88 TIP and NIRLSTHNVINAERAPGGPYRL (SEQ ID NO: 1) are substituted with amino acid residues LIP and KIELSTSNVINAEVAPGGPYRL (SEQ ID NO: 55);
b. following amino acid residues in the 150 loop of influenza B virus B/Yamagata/16/88 PNVTSRNG (SEQ ID NO: 18) are substituted with amino acid residues PFGSSNS (SEQ ID NO:56);
c. the following amino acid residues in the 160 loop of influenza B virus B/Yamagata/16/88 RDNKTA (SEQ ID NO: 5) are substituted with amino acid residues HQSGTY (SEQ ID NO: 57); and/or
d. the following amino acid residues in the 190 helix of influenza B virus B/Yamagata/16/88 NKNQMKN (SEQ ID NO: 7) are substituted with amino acid residues TTLKMHQ (SEQ ID NO: 58) or ATLKMHQ (SEQ ID NO: 70).

45. The chimeric HA polypeptide of embodiment 43 or 44, wherein the chimeric HA comprises one, two, or more amino acid substitutions outside of one, two, three, or all of the following: the 120 loop, the 150 loop, the 160 loop, and the 190 helix.

46. The chimeric HA polypeptide of any one of embodiments 43 to 45, wherein the H11 subtype is influenza A/northern shoveler/Netherlands/18/99.

47. The chimeric HA polypeptide of any one of embodiments 30 to 33, wherein the influenza A virus HA is an H12 HA subtype.

48. The chimeric HA polypeptide of embodiment 47, wherein
a. the following amino acid residues in influenza B virus B/Yamagata/16/88 TIP and NIRLSTHNVINAERAPGGPYRL (SEQ ID NO: 1) are substituted with amino acid residues YIP and RIKLSTFNVINAETAPGGPYRL (SEQ ID NO: 63);
b. the following amino acid residues in the 150 loop of influenza B virus B/Yamagata/16/88 PNVTSRNG (SEQ ID NO: 18) are substituted with amino acid residues NNTSNQGS (SEQ ID NO:64);
c. the following amino acid residues in the 160 loop of influenza B virus B/Yamagata/16/88 RDNKTA (SEQ ID NO: 5) are substituted with amino acid residues LKSGQF (SEQ ID NO: 65); and/or
d. the following amino acid residues in the 190 helix of influenza B virus B/Yamagata/16/88 NKNQMKN (SEQ ID NO: 7) are substituted with amino acid residues PTSDMQI (SEQ ID NO: 66).

49. The chimeric HA polypeptide of embodiment 47 or 48, wherein the chimeric HA comprises one, two, or more amino acid substitutions outside of one, two, three, or all of the following: the 120 loop, the 150 loop, the 160 loop, and the 190 helix.

50. The chimeric HA polypeptide of any one of embodiments 47 to 49, wherein the H12 subtype is influenza A/mallard/interior Alaska/7MP0167/2007.

51. The chimeric HA polypeptide of any one of embodiments 30 to 33, wherein the influenza A virus HA is an H13 HA subtype.

52. The chimeric HA polypeptide of embodiment 51, wherein
   a. the following amino acid residues in influenza B virus B/Yamagata/16/88 TIP and NIRLSTHNVINAER-APGGPYRL (SEQ ID NO: 1) are substituted with amino acid residues NIP and RIELSTHNVINAE-VAPGGPYRL (SEQ ID NO: 59);
   b. the following amino acid residues in the 150 loop of influenza B virus B/Yamagata/16/88 PNVTSRNG (SEQ ID NO: 18) are substituted with amino acid residues PDKGASS (SEQ ID NO:60);
   c. the following amino acid residues in the 160 loop of influenza B virus B/Yamagata/16/88 RDNKTA (SEQ ID NO: 5) are substituted with amino acid residues KRGNQY (SEQ ID NO: 61); and/or
   d. the following amino acid residues in the 190 helix of influenza B virus B/Yamagata/16/88 NKNQMKN (SEQ ID NO: 7) are substituted with amino acid residues VSTNMAK (SEQ ID NO: 62).

53. The chimeric HA polypeptide of embodiment 51 or 52, wherein the chimeric HA comprises one, two, or more amino acid substitutions outside of one, two, three, or all of the following: the 120 loop, the 150 loop, the 160 loop, and the 190 helix.

54. The chimeric HA polypeptide of any one of embodiments 51 to 53, wherein the H13 subtype is influenza A/black headed gull/Sweden/1/99.

55. A chimeric hemagglutinin (HA) polypeptide comprising the amino acid sequence set forth in SEQ ID NO: 21 or SEQ ID NO: 27, or the amino acid sequence set forth in SEQ ID NO: 21 or SEQ ID NO: 27 without the signal peptide.

56. A chimeric hemagglutinin (HA) polypeptide comprising the amino acid sequence set forth in SEQ ID NO: 23 or SEQ ID NO: 25, or the amino acid sequence set forth in SEQ ID NO: 23 or SEQ ID NO: 25 without the signal peptide.

57. A chimeric hemagglutinin (HA) polypeptide comprising the amino acid sequence of the influenza virus HA ectodomain forth in SEQ ID NO: 21 or SEQ ID NO: 27.

58. A chimeric hemagglutinin (HA) polypeptide comprising the amino acid sequence of the influenza virus HA ectodomain forth in SEQ ID NO: 23 or SEQ ID NO: 25.

59. A chimeric hemagglutinin (HA) polypeptide comprising the amino acid sequence set forth in SEQ ID NO: 44, SEQ ID NO: 46, SEQ ID NO: 48, or SEQ ID NO: 50, or the amino acid sequence set forth in SEQ ID NO: 44, SEQ ID NO: 46, SEQ ID NO: 48, or SEQ ID NO: 50 without the signal peptide.

60. A chimeric hemagglutinin (HA) polypeptide comprising the amino acid sequence of the influenza virus HA ectodomain forth in SEQ ID NO: 44, SEQ ID NO: 46, SEQ ID NO: 48, or SEQ ID NO: 50.

61. The chimeric HA polypeptide of any one of embodiments 1 to 60, which is isolated.

62. A nucleic acid sequence encoding the chimeric HA polypeptide of any one of embodiments 1 to 13, 15 to 18, 20 to 29, 59, or 60.

63. A nucleic acid sequence encoding the chimeric HA polypeptide of any one of embodiments 30 to 55, or 57.

64. A nucleic acid sequence encoding the chimeric HA polypeptide of any one of embodiments 14, 18, 56 or 58.

65. A nucleic acid sequence comprising the nucleotide sequence set forth in SEQ ID NO: 20 or SEQ ID NO: 26, or a complement thereof.

66. A nucleic acid sequence comprising the nucleotide sequence set forth in SEQ ID NO: 22 or SEQ ID NO: 24, or a complement thereof.

67. A nucleic acid sequence comprising the nucleotide sequence set forth in SEQ ID NO: 43, SEQ ID NO: 45, SEQ ID NO: 47, or SEQ ID NO: 49, or a complement thereof.

68. The nucleic acid sequence of embodiment 62 or 67, further comprising a nucleotide sequence comprising the 5' and 3' non-coding regions of an influenza B virus.

69. The nucleic acid sequence of any one of embodiments 62 to 68, wherein the nucleic acid sequence is cDNA.

70. The nucleic acid sequence of any one of embodiments 62 to 69, which is isolated.

71. An expression vector comprising the nucleic acid sequence of any one of embodiments 62 to 69.

72. A viral vector comprising the nucleic acid sequence of any one of embodiments 62 to 69.

73. An influenza B virus engineered to express the nucleic acid sequence of embodiment 62, 67 or 68.

74. An influenza A virus engineered to express the nucleic acid sequence of embodiment 63 or 65.

75. An influenza virus engineered to express the chimeric HA polypeptide of any one of embodiments 1 to 13, 15 to 18, 20 to 29, 59 or 60.

76. The influenza virus of embodiment 75, wherein the influenza virus is an influenza B virus.

77. The influenza virus of embodiment 76, wherein the chimeric HA polypeptide is encoded by a nucleotide sequence comprising 5' and 3' noncoding regions of an influenza B virus.

78. An influenza B virus comprising the chimeric HA polypeptide of any one of embodiments 1 to 13, 15 to 18, 20 to 29, 59 or 60.

79. An influenza A virus engineered to express the chimeric HA polypeptide of any one of embodiments 1, 2, 30 to 55, or 57.

80. An influenza A virus comprising the chimeric HA polypeptide of any one of embodiments 1, 2, 30 to 55, or 57.

81. The influenza virus of embodiment 74 or 79, wherein the chimeric HA polypeptide is encoded by a nucleotide sequence comprising 5' and 3' noncoding regions of an influenza A virus.

82. The influenza virus of any one of embodiments 73 to 81, which is attenuated.

83. The influenza virus of embodiment 78 or 80, which is inactivated.

84. A virus-like particle comprising the chimeric HA polypeptide of any one of embodiments 1 to 60.

85. A subunit vaccine comprising the chimeric HA polypeptide of any one of embodiments 1 to 61.

86. A split vaccine comprising the chimeric HA polypeptide of any one of embodiments 1 to 61.

87. An immunogenic composition comprising the chimeric HA polypeptide of any one of embodiments 1 to 61.

88. An immunogenic composition comprising the influenza virus of any one of embodiments 73 to 83.

89. An immunogenic composition comprising the virus-like particle of embodiment 84.

90. The immunogenic composition of any one of embodiments 87 to 89, comprising an adjuvant.

91. The subunit vaccine of embodiment 85, comprising an adjuvant.

92. The split vaccine of embodiment 86, comprising an adjuvant.

93. A method of inducing an immune response against influenza B virus in a subject, comprising administering to the subject the immunogenic composition of any one of embodiments 87 to 90.

94. A method of inducing an immune response against influenza B virus in a subject, comprising administering to the subject the subunit vaccine of embodiment 85 or 91.

95. A method of inducing an immune response against influenza B virus in a subject, comprising administering to the subject the split vaccine of embodiment 86 or 92.

96. A method of inducing an immune response against influenza B virus in a subject comprising
   a. administering to the subject a first immunogenic composition comprising a first chimeric HA, which is the chimeric HA of any one of embodiments 1 to 61; and
   b. a certain period of time after the administration of the first immunogenic composition, administering to the subject a second immunogenic composition comprising a second chimeric HA, which is the chimeric HA of any one of embodiments 1 to 61, wherein the first and second chimeric HAs are not the same.

97. A method of inducing an immune response against influenza B virus in a subject that has been administered a first immunogenic composition, comprising administering to the subject a second immunogenic composition comprising a second chimeric HA, which is the chimeric HA of any one of embodiments 1 to 61, wherein the first immunogenic composition comprising a first chimeric HA, which is the chimeric HA of any one of embodiments 1 to 61, and wherein the first and second chimeric HAs are not the same.

98. The method of embodiment 96 or 97, wherein the first and second chimeric HAs comprise an ectodomain of an influenza B virus comprising the same stem domain but with one, two, three, or all of the following: (i) different 120 loops, (ii) different 150 loops, (iii) different 160 loops, and/or (iv) different 190 helices.

99. The method of embodiment 96 to 98, wherein the method further comprises administering to the subject a third immunogenic composition comprising a third chimeric HA, which is the chimeric HA of any one of embodiments 1 to 61, wherein the first, second, and third chimeric HAs are not the same.

100. The method of embodiment 99, wherein the first, second, and third chimeric HAs comprise an ectodomain of an influenza B virus comprising the same stem domain but with one, two, three, or all of the following: (i) different 120 loops, (ii) different 150 loops, (iii) different 160 loops, and/or (iv) different 190 helices.

101. The method of embodiment 99 or 100, wherein the third immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the second immunogenic composition.

102. The method of any one of embodiments 96 to 101, wherein the second immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the first immunogenic composition.

103. A method of inducing an immune response against influenza B virus in a subject, comprising:
   a. a first administration of a first immunogenic composition comprising a first chimeric HA polypeptide to the subject, wherein the first chimeric HA polypeptide comprises a first ectodomain of a a first influenza B virus comprising:
      i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a first subtype;
      ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the first subtype;
      iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the first subtype; and
      iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the first subtype; and
   b. a second administration of a second immunogenic composition comprising a second chimeric HA polypeptide to the subject a first period of time after the first administration, wherein the second chimeric HA polypeptide comprises a second ectodomain of a second influenza B virus comprising:
      i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a second subtype;
      ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the second subtype;
  iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the second subtype; and
  iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the second subtype; and
 c. a third administration of a third immunogenic composition comprising a third chimeric HA polypeptide to the subject a second period of time after the second administration, wherein the third chimeric HA polypeptide comprises a third ectodomain of a third influenza B virus comprising:
  i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a third subtype;
  ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the third subtype;
  iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the third subtype; and
  iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the third subtype.

104. The method of embodiment 103, wherein first chimeric HA polypeptide is administered to the subject as a nucleic acid encoding the polypeptide.

105. The method of embodiment 103, wherein the first chimeric HA polypeptide is administered to the subject as part of an influenza virus.

106. The method of any one of embodiments 103 to 105, wherein the first, second and third subtypes are different.

107. The method of embodiment 106, wherein the subtypes are selected from the group consisting of H4, H5, H6, H7, H8, H9, H10, H11, H12, H13, H14, H15, H16, H17 and H18.

108. The method of embodiment 106, wherein the subtypes are selected from the group consisting of H5, H8, H11, H12, and H13.

109. The method of any one of embodiments 103 to 105, wherein the first period of time is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the first administration.

110. The method of any one of embodiments 103 to 105, wherein the second period of time is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the second administration.

111. The method of any one of embodiments 93 to 110, wherein the subject is human.

112. An immunogenic composition of any one of embodiments 87 to 90 for use in a method of inducing an immune response against influenza B virus in a subject, wherein the method comprises administering to the subject said immunogenic composition.

113. A subunit vaccine of embodiment 85 or 91 for use in a method of inducing an immune response against influenza B virus in a subject, wherein the method comprises administering to the subject said subunit vaccine.

114. A split vaccine of embodiment 86 or 92 for use in a method of inducing an immune response against influenza B virus in a subject, wherein the method comprises administering to the subject said split vaccine.

115. A first immunogenic composition for use in a method of inducing an immune response against influenza B virus in a subject, wherein the method comprises:
 a. administering to the subject said first immunogenic composition, wherein said first immunogenic composition comprises a first chimeric HA, which is the chimeric HA of any one of embodiments 1 to 61; and
 b. a certain period of time after the administration of the first immunogenic composition, administering to the subject a second immunogenic composition comprising a second chimeric HA, which is the chimeric HA of any one of embodiments 1 to 61, wherein the first and second chimeric HAs are not the same.

116. A second immunogenic composition for use in a method of inducing an immune response against influenza B virus in a subject that has been administered a first immunogenic composition, wherein the method comprises administering to the subject said second immunogenic composition, wherein said second immunogenic composition comprises a second chimeric HA, which is the chimeric HA of any one of embodiments 1 to 61, wherein the first immunogenic composition comprising a first chimeric HA, which is the chimeric HA of any one of embodiments 1 to 61, and wherein the first and second chimeric HAs are not the same.

117. The first immunogenic composition for use of embodiment 115, wherein the first and second chimeric HAs comprise an ectodomain of an influenza B virus comprising the same stem domain but with one, two, three, or all of the following: (i) different 120 loops, (ii) different 150 loops, (iii) different 160 loops, and/or (iv) different 190 helices.

118. The second immunogenic composition for use of embodiment 116, wherein the first and second chimeric HAs comprise an ectodomain of an influenza B virus comprising the same stem domain but with one, two, three, or all of the following: (i) different 120 loops, (ii) different 150 loops, (iii) different 160 loops, and/or (iv) different 190 helices.

119. The first immunogenic composition for use of embodiment 115 or 117, wherein the method further comprises administering to the subject a third immunogenic composition comprising a third chimeric HA, which is the chimeric HA of any one of embodiments 1 to 61, wherein the first, second, and third chimeric HAs are not the same.

120. The second immunogenic composition of embodiment 116 or 118, wherein the method further comprises administering to the subject a third immunogenic composition comprising a third chimeric HA, which is the chimeric HA of any one of embodiments 1 to 61, wherein the first, second, and third chimeric HAs are not the same.

121. The first immunogenic composition for use of embodiment 119, wherein the first, second, and third chimeric HAs comprise an ectodomain of an influenza B virus comprising the same stem domain but with one, two, three, or all of the following: (i) different 120 loops, (ii) different 150 loops, (iii) different 160 loops, and/or (iv) different 190 helices.

122. The second immunogenic composition for use of embodiment 120, wherein the first, second, and third chimeric HAs comprise an ectodomain of an influenza B virus comprising the same stem domain but with one, two, three, or all of the following: (i) different 120 loops, (ii) different 150 loops, (iii) different 160 loops, and/or (iv) different 190 helices.

123. The first immunogenic composition for use of embodiment 119 or 121, wherein the third immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the second immunogenic composition.

124. The second immunogenic composition for use of embodiment 120 or 122, wherein the third immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the second immunogenic composition.

125. The first immunogenic composition for use of embodiment 115, 117, 119 or 121, wherein the second immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the first immunogenic composition.

126. The second immunogenic composition for use of embodiment 116, 118, 120 or 122, wherein the second immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the first immunogenic composition.

127. A first immunogenic composition for use in a method of inducing an immune response against influenza B virus in a subject, wherein the method comprises:
   a. a first administration of the first immunogenic composition, wherein the first immunogenic composition comprises a first chimeric HA polypeptide to the subject, and wherein the first chimeric HA polypeptide comprises a first ectodomain of a a first influenza B virus comprising:
      i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a first subtype;
      ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the first subtype;
      iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the first subtype; and
      iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the first subtype; and
   b. a second administration of a second immunogenic composition comprising a second chimeric HA polypeptide to the subject a first period of time after the first administration, wherein the second chimeric HA polypeptide comprises a second ectodomain of a second influenza B virus comprising:
      i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a second subtype;

ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the second subtype;

iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the second subtype; and iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the second subtype; and c. a third administration of a third immunogenic composition comprising a third chimeric HA polypeptide to the subject a second period of time after the second administration, wherein the third chimeric HA polypeptide comprises a third ectodomain of a third influenza B virus comprising:

i. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA of a third subtype;

ii. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA of the third subtype;

iii. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA of the third subtype; and iv. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA of the third subtype.

128. The first immunogenic composition for use of embodiment 127, wherein first chimeric HA polypeptide is administered to the subject as a nucleic acid encoding the polypeptide.

129. The first immunogenic composition for use of embodiment 127, wherein the first chimeric HA polypeptide is administered to the subject as part of an influenza virus.

130. The first immunogenic composition for use of any one of embodiments 127 to 129, wherein the first, second and third subtypes are different.

131. The first immunogenic composition for use of embodiment 130, wherein the subtypes are selected from the group consisting of H4, H5, H6, H7, H8, H9, H10, H11, H12, H13, H14, H15, H16, H17 and H18.

132. The first immunogenic composition for use of embodiment 130, wherein the subtypes are selected from the group consisting of H5, H8, H11, H12, and H13.

133. The first immunogenic composition for use of any one of embodiments 127 to 132, wherein the first period of time is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the first administration.

134. The first immunogenic composition for use of any one of embodiments 127 to 133, wherein the second period of time is 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the second administration.

135. The immunogenic composition for use of any one of embodiments 112 or 115 to 134, or the vaccine for use of 113 or 114, wherein the subject is human.

8. EQUIVALENTS

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The invention claimed is:

1. A nucleic acid sequence encoding a chimeric hemagglutinin (HA) polypeptide, wherein the chimeric HA polypeptide comprises a hemagglutinin ectodomain from influenza B virus B/Yamagata/16/88, and wherein:

I. a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues FIP and KIQLSTKNVINAEHAPGGPYRL (SEQ ID NO: 2);

b. the following amino acid residues in the 150 loop of the globular head domain of influenza B virus B/Yamagata/16/88 hemagglutinin PNVTSRNG (SEQ ID NO: 18) are substituted with amino acid residues PYQGKSS (SEQ ID NO:19);

c. the following amino acid residues in the 160 loop of the globular head domain of influenza B virus B/Yamagata/16/88 hemagglutinin RDNKTA (SEQ ID NO: 5) are substituted with amino acid residues KKNSTY (SEQ ID NO: 6); and d. the following amino acid residues in the 190 helix of the globular head domain of influenza B virus B/Yamagata/16/88 hemagglutinin NKNQMKN (SEQ ID NO: 7) are substituted with amino acid residues NDAAMQT (SEQ ID NO: 8);

II. a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues HIP and RIRLSTYNVINAETAPGGPYRL (SEQ ID NO: 51);

b the following amino acid residues in the 150 loop of the globular head domain of influenza B virus B/Yamagata/16/88 hemagglutinin PNVTSRNG (SEQ ID NO: 18) are substituted with amino acid residues NASTGGQS (SEQ ID NO: 52);

c. the following amino acid residues in the 160 loop of the globular head domain of influenza B virus B/Yamagata/16/88 hemagglutinin RDNKTA (SEQ ID NO: 5) are substituted with amino acid residues KKKADTY (SEQ ID NO: 53); and d. the following amino acid residues in the 190 helix of the globular head domain of influenza B virus B/Yamagata/16/88 hemagglutinin NKNQMKN (SEQ ID NO: 7) are substituted with amino acid residues ADAKMQT (SEQ ID NO: 54);

III. a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues LIP and KIELSTSNVINAEVAPGGPYRL (SEQ ID NO: 55);

b. the following amino acid residues in the 150 loop of the globular head domain of influenza B virus B/Yamagata/16/88 hemagglutinin PNVTSRNG (SEQ ID NO: 18) are substituted with amino acid residues PFGSSNS (SEQ ID NO:56);

c. the following amino acid residues in the 160 loop of the globular head domain of influenza B virus B/Yamagata/16/88 hemagglutinin RDNKTA (SEQ ID NO: 5) are substituted with amino acid residues HQSGTY (SEQ ID NO: 57); and d. the following amino acid residues in the 190 helix of the globular head domain of influenza B virus B/Yamagata/16/88 hemagglutinin NKNQMKN (SEQ ID NO: 7) are substituted with amino acid residues TTLKMHQ (SEQ ID NO: 58) or ATLKMHQ (SEQ ID NO: 70); or IV. a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues NIP and RIELSTHNVINAEVAPGGPYRL (SEQ ID NO: 59);

b. the following amino acid residues in the 150 loop of the globular head domain of influenza B virus B/Yamagata/16/88 hemagglutinin PNVTSRNG (SEQ ID NO: 18) are substituted with amino acid residues PDKGASS (SEQ ID NO:60);

c. the following amino acid residues in the 160 loop of the globular head domain of influenza B virus B/Yamagata/16/88 hemagglutinin RDNKTA (SEQ ID NO: 5) are substituted with amino acid residues KRGNQY (SEQ ID NO: 61); and d. the following amino acid residues in the 190 helix of the globular head domain of influenza B virus B/Yamagata/16/88 hemagglutinin NKNQMKN (SEQ ID NO: 7) are substituted with amino acid residues VSTNMAK (SEQ ID NO: 62).

2. The nucleic acid sequence of claim 1, wherein the chimeric HA polypeptide further comprises the transmembrane and cytoplasmic tail domains of the influenza B virus hemagglutinin.

3. The nucleic acid sequence of claim 1, wherein:

a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues FIP and KIQLSTKNVINAEHAPGGPYRL (SEQ ID NO: 2);

b. the following amino acid residues in the 150 loop of the globular head domain of influenza B virus B/Yamagata/16/88 hemagglutinin PNVTSRNG (SEQ ID NO: 18) are substituted with amino acid residues PYQGKSS (SEQ ID NO:19);

c. the following amino acid residues in the 160 loop of the globular head domain of influenza B virus B/Yamagata/16/88 hemagglutinin RDNKTA (SEQ ID NO: 5) are substituted with amino acid residues KKNSTY (SEQ ID NO: 6); and d. the following amino acid residues in the 190 helix of the globular head domain of influenza B virus B/Yamagata/16/88 hemagglutinin NKNQMKN (SEQ ID NO: 7) are substituted with amino acid residues NDAAMQT (SEQ ID NO: 8).

4. The nucleic acid sequence of claim 1, wherein:

a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues HIP and RIRLSTYNVINAETAPGGPYRL (SEQ ID NO: 51);

b. the following amino acid residues in the 150 loop of the globular head domain of influenza B virus B/Yamagata/16/88 hemagglutinin PNVTSRNG (SEQ ID NO: 18) are substituted with amino acid residues NASTGGQS (SEQ ID NO: 52);

c. the following amino acid residues in the 160 loop of the globular head domain of influenza B virus B/Yamagata/16/88 hemagglutinin RDNKTA (SEQ ID NO: 5) are substituted with amino acid residues KKKADTY (SEQ ID NO: 53); and d. the following amino acid residues in the 190 helix of the globular head domain of influenza B virus B/Yamagata/16/88 hemagglutinin NKNQMKN (SEQ ID NO: 7) are substituted with amino acid residues ADAKMQT (SEQ ID NO: 54).

5. The nucleic acid sequence of claim 1, wherein:

a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues LIP and KIELSTSNVINAEVAPGGPYRL (SEQ ID NO: 55);

b. the following amino acid residues in the 150 loop of the globular head domain of influenza B virus B/Yamagata/16/88 hemagglutinin PNVTSRNG (SEQ ID NO: 18) are substituted with amino acid residues PFGSSNS (SEQ ID NO:56);

c. the following amino acid residues in the 160 loop of the globular head domain of influenza B virus B/Yamagata/16/88 hemagglutinin RDNKTA (SEQ ID NO: 5) are substituted with amino acid residues HQSGTY (SEQ ID NO: 57); and d. the following amino acid residues in the 190 helix of the globular head domain of influenza B virus B/Yamagata/16/88 hemagglutinin NKNQMKN (SEQ ID NO: 7) are substituted with amino acid residues TTLKMHQ (SEQ ID NO: 58).

6. The nucleic acid sequence of claim 1, wherein:

a. the following amino acid residues in the 120 loop of the globular head domain of influenza B virus B/Yamagata/16/88 hemagglutinin TIP and NIRLSTHNVINAERAPGGPYRL (SEQ ID NO: 1) are substituted with amino acid residues NIP and RIELSTHNVINAEVAPGGPYRL (SEQ ID NO: 59);

b. the following amino acid residues in the 150 loop of the globular head domain of influenza B virus B/Yamagata/16/88 hemagglutinin PNVTSRNG (SEQ ID NO: 18) are substituted with amino acid residues PDKGASS (SEQ ID NO:60);

c. the following amino acid residues in the 160 loop of the globular head domain of influenza B virus B/Yamagata/16/88 hemagglutinin RDNKTA (SEQ ID NO: 5) are substituted with amino acid residues KRGNQY (SEQ ID NO: 61); and d. the following amino acid residues in the 190 helix of the globular head domain of influenza B virus B/Yamagata/16/88 hemagglutinin NKNQMKN (SEQ ID NO: 7) are substituted with amino acid residues VSTNMAK (SEQ ID NO: 62).

7. A nucleic acid sequence encoding a chimeric hemagglutinin (HA) polypeptide, wherein the chimeric HA polypeptide comprises:

a. the amino acid sequence set forth in SEQ ID NO: 21, or the amino acid set forth in SEQ ID NO: 21 without the signal peptide;

b. the amino acid sequence set forth in SEQ ID NO: 23 or SEQ ID NO: 25, or the amino acid sequence set forth in SEQ ID NO: 23 or SEQ ID NO: 25 without the signal peptide;

c. the amino acid sequence of the influenza virus HA ectodomain set forth in SEQ ID NO: 21;

d. the amino acid sequence of the influenza virus HA ectodomain set forth in SEQ ID NO: 23 or SEQ ID NO: 25;

e. the amino acid sequence set forth in SEQ ID NO: 44, SEQ ID NO: 46, SEQ ID NO: 48, or SEQ ID NO: 50, or the amino acid sequence set forth in SEQ ID NO: 44, SEQ ID NO: 46, SEQ ID NO: 48, or SEQ ID NO: 50 without the signal peptide; or f. the amino acid sequence of the influenza virus HA ectodomain set forth in SEQ ID NO: 44, SEQ ID NO: 46, SEQ ID NO: 48, or SEQ ID NO: 50.

8. The chimeric HA polypeptide of claim 7, wherein the chimeric HA polypeptide comprises the amino acid sequence set forth in SEQ ID NO: 44.

9. The nucleic acid sequence of claim 7, wherein the chimeric HA polypeptide comprises the amino acid sequence set forth in SEQ ID NO: 44 without the signal peptide.

10. The nucleic acid sequence of claim 7, wherein the chimeric HA polypeptide comprises the amino acid sequence of the influenza virus HA ectodomain set forth in SEQ ID NO: 44.

11. The nucleic acid sequence of claim 1, which is isolated.

12. The nucleic acid sequence of claim 1, wherein the nucleic acid sequence is RNA or cDNA.

13. An isolated nucleic acid sequence encoding a chimeric hemagglutinin (HA) polypeptide, wherein the chimeric HA polypeptide comprises a hemagglutinin ectodomain from an influenza B virus comprising the following:

a. 2, 3, 4, 5, 6, 7, 8, 9, 10, 11, 12, 13, 14, 15, 16, 17, 18, 19, 20 or more amino acid substitutions within the 120 loop of the globular head domain of the influenza B virus HA, wherein the amino acid substitutions substitute 2, 3, 4, 5, 6, 7, 8, 9, 10, 11, 12, 13, 14, 15, 16, 17, 18, 19, 20 or more amino acid residues in the 120 loop of the globular head of the influenza B virus HA with amino acid residues found in a corresponding region of the globular domain of an influenza A virus HA;

b. 2, 3, 4, 5, 6, 7, 8, 9 or more amino acid substitutions within the 150 loop of the globular head domain of the influenza B virus HA, wherein the amino acid substitutions substitute 2, 3, 4, 5, 6, 7, 8, 9 or more amino acid residues in the 150 loop of the globular head of the influenza B virus HA with amino acid residues found in a corresponding region of the globular domain of an influenza A virus HA;

c. 2, 3, 4, 5 or more amino acid substitutions within the 160 loop of the globular head domain of the influenza B virus HA, wherein the amino acid substitutions substitute 2, 3, 4, 5 or more amino acid residues in the 160 loop of the globular head of the influenza B virus HA with amino acid residues found in a corresponding region of the globular domain of an influenza A virus HA; and d. 2, 3, 4, 5, 6, 7, 8 or more amino acid substitutions within the 190 helix of the globular head domain of the influenza B virus HA, wherein the amino acid substitutions substitute 2, 3, 4, 5, 6, 7, 8 or more amino acid residues in the 190 helix of the globular head of the influenza B virus HA with amino acid residues found in a corresponding region of the globular domain of an influenza A virus HA.

14. The nucleic acid sequence of claim 12, wherein the chimeric HA polypeptide further comprises the transmembrane and cytoplasmic tail domains of the influenza B virus hemagglutinin.

15. A nucleic acid sequence encoding a chimeric hemagglutinin (HA) polypeptide, wherein the nucleic acid sequence comprises:

a. the nucleotide sequence set forth in SEQ ID NO: 20, or a complement thereof, b. the nucleotide sequence set forth in SEQ ID NO: 22 or SEQ ID NO: 24, or a complement thereof, or c. the nucleotide sequence set forth in SEQ ID NO: 43, SEQ ID NO: 45, SEQ ID NO: 47, or SEQ ID NO: 49, or a complement thereof.

16. The nucleic acid sequence of claim 15, further comprising a nucleotide sequence comprising the 5' non-coding region of an influenza B virus and a nucleotide sequence comprising the 3' non-coding region of an influenza B virus.

17. The nucleic acid sequence of claim 15, wherein the nucleic acid sequence is RNA or cDNA.

18. The nucleic acid sequence of claim 15, which is isolated.

19. An expression vector comprising the nucleic acid sequence of claim 1.

20. The expression vector of claim 19, wherein the expression vector is a plasmid or a viral vector.

21. An influenza B virus comprising an HA segment that comprises the nucleic acid sequence of claim 1.

22. An isolated host cell comprising the expression vector of claim 19.

23. A method for producing an influenza virus comprising the nucleic acid sequence of claim 1, comprising propagating the virus in a substrate that allows the virus to grow.

24. The nucleic acid sequence of claim 13, wherein the chimeric HA polypeptide further comprises the transmembrane and cytoplasmic tail domains of the influenza B virus hemagglutinin.

25. The nucleic acid sequence of claim 13, wherein the globular head domain of the hemagglutinin ectodomain further comprises 1, 2, 3, 4, or 5 amino acid substitutions outside of the 120 loop, 150 loop, 160 loop, and/or 190 helix.

26. The nucleic acid sequence of claim 1, wherein the globular head domain of the hemagglutinin ectodomain further comprises 1, 2, 3, 4, or 5 amino acid substitutions outside of the 120 loop, 150 loop, 160 loop, and/or 190 helix.

27. An influenza B virus comprising the nucleic acid sequence of claim 13.

* * * * *